(12) United States Patent
Liew et al.

(10) Patent No.: US 11,053,551 B2
(45) Date of Patent: **\*Jul. 6, 2021**

(54) METHOD AND APPARATUS FOR DETERMINING A PROBABILITY OF COLORECTAL CANCER IN A SUBJECT

(71) Applicant: GeneNews, Inc., Markham (CA)

(72) Inventors: Choong-Chin Liew, Toronto (CA); Samuel Chao, Concord (CA)

(73) Assignee: StageZero Life Sciences Ltd., Richmond Hill (CA)

( * ) Notice: Subject to any disclaimer, the term of this patent is extended or adjusted under 35 U.S.C. 154(b) by 62 days.

This patent is subject to a terminal disclaimer.

(21) Appl. No.: 15/883,637

(22) Filed: Jan. 30, 2018

(65) Prior Publication Data

US 2018/0163276 A1  Jun. 14, 2018

Related U.S. Application Data

(63) Continuation of application No. 14/546,433, filed on Nov. 18, 2014, now abandoned, which is a continuation of application No. 12/384,914, filed on Apr. 10, 2009, now Pat. No. 8,921,074.

(60) Provisional application No. 61/123,798, filed on Apr. 10, 2008, provisional application No. 61/123,831, filed on Apr. 11, 2008.

(51) Int. Cl.
| | |
|---|---|
| *C12Q 1/6886* | (2018.01) |
| *G01N 33/574* | (2006.01) |
| *G16B 25/00* | (2019.01) |
| *G16B 5/00* | (2019.01) |
| *G16B 40/00* | (2019.01) |

(52) U.S. Cl.
CPC ..... *C12Q 1/6886* (2013.01); *G01N 33/57419* (2013.01); *G16B 5/00* (2019.02); *C12Q 2600/118* (2013.01); *C12Q 2600/158* (2013.01); *C12Q 2600/16* (2013.01); *C12Q 2600/166* (2013.01); *G01N 2800/50* (2013.01); *G01N 2800/56* (2013.01); *G16B 25/00* (2019.02); *G16B 40/00* (2019.02)

(58) Field of Classification Search
CPC ............ C12Q 1/6886; C12Q 2600/118; C12Q 2600/158; C12Q 2600/16; C12Q 2600/166; G01N 2800/50; G01N 2800/56; G01N 33/57419; G16B 25/00; G16B 40/00; G16B 5/00
USPC ....................................................... 435/91.2
See application file for complete search history.

(56) References Cited

U.S. PATENT DOCUMENTS

| | | | |
|---|---|---|---|
| 8,071,293 B2 | 12/2011 | High et al. | |
| 8,921,074 B2 | 12/2014 | Liew et al. | |
| 2003/0008284 A1 | 1/2003 | Kennedy et al. | |
| 2005/0014165 A1* | 1/2005 | Lee | C12Q 1/6886 435/6.14 |
| 2006/0019256 A1 | 1/2006 | Clarke et al. | |
| 2006/0199179 A1 | 9/2006 | Nakamura et al. | |
| 2007/0054282 A1 | 3/2007 | Liew | |
| 2007/0117164 A1 | 5/2007 | Raskov et al. | |

FOREIGN PATENT DOCUMENTS

| | | |
|---|---|---|
| CA | 2530191 | 12/2004 |
| CA | 2626604 | 4/2007 |
| EP | 2 868 754 | 5/2015 |
| WO | WO 2004/090550 | 10/2004 |
| WO | WO 2005/054508 | 6/2005 |
| WO | WO 2007/048074 | 4/2007 |
| WO | WO 2007/149269 | 12/2007 |
| WO | WO 2009/125303 | 10/2009 |

OTHER PUBLICATIONS

Bates, Six-gene cluster Stratifies Need for Colonoscopy, International Medical News Group, Jul. 2008.
Hamm et al., Frequent expression loss of Inter-alpha-trypsin inhibitor heavy chain (ITIH) genes in multiple human solid tumors: A systematic expression analysis, BMC Cancer, vol. 8, No. 25, XP021034655, Jan. 28, 2008.
Han et al.. "Novel blood biomarker panel detects human colorectal cancer", Journal of Clinical Oncology, 2006 ASCO Annual Meeting Proceedings , vol. 24, No. 18S, 3611, XP002642644, Jun. 2006.
Han et al., Novel Blood-Based, Five-Gene Biomarker Set for the Detection of Colorectal Cancer, Clinical Cancer Research, vol. 14, No. 2, pp. 455-460, XP002642643, Jan. 15, 2008.
Kulman, et al., Identification of two novel transmembrane γ-carboxyglutamic acid proteins expressed broadly in fetal and adult tissues, Proceedings of the National Academy of Sciences of the USA, vol. 98, No. 4, pp. 1370-1375, Feb. 13, 2001.
Lelliott et al., Lamin expression in human adipose cells in relation to anatomical site and differentiation state, Journal of Clinical Endocrinology & Metabolism, vol. 87, No. 2, pp. 728-734, Feb. 2002.

(Continued)

*Primary Examiner* — Cynthia B Wilder
(74) *Attorney, Agent, or Firm* — Sunstein LLP

(57) ABSTRACT

A method of determining a probability that a human test subject has colorectal cancer as opposed to not having colorectal cancer is disclosed. The method comprises, for each gene of a set of one or more genes selected from the group consisting of ANXA3, CLEC4D, IL2RB, LMNB1, PRRG4, TNFAIP6 and VNN1: determining a level of RNA encoded by the gene in blood of the test subject, thereby generating test data; providing positive control data representing levels of RNA encoded by the gene in blood of human control subjects having colorectal cancer, and providing negative control data representing levels of RNA encoded by the gene in blood of human control subjects not having colorectal cancer; and determining a probability that the test data corresponds to the positive control data and not to the negative control data, where the probability that the test data corresponds to the positive control data and not to the negative control data represents the probability that the test subject has colorectal cancer as opposed to not having colorectal cancer.

3 Claims, 9 Drawing Sheets

Specification includes a Sequence Listing.

(56) References Cited

OTHER PUBLICATIONS

Marshall et al., Stratification of colorectal cancer probability using six genes from whole blood, AACR Annual Meeting, San Diego, CA, Apr. 12-16, 2008, Cancer Research vol. 68: LB-214, May 1, 2008.

Marshall et al., A blood-based biomarker panel for stratifying current risk for colorectal cancer, International Journal of Cancer, vol. 126, pp. 1177-1186, 2010.

Morrow, Biomarker Panel for Colon Cancer Rivals Fecal Occult Blood Test, Managed Care, http://www.managedcaremag.com/archives/1205/1205.biotech.html, May 2012.

Rubie et al., Housekeeping gene variability in normal and cancerous colorectal, pancreatic, esophageal, gastric and hepatic tissues, Molecular and Cellular Probes, vol. 19, pp. 101-109, XP004725272, 2005.

Schneider et al., Improved sensitivity in the diagnosis of gastrointestinal tumors by fuzzy logic-based tumor marker profiles including the tumor M2-PK, Anticancer Research, vol. 25, No. 3A, pp. 1507-1515, May 1, 2005.

Yip et al., A case-controlled validation study of a blood-based seven-gene biomarker panel for colorectal cancer in Malaysia, Journal of Experimental & Clinical Cancer Research, vol. 29, No. 1, p. 128, Sep. 2010.

Canadian Intellectual Property Office, International Search Report WO2009125303, International Application No. PCT/IB2009/005782 together with the Written Opinion, 19 pages, dated Dec. 22, 2009.

European Patent Office, Supplementary European Search Report, Application No. EP 09 73 0647, 8 pages, completed Jun. 16, 2011 and dated Jul. 8, 2011.

European Patent Office, Extended European Search Report, Application No. 14196147.4, 6 pages, dated Apr. 9, 2015.

* cited by examiner

ACTB: actin, beta SEQ ID NO: 73

```
   1 accgccgaga ccgcgtccgc cccgcgagca cagagcctcg cctttgccga tccgccgcc
  61 gtccacaccc gccgccagct caccatggat gatgatatcg ccgcgctcgt cgtcgacaac
 121 ggctccggca tgtgcaaggc cggcttcgcg ggcgacgatg ccccccgggc cgtcttcccc
 181 tccatcgtgg ggcgccccag gcaccagggc gtgatggtgg gcatgggtca gaaggattcc
 241 tatgtgggcg acgaggccca gagcaagaga ggcatcctca ccctgaagta ccccatcgag
 301 cacggcatcg tcaccaactg ggacgacatg gagaaaatct ggcaccacac cttctacaat
 361 gagctgcgtg tggctcccga ggagcacccc gtgctgctga ccgaggcccc ctgaacccc
 421 aaggccaacc gcgagaagat gacccagatc atgtttgaga ccttcaacac cccagccatg
 481 tacgttgcta tccaggctgt gctatcctg tacgcctctg gccgtaccac tggcatcgtg
 541 atggactccg gtgacggggt cacccacact gtgcccatct acgagggta tgccctcccc
 601 catgccatcc tgcgtctgga cctggctggc cgggacctga ctgactacct catgaagatc
 661 ctcaccgagc gcggctacag cttcaccacc acggccgagc gggaaatcgt gcgtgacatt
 721 aaggagaagc tgtgctacgt cgccctggac ttcgagcaag agatggccac ggctgcttcc
 781 agctcctccc tggagaagag ctacgagctg cctgacggcc aggtcatcac cattggcaat
 841 gagcggttcc gctgccctga ggcactcttc cagccttcct tcctgggcat ggagtcctgt
 901 ggcatccacg aaactacctt caactccatc atgaagtgtg acgtggacat ccgcaaagac
 961 ctgtacgcca acacagtgct gtctggcggc accaccatgt accctggcat tgccgacagg
1021 atgcagaagg agatcactgc cctggcaccc agcacaatga agatcaagat cattgctcct
1081 cctgagcgca agtactccgt gtggatcggc ggctccatcc tggcctcgct gtccaccttc
1141 cagcagatgt ggatcagcaa gcaggagtat gacgagtccg cccctccat cgtccaccgc
1201 aaatgcttct aggcggacta tgacttagtt gcgttacacc ctttcttgac aaaacctaac
1261 ttgcgcagaa aacaagatga gattggcatg gctttatttg ttttttttgt tttgttttgg
1321 tttttttttt ttttttggct tgactcagga tttaaaaact ggaacggtga aggtgacagc
1381 agtcggttgg agcgagcatc ccccaaagtt cacaatgtgg ccgaggactt tgattgcaca
1441 ttgttgtttt tttaatagtc attccaaata tgagatgcgt tgttacagga agtcccttgc
1501 catcctaaaa gccaccccac ttctctctaa ggagaatggc ccagtcctct cccaagtcca
1561 cacaggggag gtgatagcat tgctttcgtg taaattatgt aatgcaaaat ttttttaatc
1621 ttcgccttaa tacttttta ttttgtttta tttgaatga tgagccttcg tgccccccct
1681 tccccctttt ttgtccccca acttgagatg tatgaaggct tttggtctcc ctgggagtgg
1741 gtggaggcag ccaggctta cctgtacact gacttgagac cagttgaata aaagtgcaca
1801 ccttaaaaat gaaaaaaaaa aaaaaaaaa aaaaaaaaaa aaaaaaaaaa aa
```

FIG. 1A

ANXA3: annexin A3  SEQ ID NO: 74

```
   1 gggtggggaa gcttagagac cggtgaggga gcagagctgg ggcgcctgtg tacagggata
  61 gagcccggcg gcagcagggc gcggcttccc tttcccgggg cctggggccg caatcaggtg
 121 gagtcgagag gccggaggag gggcaggagg aaggggtgcg gtcgcgatcc ggacccggag
 181 ccagcgcgga gcacctgcgc ccgcggctga caccttcgct cgcagtttgt tcgcagttta
 241 ctcgcacacc agtttccccc accgcgcttt ggattagtgt gatctcagct caaggcaaag
 301 gtgggatatc atggcatcta tctgggttgg acaccgagga acagtaagag attatccaga
 361 ctttagccca tcagtggatg ctgaagctat tcagaaagca atcagaggaa ttggaactga
 421 tgagaaaatg ctcatcagca ttctgactga gaggtcaaat gcacagcggc agctgattgt
 481 taaggaatat caagcagcat atggaaagga gctgaaagat gacttgaagg gtgatctctc
 541 tggccacttt gagcatctca tggtggccct agtgactcca ccagcagtct tgatgcaaa
 601 gcagctaaag aaatccatga agggcgcggg aacaaacgaa gatgccttga ttgaaatctt
 661 aactaccagg acaagcaggc aaatgaagga tatctctcaa gcctattata cagtatacaa
 721 gaagagtctt ggagatgaca ttagttccga aacatctggt gacttccgga agctctgtt
 781 gactttggca gatggcagaa gagatgaaag tctgaaagtg gatgagcatc tggccaaaca
 841 agatgcccag attctctata aagctggtga gaacagatgg ggcacggatg aagacaaatt
 901 cactgagatc ctgtgtttaa ggagctttcc tcaattaaaa ctaacatttg atgaatacag
 961 aaatatcagc caaaggaca ttgtggacag cataaaagga gaattatctg ggcattttga
1021 agacttactg ttggccatag ttaattgtgt gaggaacacg ccggcctttt tagccgaaag
1081 actgcatcga gccttgaagg gtattggaac tgatgagttt actctgaacc gaataatggt
1141 gtccagatca gaaattgacc ttttggacat tcgaacagag ttcaagaagc attatggcta
1201 ttccctatat tcagcaatta aatcggatac ttctggagac tatgaaatca cactcttaaa
1261 aatctgtggt ggagatgact gaaccaagaa gataatctcc aaaggtccac gatgggcttt
1321 cccaacagct ccaccttact tcttctcata ctatttaaga gaacaagcaa atataaacag
1381 caacttgtgt tcctaacagg aattttcatt gttctataac aacaacaaca aaagcgatta
1441 ttattttaga gcatctcatt tataatgtag cagctcataa atgaaattga aatggtatt
1501 aaagatctgc aactactatc caacttatat ttctgctttc aaagttaaga atctttatag
1561 ttctactcca ttaaatataa agcaagataa taaaaattgt tgcttttgtt aaagtaaaa
1621 aaaaaaaaa aaaa
```

FIG. 1B

CLEC4D: C-type lectin domain family 4, member D (SEQ ID NO:75)

```
   1 ctttgaaaaa gacttctttt gagctaactt tcttatactg gtaccttct aatctcacta
  61 caatatgtaa cattggtgtt cgatctcaag tatttctgaa tatattcccc tatccacaga
 121 aatatactct gggggaaaaa aaatagaaca aattcttgcc gtcctgacca ttgaacaaga
 181 gactaattag acaatggggc tagaaaaacc tcaaagtaaa ctggaaggag gcatgcatcc
 241 ccagctgata ccttcggtta ttgctgtagt tttcatctta cttctcagtg tctgttttat
 301 tgcaagttgt ttggtgactc atcacaactt ttcacgctgt aagagaggca caggagtgca
 361 caagttagag caccatgcaa agctcaaatg catcaaagag aaatcagaac tgaaaagtgc
 421 tgaagggagc acctggaact gttgtcctat tgactggaga gccttccagt ccaactgcta
 481 ttttcctctt actgacaaca agacgtgggc tgagagtgaa aggaactgtt cagggatggg
 541 ggcccatctg atgaccatca gcacggaagc tgagcagaac tttattattc agtttctgga
 601 tagacggctt tcctatttcc ttggacttag agatgagaat gccaaaggtc agtggcgttg
 661 ggtggaccag acgccattta acccacgcag agtattctgg cataagaatg aacccgacaa
 721 ctctcaggga gaaaactgtg ttgttcttgt ttataaccaa gataaatggg cctggaatga
 781 tgttccttgt aactttgaag caagtaggat ttgtaaaata cctggaacaa cattgaacta
 841 gaaactcaga aagtggtcct tgtgatggaa agagaaaaga aaaccaatt agaataaggc
 901 agaatgtacg tgcgtcattg gaacacagaa aacatgctgg ttcatacagc gtttttagtc
 961 ataatggtct tttttatttt gtttgattca ttcgagacaa catgtgtgta tgtgtgtgtg
1021 tgtgtgtgta gataatgtgg tttttgtatg gtgtttgatg gaaggaataa tctttctttg
1081 ctttcttagt agtatttcaa ggtgtttact tttcaattgg tgtgcactga atgcatgtat
1141 ggaagaatag cgtgaataat gcaatctctt tgtcattttt ccccttctca gactcttagc
1201 tcttaaaatt caaagatggg atattctaac tggtagtggt gcatcatttt taacccaaat
1261 attgcaagca ctttaaagat ttgaaaccac attttattg tttgatgttt cattttcaga
1321 cttttttaatg tcagtcatta caattacatt gcatgaggaa aattttcca gaacaacagt
1381 gtggaatagt tctgaattat gctgttctac agatagaaaa aaagtccaaa tgcctttaaa
1441 aatttacttc ttactccacc caacacgttt ttgcaaagca agaagtcttt gtaagacacc
1501 ttaaacaaag tccttcaatt ctacagcaga ggaaataaaa tcccccagaa gccaagggc
1561 tcaccttcac attgttagtt catgacagac ccaggtgtgc ttcattagag ataacataca
1621 ttcccttttgg tatcacagga agttactggg gattactcga cctcattact tagctaacga
1681 ctggataaaa tttcttaatt gtttgaagta acattgtatt cgtgtttgca ttattaattt
1741 gaatagaaaa taatcacatt ttcaacccat ttatacaaat tgttaatgtt tctttagagc
1801 tgtataacta tagtttgaac tagcaaggaa gttattgttt tgacaaccag aaattatgct
1861 tttctggtgc atgaaacatt aattgcaaag ggcagtcaca tccaacttta ataaaatatg
1921 gtggtctttc ttaaaaaaaa aaaaaaaaaa aaaaaaaaaa aaa
```

FIG. 1C (IL2RB: interleukin 2 receptor,
beta (SEQ ID NO:76)

```
   1 gcagccagag ctcagcaggg ccctggagag atggccacgg tcccagcacc ggggaggact ggagagcgcg
  71 cgctgccacc gccccatgtc tcagccaggg cttccttcct cggctccacc ctgtggatgt aatggcggcc
 141 cctgctctgt cctggcgtct gcccctcctc atcctcctcc tgccctggc tacctcttgg gcatctgcag
 211 cggtgaatgg cacttcccag ttcacatgct tctacaactc gagagccaac atctcctgtg tctggagcca
 281 agatggggct ctgcaggaca cttcctgcca agtccatgcc tggccggaca gacggcggtg gaaccaaacc
 351 tgtgagctgc tccccgtgag tcaagcatcc tgggcctgca acctgatcct cggagcccca gattctcaga
 421 aactgaccac agttgacatc gtcaccctga gggtgctgtg ccgtgagggg gtgcgatgga gggtgatggc
 491 catccaggac ttcaagccct tgagaacct tcgcctgatg gccccatct ccctccaagt tgtccacgtg
 561 gagacccaca gatgcaacat aagctgggaa atctcccaag cctcccacta cttttgaaaga cacctggagt
 631 tcgaggcccg gacgctgtcc ccaggccaca cctgggagga ggccccctg ctgactctca agcagaagca
 701 ggaatggatc tgcctggaga cgctcacccc agacacccag tatgagtttc aggtgcgggt caagcctctg
 771 caaggcgagt tcacgacctg gagcccctgg agccagcccc tggccttcag gacaaagcct gcagcccttg
 841 ggaaggacac cattccgtgg ctcggccacc tcctcgtggg cctcagcggg gcttttggct tcatcatctt
 911 agtgtacttg ctgatcaact gcaggaacac cgggccatgg ctgaagaagg tcctgaagtg taacacccca
 981 gacccctcga agttcttttc ccagctgagc tcagagcatg gaggagacgt ccagaagtgg ctctcttcgc
1051 ccttcccctc atcgtccttc agccctggcg gcctggcacc tgagatctcg ccactagaag tgctggagag
1121 ggacaaggtg acgcagctgc tcctgcagca ggacaaggtg cctgagcccg catccttaag cagcaaccac
1191 tcgctgacca gctgcttcac caaccagggt tacttcttct tccacctccc ggatgccttg gagatagagg
1261 cctgccaggt gtactttact tacgacccct actcaggaga agaccctgat gagggtgtgg ccgggggcacc
1331 cacagggtct tcccccaac ccctgcagcc tctgtcaggg gaggacgacg cctactgcac cttccctcc
1401 agggatgacc tgctgctctt ctccccagt ctcctcggtg gccccagccc ccaagcact gccctgggg
1471 gcagtggggc cggtgaagag aggatgcccc cttctttgca agaaagagtc cccagagact gggaccccca
1541 gcccctgggg cctcccaccc caggagtccc agacctggtg gatttcagc caccccctga gctggtgctg
1611 cgagaggctg ggaggaggt ccctgacgct ggcccaggg agggagtcag tttcccctgg tccaggcctc
1681 ctgggcaggg ggagttcagg gcccttaatg ctcgcctgcc cctgaacact gatgcctact tgtccctcca
1751 agaactccag ggtcaggacc caactcactt ggtgtagaca gatggccagg gtgggaggca ggcagctgcc
1821 tgctctgcgc cgagcctcag aaggaccctg ttgagggtcc tcagtccact gctgaggaca ctcagtgtcc
1891 agttgcagct ggacttctcc acccggatgg cccccaccca gtcctgcaca cttggtccat ccatttccaa
1961 acctccactg ctgctcccgg gtcctgctgc ccgagccagg aactgtgtgt gttgcagggg ggcagtaact
2031 ccccaactcc ctcgttaatc acaggatccc acgaatttag gctcagaagc atcgctcctc tccagccctg
2101 cagctattca ccaatatcag tcctcgcggc tctccagggc tccctgccct gacctcttcc ctgggttttc
2171 tgcccagcc tcctccttcc ctcccctccc cgtccacagg gcagcctgag cgtgctttcc aaaacccaaa
2241 tatggccacg ctcccccctg gttcaaaacc ttgcacaggt cccactgccc tcagcccac ttctcagcct
2311 ggtacttgta cctccggtgt cgtgtgggga catcccttc tgcaatcctc cctaccgtcc tcctgagcca
2381 ctcagagctc cctcacaccc cctctgttgc acatgctatt ccctgggct gctgtgcgct ccccctcatc
2451 taggtgacaa acttccctga ctcttcaagt gccggttttg cttctcctgg agggaagcac tgcctccctt
2521 aatctgccag aaacttctag cgtcagtgct ggaggagaa gctgtcaggg acccagggcg cctggagaaa
2591 gaggccctgt tactattcct ttgggatctc tgaggcctca gagtgcttgg ctgctgtatc tttaatgctg
2661 gggcccaagt aagggcacag atcccccac aaagtggatg cctgctgcat cttcccacag tggcttcaca
2731 gacccacaag agaagctgat ggggagtaaa ccctggagtc cgaggcccag gcagcagccc cgcctagtgg
2801 tgggccctga tgctgccagg cctggaccct cccactgccc cctccactgg aggggtctcc tctgcagctc
2871 agggactggc acactggcct ccagaaggc agctccacag ggcagggcct cattatttt cactgcccca
2941 gacacagtgc ccaacacccc gtcgtatacc ctggatgaac gaattaatta cctggcacca cctcgtctgg
3011 gctccctgcg cctgacattc acacagagag gcagagtccc gtgcccatta ggtctggcat gccccctcct
3081 gcaagggct caaccccta ccccgacccc tccacgtatc tttcctaggc agatcacgtt gcaatgcctc
3151 aaacaacatt ccacccagc aggacagtga cccagtccc agctaactct gacctgggag ccctcaggca
3221 cctgcactta caggccttgc tcacagctga ttgggcacct gaccacacgc ccccacaggc tctgaccagc
3291 agcctatgag ggggttttggc accaagctct gtccaatcag gtaggctggg cctgaactag ccaatcagat
3361 caactctgtc ttgggcgttt gaactcaggg agggaggccc ttgggagcag gtgcttgtgg acaaggctcc
3431 acaagcgttg agccttggaa aggtagacaa gcgttgagcc actaagcaga ggacctgggg ttcccaatac
3501 aaaaatacct actgctgaga gggctgctga ccatttggtc aggattcctg ttgcctttat atccaaaata
3571 aactcccctt tcttgaggtt gtctgagtct tgggtctatg ccttgaaaaa agctgaatta ttggacagtc
3641 tcacctcctg ccatagggtc ctgaatgttt cagaccacaa ggggctccac acctttgctg tgtgttctgg
3711 ggcaacctac taatcctctc tgcaagtcgg tctccttatc cccccaaatg gaaattgtat ttgccttctc
3781 cactttggga ggctcccact tcttgggagg gttacatttt ttaagtctta atcatttgtg acatatgtat
3851 ctatacatcc gtatcttta atgatccgtg tgtaccatct ttgtgattat ttccttaata ttttttcttt
3921 aagtcagttc attttcgttg aaatacattt atttaaagaa aaatctttgt tactctgtaa atgaaaaaac
3991 ccattttcgc tataaataaa aggtaactgt acaaaataag tacaatgcaa caaaa
```

FIG. 1D

LMNB1: lamin B1 (SEQ ID NO:77)

```
   1 gtgcagcctg agaggaaaca aagtgctgcg agcaggagac ggcggcggcg cgaaccctgc
  61 tgggcctcca gtcaccctcg tcttgcattt tcccgcgtgc gtgtgtgagt gggtgtgtgt
 121 gttttcttac aaagggtatt tcgcgatcga tcgattgatt cgtagttccc ccccgcgcgc
 181 ctttgccctt tgtgctgtaa tcgagctccc gccatcccag gtgcttctcc gttcctctaa
 241 acgccagcgt ctggacgtga gcgcaggtcg ccggtttgtg ccttcggtcc ccgcttcgcc
 301 ccctgccgtc ccctccttat cacggtcccg ctcgcggcct cgccgccccg ctgtctccgc
 361 cgcccgccat ggcgactgcg accccgtgc cgccgcggat gggcagccgc gctggcggcc
 421 ccaccacgcc gctgagcccc acgcgcctgt cgcggctcca ggagaaggag gagctgcgcg
 481 agctcaatga ccggctggcg gtgtacatcg acaaggtgcg cagcctggag acggagaaca
 541 gcgcgctgca gctgcaggtg acggagcgcg aggaggtgcg cggccgtgag ctcaccggcc
 601 tcaaggcgct ctacgagacc gagctggccg acgcgcgacg cgcgctcgac gacacggccc
 661 gcgagcgcgc caagctgcag atcgagctgg gcaagtgcaa ggcggaacac gaccagctgc
 721 tcctcaacta tgctaagaag gaatctgatc ttaatggcgc ccagatcaag cttcgagaat
 781 atgaagcagc actgaattcg aaagatgcag ctcttgctac tgcacttggt gacaaaaaaa
 841 gtttagaggg agatttggag gatctgaagg atcagattgc ccagttggaa gcctccttag
 901 ctgcagccaa aaaacagtta gcagatgaaa ctttacttaa agtagatttg gagaatcgtt
 961 gtcagagcct tactgaggac ttggagtttc gcaaaagcat gtatgaagag gagattaacg
1021 agaccagaag gaagcatgaa acgcgcttgg tagaggtgga ttctgggcgt caaattgagt
1081 atgagtacaa gctggcgcaa gcccttcatg agatgagaga gcaacatgat gcccaagtga
1141 ggctgtataa ggaggagctg gagcagactt accatgccaa acttgagaat gccagactgt
1201 catcagagat gaatacttct actgtcaaca gtgccaggga agaactgatg gaaagccgca
1261 tgagaattga gagcctttca tcccagcttt ctaatctaca gaaagagtct agagcatgtt
1321 tggaaaggat tcaagaatta gaggacttgc ttgctaaaga aaaagacaac tctcgtcgca
1381 tgctgacaga caaagagaga gagatggcgg aaataaggga tcaaatgcag caacagctga
1441 atgactatga acagcttctt gatgtaaagt tagccctgga catggaaatc agtgcttaca
1501 ggaaactctt agaaggcgaa gaagagaggt tgaagctgtc tccaagccct tcttcccgtg
1561 tgacagtatc ccgagcatcc tcaagtcgta gtgtacgtac aactagagga aagcggaaga
1621 gggttgatgt ggaagaatca gaggcgagta gtagtgttag catctctcat tccgcctcag
1681 ccactggaaa tgtttgcatc gaagaaattg atgttgatgg gaaatttatc cgcttgaaga
1741 acacttctga acaggatcaa ccaatgggag ctgggagat gatcagaaaa attggagaca
1801 catcagtcag ttataaatat acctcaagat atgtgctgaa ggcaggccag actgttacaa
1861 tttggctgc aaacgctggt gtcacagcca gcccccaac tgacctcatc tggaagaacc
1921 agaactcgtg gggcactggc gaagatgtga aggttatatt gaaaaattct cagggagagg
1981 aggttgctca agaagtaca gtctttaaaa caaccatacc tgaagaagag gaggaggagg
2041 aagaagcagc tggagtggtt gttgaggaag aacttttcca ccagcaggga accccaagag
2101 catccaatag aagctgtgca attatgtaaa attttcaact gtcttcctca aaataaagaa
2161 gtatggtaat ccttacctgt atacagtgca gagccttctc agaagcacag aatattttta
2221 tatttccttt atgtgaattt ttaagctgca aatctgatgg ccttaatttc cttttgaca
2281 ctgaaagttt tgtaaaagaa atcatgtcca tacactttgt tgcaagatgt gaattattga
2341 cactgaactt aataactgtg tactgttcgg aaggggttcc tcaaattttt tgactttttt
2401 tgtatgtgtg ttttttcttt tttttaagt tcttatgagg aggggaggg aaataaacca
2461 ctgtgcgtct tggtgtaatt tgaagattgc cccatctaga ctagcaatct cttcattatt
2521 ctctgctata tataaaacgg tgctgtgagg gaggggaaaa gcattttca atatattgaa
2581 cttttgtact gaattttttt gtaataagca atcaaggtta taatttttt taaaatagaa
2641 attttgtaag aaggcaatat taacctaatc accatgtaag cactctggat gatggattcc
2701 acaaaacttg gttttatggt tacttcttct cttagattct taattcatga ggagggtggg
2761 ggagggaggt ggagggaggg aagggtttct ctattaaaat gcattcgttg tgttttttaa
2821 gatagtgtaa cttgcttaaa tttcttatgt gacattaaca aataaaaag ctcttttaat
2881 at
```

FIG. 1E

PRRG4: proline rich Gla (G-carboxyglutamic acid) 4 (transmembrane) (SEQ ID NO:78)

```
   1 cccggaccga ggcaggacct caccccgcgc gtgttccccg ggcgccccte tgcgaacccc
  61 aggcccttcc caggtttgcg cgcggggggcc atccagaccc tgcggagagc gaggcccgga
 121 gcgtcgccga ggtttgaggg cgccggagac cgagggcctg gcggccgaag gaaccgcccc
 181 aagaagagcc tctggcccgg gggctgctgg aacatgtgcg gggggacaca gtttgtttga
 241 cagttgccag actatgttta cgcttctggt tctactcagc caactgccca cagttaccct
 301 ggggtttcct cattgcgcaa gaggtccaaa ggcttctaag catgcgggag aagaagtgtt
 361 tacatcaaaa gaagaagcaa acttttttcat acatagacgc cttctgtata atagatttga
 421 tctggagctc ttcactcccg gcaacctaga aagagagtgc aatgaagaac tttgcaatta
 481 tgaggaagcc agagagattt ttgtggatga agataaaacg attgcatttt ggcaggaata
 541 ttcagctaaa ggaccaacca caaaatcaga tggcaacaga gagaaaatag atgttatggg
 601 ccttctgact ggattaattg ctgctggagt attttttggtt attttttggat tacttggcta
 661 ctatctttgt atcactaagt gtaataggct acaacatcca tgctcttcag ccgtctatga
 721 aaggggggagg cacactccct ccatcatttt cagaagacct gaggaggctg ccttgtctcc
 781 attgccgcct tctgtggagg atgcaggatt accttcttat gaacaggcag tggcgctgac
 841 cagaaaacac agtgtttcac caccaccacc atatcctggg cacacaaaag gatttagggt
 901 atttaaaaaa tctatgtctc tcccatctca ctgactacct tgtcattttg gtataagaaa
 961 tttgtgttat ttgataggcc gggcatggtg gctcatgcct gtaatcccag cactttggga
1021 ggccaggagt tcgagaccag cctggccaac atggtgaaac ccggtctcta ctaaaaattc
1081 aaaaattacc taggcgtcat ggggcatgcc tgtagtccca cctacttggg aggctgaagc
1141 aggagaattg ctcgaacctg ggaggcagag gttgcagtaa gctgagatca cgccactgca
1201 ttccagcctg ggcgacagag caagactcca tctcaaaaat aaaataaaaa aagaaagaaa
1261 gaaaagaaga agaaaagaga agaaggagaa ggagatgaag gaggaggagg aggagaagga
1321 gaagaagaag aagaagaaga ccacaaaaga catgactatc caactttttta tgacaaactg
1381 caaggaataa aggaagaata agtccatgta ctgtaccaca gaagttctgt ctgcatcttg
1441 gacctgaact tgatcattat cagcttgata agagacttttt tgactctata tccttgcagt
1501 taagaagaaa gcactttttt gtaatgtttg ttttaatggt tcaaaaaaaa tctttcttat
1561 aaagagcata ggtagaatta gtgaactctt tggatccttt gtacagataa aggttataga
1621 tttcttgtgt tgaatattaa aaaagcaagg atgtctaacc attaagatta tccaaagtca
1681 ggctgggcgc agtggctcac gcctgtaatc ccagcacttt gggagggata ggtgggcgga
1741 tcacctgagg tcaggagttt gagaccagcc tggccaacat ggcaaaaccc cgtctctaca
1801 aaaatacaaa agaaattagc cagacatgat ggcgggtgcc tctaatccca gctactgggg
1861 aggctgaggt gggagaatcg cttgaactcg ggaggtggag gttgtagtga ggcgagattg
1921 tgccattgca ctccaacctg ggcgacagag tgagactcca tctcaaaaaa aaaaaaaaaa
1981 aaaaaaaaaa aaaaaaaaaa aaaaaaaaaa aaaaa
```

FIG. 1F

TNFAIP6: tumor necrosis factor, alpha-induced protein 6 (SEQ ID NO:79)

```
   1 cagtcacatt tcagccactg ctctgagaat ttgtgagcag cccctaacag gctgttactt
  61 cactacaact gacgatatga tcatcttaat ttacttattt ctcttgctat gggaagacac
 121 tcaaggatgg ggattcaagg atggaatttt tcataactcc atatggcttg aacgagcagc
 181 cggtgtgtac cacagagaag cacggtctgg caaatacaag ctcacctacg cagaagctaa
 241 ggcggtgtgt gaatttgaag gcggccatct cgcaacttac aagcagctag aggcagccag
 301 aaaaattgga tttcatgtct gtgctgctgg atggatggct aagggcagag ttggataccc
 361 cattgtgaag ccagggccca actgtggatt tggaaaaact ggcattattg attatggaat
 421 ccgtctcaat aggagtgaaa gatgggatgc ctattgctac aacccacacg caaggagtg
 481 tggtggcgtc tttacagatc caaagcaaat ttttaaatct ccaggcttcc caaatgagta
 541 cgaagataac caaatctgct actggcacat tagactcaag tatggtcagc gtattcacct
 601 gagtttttta gattttgacc ttgaagatga cccaggttgc ttggctgatt atgttgaaat
 661 atatgacagt tacgatgatg tccatggctt tgtgggaaga tactgtggag atgagcttcc
 721 agatgacatc atcagtacag gaaatgtcat gaccttgaag tttctaagtg atgcttcagt
 781 gacagctgga ggtttccaaa tcaaatatgt tgcaatggat cctgtatcca atccagtca
 841 aggaaaaaat acaagtacta cttctactgg aaataaaaac tttttagctg gaagatttag
 901 ccacttataa aaaaaaaaaa aaggatgatc aaaacacaca gtgtttatgt tggaatcttt
 961 tggaactcct ttgatctcac tgttattatt aacatttatt tattattttt ctaaatgtga
1021 aagcaataca taatttaggg aaaattggaa aatataggaa actttaaacg agaaaatgaa
1081 acctctcata atcccactgc atagaaataa caagcgttaa cattttcata ttttttttctt
1141 tcagtcattt ttctatttgt ggtatatgta tatatgtacc tatatgtatt tgcatttgaa
1201 attttggaat cctgctctat gtacagtttt gtattatact ttttaaatct tgaactttat
1261 aaacattttc tgaaatcatt gattattcta caaaaacatg attttaaaca gctgtaaaat
1321 attctatgat atgaatgttt tatgcattat ttaagcctgt ctctattgtt ggaatttcag
1381 gtcattttca taaatattgt tgcaataaat atccttgaac acaaaaaaaa aaaaaaaaa
```

FIG. 1G

VNN1: vanin 1 (SEQ ID NO: 80)

```
   1 cattggactt cagcatgact actcagttgc cagcttacgt ggcaattttg cttttctatg
  61 tctcaagagc cagctgccag gacactttca ttgcagctgt ttatgagcat gcagcgatat
 121 tgcccaatgc caccctaaca ccagtgtctc gtgaggaggc tttggcatta atgaatcgga
 181 atctggacat tttggaagga gcgatcacat cagcagcaga tcagggtgcg catattattg
 241 tgactccaga agatgctatt tatggctgga acttcaacag ggactctctc tacccatatt
 301 tggaggacat cccagaccct gaagtaaact ggatcccctg taataatcgt aacagatttg
 361 gccagacccc agtacaagaa agactcagct gcctggccaa gaacaactct atctatgttg
 421 tggcaaatat tggggacaag aagccatgcg ataccagtga tcctcagtgt cccctgatg
 481 gccgttacca atacaacact gatgtggtat ttgattctca aggaaaactg gtggcacgct
 541 accataagca aaaccttttc atgggtgaaa atcaattcaa tgtacccaag gagcctgaga
 601 ttgtgacttt caataccacc tttggaagtt ttggcatttt cacatgcttt gatatactct
 661 tccatgatcc tgctgttacc ttggtgaaag atttccacgt ggacaccata gtattcccaa
 721 cagcttggat gaatgttttg ccacatttgt cagctgttga attccactca gcttgggcta
 781 tgggcatgag ggtcaatttc cttgcatcca acatacatta cccctcaaag aaaatgacag
 841 gaagtggcat ctatgcaccc aattcttcaa gagcatttca ttatgatatg aagacagaag
 901 agggaaaact cctcctctcg caactggatt cccacccatc ccattctgca gtggtgaact
 961 ggacttccta tgccagcagt atagaagcgc tctcatcagg aaacaaggaa tttaaaggca
1021 ctgtcttttt cgatgaattc acttttgtga agctcacagg agttgcagga aattatacag
1081 tttgtcagaa agatctctgc tgtcatttaa gctacaaaat gtctgagaac ataccaaatg
1141 aagtgtacgc tctaggggca tttgacggac tgcacactgt ggaagggcgc tattatctac
1201 agatttgtac cctgttgaaa tgtaaaacga ctaatttaaa cacttgcggt gactcagctg
1261 aaacagcttc taccaggttt gaatgttctc cctcagtgg cactttcgga acccagtatg
1321 tctttcctga ggtgttgctg agtgaaaatc agcttgcacc tggagaattt caggtgtcaa
1381 ctgacggacg cttgtttagt ctgaagccaa catccggacc tgtcttaaca gtaactctgt
1441 ttgggaggtt gtatgagaag gactggcat caaatgcttc atcaggcctc acagcacaag
1501 caagaataat aatgctaata gttatagcac ctattgtatg tcattaagt tggtagaata
1561 ttgacttttt ctctttttta tttgggataa tttaaaaaat gatggatgag aaaagaaaga
1621 ttggtccggg ttaatattat cctctagtat aagtgaatta ctagtttctc tttatttaga
1681 caaacacaca cacaccagat aatataaact taataaatta tctgttaatg tagattttat
1741 ttaaaaaact atatttgaac attggtcttt cttggacgtg agctaattat atcaaataag
1801 tatcacaaat cttttacgca gaagaaataa aaactacggg tagaaaacat aagaactatc
1861 ataaaattta cttacaagga ggctgctctt gttaccactt ttattatatt acgtatcact
1921 tattcagctc tgctgaaaat ttccaatgac tttgtttgtt tgctctttta gttttttacc
1981 taaacaatac attttgattc tcttgtgggt tgataatgtc tccccaaaat ttacatgttg
2041 aagcacctca gaatgtgact gtatttggag acagggtctt taagaggta aaataaggtc
2101 attaggatag accctaattc aatatgactg atgatcataa aagaagaggc gagtagggca
2161 caacaggcac aagggagac cataaggaga cacagaggaa ggacaactct ttacaagcta
2221 agaagagagg gcctcagaag aaaccaaccc tgccaacacc ttgatcttgg acttccagcc
2281 tccaaaacta tgagaaataa atttctattg tttaagtcac ccagtccatg gtactttgtt
2341 aggcagccct ggcaaatgaa tcaaagaccc attcctgttc ctctccccac cactactgtt
2401 ttctactgta atctgaagct tcaacaaaag gcttacctgg taagaatatt cagctggtct
2461 gggtcctcaa gactccaata gacactctta aagaaggatt gctgatggat tgatagtgaa
2521 accattagat cattgaattc ctctggaatt agaaaaccag agagtcccat tttaagaaat
2581 tagatattta atatagcatt gtgtgttcta ttttagtaac agcagaatct cttgacatta
2641 cacaactcag tgaaacaaca tcatttaagc caaatatct cccaactgac tgatagactc
2701 tgagcactaa tatcatagtg ctgtgatgat ggacaattac atagtaccga taacagccat
2761 gcactgtgca aagcatgccc ttctgcacag gagagcaagg cacttgcagt agtgatctat
2821 gccagcaaaa catcattttg agacaaacat ttttgtggca gatgttttc ctaaaaagta
2881 ctatatcatc caagaaatat ttgagtaaaa tcccttgttc ttttgggtga cattaactga
2941 catttgcttt ttttcaagac ctaatagaaa ataagaaagc ccataatgta tttagaaaca
3001 ggaatcctca gagcaattct ctgtattctc atataatttc aatgtaaaac agaaaacata
3061 ttgatgtgtt ggtgataggc ttgaattatt aaaaacttca aaacaaaa
```

FIG. 1H

SEQUENCE LISTING

<160> NUMBER OF SEQ ID NOS: 80

<210> SEQ ID NO 1
<211> LENGTH: 24
<212> TYPE: DNA
<213> ORGANISM: Artificial Sequence
<220> FEATURE:
<223> OTHER INFORMATION: 5' Primer for ACTB gene

<400> SEQUENCE: 1
caccacacct tctacaatga gctg                                          24

<210> SEQ ID NO 2
<211> LENGTH: 22
<212> TYPE: DNA
<213> ORGANISM: Artificial Sequence
<220> FEATURE:
<223> OTHER INFORMATION: 3' Primer for ACTB gene

<400> SEQUENCE: 2
acagcctgga tagcaacgta ca                                            22

<210> SEQ ID NO 3
<211> LENGTH: 26
<212> TYPE: DNA
<213> ORGANISM: Artificial Sequence
<220> FEATURE:
<223> OTHER INFORMATION: probe for ACTB gene

<400> SEQUENCE: 3
aaccgcgaga agatgaccca gatcat                                        26

<210> SEQ ID NO 4
<211> LENGTH: 20
<212> TYPE: DNA
<213> ORGANISM: Artificial Sequence
<220> FEATURE:
<223> OTHER INFORMATION: 5' primer for ACTB gene

<400> SEQUENCE: 4
accttctaca atgagctgcg                                               20

<210> SEQ ID NO 5
<211> LENGTH: 22
<212> TYPE: DNA
<213> ORGANISM: Artificial Sequence
<220> FEATURE:
<223> OTHER INFORMATION: 3' primer for ACTB gene

<400> SEQUENCE: 5
ggtctcaaac atgatctggg tc                                            22

<210> SEQ ID NO 6
<211> LENGTH: 20
<212> TYPE: DNA
<213> ORGANISM: Artificial Sequence
<220> FEATURE:
<223> OTHER INFORMATION: Probe for ACTB gene

<400> SEQUENCE: 6
aaggccaacc gcgagaagat                                               20

<210> SEQ ID NO 7
<211> LENGTH: 20
<212> TYPE: DNA
<213> ORGANISM: Artificial Sequence

```
<220> FEATURE:
<223> OTHER INFORMATION: 5' primer for ACTB gene

<400> SEQUENCE: 7
cacccagcac aatgaagatc                                                 20

<210> SEQ ID NO 8
<211> LENGTH: 20
<212> TYPE: DNA
<213> ORGANISM: Artificial Sequence
<220> FEATURE:
<223> OTHER INFORMATION: 3' primer for ACTB gene

<400> SEQUENCE: 8
ctgcttgctg atccacatct                                                 20

<210> SEQ ID NO 9
<211> LENGTH: 20
<212> TYPE: DNA
<213> ORGANISM: Artificial Sequence
<220> FEATURE:
<223> OTHER INFORMATION: Probe for ACTB gene

<400> SEQUENCE: 9
atcattgctc ctcctgagcg                                                 20

<210> SEQ ID NO 10
<211> LENGTH: 20
<212> TYPE: DNA
<213> ORGANISM: Artificial Sequence
<220> FEATURE:
<223> OTHER INFORMATION: 5' primer for ANXA3 gene

<400> SEQUENCE: 10
gaaacatctg gtgacttccg                                                 20

<210> SEQ ID NO 11
<211> LENGTH: 18
<212> TYPE: DNA
<213> ORGANISM: Artificial Sequence
<220> FEATURE:
<223> OTHER INFORMATION: 3' Primer for ANXA3 gene

<400> SEQUENCE: 11
tctgggcatc ttgtttgg                                                   18

<210> SEQ ID NO 12
<211> LENGTH: 21
<212> TYPE: DNA
<213> ORGANISM: Artificial Sequence
<220> FEATURE:
<223> OTHER INFORMATION: Probe for ANXA3 gene

<400> SEQUENCE: 12
ttgactttgg cagatggcag a                                               21

<210> SEQ ID NO 13
<211> LENGTH: 21
<212> TYPE: DNA
<213> ORGANISM: Artificial Sequence
<220> FEATURE:
<223> OTHER INFORMATION: 5' primer for ANXA3 gene

<400> SEQUENCE: 13
ggaacaaacg aagatgcctt g                                               21
```

<210> SEQ ID NO 14
<211> LENGTH: 20
<212> TYPE: DNA
<213> ORGANISM: Artificial Sequence
<220> FEATURE:
<223> OTHER INFORMATION: 3' primer for ANXA3

<400> SEQUENCE: 14
aagtcaccag atgtttcgga                                           20

<210> SEQ ID NO 15
<211> LENGTH: 26
<212> TYPE: DNA
<213> ORGANISM: Artificial Sequence
<220> FEATURE:
<223> OTHER INFORMATION: probe for ANXA3

<400> SEQUENCE: 15
atcttaacta ccaggacaag caggca                                    26

<210> SEQ ID NO 16
<211> LENGTH: 20
<212> TYPE: DNA
<213> ORGANISM: Artificial Sequence
<220> FEATURE:
<223> OTHER INFORMATION: 5' primer for anxa3

<400> SEQUENCE: 16
ctaccaggac aagcaggcaa                                           20

<210> SEQ ID NO 17
<211> LENGTH: 19
<212> TYPE: DNA
<213> ORGANISM: Artificial Sequence
<220> FEATURE:
<223> OTHER INFORMATION: 3' primer for ANXA3

<400> SEQUENCE: 17
ttctgccatc tgccaaagt                                            19

<210> SEQ ID NO 18
<211> LENGTH: 22
<212> TYPE: DNA
<213> ORGANISM: Artificial Sequence
<220> FEATURE:
<223> OTHER INFORMATION: probe for ANXA3

<400> SEQUENCE: 18
tccgaaacat ctggtgactt cc                                        22

<210> SEQ ID NO 19
<211> LENGTH: 19
<212> TYPE: DNA
<213> ORGANISM: Artificial Sequence
<220> FEATURE:
<223> OTHER INFORMATION: 5' primer for CLEC4D

<400> SEQUENCE: 19
ccatttaacc cacgcagag                                            19

<210> SEQ ID NO 20
<211> LENGTH: 20
<212> TYPE: DNA
<213> ORGANISM: Artificial Sequence
<220> FEATURE:
<223> OTHER INFORMATION: 3' primer for CLEC4D

```
<400> SEQUENCE: 20
caggcccatt tatcttggtt                                              20

<210> SEQ ID NO 21
<211> LENGTH: 23
<212> TYPE: DNA
<213> ORGANISM: Artificial Sequence
<220> FEATURE:
<223> OTHER INFORMATION: probe for CLEC4D

<400> SEQUENCE: 21
ctggcataag aatgaacccg aca                                          23

<210> SEQ ID NO 22
<211> LENGTH: 22
<212> TYPE: DNA
<213> ORGANISM: Artificial Sequence
<220> FEATURE:
<223> OTHER INFORMATION: 5' primer for CLEC4D

<400> SEQUENCE: 22
tccgaaacat ctggtgactt cc                                           22

<210> SEQ ID NO 23
<211> LENGTH: 20
<212> TYPE: DNA
<213> ORGANISM: Artificial Sequence
<220> FEATURE:
<223> OTHER INFORMATION: 3' primer for CLEC4D

<400> SEQUENCE: 23
tcctttcact ctcagcccac                                              20

<210> SEQ ID NO 24
<211> LENGTH: 20
<212> TYPE: DNA
<213> ORGANISM: Artificial Sequence
<220> FEATURE:
<223> OTHER INFORMATION: probe for CLEC4D

<400> SEQUENCE: 24
atgaccatca gcacggaagc                                              20

<210> SEQ ID NO 25
<211> LENGTH: 20
<212> TYPE: DNA
<213> ORGANISM: Artificial Sequence
<220> FEATURE:
<223> OTHER INFORMATION: 5' primer for CLEC4D

<400> SEQUENCE: 25
gggctgagag tgaaaggaac                                              20

<210> SEQ ID NO 26
<211> LENGTH: 19
<212> TYPE: DNA
<213> ORGANISM: Artificial Sequence
<220> FEATURE:
<223> OTHER INFORMATION: 3' primer for CLEC4D

<400> SEQUENCE: 26
ccactgacct ttggcattc                                               19

<210> SEQ ID NO 27
```

```
<211> LENGTH: 20
<212> TYPE: DNA
<213> ORGANISM: Artificial Sequence
<220> FEATURE:
<223> OTHER INFORMATION: probe for CLEC4D

<400> SEQUENCE: 27
atgaccatca gcacggaagc                                               20

<210> SEQ ID NO 28
<211> LENGTH: 19
<212> TYPE: DNA
<213> ORGANISM: Artificial Sequence
<220> FEATURE:
<223> OTHER INFORMATION: 5' primer for IL2RB

<400> SEQUENCE: 28
aaatctccca agcctccca                                                19

<210> SEQ ID NO 29
<211> LENGTH: 19
<212> TYPE: DNA
<213> ORGANISM: Artificial Sequence
<220> FEATURE:
<223> OTHER INFORMATION: 3' primer for IL2RB

<400> SEQUENCE: 29
aggcagatcc attcctgct                                                19

<210> SEQ ID NO 30
<211> LENGTH: 21
<212> TYPE: DNA
<213> ORGANISM: Artificial Sequence
<220> FEATURE:
<223> OTHER INFORMATION: probe for IL2RB

<400> SEQUENCE: 30
ttgaaagaca cctggagttc g                                             21

<210> SEQ ID NO 31
<211> LENGTH: 21
<212> TYPE: DNA
<213> ORGANISM: Artificial Sequence
<220> FEATURE:
<223> OTHER INFORMATION: 5' primer for IL2RB

<400> SEQUENCE: 31
gacccacaga tgcaacataa g                                             21

<210> SEQ ID NO 32
<211> LENGTH: 20
<212> TYPE: DNA
<213> ORGANISM: Artificial Sequence
<220> FEATURE:
<223> OTHER INFORMATION: 3' primer for IL2RB

<400> SEQUENCE: 32
gcttctgctt gagagtcagc                                               20

<210> SEQ ID NO 33
<211> LENGTH: 20
<212> TYPE: DNA
<213> ORGANISM: Artificial Sequence
<220> FEATURE:
<223> OTHER INFORMATION: Probe for IL2RB

<400> SEQUENCE: 33
```
aaatctccca agcctcccac                                              20

<210> SEQ ID NO 34
<211> LENGTH: 19
<212> TYPE: DNA
<213> ORGANISM: Artificial Sequence
<220> FEATURE:
<223> OTHER INFORMATION: 5' primer for IL2RB

<400> SEQUENCE: 34
tggagaccca cagatgcaa                                               19

<210> SEQ ID NO 35
<211> LENGTH: 20
<212> TYPE: DNA
<213> ORGANISM: Artificial Sequence
<220> FEATURE:
<223> OTHER INFORMATION: 3' primer for IL2RB

<400> SEQUENCE: 35
gcttctgctt gagagtcagc                                              20

<210> SEQ ID NO 36
<211> LENGTH: 20
<212> TYPE: DNA
<213> ORGANISM: Artificial Sequence
<220> FEATURE:
<223> OTHER INFORMATION: probe for IL2RB

<400> SEQUENCE: 36
aaatctccca agcctcccac                                              20

<210> SEQ ID NO 37
<211> LENGTH: 21
<212> TYPE: DNA
<213> ORGANISM: Artificial Sequence
<220> FEATURE:
<223> OTHER INFORMATION: 5' primer for LMNB1

<400> SEQUENCE: 37
ggagtggttg ttgaggaaga a                                            21

<210> SEQ ID NO 38
<211> LENGTH: 21
<212> TYPE: DNA
<213> ORGANISM: Artificial Sequence
<220> FEATURE:
<223> OTHER INFORMATION: 3' primer for LMNB1

<400> SEQUENCE: 38
ctgagaaggc tctgcactgt a                                            21

<210> SEQ ID NO 39
<211> LENGTH: 21
<212> TYPE: DNA
<213> ORGANISM: Artificial Sequence
<220> FEATURE:
<223> OTHER INFORMATION: probe for LMNB1

<400> SEQUENCE: 39
aaccccaaga gcatccaata g                                            21

<210> SEQ ID NO 40
<211> LENGTH: 19
<212> TYPE: DNA

```
<213> ORGANISM: Artificial Sequence
<220> FEATURE:
<223> OTHER INFORMATION: 5' primer for LMNB1

<400> SEQUENCE: 40
ctggcgaaga tgtgaaggt                                             19

<210> SEQ ID NO 41
<211> LENGTH: 20
<212> TYPE: DNA
<213> ORGANISM: Artificial Sequence
<220> FEATURE:
<223> OTHER INFORMATION: 3' primer for LMNB1

<400> SEQUENCE: 41
cttcctcaac aaccactcca                                            20

<210> SEQ ID NO 42
<211> LENGTH: 22
<212> TYPE: DNA
<213> ORGANISM: Artificial Sequence
<220> FEATURE:
<223> OTHER INFORMATION: probe

<400> SEQUENCE: 42
aattctcagg gagaggaggt tg                                         22

<210> SEQ ID NO 43
<211> LENGTH: 22
<212> TYPE: DNA
<213> ORGANISM: Artificial Sequence
<220> FEATURE:
<223> OTHER INFORMATION: 5' primer for LMNB1

<400> SEQUENCE: 43
aggcgaagaa gagaggttga ag                                         22

<210> SEQ ID NO 44
<211> LENGTH: 21
<212> TYPE: DNA
<213> ORGANISM: Artificial Sequence
<220> FEATURE:
<223> OTHER INFORMATION: 3' primer ofr LMNB1

<400> SEQUENCE: 44
ccgctttcct ctagttgtac g                                          21

<210> SEQ ID NO 45
<211> LENGTH: 20
<212> TYPE: DNA
<213> ORGANISM: Artificial Sequence
<220> FEATURE:
<223> OTHER INFORMATION: probe for LMNB1

<400> SEQUENCE: 45
tgtctccaag cccttcttcc                                            20

<210> SEQ ID NO 46
<211> LENGTH: 22
<212> TYPE: DNA
<213> ORGANISM: Artificial Sequence
<220> FEATURE:
<223> OTHER INFORMATION: 5' primer for PRRG4

<400> SEQUENCE: 46
atgcgggaga agaagtgttt ac                                         22
```

<210> SEQ ID NO 47
<211> LENGTH: 21
<212> TYPE: DNA
<213> ORGANISM: Artificial Sequence
<220> FEATURE:
<223> OTHER INFORMATION: 3' primer for PRRG4

<400> SEQUENCE: 47
ctctggcttc ctcataattg c                                    21

<210> SEQ ID NO 48
<211> LENGTH: 24
<212> TYPE: DNA
<213> ORGANISM: Artificial Sequence
<220> FEATURE:
<223> OTHER INFORMATION: probe for PRRG4

<400> SEQUENCE: 48
ctcttcactc ccggcaacct agaa                                 24

<210> SEQ ID NO 49
<211> LENGTH: 20
<212> TYPE: DNA
<213> ORGANISM: Artificial Sequence
<220> FEATURE:
<223> OTHER INFORMATION: 5' primer for PRRG4

<400> SEQUENCE: 49
tgctgctgga gtattttgg                                       20

<210> SEQ ID NO 50
<211> LENGTH: 19
<212> TYPE: DNA
<213> ORGANISM: Artificial Sequence
<220> FEATURE:
<223> OTHER INFORMATION: 3' primer for PRRG4

<400> SEQUENCE: 50
aatgatggag ggagtgtgc                                       19

<210> SEQ ID NO 51
<211> LENGTH: 20
<212> TYPE: DNA
<213> ORGANISM: Artificial Sequence
<220> FEATURE:
<223> OTHER INFORMATION: probe for PRRG4

<400> SEQUENCE: 51
aacatccatg ctcttcagcc                                      20

<210> SEQ ID NO 52
<211> LENGTH: 20
<212> TYPE: DNA
<213> ORGANISM: Artificial Sequence
<220> FEATURE:
<223> OTHER INFORMATION: 5' primer for PRRG4

<400> SEQUENCE: 52
actcccggca acctagaaag                                      20

<210> SEQ ID NO 53
<211> LENGTH: 22
<212> TYPE: DNA
<213> ORGANISM: Artificial Sequence
<220> FEATURE:

<223> OTHER INFORMATION: 3' primer for PRRG4

<400> SEQUENCE: 53
gtcagaaggc ccataacatc ta					22

<210> SEQ ID NO 54
<211> LENGTH: 20
<212> TYPE: DNA
<213> ORGANISM: Artificial Sequence
<220> FEATURE:
<223> OTHER INFORMATION: probe for prrg4

<400> SEQUENCE: 54
aacgattgca ttttggcagg					20

<210> SEQ ID NO 55
<211> LENGTH: 20
<212> TYPE: DNA
<213> ORGANISM: Artificial Sequence
<220> FEATURE:
<223> OTHER INFORMATION: 5' primer for TNFAIP6

<400> SEQUENCE: 55
gcctattgct acaacccaca					20

<210> SEQ ID NO 56
<211> LENGTH: 19
<212> TYPE: DNA
<213> ORGANISM: Artificial Sequence
<220> FEATURE:
<223> OTHER INFORMATION: 3' primer for TNFAIP6

<400> SEQUENCE: 56
tgggaagcct ggagattta					19

<210> SEQ ID NO 57
<211> LENGTH: 23
<212> TYPE: DNA
<213> ORGANISM: Artificial Sequence
<220> FEATURE:
<223> OTHER INFORMATION: probe for TNFAIP6

<400> SEQUENCE: 57
aaggagtgtg gtggcgtctt tac					23

<210> SEQ ID NO 58
<211> LENGTH: 21
<212> TYPE: DNA
<213> ORGANISM: Artificial Sequence
<220> FEATURE:
<223> OTHER INFORMATION: 5' primer for TNFAIP6

<400> SEQUENCE: 58
caggttgctt ggctgattat g					21

<210> SEQ ID NO 59
<211> LENGTH: 20
<212> TYPE: DNA
<213> ORGANISM: Artificial Sequence
<220> FEATURE:
<223> OTHER INFORMATION: 3' primer for TNFAIP6

<400> SEQUENCE: 59
ttgatttgga aacctccagc					20

```
<210> SEQ ID NO 60
<211> LENGTH: 24
<212> TYPE: DNA
<213> ORGANISM: Artificial Sequence
<220> FEATURE:
<223> OTHER INFORMATION: probe for TNFAIP6

<400> SEQUENCE: 60
tggctttgtg ggaagatact gtgg                                              24

<210> SEQ ID NO 61
<211> LENGTH: 24
<212> TYPE: DNA
<213> ORGANISM: Artificial Sequence
<220> FEATURE:
<223> OTHER INFORMATION: 5' primer for TNFAIP6

<400> SEQUENCE: 61
cattagactc aagtatggtc agcg                                              24

<210> SEQ ID NO 62
<211> LENGTH: 22
<212> TYPE: DNA
<213> ORGANISM: Artificial Sequence
<220> FEATURE:
<223> OTHER INFORMATION: 3' primer for TNFAIP6

<400> SEQUENCE: 62
tccacagtat cttcccacaa ag                                                22

<210> SEQ ID NO 63
<211> LENGTH: 22
<212> TYPE: DNA
<213> ORGANISM: Artificial Sequence
<220> FEATURE:
<223> OTHER INFORMATION: probe for TNFAIP6

<400> SEQUENCE: 63
caggttgctt ggctgattat gt                                                22

<210> SEQ ID NO 64
<211> LENGTH: 20
<212> TYPE: DNA
<213> ORGANISM: Artificial Sequence
<220> FEATURE:
<223> OTHER INFORMATION: 5' primer for VNN1

<400> SEQUENCE: 64
tgacaggaag tggcatctat                                                   20

<210> SEQ ID NO 65
<211> LENGTH: 20
<212> TYPE: DNA
<213> ORGANISM: Artificial Sequence
<220> FEATURE:
<223> OTHER INFORMATION: 3' primer for VNN1

<400> SEQUENCE: 65
tactgctggc ataggaagtc                                                   20

<210> SEQ ID NO 66
<211> LENGTH: 25
<212> TYPE: DNA
<213> ORGANISM: Artificial Sequence
<220> FEATURE:
<223> OTHER INFORMATION: probe for VNN1
```

<400> SEQUENCE: 66
agaagaggga aaactcctcc tctcg                                      25

<210> SEQ ID NO 67
<211> LENGTH: 20
<212> TYPE: DNA
<213> ORGANISM: Artificial Sequence
<220> FEATURE:
<223> OTHER INFORMATION: 5' primer for VNN1

<400> SEQUENCE: 67
ctggagaatt tcaggtgtca                                            20

<210> SEQ ID NO 68
<211> LENGTH: 20
<212> TYPE: DNA
<213> ORGANISM: Artificial Sequence
<220> FEATURE:
<223> OTHER INFORMATION: 3' primer for VNN1

<400> SEQUENCE: 68
atgcccagtc cttctcatac                                            20

<210> SEQ ID NO 69
<211> LENGTH: 25
<212> TYPE: DNA
<213> ORGANISM: Artificial Sequence
<220> FEATURE:
<223> OTHER INFORMATION: probe for VNN1

<400> SEQUENCE: 69
actgacggac gcttgtttag tctga                                      25

<210> SEQ ID NO 70
<211> LENGTH: 20
<212> TYPE: DNA
<213> ORGANISM: Artificial Sequence
<220> FEATURE:
<223> OTHER INFORMATION: 5' primer for VNN1

<400> SEQUENCE: 70
gtattcccaa cagcttggat                                            20

<210> SEQ ID NO 71
<211> LENGTH: 20
<212> TYPE: DNA
<213> ORGANISM: Artificial Sequence
<220> FEATURE:
<223> OTHER INFORMATION: 3' primer for VNN1

<400> SEQUENCE: 71
atagatgcca cttcctgtca                                            20

<210> SEQ ID NO 72
<211> LENGTH: 24
<212> TYPE: DNA
<213> ORGANISM: Artificial Sequence
<220> FEATURE:
<223> OTHER INFORMATION: probe for VNN1

<400> SEQUENCE: 72
catgagggtc aatttccttg catc                                       24

<210> SEQ ID NO 73
<211> LENGTH: 1852

<212> TYPE: DNA
<213> ORGANISM: Homo sapiens

<400> SEQUENCE: 73

| | | | | | |
|---|---|---|---|---|---|
| accgccgaga | ccgcgtccgc | cccgcgagca | cagagcctcg | cctttgccga | tccgccgccc | 60 |
| gtccacaccc | gccgccagct | caccatggat | gatgatatcg | ccgcgctcgt | cgtcgacaac | 120 |
| ggctccggca | tgtgcaaggc | cggcttcgcg | ggcgacgatg | ccccccgggc | cgtcttcccc | 180 |
| tccatcgtgg | ggcgccccag | gcaccagggc | gtgatggtgg | gcatgggtca | gaaggattcc | 240 |
| tatgtgggcg | acgaggccca | gagcaagaga | ggcatcctca | ccctgaagta | ccccatcgag | 300 |
| cacggcatcg | tcaccaactg | ggacgacatg | gagaaaatct | ggcaccacac | cttctacaat | 360 |
| gagctgcgtg | tggctcccga | ggagcacccc | gtgctgctga | ccgaggcccc | cctgaacccc | 420 |
| aaggccaacc | gcgagaagat | gacccagatc | atgtttgaga | ccttcaacac | cccagccatg | 480 |
| tacgttgcta | tccaggctgt | gctatccctg | tacgcctctg | gccgtaccac | tggcatcgtg | 540 |
| atggactccg | tgacgggggt | cacccacact | gtgcccatct | acgagggggta | tgccctcccc | 600 |
| catgccatcc | tgcgtctgga | cctggctggc | cgggacctga | ctgactacct | catgaagatc | 660 |
| ctcaccgagc | gcggctacag | cttcaccacc | acggccgagc | gggaaatcgt | gcgtgacatt | 720 |
| aaggagaagc | tgtgctacgt | cgccctggac | ttcgagcaag | agatggccac | ggctgcttcc | 780 |
| agctcctccc | tggagaagag | ctacgagctg | cctgacggcc | aggtcatcac | cattggcaat | 840 |
| gagcggttcc | gctgccctga | ggcactcttc | cagccttcct | tcctgggcat | ggagtcctgt | 900 |
| ggcatccacg | aaactacctt | caactccatc | atgaagtgtg | acgtggacat | ccgcaaagac | 960 |
| ctgtacgcca | acacagtgct | gtctggcggc | accaccatgt | accctggcat | tgccgacagg | 1020 |
| atgcagaagg | agatcactgc | cctggcaccc | agcacaatga | agatcaagat | cattgctcct | 1080 |
| cctgagcgca | agtactccgt | gtggatcggc | ggctccatcc | tggcctcgct | gtccaccttc | 1140 |
| cagcagatgt | ggatcagcaa | gcaggagtat | gacgagtccg | gccccatccat | cgtccaccgc | 1200 |
| aaatgcttct | aggcggacta | tgacttagtt | gcgttacacc | ctttcttgac | aaaacctaac | 1260 |
| ttgcgcagaa | acaagatgag | attggcatg | gcttatttg | ttttttttgt | tttgttttgg | 1320 |
| tttttttttt | tttttggct | tgactcagga | tttaaaaact | ggaacggtga | aggtgacagc | 1380 |
| agtcggttgg | agcgagcatc | ccccaaagtt | cacaatgtgg | ccgaggactt | tgattgcaca | 1440 |
| ttgttgtttt | tttaatagtc | attccaaata | tgagatgcgt | tgttacagga | agtcccttgc | 1500 |
| catcctaaaa | gccaccccac | ttctctctaa | ggagaatggc | ccagtcctct | cccaagtcca | 1560 |
| cacaggggag | gtgatagcat | tgctttcgtg | taaattatgt | aatgcaaaat | ttttttaatc | 1620 |
| ttcgccttaa | tactttttta | ttttgtttta | ttttgaatga | tgagccttcg | tgcccccct | 1680 |
| tccccctttt | ttgtccccca | acttgagatg | tatgaaggct | tttggtctcc | ctgggagtgg | 1740 |
| gtggaggcag | ccagggctta | cctgtacact | gacttgagac | cagttgaata | aaagtgcaca | 1800 |
| ccttaaaaat | gaaaaaaaaa | aaaaaaaaaa | aaaaaaaaaa | aaaaaaaaaa | aa | 1852 |

<210> SEQ ID NO 74
<211> LENGTH: 1634
<212> TYPE: DNA
<213> ORGANISM: Homo sapiens

<400> SEQUENCE: 74

| | | | | | |
|---|---|---|---|---|---|
| gggtggggaa | gcttagagac | cggtgaggga | gcagagctgg | ggcgcctgtg | tacagggata | 60 |
| gagcccggcg | gcagcagggc | gcggcttccc | tttcccgggg | cctggggccg | caatcaggtg | 120 |

| | |
|---|---|
| gagtcgagag gccggaggag gggcaggagg aaggggtgcg gtcgcgatcc ggacccggag | 180 |
| ccagcgcgga gcacctgcgc ccgcggctga caccttcgct cgcagtttgt tcgcagttta | 240 |
| ctcgcacacc agtttccccc accgcgcttt ggattagtgt gatctcagct caaggcaaag | 300 |
| gtgggatatc atggcatcta tctgggttgg acaccgagga acagtaagag attatccaga | 360 |
| ctttagccca tcagtggatg ctgaagctat tcagaaagca atcagaggaa ttggaactga | 420 |
| tgagaaaatg ctcatcagca ttctgactga gaggtcaaat gcacagcggc agctgattgt | 480 |
| taaggaatat caagcagcat atggaaagga gctgaaagat gacttgaagg gtgatctctc | 540 |
| tggccacttt gagcatctca tggtggccct agtgactcca ccagcagtct ttgatgcaaa | 600 |
| gcagctaaag aaatccatga agggcgcggg aacaaacgaa gatgccttga ttgaaatctt | 660 |
| aactaccagg acaagcaggc aaatgaagga tatctctcaa gcctattata cagtatacaa | 720 |
| gaagagtctt ggagatgaca ttagttccga acatctggt gacttccgga aagctctgtt | 780 |
| gactttggca gatggcagaa gagatgaaag tctgaaagtg gatgagcatc tggccaaaca | 840 |
| agatgcccag attctctata aagctggtga aacagatgg ggcacggatg aagacaaatt | 900 |
| cactgagatc ctgtgtttaa ggagctttcc tcaattaaaa ctaacatttg atgaatacag | 960 |
| aaatatcagc caaaaggaca ttgtggacag cataaaagga gaattatctg gcattttga | 1020 |
| agacttactg ttggccatag ttaattgtgt gaggaacacg ccggcctttt tagccgaaag | 1080 |
| actgcatcga gccttgaagg gtattggaac tgatgagttt actctgaacc gaataatggt | 1140 |
| gtccagatca gaaattgacc ttttggacat tcgaacagag ttcaagaagc attatggcta | 1200 |
| ttccctatat tcagcaatta aatcggatac ttctggagac tatgaaatca cactcttaaa | 1260 |
| aatctgtggt ggagatgact gaaccaagaa gataatctcc aaaggtccac gatgggcttt | 1320 |
| cccaacagct ccaccttact tcttctcata ctatttaaga gaacaagcaa atataaacag | 1380 |
| caacttgtgt tcctaacagg aattttcatt gttctataac aacaacaaca aaagcgatta | 1440 |
| ttatttaga gcatctcatt tataatgtag cagctcataa atgaaattga aaatggtatt | 1500 |
| aaagatctgc aactactatc caacttatat ttctgctttc aaagttaaga atctttatag | 1560 |
| ttctactcca ttaaatataa agcaagataa taaaaattgt tgcttttgtt aaaagtaaaa | 1620 |
| aaaaaaaaaa aaaa | 1634 |

<210> SEQ ID NO 75
<211> LENGTH: 2933
<212> TYPE: DNA
<213> ORGANISM: Homo sapiens

<400> SEQUENCE: 75

| | |
|---|---|
| ctttgaaaaa gacttctttt gagctaactt tcttatactg gtacctttct aatctcacta | 60 |
| caatatgtaa cattggtgtt cgatctcaag tatttctgaa tatattcccc tatccacaga | 120 |
| aatatactct gggggaaaaa aaatagaaca aattcttgcc gtcctgacca ttgaacaaga | 180 |
| gactaattag acaatggggc tagaaaaacc tcaaagtaaa ctggaaggag gcatgcatcc | 240 |
| ccagctgata ccttcggtta ttgctgtagt tttcatctta cttctcagtg tctgtttat | 300 |
| tgcaagttgt ttggtgactc atcacaactt ttcacgctgt aagagaggca caggagtgca | 360 |
| caagttagag caccatgcaa agctcaaatg catcaaagag aaatcagaac tgaaaagtgc | 420 |
| tgaagggagc acctggaact gttgtcctat tgactggaga gccttccagt ccaactgcta | 480 |
| ttttcctctt actgacaaca agacgtgggc tgagagtgaa aggaactgtt cagggatggg | 540 |
| ggcccatctg atgaccatca gcacggaagc tgagcagaac tttattattc agtttctgga | 600 |

```
tagacggctt tcctatttcc ttggacttag agatgagaat gccaaaggtc agtggcgttg      660
ggtggaccag acgccattta acccacgcag agtattctgg cataagaatg aacccgacaa      720
ctctcaggga gaaaactgtg ttgttcttgt ttataaccaa gataaatggg cctggaatga      780
tgttccttgt aactttgaag caagtaggat ttgtaaaata cctggaacaa cattgaacta      840
gaaactcaga aagtggtcct tgtgatggaa agagaaaaga aaaccaatt agaataaggc       900
agaatgtacg tgcgtcattg gaacacagaa aacatgctgg ttcatacagc gtttttagtc      960
cttgaaaaa gacttctttt gagctaactt tcttatactg gtacctttct aatctcacta     1020
caatatgtaa cattggtgtt cgatctcaag tatttctgaa tatattcccc tatccacaga     1080
aatatactct gggggaaaaa aaatagaaca aattcttgcc gtcctgacca ttgaacaaga     1140
gactaattag acaatggggc tagaaaaacc tcaaagtaaa ctggaaggag gcatgcatcc     1200
ccagctgata ccttcggtta ttgctgtagt tttcatctta cttctcagtg tctgttttat     1260
tgcaagttgt ttggtgactc atcacaactt ttcacgctgt aagagaggca caggagtgca     1320
caagttagag caccatgcaa agctcaaatg catcaaagag aaatcagaac tgaaaagtgc     1380
tgaagggagc acctggaact gttgtcctat tgactggaga gccttccagt ccaactgcta     1440
ttttcctctt actgacaaca agacgtgggc tgagagtgaa aggaactgtt cagggatggg     1500
ggcccatctg atgaccatca gcacggaagc tgagcagaac tttattattc agttctgga      1560
tagacggctt tcctatttcc ttggacttag agatgagaat gccaaaggtc agtggcgttg     1620
ggtggaccag acgccattta acccacgcag agtattctgg cataagaatg aacccgacaa     1680
ctctcaggga gaaaactgtg ttgttcttgt ttataaccaa gataaatggg cctggaatga     1740
tgttccttgt aactttgaag caagtaggat ttgtaaaata cctggaacaa cattgaacta     1800
gaaactcaga aagtggtcct tgtgatggaa agagaaaaga aaaccaatt agaataaggc      1860
agaatgtacg tgcgtcattg gaacacagaa aacatgctgg ttcatacagc gtttttagtc     1920
ataatggtct ttttttatttt gtttgattca ttcgagacaa catgtgtgta tgtgtgtgtg    1980
tgtgtgtgta gataatgtgg ttttttgtatg gtgtttgatg gaaggaataa tctttctttg    2040
ctttcttagt agtatttcaa ggtgtttact tttcaattgg tgtgcactga atgcatgtat     2100
ggaagaatag cgtgaataat gcaatctctt tgtcattttt cccttctca gactcttagc      2160
tcttaaaatt caaagatggg atattctaac tggtagtggt gcatcatttt taacccaaat     2220
attgcaagca ctttaaagat ttgaaaccac attttttattg tttgatgttt cattttcaga    2280
cttttttaatg tcagtcatta caattacatt gcatgaggaa aattttttcca gaacaacagt   2340
gtggaatagt tctgaattat gctgttctac agatagaaaa aaagtccaaa tgcctttaaa     2400
aatttacttc ttactccacc caacacgttt ttgcaaagca agaagtcttt gtaagacacc     2460
ttaaacaaag tccttcaatt ctacagcaga ggaaataaaa tcccccagaa gccaagggc      2520
tcaccttcac attgttagtt catgacagac ccaggtgtgc ttcattagag ataacataca     2580
ttcccttttgg tatcacagga agttactggg gattactcga cctcattact tagctaacga    2640
ctggataaaa tttcttaatt gtttgaagta acattgtatt cgtgtttgca ttattaattt     2700
gaatagaaaa taatcacatt ttcaacccat ttatacaaat tgttaatgtt tctttagagc     2760
tgtataacta tagtttgaac tagcaaggaa gttattgttt tgacaaccag aaattatgct     2820
tttctggtgc atgaaacatt aattgcaaag ggcagtcaca tccaacttta ataaaatatg     2880
gtggtctttc ttaaaaaaaa aaaaaaaaaa aaaaaaaaa  aaaaaaaaaa aaa            2933
```

<210> SEQ ID NO 76
<211> LENGTH: 4045
<212> TYPE: DNA
<213> ORGANISM: Homo sapiens

<400> SEQUENCE: 76

| | | | | | |
|---|---|---|---|---|---|
| gcagccagag | ctcagcaggg | ccctggagag | atggccacgg | tcccagcacc | ggggaggact | 60 |
| ggagagcgcg | cgctgccacc | gccccatgtc | tcagccaggg | cttccttcct | cggctccacc | 120 |
| ctgtggatgt | aatggcggcc | cctgctctgt | cctggcgtct | gccctcctc | atcctcctcc | 180 |
| tgcccctggc | tacctcttgg | gcatctgcag | cggtgaatgg | cacttcccag | ttcacatgct | 240 |
| tctacaactc | gagagccaac | atctcctgtg | tctggagcca | agatggggct | ctgcaggaca | 300 |
| cttcctgcca | agtccatgcc | tggccggaca | gacggcggtg | gaaccaaacc | tgtgagctgc | 360 |
| tccccgtgag | tcaagcatcc | tgggcctgca | acctgatcct | cggagcccca | gattctcaga | 420 |
| aactgaccac | agttgacatc | gtcaccctga | gggtgctgtg | ccgtgagggg | gtgcgatgga | 480 |
| gggtgatggc | catccaggac | ttcaagccct | ttgagaacct | tcgcctgatg | gccccatct | 540 |
| ccctccaagt | tgtccacgtg | gagacccaca | gatgcaacat | aagctgggaa | atctcccaag | 600 |
| cctcccacta | ctttgaaaga | cacctggagt | tcgaggcccg | gacgctgtcc | ccaggccaca | 660 |
| cctgggagga | ggccccctg | ctgactctca | agcagaagca | ggaatggatc | tgcctggaga | 720 |
| cgctcacccc | agacacccag | tatgagtttc | aggtgcgggt | caagcctctg | caaggcgagt | 780 |
| tcacgacctg | gagccctgg | agccagccc | tggccttcag | gacaaagcct | gcagcccttg | 840 |
| ggaaggacac | cattccgtgg | ctcggccacc | tcctcgtggg | cctcagcggg | gcttttggct | 900 |
| tcatcatctt | agtgtacttg | ctgatcaact | gcaggaacac | cgggccatgg | ctgaagaagg | 960 |
| tcctgaagtg | taacaccccca | gaccctcga | agttctttc | ccagctgagc | tcagagcatg | 1020 |
| gaggagacgt | ccagaagtgg | ctctcttcgc | ccttcccctc | atcgtccttc | agccctggcg | 1080 |
| gcctggcacc | tgagatctcg | ccactagaag | tgctggagag | gacaaggtg | acgcagctgc | 1140 |
| tcctgcagca | ggacaaggtg | cctgagcccg | catccttaag | cagcaaccac | tcgctgacca | 1200 |
| gctgcttcac | caaccagggt | tacttcttct | tccaccctcc | ggatgccttg | agatagagg | 1260 |
| cctgccaggt | gtactttact | tacgacccct | actcagagga | agaccctgat | gagggtgtgg | 1320 |
| ccggggcacc | cacagggtct | tccccccaac | ccctgcagcc | tctgtcaggg | gaggacgacg | 1380 |
| cctactgcac | cttcccctcc | agggatgacc | tgctgctctt | ctcccccagt | ctcctcggtg | 1440 |
| gcccagccc | ccaagcact | gcccctgggg | gcagtgggc | cggtgaagag | aggatgcccc | 1500 |
| cttctttgca | agaaagagtc | cccagagact | gggaccccca | gccctgggg | cctcccaccc | 1560 |
| caggagtccc | agacctggtg | gattttcagc | cacccccgga | gctggtgctg | cgagaggctg | 1620 |
| gggaggaggt | ccctgacgct | ggccccaggg | agggagtcag | tttccctgg | tccaggcctc | 1680 |
| ctgggcaggg | ggagttcagg | gcccttaatg | ctcgcctgcc | cctgaacact | gatgcctact | 1740 |
| tgtccctcca | agaactccag | ggtcaggacc | caactcactt | ggtgtagaca | gatggccagg | 1800 |
| gtgggaggca | ggcagctgcc | tgctctgcgc | cgagcctcag | aaggaccctg | ttgagggtcc | 1860 |
| tcagtccact | gctgaggaca | ctcagtgtcc | agttgcagct | ggacttctcc | accggatgg | 1920 |
| ccccccaccca | gtcctgcaca | cttggtccat | ccatttccaa | acctccactg | ctgctcccgg | 1980 |
| gtcctgctgc | ccgagccagg | aactgtgtgt | gttgcagggg | ggcagtaact | ccccaactcc | 2040 |
| ctcgttaatc | acaggatccc | acgaatttag | gctcagaagc | atcgctcctc | tccagccctg | 2100 |
| cagctattca | ccaatatcag | tcctcgcggc | tctccagggc | tccctgccct | gacctcttcc | 2160 |

```
ctgggttttc tgccccagcc tcctccttcc ctcccctccc cgtccacagg gcagcctgag   2220
cgtgctttcc aaaacccaaa tatggccacg ctccccctcg gttcaaaacc ttgcacaggt   2280
cccactgccc tcagcccac  ttctcagcct ggtacttgta cctccggtgt cgtgtgggga   2340 catcccttc  tgcaatcctc cctaccgtcc tcctgagcca ctcagagctc cctcacaccc   2400
cctctgttgc acatgctatt ccctgggggct gctgtgcgct cccctcatc  taggtgacaa   2460 acttccctga ctcttcaagt gccggttttg cttctcctgg agggaagcac tgcctcccctt  2520 aatctgccag aaacttctag cgtcagtgct ggagggagaa gctgtcaggg acccagggcg   2580
cctggagaaa gaggccctgt tactattcct ttgggatctc tgaggcctca gagtgcttgg   2640
ctgctgtatc tttaatgctg gggcccaagt aagggcacag atcccccac  aaagtggatg   2700 cctgctgcat cttcccacag tggcttcaca gacccacaag agaagctgat ggggagtaaa   2760
ccctggagtc cgaggcccag gcagcagccc cgcctagtgg tgggccctga tgctgccagg   2820
cctgggacct cccactgccc cctccactgg aggggtctcc tctgcagctc agggactggc   2880
acactggcct ccagaagggc agctccacag ggcagggcct cattattttt cactgcccca   2940
gacacagtgc ccaacacccc gtcgtatacc ctggatgaac gaattaatta cctggcacca   3000
cctcgtctgg gctccctgcg cctgacattc acacagagag gcagagtccc gtgcccatta   3060
ggtctggcat gccccctcct gcaagggggct caacccccta cccgaccccc tccacgtatc   3120
tttcctaggc agatcacgtt gcaatggctc aaacaacatt ccaccccagc aggacagtga   3180
ccccagtccc agctaactct gacctgggag ccctcaggca cctgcactta caggccttgc   3240
tcacagctga ttgggcacct gaccacacgc ccccacaggc tctgaccagc agcctatgag   3300
ggggtttggc accaagctct gtccaatcag gtaggctggg cctgaactag ccaatcagat   3360
caactctgtc ttgggcgttt gaactcaggg agggaggccc ttgggagcag gtgcttgtgg   3420
acaaggctcc acaagcgttg agccttggaa aggtagacaa gcgttgagcc actaagcaga   3480
ggaccttggg ttcccaatac aaaaatacct actgctgaga gggctgctga ccatttggtc   3540
aggattcctg ttgcctttat atccaaaata aactccccctt tcttgaggtt gtctgagtct   3600
tgggtctatg ccttgaaaaa agctgaatta ttggacagtc tcacctcctg ccatagggtc   3660
ctgaatgttt cagaccacaa ggggctccac acctttgctg tgtgttctgg ggcaacctac   3720
taatcctctc tgcaagtcgg tctccttatc cccccaaatg gaaattgtat ttgccttctc   3780
cactttggga ggctcccact tcttgggagg gttacatttt ttaagtctta atcatttgtg   3840
acatatgtat ctatacatcc gtatctttta atgatccgtg tgtaccatct ttgtgattat   3900
ttccttaata ttttttcttt aagtcagttc attttcgttg aaatacattt atttaaagaa   3960
aaatctttgt tactctgtaa atgaaaaaac ccattttcgc tataaataaa aggtaactgt   4020
acaaaataag tacaatgcaa caaaa                                         4045
```

<210> SEQ ID NO 77
<211> LENGTH: 2882
<212> TYPE: DNA
<213> ORGANISM: Homo sapiens

<400> SEQUENCE: 77

```
gtgcagcctg agaggaaaca aagtgctgcg agcaggagac ggcggcggcg cgaaccctgc     60
tgggcctcca gtcaccctcg tcttgcattt tcccgcgtgc gtgtgtgagt gggtgtgtgt    120
gttttcttac aaagggtatt tcgcgatcga tcgattgatt cgtagttccc cccgcgcgc    180
```

```
ctttgccctt tgtgctgtaa tcgagctccc gccatcccag gtgcttctcc gttcctctaa    240
acgccagcgt ctggacgtga gcgcaggtcg ccggtttgtg ccttcggtcc ccgcttcgcc    300
ccctgccgtc ccctccttat cacggtcccg ctcgcggcct cgccgccccg ctgtctccgc    360
cgccgccat ggcgactgcg accccgtgc cgccgcggat gggcagccgc gctggcggcc     420
ccaccacgcc gctgagcccc acgcgcctgt cgcggctcca ggagaaggag gagctgcgcg    480
agctcaatga ccggctggcg gtgtacatcg acaaggtgcg cagcctggag acggagaaca    540
gcgcgctgca gctgcaggtg acggagcgcg aggaggtgcg cggccgtgag ctcaccggcc    600
tcaaggcgct ctacgagacc gagctggccg acgcgcgacg cgcgctcgac gacacggccc    660
gcgagcgcgc caagctgcag atcgagctgg gcaagtgcaa ggcggaacac gaccagctgc    720
tcctcaacta tgctaagaag gaatctgatc ttaatggcgc ccagatcaag cttcgagaat    780
atgaagcagc actgaattcg aaagatgcag ctcttgctac tgcacttggt gacaaaaaaa    840
gtttagaggg agatttggag gatctgaagg atcagattgc ccagttggaa gcctccttag    900
ctgcagccaa aaaacagtta gcagatgaaa ctttacttaa agtagatttg gagaatcgtt    960
gtcagagcct tactgaggac ttggagtttc gcaaaagcat gtatgaagag gagattaacg   1020
agaccagaag gaagcatgaa acgcgcttgg tagaggtgga ttctgggcgt caaattgagt   1080
atgagtacaa gctggcgcaa gcccttcatg agatgagaga gcaacatgat gcccaagtga   1140
ggctgtataa ggaggagctg gagcagactt accatgccaa acttgagaat gccagactgt   1200
catcagagat gaatacttct actgtcaaca gtgccaggga gaactgatg gaaagccgca    1260
tgagaattga gagcctttca tcccagcttt ctaatctaca gaaagagtct agagcatgtt   1320
tggaaaggat tcaagaatta gaggacttgc ttgctaaaga aaaagacaac tctcgtcgca   1380
tgctgacaga caaagagaga gagatggcgg aaataaggga tcaaatgcag caacagctga   1440
atgactatga acagcttctt gatgtaaagt tagccctgga catggaaatc agtgcttaca   1500
ggaaactctt agaaggcgaa gaagagaggt tgaagctgtc tccaagccct tcttcccgtg   1560
tgacagtatc ccgagcatcc tcaagtcgta gtgtacgtac aactagagga aagcggaaga   1620
gggttgatgt ggaagaatca gaggcgagta gtagtgttag catctctcat tccgcctcag   1680
ccactggaaa tgtttgcatc gaagaaattg atgttgatgg gaaatttatc cgcttgaaga   1740
acacttctga acaggatcaa ccaatgggag gctgggagat gatcagaaaa attggagaca   1800
catcagtcag ttataaatat acctcaagat atgtgctgaa ggcaggccag actgttacaa   1860
tttgggctgc aaacgctggt gtcacagcca gcccccaac tgacctcatc tggaagaacc    1920
agaactcgtg gggcactggc gaagatgtga aggttatatt gaaaaattct cagggagagg   1980
aggttgctca agaagtaca gtctttaaaa caaccatacc tgaagaagag gaggaggagg    2040
aagaagcagc tggagtggtt gttgaggaag aactttccca ccagcaggga accccaagag   2100
catccaatag aagctgtgca attatgtaaa attttcaact gtcttcctca aaataaagaa   2160
gtatggtaat ccttacctgt atacagtgca gagccttctc agaagcacag aatatttta    2220
tatttccttt atgtgaattt ttaagctgca aatctgatgg ccttaatttc ctttttgaca   2280
ctgaaagttt tgtaaaagaa atcatgtcca tacactttgt tgcaagatgt gaattattga   2340
cactgaactt aataactgtg tactgttcgg aaggggttcc tcaaattttt tgactttttt   2400
tgtatgtgtg ttttttcttt ttttttaagt tcttatgagg agggagggt aaataaacca    2460
ctgtgcgtct tggtgtaatt tgaagattgc cccatctaga ctagcaatct cttcattatt   2520
ctctgctata tataaaacgg tgctgtgagg gaggggaaaa gcatttttca atatattgaa   2580
```

```
cttttgtact gaattttttt gtaataagca atcaaggtta taatttttt taaaatagaa      2640 attttgtaag aaggcaatat taacctaatc accatgtaag cactctggat gatggattcc     2700
acaaaacttg gttttatggt tacttcttct cttagattct taattcatga ggagggtggg     2760
ggagggaggt ggagggaggg aagggtttct ctattaaaat gcattcgttg tgttttttaa     2820
gatagtgtaa cttgcttaaa tttcttatgt gacattaaca aataaaaaag ctcttttaat     2880
at                                                                   2882
```

<210> SEQ ID NO 78
<211> LENGTH: 2015
<212> TYPE: DNA
<213> ORGANISM: Homo sapiens

<400> SEQUENCE: 78

```
cccggaccga ggcaggacct caccccgcgc gtgttccccg ggcgcccctc tgcgaaccec      60 aggcccttcc caggtttgcg cgcggggcc atccagaccc tgcggagagc gaggcccgga     120
gcgtcgccga ggtttgaggg cgccggagac cgagggcctg gcggccgaag aaccgcccc     180 aagaagagcc tctggcccgg gggctgctgg aacatgtgcg gggggacaca gtttgtttga     240
cagttgccag actatgttta cgcttctggt tctactcagc caactgccca cagttaccct     300
ggggtttcct cattgcgcaa gaggtccaaa ggcttctaag catgcgggag aagaagtgtt     360
tacatcaaaa gaagaagcaa acttttttcat acatagacgc cttctgtata atagatttga     420
tctggagctc ttcactcccg gcaacctaga aagagagtgc aatgaagaac tttgcaatta     480
tgaggaagcc agagagattt tgtggatga agataaaacg attgcatttt ggcaggaata     540
ttcagctaaa ggaccaacca caaaatcaga tggcaacaga gagaaaatag atgttatggg     600
ccttctgact ggattaattg ctgctggagt atttttggtt atttttggat tacttggcta     660
ctatctttgt atcactaagt gtaataggct acaacatcca tgctcttcag ccgtctatga     720
aagggggagg cacactccct ccatcatttt cagaagacct gaggaggctg ccttgtctcc     780
attgccgcct tctgtggagg atgcaggatt accttcttat gaacaggcag tggcgctgac     840
cagaaaacac agtgtttcac caccaccacc atatcctggg cacacaaaag gatttagggt     900
atttaaaaaa tctatgtctc tcccatctca ctgactacct tgtcattttg gtataagaaa     960
tttgtgttat ttgataggcc gggcatggtg gctcatgcct gtaatcccag cactttggga    1020
ggccaggagt tcgagaccag cctggccaac atggtgaaac ccggtctcta ctaaaaattc    1080
aaaaattacc taggcgtcat ggggcatgcc tgtagtccca cctacttggg aggctgaagc    1140
aggagaattg ctcgaacctg ggaggcagag gttgcagtaa gctgagatca cgccactgca    1200
ttccagcctg ggcgacagag caagactcca tctcaaaaat aaaataaaaa aagaaagaaa    1260
gaaaagaaga agaaaagaga agaaggagaa ggagatgaag gaggaggagg aggagaagga    1320
gaagaagaag aagaagaaga ccacaaaaga catgactatc caacttttta tgacaaactg    1380
caaggaataa aggaagaata agtccatgta ctgtaccaca gaagttctgt ctgcatcttg    1440
gacctgaact tgatcattat cagcttgata agagactttt tgactctata tccttgcagt    1500
taagaagaaa gcactttttt gtaatgtttg ttttaatggt tcaaaaaaaa tctttcttat    1560
aaagagcata ggtagaatta gtgaactctt tggatccttt gtacagataa aggttataga    1620
tttcttgtgt tgaatattaa aaaagcaagg atgtctaacc attaagatta tccaaagtca    1680
ggctgggcgc agtggctcac gcctgtaatc ccagcacttt gggagggata ggtgggcgga    1740
```

| | |
|---|---|
| tcacctgagg tcaggagttt gagaccagcc tggccaacat ggcaaaaccc cgtctctaca | 1800 |
| aaaatacaaa agaaattagc cagacatgat ggcgggtgcc tctaatccca gctactgggg | 1860 |
| aggctgaggt gggagaatcg cttgaactcg ggaggtggag gttgtagtga ggcgagattg | 1920 |
| tgccattgca ctccaacctg ggcgacagag tgagactcca tctcaaaaaa aaaaaaaaa | 1980 |
| aaaaaaaaaa aaaaaaaaaa aaaaaaaaaa aaaaa | 2015 |

<210> SEQ ID NO 79
<211> LENGTH: 1440
<212> TYPE: DNA
<213> ORGANISM: Homo sapiens

<400> SEQUENCE: 79

| | |
|---|---|
| cagtcacatt tcagccactg ctctgagaat ttgtgagcag ccctaacag gctgttactt | 60 |
| cactacaact gacgatatga tcatcttaat ttacttattt ctcttgctat gggaagacac | 120 |
| tcaaggatgg ggattcaagg atggaatttt tcataactcc atatggcttg aacgagcagc | 180 |
| cggtgtgtac cacagagaag cacggtctgg caaatacaag ctcacctacg cagaagctaa | 240 |
| ggcggtgtgt gaatttgaag gcggccatct cgcaacttac aagcagctag aggcagccag | 300 |
| aaaaattgga tttcatgtct gtgctgctgg atggatggct aagggcagag ttggataccc | 360 |
| cattgtgaag ccagggccca actgtggatt tggaaaaact ggcattattg attatggaat | 420 |
| ccgtctcaat aggagtgaaa gatgggatgc ctattgctac aacccacacg caaaggagtg | 480 |
| tggtggcgtc tttacagatc caaagcaaat ttttaaatct ccaggcttcc caatgagta | 540 |
| cgaagataac caaatctgct actggcacat tagactcaag tatggtcagc gtattcacct | 600 |
| gagttttta gattttgacc ttgaagatga cccaggttgc ttggctgatt atgttgaaat | 660 |
| atatgacagt tacgatgatg tccatggctt tgtgggaaga tactgtggag atgagcttcc | 720 |
| agatgacatc atcagtacag gaaatgtcat gaccttgaag tttctaagtg atgcttcagt | 780 |
| gacagctgga ggtttccaaa tcaaatatgt tgcaatggat cctgtatcca aatccagtca | 840 |
| aggaaaaaat acaagtacta cttctactgg aaataaaaac ttttagctg gaagatttag | 900 |
| ccacttataa aaaaaaaaa aaggatgatc aaaacacaca gtgtttatgt tggaatcttt | 960 |
| tggaactcct ttgatctcac tgttattatt aacatttatt tattattttt ctaaatgtga | 1020 |
| aagcaataca taatttaggg aaaattggaa aatataggaa actttaaacg agaaaatgaa | 1080 |
| acctctcata atcccactgc atagaaataa caagcgttaa cattttcata tttttttctt | 1140 |
| tcagtcattt ttctatttgt ggtatatgta tatatgtacc tatatgtatt tgcatttgaa | 1200 |
| attttggaat cctgctctat gtacagtttt gtattatact tttaaatct tgaactttat | 1260 |
| aaacattttc tgaaatcatt gattattcta caaaacatg attttaaaca gctgtaaaat | 1320 |
| attctatgat atgaatgttt tatgcattat ttaagcctgt ctctattgtt ggaatttcag | 1380 |
| gtcattttca taaatattgt tgcaataaat atccttgaac acaaaaaaaa aaaaaaaaa | 1440 |

<210> SEQ ID NO 80
<211> LENGTH: 3109
<212> TYPE: DNA
<213> ORGANISM: Homo sapiens

<400> SEQUENCE: 80

| | |
|---|---|
| cattggactt cagcatgact actcagttgc cagcttacgt ggcaattttg cttttctatg | 60 |
| tctcaagagc cagctgccag gacactttca ttgcagctgt ttatgagcat gcagcgatat | 120 |
| tgcccaatgc caccctaaca ccagtgtctc gtgaggaggc tttggcatta atgaatcgga | 180 |

```
atctggacat tttggaagga gcgatcacat cagcagcaga tcagggtgcg catattattg    240
tgactccaga agatgctatt tatggctgga acttcaacag ggactctctc tacccatatt    300
tggaggacat cccagaccct gaagtaaact ggatcccctg taataatcgt aacagatttg    360
gccagacccc agtacaagaa agactcagct gcctggccaa gaacaactct atctatgttg    420
tggcaaatat tggggacaag aagccatgcg ataccagtga tcctcagtgt ccccctgatg    480
gccgttacca atacaacact gatgtggtat ttgattctca aggaaaactg gtggcacgct    540
accataagca aaaccttttc atgggtgaaa atcaattcaa tgtacccaag gagcctgaga    600
ttgtgacttt caataccacc tttgaagttt tggcattttt cacatgcttt gatatactct    660
tccatgatcc tgctgttacc ttggtgaaag atttccacgt ggacaccata gtattcccaa    720
cagcttggat gaatgttttg ccacatttgt cagctgttga attccactca gcttgggcta    780
tgggcatgag ggtcaatttc cttgcatcca acatacatta cccctcaaag aaaatgacag    840
gaagtggcat ctatgcaccc aattcttcaa gagcatttca ttatgatatg aagacagaag    900
agggaaaact cctcctctcg caactggatt cccacccatc ccattctgca gtggtgaact    960
ggacttccta tgccagcagt atagaagcgc tctcatcagg aaacaaggaa tttaaaggca    1020
ctgtcttttt cgatgaattc acttttgtga agctcacagg agttgcagga aattatacag    1080
tttgtcagaa agatctctgc tgtcatttaa gctacaaaat gtctgagaac ataccaaatg    1140
aagtgtacgc tctaggggca tttgacggac tgcacactgt ggaagggcgc tattatctac    1200
agatttgtac cctgttgaaa tgtaaaacga ctaatttaaa cacttgcggt gactcagctg    1260
aaacagcttc taccaggttt gaaatgttct ccctcagtgg cactttcgga acccagtatg    1320
tctttcctga ggtgttgctg agtgaaaatc agcttgcacc tggagaattt caggtgtcaa    1380
ctgacggacg cttgtttagt ctgaagccaa catccggacc tgtcttaaca gtaactctgt    1440
ttgggaggtt gtatgagaag gactgggcat caaatgcttc atcaggcctc acagcacaag    1500
caagaataat aatgctaata gttatagcac ctattgtatg ctcattaagt tggtagaata    1560
ttgacttttt ctctttttta tttgggataa tttaaaaaat gatggatgag aaaagaaaga    1620
ttggtccggg ttaatattat cctctagtat aagtgaatta ctagtttctc tttatttaga    1680
caaacacaca cacaccagat aatataaact aataaaatta tctgttaatg tagattttat    1740
ttaaaaaact atatttgaac attggtcttt cttggacgtg agctaattat atcaaataag    1800
tatcacaaat cttttacgca gaagaaataa aaactacggg tagaaaacat aagaactatc    1860
ataaaattta cttacaagga ggctgctctt gttaccactt ttattatatt acgtatcact    1920
tattcagctc tgctgaaaat ttccaatgac tttgtttgtt tgctcttttta gttttttacc    1980 taaacaatac atttttgattc tcttgtgggt tgataatgtc tccccaaaat ttacatgttg    2040
aagcacctca gaatgtgact gtatttggag acagggtctt taagaggta aataaggtc    2100 attaggatag accctaattc aatatgactg atgatcataa agaagaggc gagtagggca    2160 caacaggcac aaagggagac cataaggaga cacagaggaa ggacaactct ttacaagcta    2220
agaagagagg gcctcagaag aaaccaaccc tgccaacacc ttgatcttgg acttccagcc    2280
tccaaaacta tgagaaataa atttctattg tttaagtcac ccagtccatg gtactttgtt    2340
aggcagccct ggcaaatgaa tcaaagaccc attcctgttc ctctcccac cactactgtt    2400 ttctactgta atctgaagct tcaacaaaag gcttacctgg taagaatatt cagctggtct    2460
gggtcctcaa gactccaata gacactctta aagaaggatt gctgatggat tgatagtgaa    2520
```

-continued

```
accattagat cattgaattc ctctggaatt agaaaaccag agagtcccat tttaagaaat    2580
tagatattta atatagcatt gtgtgttcta ttttagtaac agcagaatct cttgacatta    2640
cacaactcag tgaaacaaca tcatttaagc caaaatatct cccaactgac tgatagactc    2700
tgagcactaa tatcatagtg ctgtgatgat ggacaattac atagtaccga taacagccat    2760
gcactgtgca aagcatgccc ttctgcacag gagagcaagg cacttgcagt agtgatctat    2820
gccagcaaaa catcattttg agacaaacat ttttgtggca gatgttttc ctaaaaagta    2880 ctatatcatc caagaaatat ttgagtaaaa tcccttgttc ttttgggtga cattaactga    2940
catttgcttt ttttcaagac ctaatagaaa ataagaaagc ccataatgta tttagaaaca    3000
ggaatcctca gagcaattct ctgtattctc atataatttc aatgtaaaac agaaaacata    3060
ttgatgtgtt ggtgataggc ttgaattatt aaaaacttca aaaacaaaa                3109
```

METHOD AND APPARATUS FOR DETERMINING A PROBABILITY OF COLORECTAL CANCER IN A SUBJECT

This application is a continuation application of U.S. non-provisional application Ser. No. 14/546,433, filed Nov. 18, 2014, which is a continuation application of U.S. non-provisional application Ser. No. 12/384,914, filed Apr. 10, 2009, which itself claims the benefit of U.S. provisional application 61/123,798, filed Apr. 10, 2008 and of U.S. provisional application 61/123,831, filed Apr. 11, 2008. The entire contents of both non-provisional applications and both provisional applications are incorporated by reference herein.

TECHNICAL FIELD

The disclosure relates to apparatuses, kits and methods for determining a probability of colorectal cancer in a test subject. More particularly, the disclosure relates to apparatuses, kits and methods for diagnosing colorectal cancer in a test subject by measuring a level of one or more gene products in blood of the test subject.

BACKGROUND

Colorectal cancer causes 655,000 deaths worldwide per year, making it the second-leading cause of cancer-related deaths. It is the third most frequently diagnosed cancer in men and women in the United States and carries an overall population lifetime risk of 6%. (American Cancer Society. Cancer Facts and Figures. 2008. Atlanta: American Cancer Society). The American Cancer Society estimates that about 108,070 new cases of colon cancer (53,760 in men and 54,310 in women) and 40,740 new cases of rectal cancer (23,490 in men and 17,250 in women) will be diagnosed in 2008. Of those diagnosed, nearly half are expected to die within five years. In the United States in 2008 an estimated 50,000 men and women will die of cancer of the colon and rectum. (American Cancer Society 2008). This high mortality rate is due at least in part to the fact that a large proportion of cancers are detected at relatively late stages, such as following onset of overt symptoms, when the cancer is more difficult to treat. In addition, identification of colorectal cancer at later stages concomitantly necessitates harsher treatment, such as radical colostomy. It has been shown that the identification and treatment of colorectal cancer at earlier stages significantly reduces the risk of developing more advanced disease, and hence risk of death from the disease. Stage at detection is critically related to patient survival. Localized cancers (Dukes's Stage A or B) have an excellent prognosis of 82%-93% at five years. Regional (Dukes's Stage C) patients have a five year survival rates of 55% to 60%; and only 5% to 8% of patients with late stage cancer will survive the five year span. (O'Connell J B, Maggard M, Ko C Y. Colon cancer survival rates with the new American Joint Committee on cancer sixth edition staging. JNCI. 2004; 96: 1420-1425). Therefore, a test to screen for colorectal cancer so as to allow earlier treatment should markedly reduce the incidence of advanced-stage colorectal cancer (Ransohoff D F. Colorectal cancer screening in 2005: status and challenges. Gastroenterology. 2005 May; 128(6):1685-95) and decrease the current costs to the medical system. Thus, the American Cancer Society recommends that all Americans age 50 and older be screened regularly for colorectal cancer. Unfortunately, only a small fraction of the population at risk is screened for the disease (Mitka M. Colorectal cancer screening rates still fall far short of recommended levels. JAMA. 2008 Feb. 13; 299(6):622), as currently available screening methods require insufficiently available and/or costly resources, are associated with unacceptably low patient compliance, and/or are associated with significant health risks.

Currently utilized screening technologies to test for colorectal cancer include fecal occult blood test (FOBT), flexible sigmoidoscopy, double contrast barium enema (DCBE), and colonoscopy. The current recommended standards for screening for colorectal cancer in individuals over the age of 50 and who are considered part of an average risk population include: an FOBT yearly, a sigmoidoscopy every five years, a colonoscopy every ten years and a DCBE every five years. For a high risk population where one or more family members have had colorectal cancer, a colonoscopy is recommended every two years as a follow up to FOBT or sigmoidoscopy. Each of these tests suffers significant disadvantages. Fecal occult blood testing suffers from low sensitivity, requires significant dietary and other restrictions prior to testing and is associated with poor patient compliance. Sigmoidoscopy and colonoscopy are more sensitive than the other standard methods since they involve direct visualization of the lumen of the colon, however these methods are also associated with various significant disadvantages. Sigmoidoscopy and colonoscopy are both highly invasive procedures which cause significant levels of discomfort, causing many individuals to opt not to undergo these recommended screening procedures. Sigmoidoscopy only allows visualization of the distal part of the colon and hence cannot detect a relatively large fraction of cancers, and colonoscopy, despite allowing examination essentially along the entire length of the colon, is associated with a significant failure rate for detection of colorectal cancer. In addition, sigmoidoscopy and colonoscopy are costly, are insufficiently available, and may result in potentially lethal complications, such as accidental intestinal perforation.

Various approaches have been proposed in the prior art for colorectal cancer testing using identification and analysis of markers of this disease in blood (reviewed in Hundt S. et al. Blood markers for early detection of colorectal cancer: a systematic review. Cancer Epidemiol Biomarkers Prev. 2007 October; 16(10):1935-53). Such approaches, if successful, would have the advantage of circumventing critical disadvantages of the standard prior art methods, by virtue, for example, of being relatively non-invasive, minimally cumbersome, essentially risk-free and hence likely to be associated with increased patient screening compliance rates. However, none of these approaches has demonstrated an optimal capacity for diagnosing colorectal cancer.

Thus, there is a longstanding and urgent need for an improved method of determining a probability of colorectal cancer in a subject based on analysis of blood markers.

SUMMARY

The invention discloses novel methods, apparatuses and kits for determining a probability of colorectal cancer in a subject, based on novel blood markers of colorectal cancer. This use can be effected in a variety of ways as further described and exemplified herein.

According to one aspect of the invention there is provided a method of determining a probability that a human test subject has colorectal cancer as opposed to not having colorectal cancer, the method comprising, for each gene of a set of one or more genes selected from the group consisting of ANXA3, CLEC4D, IL2RB, LMNB1, PRRG4, TNFAIP6 and VNN1: (a) determining a level of RNA encoded by the gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, wherein the probability that the test data corresponds to the positive control data and not to the negative control data represents the probability that the test subject has colorectal cancer as opposed to not having colorectal cancer.

According to another aspect of the invention there is provided a method of determining a probability that a human test subject has colorectal cancer as opposed to not having colorectal cancer, the method comprising: (a) determining a level of RNA encoded by a ANXA3 gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, wherein the probability that the test data corresponds to the positive control data and not to the negative control data represents the probability that the test subject has colorectal cancer as opposed to not having colorectal cancer.

According to yet another aspect of the invention there is provided a method of determining a probability that a human test subject has colorectal cancer as opposed to not having colorectal cancer, the method comprising: (a) determining a level of RNA encoded by a CLEC4D gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, wherein the probability that the test data corresponds to the positive control data and not to the negative control data represents the probability that the test subject has colorectal cancer as opposed to not having colorectal cancer.

According to one aspect of the invention there is provided a method of determining a probability that a human test subject has colorectal cancer as opposed to not having colorectal cancer, the method comprising: (a) determining a level of RNA encoded by a IL2RB gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, wherein the probability that the test data corresponds to the positive control data and not to the negative control data represents the probability that the test subject has colorectal cancer as opposed to not having colorectal cancer.

According to still another aspect of the invention there is provided a method of determining a probability that a human test subject has colorectal cancer as opposed to not having colorectal cancer, the method comprising: (a) determining a level of RNA encoded by a LMNB1 gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, wherein the probability that the test data corresponds to the positive control data and not to the negative control data represents the probability that the test subject has colorectal cancer as opposed to not having colorectal cancer.

According to a further aspect of the invention there is provided a method of determining a probability that a human test subject has colorectal cancer as opposed to not having colorectal cancer, the method comprising: (a) determining a level of RNA encoded by a PRRG4 gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, wherein the probability that the test data corresponds to the positive control data and not to the negative control data represents the probability that the test subject has colorectal cancer as opposed to not having colorectal cancer.

According to yet a further aspect of the invention there is provided a method of determining a probability that a human test subject has colorectal cancer as opposed to not having colorectal cancer, the method comprising: (a) determining a level of RNA encoded by a TNFAIP6 gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, wherein the probability that the test data corresponds to the positive control data and not to the negative control data represents the probability that the test subject has colorectal cancer as opposed to not having colorectal cancer.

According to still a further aspect of the invention there is provided a method of determining a probability that a human test subject has colorectal cancer as opposed to not having colorectal cancer, the method comprising: (a) determining a level of RNA encoded by a VNN1 gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, wherein the probability that the test data corresponds to the positive control data and not to the negative control data represents the probability that the test subject has colorectal cancer as opposed to not having colorectal cancer.

According to further features of the invention described below, the determining of the level of RNA encoded by the gene in blood of the test subject is effected by determining the level of RNA encoded by the gene in a blood sample isolated from the test subject.

According to further features of the invention described below, the method of determining the probability that the human test subject has colorectal cancer as opposed to not having colorectal cancer further comprises determining levels of RNA encoded by the gene in blood of a population of human subjects having colorectal cancer, thereby providing the positive control data representing the levels of RNA encoded by the gene in blood of human control subjects having colorectal cancer, and determining levels of RNA encoded by the gene in blood of a population of human subjects not having colorectal cancer, thereby providing the negative control data representing the levels of RNA encoded by the gene in blood of human control subjects not having colorectal cancer.

According to further features of the invention described below, the determining of the probability that the test data corresponds to the positive control data and not to the negative control data is effected by applying to the test data a mathematical model derived from the positive control data and from the negative control data, wherein the mathematical model is for determining the probability that data representing a level of RNA encoded by the gene corresponds to the positive control data and not to the negative control data.

According to another aspect of the invention there is provided a computer-based method of determining a probability that a human test subject has colorectal cancer as opposed to not having colorectal cancer, from test data representing a level of RNA encoded by a ANXA3 gene in blood of the test subject, the method comprising, for each gene of a set of one or more genes selected from the group consisting of ANXA3, CLEC4D, IL2RB, LMNB1, PRRG4, TNFAIP6 and VNN1 computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, wherein the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, wherein the probability that the test data corresponds to the positive control data and not to the negative control data represents the probability that the test subject has colorectal cancer as opposed to not having colorectal cancer.

According to another aspect of the invention there is provided a computer-based method of determining a probability that a human test subject has colorectal cancer as opposed to not having colorectal cancer, from test data representing a level of RNA encoded by a ANXA3 gene in blood of the test subject, the method comprising computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, wherein the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, wherein the probability that the test data corresponds to the positive control data and not to the negative control data represents the probability that the test subject has colorectal cancer as opposed to not having colorectal cancer.

According to another aspect of the invention there is provided a computer-based method of determining a probability that a human test subject has colorectal cancer as opposed to not having colorectal cancer, from test data representing a level of RNA encoded by a ANXA3 gene in blood of the test subject, the method comprising computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, wherein the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, wherein the probability that the test data corresponds to the positive control data and not to the negative control data represents the probability that the test subject has colorectal cancer as opposed to not having colorectal cancer.

According to another aspect of the invention there is provided a computer-based method of determining a probability that a human test subject has colorectal cancer as opposed to not having colorectal cancer, from test data representing a level of RNA encoded by a ANXA3 gene in blood of the test subject, the method comprising computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, wherein the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, wherein the probability that the test data corresponds to the positive control data and not to the negative control data represents the probability that the test subject has colorectal cancer as opposed to not having colorectal cancer.

According to another aspect of the invention there is provided a computer-based method of determining a probability that a human test subject has colorectal cancer as opposed to not having colorectal cancer, from test data representing a level of RNA encoded by a ANXA3 gene in blood of the test subject, the method comprising computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, wherein the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, wherein the probability that the test data corresponds to the positive control data and not to the negative control data represents the probability that the test subject has colorectal cancer as opposed to not having colorectal cancer.

According to another aspect of the invention there is provided a computer-based method of determining a probability that a human test subject has colorectal cancer as opposed to not having colorectal cancer, from test data representing a level of RNA encoded by a ANXA3 gene in blood of the test subject, the method comprising computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, wherein the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, wherein the probability that the test data corresponds to the positive control data and not to the negative control data represents the probability that the test subject has colorectal cancer as opposed to not having colorectal cancer.

According to another aspect of the invention there is provided a computer-based method of determining a probability that a human test subject has colorectal cancer as opposed to not having colorectal cancer, from test data representing a level of RNA encoded by a ANXA3 gene in blood of the test subject, the method comprising computer-implemented steps of: applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, wherein the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, wherein the probability that the test data corresponds to the positive control data and not to the negative control data represents the probability that the test subject has colorectal cancer as opposed to not having colorectal cancer.

According to another aspect of the present invention there is provided a method of classifying a human test subject as more likely to have colorectal cancer than to not have colorectal cancer, the method comprising: (a) determining a level of RNA encoded by a ANXA3 gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to another aspect of the present invention there is provided a method of classifying a human test subject as more likely to have colorectal cancer than to not have colorectal cancer, the method comprising: (a) determining a level of RNA encoded by a CLEC4D gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to yet another aspect of the present invention there is provided a method of classifying a human test subject as more likely to have colorectal cancer than to not have colorectal cancer, the method comprising: (a) determining a level of RNA encoded by a IL2RB gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, wherein an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer.

According to still another aspect of the present invention there is provided a method of classifying a human test subject as more likely to have colorectal cancer than to not have colorectal cancer, the method comprising: (a) determining a level of RNA encoded by a LMNB1 gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to a further aspect of the present invention there is provided a method of classifying a human test subject as more likely to have colorectal cancer than to not have colorectal cancer, the method comprising: (a) determining a level of RNA encoded by a PRRG4 gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to yet a further aspect of the present invention there is provided a method of classifying a human test subject as more likely to have colorectal cancer than to not have colorectal cancer, the method comprising: (a) determining a level of RNA encoded by a TNFAIP6 gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to still a further aspect of the present invention there is provided a method of classifying a human test subject as more likely to have colorectal cancer than to not have colorectal cancer, the method comprising: (a) determining a level of RNA encoded by a VNN1 gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to an additional aspect of the present invention there is provided a computer-based method of classifying a human test subject as more likely to have colorectal cancer than to not have colorectal cancer, the method comprising computer-implemented steps of: (a) applying to test data representing a level of RNA encoded by a ANXA3 gene in blood of the test subject, and to negative control data representing a level of RNA encoded by the gene in blood of human control subjects not having colorectal cancer, a mathematical formula for generating a value indicating whether the level of RNA encoded by the gene in blood of the test subject is higher than the level of RNA encoded by the gene in blood of human control subjects not having colorectal cancer; and (b) outputting the value, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to yet an additional aspect of the present invention there is provided a computer-based method of classifying a human test subject as more likely to have colorectal cancer than to not have colorectal cancer, the method comprising computer-implemented steps of: (a) applying to test data representing a level of RNA encoded by a CLEC4D gene in blood of the test subject, and to negative control data representing a level of RNA encoded by the gene in blood of human control subjects not having colorectal cancer, a mathematical formula for generating a value indicating whether the level of RNA encoded by the gene in blood of the test subject is higher than the level of RNA encoded by the gene in blood of human control subjects not having colorectal cancer; and (b) outputting the value, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to still an additional aspect of the present invention there is provided a computer-based method of classifying a human test subject as more likely to have colorectal cancer than to not have colorectal cancer, the method comprising computer-implemented steps of: (a) applying to test data representing a level of RNA encoded by a IL2RB gene in blood of the test subject, and to negative control data representing a level of RNA encoded by the gene in blood of human control subjects not having colorectal cancer, a mathematical formula for generating a value indicating whether the level of RNA encoded by the gene in blood of the test subject is lower than the level of RNA encoded by the gene in blood of human control subjects not having colorectal cancer; and (b) outputting the value, wherein an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer.

According to yet still an additional aspect of the present invention there is provided a computer-based method of classifying a human test subject as more likely to have colorectal cancer than to not have colorectal cancer, the method comprising computer-implemented steps of: (a) applying to test data representing a level of RNA encoded by a LMNB1 gene in blood of the test subject, and to negative control data representing a level of RNA encoded by the gene in blood of human control subjects not having colorectal cancer, a mathematical formula for generating a value indicating whether the level of RNA encoded by the gene in blood of the test subject is higher than the level of RNA encoded by the gene in blood of human control subjects not having colorectal cancer; and (b) outputting the value, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to another aspect of the present invention there is provided a computer-based method of classifying a human test subject as more likely to have colorectal cancer than to not have colorectal cancer, the method comprising computer-implemented steps of: (a) applying to test data representing a level of RNA encoded by a PRRG4 gene in blood of the test subject, and to negative control data representing a level of RNA encoded by the gene in blood of human control subjects not having colorectal cancer, a mathematical formula for generating a value indicating whether the level of RNA encoded by the gene in blood of the test subject is higher than the level of RNA encoded by the gene in blood of human control subjects not having colorectal cancer; and (b) outputting the value, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to yet another aspect of the present invention there is provided a computer-based method of classifying a human test subject as more likely to have colorectal cancer than to not have colorectal cancer, the method comprising computer-implemented steps of: (a) applying to test data representing a level of RNA encoded by a TNFAIP6 gene in blood of the test subject, and to negative control data representing a level of RNA encoded by the gene in blood of human control subjects not having colorectal cancer, a mathematical formula for generating a value indicating whether the level of RNA encoded by the gene in blood of the test subject is higher than the level of RNA encoded by the gene in blood of human control subjects not having colorectal cancer; and (b) outputting the value, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to still another aspect of the present invention there is provided a computer-based method of classifying a human test subject as more likely to have colorectal cancer than to not have colorectal cancer, the method comprising computer-implemented steps of: (a) applying to test data representing a level of RNA encoded by a VNN1 gene in blood of the test subject, and to negative control data representing a level of RNA encoded by the gene in blood of human control subjects not having colorectal cancer, a mathematical formula for generating a value indicating whether the level of RNA encoded by the gene in blood of the test subject is higher than the level of RNA encoded by the gene in blood of human control subjects not having colorectal cancer; and (b) outputting the value, wherein an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

According to a further aspect of the present invention there is provided a method of classifying a human test subject as more likely to have colorectal cancer than to not have colorectal cancer, the method comprising, for each gene of a set of one or more genes selected from the group consisting of ANXA3, CLEC4D, IL2RB, LMNB1, PRRG4, TNFAIP6 and VNN1: (a) determining a level of RNA encoded by the gene in blood of the test subject, thereby generating test data; (b) providing negative control data representing levels of RNA encoded by the gene in blood of human control subjects not having colorectal cancer; and (c) applying to the test data and to the negative control data mathematical formula for generating a value indicating, for ANXA3, CLEC4D, LMNB1, PRRG4, TNFAIP6 and VNN1, whether the level of RNA encoded by the gene in blood of the test subject is higher than the level of RNA encoded by the gene in blood of human control subjects not having colorectal cancer, and indicating, for IL2RB, whether the level of RNA encoded by the gene in blood of the test subject is lower than the level of RNA encoded by the gene in blood of human control subjects not having colorectal cancer, wherein, for ANXA3, CLEC4D, LMNB1, PRRG4, TNFAIP6 and VNN1, an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer, and wherein, for IL2RB, an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer.

According to yet a further aspect of the present invention there is provided a computer-based method of classifying a human test subject as more likely to have colorectal cancer than to not have colorectal cancer, the method comprising, for each gene of a set of one or more genes selected from the group consisting of ANXA3, CLEC4D, IL2RB, LMNB1, PRRG4, TNFAIP6 and VNN1, computer-implemented steps of: applying to test data representing a level of RNA encoded by the gene in blood of the test subject, and to negative control data representing a level of RNA encoded by the gene in blood of human control subjects not having colorectal cancer, a formula for calculating a value indicating, for ANXA3, CLEC4D, LMNB1, PRRG4, TNFAIP6 and VNN1, whether the level of RNA encoded by the gene in blood of the test subject is higher than the level of RNA encoded by the gene in blood of human control subjects not having colorectal cancer, and indicating, for IL2RB, whether the level of RNA encoded by the gene in blood of the test subject is lower than the level of RNA encoded by the gene in blood of human control subjects not having colorectal cancer, wherein, for ANXA3, CLEC4D, LMNB1, PRRG4, TNFAIP6 and VNN1, an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer, and wherein, for IL2RB, an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer.

According to one aspect of the invention there is provided a method of diagnosing colorectal cancer in a test subject, the method comprising, for each gene of a set of one or more genes selected from the group consisting of ANXA3, CLEC4D, IL2RB, LMNB1, PRRG4, TNFAIP6 and VNN1: (a) determining a level of RNA encoded by the gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, wherein a determination that the test data corresponds to the positive control data and not to the negative control data provides an indication of colorectal cancer in the test subject.

According to a further aspect of the present invention there is provided a method of diagnosing colorectal cancer in a test subject, the method comprising, for each gene of a set of one or more genes selected from the group consisting of ANXA3, CLEC4D, IL2RB, LMNB1, PRRG4, TNFAIP6 and VNN1: (a) determining a level of RNA encoded by the gene in blood of the test subject, thereby generating test data; (b) providing negative control data representing levels of RNA encoded by the gene in blood of human control subjects not having colorectal cancer; and (c) applying to the test data and to the negative control data a mathematical formula for generating a value indicating, for ANXA3, CLEC4D, LMNB1, PRRG4, TNFAIP6 and VNN1, whether the level of RNA encoded by the gene in blood of the test subject is higher than the level of RNA encoded by the gene in blood of human control subjects not having colorectal cancer, and indicating, for IL2RB, whether the level of RNA encoded by the gene in blood of the test subject is lower than the level of RNA encoded by the gene in blood of human control subjects not having colorectal cancer, wherein, for ANXA3, CLEC4D, LMNB1, PRRG4, TNFAIP6 and VNN1, an indication by the value that the level of RNA encoded by the gene in blood of the test subject is higher than the level of RNA encoded by the gene in blood of human control subjects not having colorectal cancer provides an indication of colorectal cancer in the test subject, and wherein, for IL2RB, an indication by the value that the level of RNA encoded by the gene in blood of the test subject is lower than the level of RNA encoded by the gene in blood of human control subjects not having colorectal cancer provides an indication of colorectal cancer in the test subject.

According to another aspect of the present invention there is provided a method of determining whether a test subject is at an increased risk of having colorectal cancer relative to the general population, comprising: a) obtaining a test sample of blood from the subject; and i) determining a level of RNA encoded by a annexin A3 (ANXA3) gene in the test sample of blood, ii) comparing the level of RNA encoded by the gene as determined in step (i) with the level of the RNA encoded by the gene in control samples of blood; and b) concluding that the subject is at an increased risk of having colorectal cancer relative to the general population if the level of RNA encoded by the gene in the test sample of blood is higher than in the control samples of blood.

According to yet another aspect of the present invention there is provided a method of determining whether a test subject is at an increased risk of having colorectal cancer relative to the general population, comprising: a) obtaining a test sample of blood from the subject; and i) determining a level of RNA encoded by a C-type lectin domain family 4, member D (CLEC4D) gene in the test sample of blood, ii) comparing the level of RNA encoded by the gene as determined in step (i) with the level of the RNA encoded by the gene in control samples of blood; and b) concluding that the subject is at an increased risk of having colorectal cancer relative to the general population if the level of RNA encoded by the gene in the test sample of blood is higher than in the control samples of blood.

According to still another aspect of the present invention there is provided a method of determining whether a test subject is at an increased risk of having colorectal cancer relative to the general population, comprising: a) obtaining a test sample of blood from the subject; and i) determining a level of RNA encoded by a interleukin 2 receptor, beta (IL2RB) gene in the test sample of blood, ii) comparing the level of RNA encoded by the gene as determined in step (i) with the level of the RNA encoded by the gene in control samples of blood; and b) concluding that the subject is at an increased risk of having colorectal cancer relative to the general population if the level of RNA encoded by the gene in the test sample of blood is lower than in the control samples of blood.

According to a further aspect of the present invention there is provided a method of determining whether a test subject is at an increased risk of having colorectal cancer relative to the general population, comprising: a) obtaining a test sample of blood from the subject; and i) determining a level of RNA encoded by a lamin B1 (LMNB1) gene in the test sample of blood, ii) comparing the level of RNA encoded by the gene as determined in step (i) with the level of the RNA encoded by the gene in control samples of blood; and b) concluding that the subject is at an increased risk of having colorectal cancer relative to the general population if the level of RNA encoded by the gene in the test sample of blood is higher than in the control samples of blood.

According to yet a further aspect of the present invention there is provided a method of determining whether a test subject is at an increased risk of having colorectal cancer relative to the general population, comprising: a) obtaining a test sample of blood from the subject; and i) determining a level of RNA encoded by a proline rich Gla (G carboxy-glutamic acid) 4 (transmembrane) (PRRG4) gene in the test sample of blood, ii) comparing the level of RNA encoded by the gene as determined in step (i) with the level of the RNA encoded by the gene in control samples of blood; and b) concluding that the subject is at an increased risk of having colorectal cancer relative to the general population if the level of RNA encoded by the gene in the test sample of blood is higher than in the control samples of blood.

According to still a further aspect of the present invention there is provided a method of determining whether a test subject is at an increased risk of having colorectal cancer relative to the general population, comprising: a) obtaining a test sample of blood from the subject; and i) determining a level of RNA encoded by a tumor necrosis factor, alpha induced protein 6 (TNFAIP6) gene in the test sample of blood, ii) comparing the level of RNA encoded by as determined in step (i) with the level of the RNA encoded by the gene in control samples of blood; and b) concluding that the subject is at an increased risk of having colorectal cancer relative to the general population if the level of RNA encoded by the gene in the test sample of blood is higher than in the control samples of blood.

According to still a further aspect of the present invention there is provided a method of determining whether a test subject is at an increased risk of having colorectal cancer relative to the general population, comprising: a) obtaining a test sample of blood from the subject; and i) determining a level of RNA encoded by a vanin 1 (VNN1) gene in the test sample of blood, ii) comparing the level of RNA encoded by the gene as determined in step (i) with the level of the RNA encoded by the gene in control samples of blood; and b) concluding that the subject is at an increased risk of having colorectal cancer relative to the general population if the level of RNA encoded by the gene in the test sample of blood is higher than in the control samples of blood.

According to an additional aspect of the present invention there is provided a method of determining whether a test subject is at an increased risk of having colorectal cancer relative to the general population, comprising: a) obtaining a test sample of blood from the subject; and for each gene of a set of genes selected from the group consisting of: ANXA3, CLEC4D, IL2RB, LMNB1, PRRG4, TNFAIP6 and VNN1, i) determining a level of RNA encoded by the gene in the test sample of blood, ii) comparing the level of RNA encoded by the gene of the set as determined in step (i) with the level of RNA encoded by the gene in one or more control samples of blood; and b) concluding that the subject is at an increased risk of having colorectal cancer relative to the general population if, for ANXA3, CLEC4D, LMNB1, PRRG4, TNFAIP6 and VNN1, the level of RNA encoded by the gene in the test sample of blood is higher than in the control samples of blood, and concluding that the subject is at an increased risk of having colorectal cancer relative to the general population if, for IL2RB, the level of RNA encoded by the gene in the test sample of blood is lower than in the control samples of blood.

According to an additional aspect of the present invention there is provided a method of diagnosing colorectal cancer in a test subject, comprising: a) obtaining a test sample of blood from the subject; and for each gene of a set of genes selected from the group consisting of: ANXA3, CLEC4D, IL2RB, LMNB1, PRRG4, TNFAIP6 and VNN1, i) determining a level of RNA encoded by the gene in the test sample of blood, and ii) applying to the level of RNA encoded by the gene of the set as determined in step (i) and to the level of RNA encoded by the gene in one or more control samples of blood a mathematical formula for generating a value indicating whether, for ANXA3, CLEC4D, LMNB1, PRRG4, TNFAIP6 and VNN1, the level of RNA encoded by the gene in the test sample of blood is higher than in the control samples of blood, and, for IL2RB, the level of RNA encoded by the gene in the test sample of blood is lower than in the control samples of blood; and b) concluding that there is an indication of colorectal cancer in the test subject, if, for ANXA3, CLEC4D, LMNB1, PRRG4, TNFAIP6 and VNN1, the value indicates that the level of RNA encoded by the gene in the test sample of blood is higher than in the control samples of blood, and concluding that there is an indication of colorectal cancer in the test subject if, for IL2RB, the value indicates that the level of RNA encoded by the gene in the test sample of blood is lower than in the control samples of blood.

According to further features of the invention described below, the control samples are from individuals who have been diagnosed as not having colorectal cancer.

According to still another aspect of the invention there is provided a kit comprising packaging and containing, for each gene of a set of two or more genes selected from the group consisting of ACTB, ANXA3, CLEC4D, IL2RB, LMNB1, PRRG4, TNFAIP6 and VNN1, a primer set capable of generating an amplification product of a polynucleotide complementary to RNA encoded, in a human subject, only by the gene.

According to further features of the invention described below, the kit further contains two or more components selected from the group consisting of a thermostable polymerase, a reverse transcriptase, deoxynucleotide triphosphates, nucleotide triphosphates and enzyme buffer.

According to further features of the invention described below, the kit further contains at least one labeled probe capable of selectively hybridizing to either a sense or an antisense strand of the amplification product.

According to further features of the invention described below, the kit further contains a computer-readable medium having instructions stored thereon that are operable when executed by a computer for applying a mathematical model to test data representing a level of RNA encoded by the gene in blood of a human test subject, wherein the mathematical model is derived from positive control data representing levels of RNA encoded by the gene in blood of human control subjects having colorectal cancer, and from negative control data representing levels of RNA encoded by the gene in blood of human control subjects not having colorectal cancer, wherein the mathematical model is for determining a probability that data representing a level of RNA encoded by the gene corresponds to the positive control data and not to the negative control data, and wherein the probability that the test data corresponds to the positive control data and not to the negative control data represents the probability that the test subject has colorectal cancer as opposed to not having colorectal cancer.

According to further features of the invention described below, the kit further contains a computer-readable medium having instructions stored thereon that are operable when executed by a computer for applying, to test data representing a level of RNA encoded by the gene in blood of a human test subject, and to negative control data representing a level of RNA encoded by the gene in blood of human control subjects not having colorectal cancer, a mathematical formula for generating a value indicating, for ANXA3, CLEC4D, LMNB1, PRRG4, TNFAIP6 and VNN1, whether the level of RNA encoded by the gene in blood of the test subject is higher than the level of RNA encoded by the gene in blood of human control subjects not having colorectal cancer, and, for IL2RB, whether the level of RNA encoded by the gene in blood of the test subject is lower than the level of RNA encoded by the gene in blood of human control subjects not having colorectal cancer, wherein, for ANXA3, CLEC4D, LMNB1, PRRG4, TNFAIP6 and VNN1, an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer, and wherein, for IL2RB, an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer.

According to further features of the invention described below, the set of one or more genes consists of ACTB and one or more genes selected from the group consisting of ANXA3, CLEC4D, IL2RB, LMNB1, PRRG4, TNFAIP6 and VNN1.

According to further features of the invention described below, the set of one or more genes consists of ACTB and ANXA3.

According to further features of the invention described below, the set of one or more genes consists of ACTB and CLEC4D.

According to further features of the invention described below, the set of one or more genes consists of ACTB and IL2RB.

According to further features of the invention described below, the set of one or more genes consists of ACTB and LMNB1.

According to further features of the invention described below, the set of one or more genes consists of ACTB and PRRG4.

According to further features of the invention described below, the set of one or more genes consists of TNFAIP6 and PRRG4.

According to further features of the invention described below, the set of one or more genes consists of ACTB and VNN1.

According to further features of the invention described below, the level of RNA encoded by the gene in blood of the test subject is determined via quantitative reverse transcriptase-polymerase chain reaction analysis.

According to further features of the invention described below, the level of RNA encoded by the gene in blood of the test subject and the levels of RNA encoded by the gene in blood of the control subjects are determined via the same method.

According to further features of the invention described below, the set of one or more genes is a set of one or more genes selected from the group consisting of ANXA3, CLEC4D, IL2RB, LMNB1, PRRG4, TNFAIP6 and VNN1, wherein the level of RNA encoded by the gene in blood of the test subject is determined as a ratio to a level of RNA encoded by ACTB in blood of the test subject.

According to further features of the invention described below, the level of RNA encoded by the gene in blood of the test subject and the level of RNA encoded by ACTB in blood of the test subject are determined via duplex quantitative reverse transcriptase-polymerase chain reaction analysis of RNA encoded by the gene and of RNA encoded by ACTB.

According to further features of the invention described below, the set of one or more genes consists of IL2RB and one or more genes selected from the group consisting of ANXA3, CLEC4D, LMNB1, PRRG4, TNFAIP6 and VNN1.

According to further features of the invention described below, the set of one or more genes is a set of one or more genes selected from the group consisting of ANXA3, CLEC4D, LMNB1, PRRG4, TNFAIP6 and VNN1, and wherein the level of RNA encoded by the gene in blood of the test subject is determined as a ratio to a level of RNA encoded by IL2RB in blood of the test subject.

According to further features of the invention described below, the level of RNA encoded by the gene in blood of the test subject and the level of RNA encoded by IL2RB in blood of the test subject are determined via duplex quantitative reverse transcriptase-polymerase chain reaction analysis of RNA encoded by the gene and of RNA encoded by IL2RB.

According to further features of the invention described below, the set of one or more genes consists of ANXA3.

According to further features of the invention described below, the set of one or more genes consists of CLEC4D.

According to further features of the invention described below, the set of one or more genes consists of IL2RB.

According to further features of the invention described below, the set of one or more genes consists of LMNB1.

According to further features of the invention described below, the set of one or more genes consists of PRRG4.

According to further features of the invention described below, the set of one or more genes consists of TNFAIP6.

According to further features of the invention described below, the set of one or more genes consists of VNN1.

According to further features of the invention described below, the set of one or more genes consists of IL2RB and ANXA3.

According to further features of the invention described below, the set of one or more genes consists of IL2RB and CLEC4D.

According to further features of the invention described below, the set of one or more genes consists of IL2RB and LMNB1.

According to further features of the invention described below, the set of one or more genes consists of IL2RB and PRRG4.

According to further features of the invention described below, the set of one or more genes consists of IL2RB and TNFAIP6.

According to further features of the invention described below, the set of one or more genes consists of IL2RB and VNN1.

Definitions

As will become apparent, preferred features and characteristics of one aspect of the invention are applicable to any other aspect of the invention. It should be noted that, as used herein, the singular form "a", "an" and "the" include plural references unless the context clearly dictates otherwise.

"Encode" A polynucleotide, including a gene, is said the to "encode" a RNA and/or polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced there from.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

As used herein, a "sample" refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), organs, and also samples of in vitro cell culture constituent.

Examples of amplification techniques include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in European Patent Appl. 320 308; gap filling ligase chain reaction amplification, as disclosed in U.S. Pat. No. 5,427,930; and RNA transcription-free amplification, as disclosed in U.S. Pat. No. 6,025,134.

Examples of a primer of the invention include an oligonucleotide which is capable of acting as a point of initiation of polynucleotide synthesis along a complementary strand when placed under conditions in which synthesis of a primer extension product which is complementary to a polynucleotide is catalyzed. Such conditions include the presence of four different nucleotide triphosphates or nucleoside analogs and one or more agents for polymerization such as DNA polymerase and/or reverse transcriptase, in an appropriate buffer ("buffer" includes substituents which are cofactors, or which affect pH, ionic strength, etc.), and at a suitable temperature. A primer must be sufficiently long to prime the synthesis of extension products in the presence of an agent for polymerase. A typical primer contains at least about 5 nucleotides in length of a sequence substantially complementary to the target sequence, but somewhat longer primers are preferred.

The terms "complementary" or "complement thereof", as used herein, refer to sequences of polynucleotides which are capable of forming Watson & Crick base pairing with another specified polynucleotide throughout the entirety of the complementary region. This term is applied to pairs of polynucleotides based solely upon their sequences and does not refer to any specific conditions under which the two polynucleotides would actually bind.

A primer will always contain a sequence substantially complementary to the target sequence, that is the specific sequence to be amplified, to which it can anneal.

In the context of this invention, the term "probe" refers to a molecule which can detectably distinguish between target molecules differing in structure, such as allelic variants. Detection can be accomplished in a variety of different ways but preferably is based on detection of specific binding. Examples of such specific binding include antibody binding and nucleic acid probe hybridization.

The term "gene" as used herein is a polynucleotide which may include coding sequences, intervening sequences and regulatory elements controlling transcription and/or translation. Genes of the invention include normal alleles of the gene encoding polymorphisms, including silent alleles having no effect on the amino acid sequence of the gene's encoded polypeptide as well as alleles leading to amino acid sequence variants of the encoded polypeptide that do not substantially affect its function. These terms also may optionally include alleles having one or more mutations which affect the function of the encoded polypeptide's function.

The polynucleotide compositions, such as primers of the invention, of this invention include RNA, cDNA, DNA complementary to target cDNA of this invention or portion thereof, genomic DNA, unspliced RNA, spliced RNA, alternately spliced RNA, synthetic forms, and mixed polymers, both sense and antisense strands, and may be chemically or biochemically modified or may contain non-natural or derivatized nucleotide bases, as will be readily appreciated by those skilled in the art.

Where nucleic acid according to the invention includes RNA, reference to the sequence shown should be construed as reference to the RNA equivalent, with U substituted for T.

The term "amount" or "level" of RNA encoded by a gene of the invention, preferably a colorectal cancer biomarker gene described herein, or a housekeeping gene, encompasses the absolute amount of the RNA, the relative amount or concentration of the RNA, as well as any value or parameter which correlates thereto.

The methods of nucleic acid isolation, amplification and analysis are routine for one skilled in the art and examples of protocols can be found, for example, in the Molecular Cloning: A Laboratory Manual (3-Volume Set) Ed. Joseph Sambrook, David W. Russel, and Joe Sambrook, Cold Spring Harbor Laboratory; 3rd edition (Jan. 15, 2001), ISBN: 0879695773. Particularly useful protocol source for methods used in PCR amplification is PCR (Basics: From Background to Bench) by M. J. McPherson, S. G. Moller, R. Beynon, C. Howe, Springer Verlag; 1st edition (Oct. 15, 2000), ISBN: 0387916008.

"Kit" refers to a combination of physical elements, e.g., probes, including without limitation specific primers, labeled nucleic acid probes, antibodies, protein-capture agent(s), reagent(s), instruction sheet(s) and other elements useful to practice the invention, in particular to identify the levels of particular RNA molecules in a sample. These physical elements can be arranged in any way suitable for carrying out the invention. For example, probes and/or primers can be provided in one or more containers or in an array or microarray device.

Colorectal cancer, also called colon cancer or rectal cancer or colorectal carcinoma, is cancer that forms in either the colon or the rectum.

The present invention is useful in a diagnostic product or method to detect the level of RNA of genes of interest, in particular, the colorectal biomarkers of the present invention. Accordingly, the invention encompasses the use of diagnostic kits based on a variety of methodologies, e.g., PCR, reverse transcriptase-PCR, quantitative PCR, microarray, chip, mass-spectroscopy, which are capable of detecting RNA levels in a sample. The invention also provides an article of manufacturing comprising packaging material and an analytical agent contained within the packaging material, wherein the analytical agent can be used for determining and/or comparing the levels of RNA encoded by one or more target genes of the invention, and wherein the packaging material comprises a label or package insert which indicates that the analytical agent can be used to identify levels of RNA that correspond to a probability that a test subject has colorectal cancer, such as a probability that the test subject has colorectal cancer as opposed to not having colorectal cancer.

The present invention therefore provides kits comprising degenerate primers to amplify polymorphic alleles or variants of target genes of the invention, and instructions comprising an amplification protocol and analysis of the results. The kit may alternatively also comprise buffers, enzymes, and containers for performing the amplification and analysis of the amplification products. The kit may also be a component of a screening or prognostic kit comprising other tools such as DNA microarrays. The kit may also provides one or more control templates, such as nucleic acids isolated from sample of patients without colorectal cancer, and/or nucleic acids isolated from samples of patients with colorectal cancer.

The kit may also include instructions for use of the kit to amplify specific targets on a solid support. Where the kit contains a prepared solid support having a set of primers already fixed on the solid support, e.g. for amplifying a particular set of target polynucleotides, the kit also includes reagents necessary for conducting a PCR on a solid support, for example using an in situ-type or solid phase type PCR procedure where the support is capable of PCR amplification using an in situ-type PCR machine. The PCR reagents, included in the kit, include the usual PCR buffers, a thermostable polymerase (e.g. Taq DNA polymerase), nucleotides (e.g. dNTPs), and other components and labeling molecules (e.g. for direct or indirect labeling). The kits can be assembled to support practice of the PCR amplification method using immobilized primers alone or, alternatively, together with solution phase primers.

In one embodiment, the kit provides one or more primer pairs, each pair capable of amplifying RNA encoded by a target gene of the invention, thereby providing a kit for analysis of RNA expression of several different target genes of the invention in a biological sample in one reaction or several parallel reactions. Primers in the kits may be labeled, for example fluorescently labeled, to facilitate detection of the amplification products and consequent analysis of the RNA levels.

In one embodiment, levels of RNA encoded by more than one target gene can be determined in one analysis. A combination kit may therefore include primers capable of amplifying cDNA derived from RNA encoded by different target genes. The primers may be differentially labeled, for example using different fluorescent labels, so as to differentiate between RNA from different target genes.

Multiplex, such as duplex, real-time RT-PCR enables simultaneous quantification of 2 targets in the same reaction, which saves time, reduces costs, and conserves samples. These advantages of multiplex, real-time RT-PCR make the technique well-suited for high-throughput gene expression analysis. Multiplex qPCR assay in a real-time format facilitates quantitative measurements and minimizes the risk of false-negative results. It is essential that multiplex PCR is optimized so that amplicons of all samples are compared insub-plateau phase of PCR. Yun, Z., I. Lewensohn-Fuchs, P. Ljungman, L. Ringholm, J. Jonsson, and J. Albert. 2003. A real-time TaqMan PCR for routine quantitation of cytomegalovirus DNA in crude leukocyte lysates from stem cell transplant patients. J. Virol. Methods 110:73-79. [PubMed]. Yun, Z., I. Lewensohn-Fuchs, P. Ljungman, and A. Vahlne. 2000. Real-time monitoring of cytomegalovirus infections after stem cell transplantation using the TaqMan polymerase chain reaction assays. Transplantation 69:1733-1736. [PubMed]. Simultaneous quantification of up to 2, 3, 4, 5, 6, 7, and 8 or more targets may be useful.

The primers and probes contained within the kit may include those listed in 19, and various subcombinations thereof.

A "control population" refers to a defined group of individuals or a group of individuals with or without colorectal cancer, and may optionally be further identified by, but not limited to geographic, ethnic, race, gender, one or more other conditions or diseases, and/or cultural indices. In most cases a control population may encompass at least 10, 50, 100, 1000, or more individuals.

"Positive control data" encompasses data representing levels of RNA encoded by a target gene of the invention in each of one or more subjects having colorectal cancer of the invention, and encompasses a single data point representing an average level of RNA encoded by a target gene of the invention in a plurality of subjects having colorectal cancer of the invention.

"Negative control data" encompasses data representing levels of RNA encoded by a target gene of the invention in each of one or more subjects not having colorectal cancer of the invention, and encompasses a single data point representing an average level of RNA encoded by a target gene of the invention in a plurality of subjects having colorectal cancer of the invention.

The probability that test data of the invention "corresponds" to positive control data or negative control data of the invention refers to the probability that the test data is more likely to be characteristic of data obtained in subjects having colorectal cancer than in subjects not having any colorectal pathology, or is more likely to be characteristic of data obtained in subjects not having any colorectal pathology than in subjects having colorectal cancer, respectively.

A primer which "selectively hybridizes" to a target polynucleotide is a primer which is capable of hybridizing only, or mostly, with a single target polynucleotide in a mixture of polynucleotides consisting of RNA of human blood, or consisting of DNA complementary to RNA of human blood.

A gene expression profile of the invention for colorectal cancer found in blood at the RNA level of one or more genes comprising, but preferably not limited to, an ANXA3 gene, a CLEC4D gene, an IL2RB gene, an LMNB1 gene, a PRRG4 gene, a TNFAIP6 gene and a VNN1 gene, can be identified or confirmed using many techniques, including but preferably not limited to PCR methods, as for example discussed further in the working examples herein, Northern analyses and the microarray technique. This gene expression profile can be measured in a bodily sample, such as blood, using microarray technology. In an embodiment of this method, fluorescently labeled cDNA probes may be generated through incorporation of fluorescent nucleotides by reverse transcription of RNA extracted from blood. Labeled cDNA probes applied to the chip hybridize with specificity to each spot of DNA on the array. Quantitation of hybridization of each arrayed element allows for assessment of corresponding mRNA abundance. For example, with dual color fluorescence, separately labeled cDNA probes generated from two sources of RNA are hybridized pair wise to the array. The relative abundance of the transcripts from the two sources corresponding to each specified gene is thus determined simultaneously. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2):106-149 (1996)). Microarray analysis can be performed by commercially available equipment, following manufacturer's protocols, such as by using the Affymetrix GenChip technology, or Incyte's microarray technology.

Other features and advantages of the invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 1A-H are sequence diagrams depicting the nucleotide sequences of the following genes: ACTB, ANXA3, CLEC4D, IL2RB, LMNB1, PRRG4, TNFAIP6 and VNN1, respectively.

DETAILED DESCRIPTION

Figure 2:
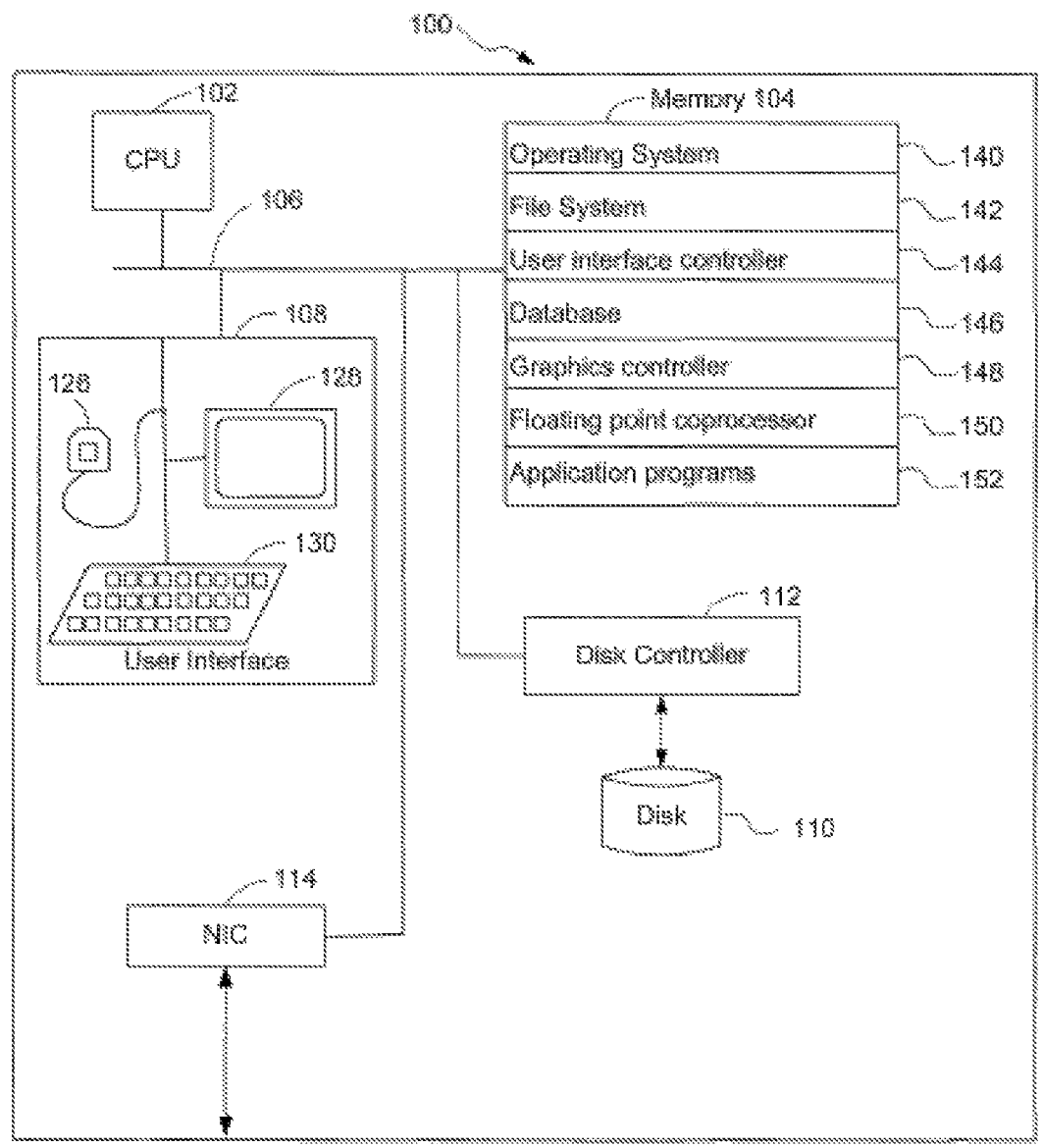
FIG. 2 is a schematic depicting an exemplary computer system for practicing certain of the methods described herein.

The invention is of methods, kits, computer systems and computer-readable media for determining a probability that a human subject has colorectal cancer. Specifically, the invention can be used to determine such a probability via analysis of novel markers of colorectal cancer in blood which are disclosed herein.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Effective methods of testing for colorectal cancer via analysis of blood markers would overcome critical disadvantages of prior art methods, which are excessively invasive, cumbersome, risky, unavailable and/or associated with low patient screening compliance rates. While various approaches have been proposed in the prior art for colorectal cancer testing via analysis of markers of this disease in blood (reviewed in Hundt S. et al. Blood markers for early detection of colorectal cancer: a systematic review. Cancer Epidemiol Biomarkers Prev. 2007 October; 16(10):1935-53), none of these approaches, however, has demonstrated a capacity to satisfactorily enable determination of the probability that a test subject has colorectal cancer as opposed to not having colorectal cancer.

Thus, the prior art fails to provide an effective method of testing a subject for colorectal cancer via analysis in a blood sample of levels of RNA encoded by one or more of the genes ANXA3, CLEC4D, LMNB1, PRRG4, TNFAIP6 and VNN1 blood markers.

While reducing the invention to practice it was surprisingly uncovered that levels of RNA encoded by the genes ANXA3, CLEC4D, LMNB1, PRRG4, TNFAIP6 and VNN1 are significantly higher in blood of subjects having colorectal cancer than in blood of subjects not having any colorectal pathology, and that levels of RNA encoded by IL2RB are significantly lower in blood of subjects having colorectal cancer than in blood of subjects not having any colorectal pathology (Example 2). While further reducing the invention to practice, it was surprisingly uncovered that mathematical models based on levels of RNA encoded by the 127 possible combinations of the colorectal cancer marker genes ANXA3, CLEC4D, IL2RB, LMNB1, PRRG4, TNFAIP6 and VNN1 in blood of a test subject could be derived capable of discriminating between subjects having colorectal cancer and subjects not having any colorectal pathology (Example 2). While further reducing the invention to practice, it was surprisingly uncovered that mathematical models based on levels of RNA encoded by the 63 possible combinations of the colorectal cancer marker genes ANXA3, CLEC4D, LMNB1, PRRG4, TNFAIP6, and VNN1 in blood of a test subject, when normalized against levels of RNA encoded by IL2RB, could be derived capable of discriminating between subjects having colorectal cancer and subjects not having any colorectal pathology (Example 3). It will be appreciated that application of such mathematical models to test data representing blood levels in a test subject of RNA encoded by the aforementioned novel colorectal cancer marker genes disclosed herein can be used to provide the probability that the test subject has colorectal cancer as opposed to not having any colorectal pathology.

While reducing the invention to practice, fold changes of blood levels of RNA encoded by ANXA3, CLEC4D, IL2RB, LMNB1, PRRG4, TNFAIP6 and VNN1, including fold-changes of levels normalized to IL2RB, in subjects having colorectal cancer relative to subjects not having any colorectal pathology were surprisingly uncovered (Example 2, Example 3 and Example 6).

Thus, according to one aspect of the invention there is provided a method of determining a probability that a human test subject has colorectal cancer as opposed to not having colorectal cancer. In a first step, the method is effected by determining, for each gene of a set of one or more of the colorectal cancer marker genes: ANXA3, CLEC4D, IL2RB, LMNB1, PRRG4, TNFAIP6 and VNN1; a level of RNA encoded by the gene in blood of the test subject, thereby generating test data. In a second step, the method is effected by determining the probability that the test data corresponds to positive control data representing levels of RNA encoded by the gene in blood of human control subjects having colorectal cancer and not to negative control data representing levels of RNA encoded by the gene in blood of human control subjects not having colorectal cancer. The probability that the test data corresponds to the positive control data and not to the negative control data represents the probability that the test subject has colorectal cancer as opposed to not having colorectal cancer.

Thus, according to an aspect of the invention, there is provided a method of classifying a test subject as being more likely to have colorectal cancer than to not have colorectal cancer. The method of classifying is effected by determining a level of RNA encoded by one or more of the set of genes consisting of ANXA3, CLEC4D, IL2RB, LMNB1, PRRG4, TNFAIP6 and/or VNN1 in blood of the test subject, to thereby generate test data and applying to the test data, and to negative control data representing a level of RNA encoded by the gene in blood of human control subjects not having colorectal cancer, a mathematical formula for generating a value indicating, for ANXA3, CLEC4D, LMNB1, PRRG4, TNFAIP6 and VNN1, whether the level of RNA encoded by the gene in blood of the test subject is higher than the level of RNA encoded by the gene in blood of human control subjects not having colorectal cancer, and indicating, for IL2RB, whether the level of RNA encoded by the gene in blood of the test subject is lower than the level of RNA encoded by the gene in blood of human control subjects not having colorectal cancer. For ANXA3, CLEC4D, LMNB1, PRRG4, TNFAIP6 and VNN1, and indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer; and where, for IL2RB, an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer.

Determining whether the level of RNA encoded by ANXA3, CLEC4D, LMNB1, PRRG4, TNFAIP6 or VNN1 in blood of the test subject is higher than the level of RNA encoded by the gene in blood of control subjects not having colorectal cancer may be effected by determining whether there is a fold-change in the level between the test subject and the control subjects not having colorectal cancer which is higher than a minimum fold-change and/or which is within a range of fold-changes.

Determining whether the level of RNA encoded by IL2RB in blood of the test subject is lower than the level of RNA encoded by the gene in blood of control subjects not having colorectal cancer may be effected by determining whether there is a fold-change in the level between the test subject and the control subjects not having colorectal cancer which is lower than a maximum fold-change and/or which is within a range of fold-changes.

Examples of suitable fold-changes and ranges of fold-changes for classifying a test subject according to the invention are provided in Example 2, Example 3 and Example 6, below, and include the following ones.

For levels of RNA encoded by ANXA3, a suitable minimum fold-change is about 1.6 fold, and a suitable range of fold-changes is about 1.6 to about 11.5 fold, relative to an average level of RNA encoded by the housekeeping gene in blood of subjects not having any colorectal pathology.

For levels of RNA encoded by CLEC4D, a suitable minimum fold-change is which is about 1.4 fold, and a suitable range of fold-changes is which is about 1.4 to about 15.9 fold, relative to an average level of RNA encoded by the housekeeping gene in blood of subjects not having any colorectal pathology.

For levels of RNA encoded by LMNB1, a suitable minimum fold-change is about 1.3 fold, and a suitable range of fold-changes is about 1.3 to about 7.0 fold, relative to an average level of RNA encoded by the housekeeping gene in blood of subjects not having any colorectal pathology.

For levels of RNA encoded by PRRG4, a suitable minimum fold-change is about 1.5 fold, and a suitable range of fold-changes is about 1.5 to about 6.3 fold, relative to an average level of RNA encoded by the housekeeping gene in blood of subjects not having any colorectal pathology.

For levels of RNA encoded by TNFAIP6, a suitable minimum fold-change is about 1.4 fold, and a suitable range of fold-changes is about 1.45 to about 16.8 fold, relative to an average level of RNA encoded by the housekeeping gene in blood of subjects not having any colorectal pathology.

For levels of RNA encoded by VNN1, a suitable minimum fold-change is about 1.5 fold, and a suitable range of fold-changes is about 1.45 to about 23.6 fold, relative to an average level of RNA encoded by the housekeeping gene in blood of subjects not having any colorectal pathology.

For levels of RNA encoded by IL2RB, a suitable maximum fold-change is about 0.8 fold, and a suitable range of fold-changes is about 0.8 to about 0.1 fold, relative to an average level of RNA encoded by the housekeeping gene in blood of subjects not having any colorectal pathology.

For levels of RNA encoded by ANXA3 normalized to IL2RB, a suitable minimum fold-change is about 1.7 fold, and a suitable range of fold-changes is about 1.7 to about 20.7 fold, relative to an average level of RNA encoded by IL2RB in blood of subjects not having any colorectal pathology.

For levels of RNA encoded by CLEC4D normalized to IL2RB, a suitable minimum fold-change is which is about 1.5 fold, and a suitable range of fold-changes is which is about 1.5 to about 12.0 fold, relative to an average level of RNA encoded by IL2RB in blood of subjects not having any colorectal pathology.

For levels of RNA encoded by LMNB1 normalized to IL2RB, a suitable minimum fold-change is about 1.5 fold, and a suitable range of fold-changes is about 1.5 to about 10.6 fold, relative to an average level of RNA encoded by IL2RB in blood of subjects not having any colorectal pathology.

For levels of RNA encoded by PRRG4 normalized to IL2RB, a suitable minimum fold-change is about 1.3 fold, and a suitable range of fold-changes is about 1.3 to about 13.1 fold, relative to an average level of RNA encoded by IL2RB in blood of subjects not having any colorectal pathology.

For levels of RNA encoded by TNFAIP6 normalized to IL2RB, a suitable minimum fold-change is about 1.5 fold, and a suitable range of fold-changes is about 1.5 to about 16.4 fold, relative to an average level of RNA encoded by IL2RB in blood of subjects not having any colorectal pathology.

For levels of RNA encoded by VNN1 normalized to IL2RB, a suitable minimum fold-change is about 1.3 fold, and a suitable range of fold-changes is about 1.3 to about 11.9 fold, relative to an average level of RNA encoded by IL2RB in blood of subjects not having any colorectal pathology.

As used herein, the term "about" refers to a variability of plus or minus 10 percent.

Thus, a test subject of the invention is classified as being more likely to have colorectal cancer than to not have colorectal cancer if, for each marker gene of the particular set of marker genes of the invention used to practice the method of classifying of the invention, the fold-change in level of RNA encoded by that gene in blood of the test subject relative to blood of the control subjects not having any colorectal cancer pathology classifies, according to the teachings of the invention, the test subject as being more likely to have colorectal cancer than to not have colorectal cancer.

Conversely, a test subject of the invention is classified as being more likely to not have colorectal cancer than to have colorectal cancer if, for each marker gene of the particular set of marker genes of the invention used to practice the method of classifying of the invention, the fold-change in level of RNA encoded by that gene in blood of the test subject relative to blood of the control subjects not having any colorectal cancer pathology does not classify, according to the teachings of the invention, the test subject as being more likely to have colorectal cancer than to not have colorectal cancer.

In one aspect of the invention, the set of one or more colorectal cancer marker genes may consist of any one of the possible combinations of one or more of ANXA3, CLEC4D, IL2RB, LMNB1, PRRG4, TNFAIP6 and VNN1 (indicated in Table 6, where each logistic regression model is based on one particular gene combination, and each gene of the combination is assigned a logistic regression coefficient value).

Sets of marker genes of the invention which consist of one or more of ANXA3, CLEC4D, IL2RB, LMNB1, PRRG4, TNFAIP6 and VNN1 which can be used to practice the invention include: ANXA3, CLEC4D, IL2RB, LMNB1, PRRG4, TNFAIP6, VNN1; ANXA3, CLEC4D, IL2RB, LMNB1, PRRG4, VNN1; ANXA3, CLEC4D, IL2RB, PRRG4; ANXA3, CLEC4D, IL2RB, LMNB1, PRRG4; ANXA3, CLEC4D, IL2RB, PRRG4, VNN1; ANXA3, IL2RB, LMNB1, PRRG4, VNN1; ANXA3, CLEC4D, IL2RB, PRRG4, TNFAIP6; ANXA3, IL2RB, LMNB1, PRRG4, TNFAIP6; ANXA3, CLEC4D, IL2RB, LMNB1, PRRG4, TNFAIP6; ANXA3, CLEC4D, IL2RB, PRRG4, TNFAIP6, VNN1; ANXA3, IL2RB, LMNB1, PRRG4, TNFAIP6, VNN1; ANXA3, IL2RB, LMNB1, PRRG4; IL2RB, PRRG4, VNN1; ANXA3, IL2RB, PRRG4, VNN1; CLEC4D, IL2RB, PRRG4, VNN1; IL2RB, LMNB1, PRRG4, VNN1; CLEC4D, IL2RB, LMNB1, PRRG4, VNN1; ANXA3, IL2RB, PRRG4, TNFAIP6; IL2RB, PRRG4, TNFAIP6, VNN1; ANXA3, IL2RB, PRRG4, TNFAIP6, VNN1; CLEC4D, IL2RB, PRRG4, TNFAIP6, VNN1; IL2RB, LMNB1, PRRG4, TNFAIP6, VNN1; CLEC4D, IL2RB, LMNB1, PRRG4, TNFAIP6, VNN1; IL2RB, PRRG4; ANXA3, IL2RB, PRRG4; CLEC4D, IL2RB, PRRG4; IL2RB, LMNB1, PRRG4; CLEC4D, IL2RB, LMNB1, PRRG4; IL2RB, PRRG4, TNFAIP6; CLEC4D, IL2RB, PRRG4, TNFAIP6; IL2RB, LMNB1, PRRG4, TNFAIP6; CLEC4D, IL2RB, LMNB1, PRRG4, TNFAIP6; ANXA3, IL2RB, VNN1; ANXA3, CLEC4D, IL2RB, VNN1; ANXA3, IL2RB, LMNB1, VNN1; ANXA3, CLEC4D, IL2RB, LMNB1, VNN1; ANXA3, CLEC4D, LMNB1, PRRG4, VNN1; ANXA3, IL2RB, TNFAIP6, VNN1; ANXA3, CLEC4D, IL2RB, TNFAIP6, VNN1; ANXA3, IL2RB, LMNB1, TNFAIP6, VNN1; ANXA3, CLEC4D, IL2RB, LMNB1, TNFAIP6, VNN1; ANXA3, CLEC4D, LMNB1, PRRG4, TNFAIP6, VNN1; ANXA3, IL2RB; ANXA3, CLEC4D, IL2RB; ANXA3, IL2RB, LMNB1; ANXA3, CLEC4D, IL2RB, LMNB1; ANXA3, CLEC4D, LMNB1, PRRG4; CLEC4D, IL2RB, LMNB1, VNN1; ANXA3, IL2RB, TNFAIP6; ANXA3, CLEC4D, IL2RB, TNFAIP6; ANXA3, IL2RB, LMNB1, TNFAIP6; ANXA3, CLEC4D, IL2RB, LMNB1, TNFAIP6; CLEC4D, IL2RB, LMNB1, TNFAIP6, VNN1; IL2RB, LMNB1, VNN1; ANXA3, LMNB1, PRRG4, VNN1; ANXA3, LMNB1, PRRG4, TNFAIP6, VNN1; ANXA3, CLEC4D, PRRG4; ANXA3, LMNB1, PRRG4; CLEC4D, IL2RB, VNN1; ANXA3, CLEC4D, PRRG4, VNN1; IL2RB, LMNB1, TNFAIP6; CLEC4D, IL2RB, LMNB1, TNFAIP6; ANXA3, CLEC4D, PRRG4, TNFAIP6; ANXA3, LMNB1, PRRG4, TNFAIP6; IL2RB, TNFAIP6, VNN1; CLEC4D, IL2RB, TNFAIP6, VNN1; ANXA3, CLEC4D, PRRG4, TNFAIP6, VNN1; IL2RB, LMNB1; CLEC4D, IL2RB, LMNB1; IL2RB, VNN1; ANXA3, CLEC4D, LMNB1, VNN1; ANXA3, CLEC4D, LMNB1, TNFAIP6, VNN1; ANXA3, CLEC4D, LMNB1; ANXA3, PRRG4; ANXA3, CLEC4D, VNN1; ANXA3, LMNB1, VNN1; ANXA3, PRRG4, VNN1; ANXA3, CLEC4D, LMNB1, TNFAIP6; ANXA3, PRRG4, TNFAIP6; ANXA3, CLEC4D, TNFAIP6, VNN1; ANXA3, LMNB1, TNFAIP6, VNN1; ANXA3, CLEC4D, TNFAIP6, VNN1; ANXA3, PRRG4, TNFAIP6, VNN1; ANXA3; ANXA3, CLEC4D; ANXA3, LMNB1; ANXA3, VNN1; ANXA3, TNFAIP6; ANXA3, CLEC4D, TNFAIP6; IL2RB, TNFAIP6; CLEC4D, IL2RB, TNFAIP6; ANXA3, LMNB1, TNFAIP6; ANXA3, TNFAIP6, VNN1; CLEC4D, IL2RB; PRRG4, VNN1; CLEC4D, PRRG4, VNN1; LMNB1, PRRG4, VNN1; CLEC4D, LMNB1, PRRG4, VNN1; PRRG4, TNFAIP6, VNN1; CLEC4D, PRRG4, TNFAIP6, VNN1; LMNB1, PRRG4, TNFAIP6, VNN1; CLEC4D, LMNB1, PRRG4, TNFAIP6, VNN1; PRRG4; CLEC4D, PRRG4; LMNB1, PRRG4; CLEC4D, LMNB1, PRRG4; PRRG4, TNFAIP6; CLEC4D, PRRG4, TNFAIP6; LMNB1, PRRG4, TNFAIP6; CLEC4D, LMNB1, PRRG4, TNFAIP6; LMNB1, TNFAIP6, VNN1; CLEC4D, VNN1; LMNB1, VNN1; CLEC4D, LMNB1, VNN1; LMNB1, TNFAIP6; LMNB1, TNFAIP6; TNFAIP6, VNN1; CLEC4D, TNFAIP6, VNN1; CLEC4D, LMNB1, TNFAIP6, VNN1; LMNB1; CLEC4D, LMNB1; VNN1; CLEC4D, TNFAIP6; TNFAIP6; CLEC4D; and IL2RB.

According to the aspect of the invention where the set of one or more colorectal cancer marker genes consists of any one of the 127 possible combinations of ANXA3, CLEC4D, IL2RB, LMNB1, PRRG4, TNFAIP6 and VNN1, the level of RNA encoded by a gene of the invention in blood of a subject of the invention may be determined as a ratio to a level of RNA encoded by a housekeeping gene in blood of the subject. It will be appreciated that such measurement of a level or RNA encoded by a gene relative to that of a housekeeping gene within individual samples can be used to control for sample to sample variability.

The housekeeping gene may be any one of various genes expressed in blood known to the ordinarily skilled artisan. In one aspect of the method, the housekeeping gene is ACTB. Alternately, the housekeeping gene may encode 18S rRNA.

Nucleotide sequences of target genes of the invention (ACTB, ANXA3, CLEC4D, IL2RB, LMNB1, PRRG4, TNFAIP6 and VNN1) are described in FIGS. 1A-H and in Table 1, below.

In another aspect of the invention, the set of one or more colorectal cancer marker genes may consist of any one of the possible combinations of one or more of ANXA3, CLEC4D, LMNB1, PRRG4, TNFAIP6 and VNN1 (indicated in Table 5, where each logistic regression model is based on one particular gene combination, and each gene of the combination is assigned a logistic regression coefficient value).

The possible combinations of one or more of ANXA3, CLEC4D, LMNB1, PRRG4, TNFAIP6 and VNN1 which can be used to practice the invention include: ANXA3, CLEC4D, LMNB1, PRRG4, TNFAIP6 and VNN1; ANXA3, LMNB1, PRRG4, TNFAIP6 and VNN1; ANXA3, CLEC4D, LMNB1, PRRG4, TNFAIP6; ANXA3, CLEC4D, LMNB1, PRRG4, TNFAIP6 and VNN1; ANXA3, PRRG4, TNFAIP6 and VNN1; CLEC4D, LMNB1, PRRG4, TNFAIP6 and VNN1; ANXA3, PRRG4 and TNFAIP6; CLEC4D, LMNB1, PRRG4 and TNFAIP6; ANXA3, CLEC4D, PRRG4, TNFAIP6 and VNN1; ANXA3, CLEC4D, PRRG4 and TNFAIP6; ANXA3, LMNB1, PRRG4 and VNN1; ANXA3, LMNB1, PRRG4 and TNFAIP6; CLEC4D, LMNB1, PRRG4 and VNN1; ANXA3, CLEC4D, LMNB1, PRRG4; ANXA3, CLEC4D, PRRG4 and VNN1; LMNB1, PRRG4 and VNN1; LMNB1, PRRG4, TNFAIP6 and VNN1; LMNB1, PRRG4 and TNFAIP6; ANXA3, CLEC4D and PRRG4; ANXA3, LMNB1 and PRRG4; ANXA3 and PRRG4; ANXA3, PRRG4 and VNN1; CLEC4D, LMNB1 and PRRG4; LMNB1 and PRRG4; CLEC4D, PRRG4, TNFAIP6 and VNN1; CLEC4D, PRRG4 and TNFAIP6; CLEC4D, PRRG4 and VNN1; CLEC4D and PRRG4; PRRG4, TNFAIP6 and VNN1; PRRG4 and VNN1; PRRG4 and TNFAIP6; PRRG4; TNFAIP6 and VNN1; VNN1; ANXA3, TNFAIP6 and VNN1; ANXA3, LMNB1, TNFAIP6 and VNN1; LMNB1, TNFAIP6 and VNN1; CLEC4D, TNFAIP6 and VNN1; ANXA3, CLEC4D, TNFAIP6 and VNN1; ANXA3, CLEC4D, LMNB1, TNFAIP6 and VNN1; CLEC4D, LMNB1, TNFAIP6 and VNN1; ANXA3 and VNN1; ANXA3, CLEC4D, LMNB1 and TNFAIP6; CLEC4D, LMNB1 and TNFAIP6; CLEC4D and VNN1; LMNB1 and VNN1; ANXA3, CLEC4D and VNN1; ANXA3, LMNB1 and VNN1; ANXA3, LMNB1 and TNFAIP6; LMNB1 and TNFAIP6; CLEC4D, LMNB1 and VNN1; ANXA3, CLEC4D, LMNB1 and VNN1; ANXA3, CLEC4D and TNFAIP6; CLEC4D and TNFAIP6; CLEC4D, LMNB1; ANXA3, CLEC4D and LMNB1; LMNB1; ANXA3 and TNFAIP6; ANXA3 and LMNB1; TNFAIP6; ANXA3 and CLEC4D; CLEC4D; and ANXA3.

According to the aspect of the invention where the set of one or more colorectal cancer marker genes consists of any one of the 63 possible combinations of ANXA3, CLEC4D, LMNB1, PRRG4, TNFAIP6 and VNN1, the level of RNA encoded by a gene of the invention in blood of a subject of the invention may be determined as a ratio to a level of RNA encoded by IL2RB in blood of the subject.

It will be appreciated that data representing levels of RNA encoded by a set of genes of the invention may be combined with data representing levels of gene products of other genes which are differently expressed in blood in subjects having colorectal cancer relative to subjects not having any colorectal pathology so as to determine a probability that a test subject has colorectal cancer versus not having any colorectal pathology.

In another aspect, the method further comprises determining levels of RNA encoded by the gene in blood of a population of control human subjects having colorectal cancer, and/or in blood of a population of human control subjects not having colorectal cancer, to thereby provide the positive control data and/or the negative control data, respectively. Alternately, it is envisaged that the level of RNA encoded by a gene of the invention in control subjects of the invention could be provided by prior art data corresponding to control data of the invention.

The method of the invention may be practiced using any one of various types of control subjects.

In an aspect of the method of the invention, the control subjects not having colon cancer are subjects having been diagnosed as not having any colorectal pathology as a result of colonoscopic examination. As is described in the Examples section which follows, the method of the invention may be practiced using subjects not having any colorectal pathology as the control subjects not having colorectal cancer.

In an aspect of the method of the invention, the control subjects having colorectal cancer are subjects having been diagnosed as having colorectal cancer as a result of colonoscopic examination. As is described in the Examples section which follows, the method of the invention may be practiced using subjects diagnosed as not having any colorectal pathology as the control subjects not having colorectal cancer.

The method of the invention may furthermore be practiced using any one of various numbers of control subjects. One of ordinary skill in the art will possess the necessary expertise to select a sufficient number of control subjects so as to obtain control data having a desired statistical significance for practicing the method of the invention with a desired level of reliability.

For example, the method of the invention can be practiced using 10 or more, 20 or more, 30 or more, 40 or more, 50 or more, 60 or more, 70 or more, 80 or more, 90 or more, 100 or more, 10 or more, 20 or more, 30 or more, 40 or more, 50 or more, 60 or more, 70 or more, 80 or more, 90 or more, 100 or more, 110 or more, 120 or more, 130 or more, 140 or more, 150 or more, 160 or more, 170 or more, 180 or more, 190 or more, or 200 or more of control subjects having colorectal cancer and/or of control subjects not having colorectal cancer.

In one aspect of the invention, the level of RNA encoded by a gene of the invention in blood of the test subject and the levels of RNA encoded by the gene in blood of the control subjects are determined via the same method. As is described in the Examples section, below, the method can be practiced where the level of RNA encoded by a gene of the invention in blood of the test subject and the levels of RNA encoded by the gene in blood of the control subjects are determined via the same method. Alternately, it is envisaged that the level of a gene of the invention in blood of a test subject of the invention and in blood of control subjects of the invention could be determined using different methods. It will be appreciated that use of the same method to determine the levels of RNA encoded by a gene of the invention in a test subject and in control subjects of the invention can be used to avoid method-to-method calibration to minimize any variability which might arise from use of different methods.

In one aspect of the method, determining of the level of RNA encoded by a gene of the invention in blood of a subject of the invention is effected by determining the level of RNA encoded by the gene in a blood sample isolated from the subject. Alternately, it is envisaged that determining of the level of RNA encoded by a gene in blood of a subject of the invention could be effected by determining the level of RNA encoded by the gene in an in-vivo sample using a suitable method for such a purpose.

In one aspect of the method, the level of RNA encoded by a gene of the invention in blood of a subject of the invention is determined in a sample of RNA isolated from blood of the subject. Alternately, it is envisaged that the level of RNA of a gene of the invention in blood of a subject of the invention could be determined in a sample which includes RNA of blood of the subject but from which RNA has not been isolated therefrom, using a suitable method for such a purpose.

Any one of various methods routinely employed in the art for isolating RNA from blood may be used to isolate RNA from blood of a subject of the invention, so as to enable practicing of the method of the invention.

In one aspect of the method, the level of RNA encoded by a gene of the invention in blood of a subject of the invention is determined in RNA of a sample of whole blood. Any one of various methods routinely employed in the art for isolating RNA from whole blood may be employed for practicing the method.

Alternately, it is envisaged that the level of RNA encoded by a gene of the invention in blood of a subject of the invention could be determined in RNA of a sample of fraction of blood which expresses the gene sufficiently specifically so as to enable the method. Examples of such blood fractions include preparations of isolated types of leukocytes, preparations of isolated peripheral blood mononuclear cells, preparations of isolated granulocytes, preparations of isolated whole leukocytes, preparations of isolated specific types of leukocytes, plasma-depleted blood, preparations of isolated lymphocytes, and the plasma fraction of blood.

In one aspect of the method, isolation of RNA from whole blood of a subject of the invention is effected by using a PAXgene Blood RNA Tube (obtainable from PreAnalytiX) in accordance with the instructions of the PAXgene Blood RNA Kit protocol. As is described in the Examples section below, the method of the invention may be practiced by determining a level of a gene of the invention in RNA isolated from blood from test and control subjects of the invention using PAXgene Blood RNA Tubes.

Determining of a level of RNA encoded by a gene of the invention in a sample of the invention may be effected in any one of various ways routinely practiced in the art.

For example, the level of RNA encoded by a gene of the invention in a sample of the invention may be determined via any one of various methods based on quantitative polynucleotide amplification which are routinely employed in the art for determining a level of RNA encoded by a gene in a sample.

Alternately, the level of RNA encoded by a gene of the invention may be determined via any one of various methods based on quantitative polynucleotide hybridization to an immobilized probe which are routinely employed in the art for determining a level of RNA encoded by a gene in a sample.

In one aspect of the method of the invention, the method based on quantitative polynucleotide amplification used to determine the level of RNA encoded by a gene of the invention is quantitative reverse transcriptase-polymerase chain reaction (PCR) analysis. Any one of various types of quantitative reverse transcriptase-PCR analyses routinely employed in the art to determine the level of RNA encoded by a gene in a sample may be used to practice the invention. For example, any one of various sets of primers may be used to perform quantitative reverse transcriptase-PCR analysis so as to practice the method of the invention.

In one aspect of the method of the invention, the quantitative reverse transcriptase-PCR analysis used to determine the level of RNA encoded by a gene of the invention is quantitative real-time PCR analysis of DNA complementary to RNA encoded by the gene using a labeled probe capable of specifically binding amplification product of DNA complementary to RNA encoded by the gene. For example, quantitative real-time PCR analysis may be performed using a labeled probe which comprises a polynucleotide capable of selectively hybridizing with a sense or antisense strand of amplification product of DNA complementary to RNA encoded by the gene. Labeled probes comprising a polynucleotide having any one of various nucleic acid sequences capable of specifically hybridizing with amplification product of DNA complementary to RNA encoded by the gene may be used to practice the method of the invention.

Quantitative real-time PCR analysis of a level of RNA encoded by a gene of the invention may be performed in any one of various ways routinely employed in the art.

In one aspect of the method of the invention, quantitative real-time PCR analysis is performed by analyzing complementary DNA prepared from RNA of blood a subject of the invention, using the QuantiTect™ Probe RT-PCR system (Qiagen, Valencia, Calif.; Product Number 204345), a TaqMan dual labelled probe, and a Real-Time PCR System 7500 instrument (Applied Biosystems). As is described in the Examples section which follows, such quantitative real-time PCR analysis may be used to practice the method of the invention.

As specified above, the level of RNA encoded by a gene of the invention may be determined via a method based on quantitative polynucleotide hybridization to an immobilized probe.

In one aspect, determining of the level of RNA encoded by a gene of the invention via a method based on quantitative polynucleotide hybridization is effected using a microarray, such as an Affymetrix U133Plus 2.0 GeneChip oligonucleotide array (Affymetrix; Santa Clara, Calif.).

As specified above, the level of RNA encoded by a gene of the invention in a sample of the invention may be determined via quantitative reverse transcriptase-PCR analysis using any one of various sets of primers and labeled probes to amplify and quantitate DNA complementary to RNA encoded by a marker gene of the invention produced during such analysis. Examples of suitable primers for use in quantitative reverse transcriptase-PCR analysis of the level of RNA encoded by a target gene of the invention are listed in Table 19. This table further lists examples of suitable polynucleotides comprised in labeled probes for practicing quantitative real-time PCR analysis according to the method of the invention.

TABLE 19

PCR primers and matching polynucleotides of labeled probes for quantitative PCR analysis.

| Gene encoding amplified cDNA | Assay reagent | Nucleic acid sequences of PCR primers and matching polynucleotides comprised in labeled probes | Primer/ probe position | Amplicon size (bp) |
|---|---|---|---|---|
| ACTB | 5' primer | 5'-CACCACACCTTCTACAATGAGCTG-3' (SEQ ID NO: 1) | 259 | 158 |
| | 3' primer | 5'-ACAGCCTGGATAGCAACGTACA-3' (SEQ ID NO: 2) | 416 | |
| | probe | 5'-AACCGCGAGAAGATGACCCAGATCAT-3' (SEQ ID NO: 3) | 343 | |
| | 5' primer | 5'-ACCTTCTACAATGAGCTGCG-3' (SEQ ID NO: 4) | 337 | 114 |
| | 3' primer | 5'-GGTCTCAAACATGATCTGGGTC-3' (SEQ ID NO: 5) | 450 | |
| | probe | 5'-AAGGCCAACCGCGAGAAGAT-3' (SEQ ID NO: 6) | 409 | |
| | 5' primer | 5'-CACCCAGCACAATGAAGATC-3' (SEQ ID NO: 7) | 1034 | 119 |

TABLE 19-continued

PCR primers and matching polynucleotides
of labeled probes for quantitative PCR analysis.

| Gene encoding amplified cDNA | Assay reagent | Nucleic acid sequences of PCR primers and matching polynucleotides comprised in labeled probes | Primer/ probe position | Amplicon size (bp) |
|---|---|---|---|---|
| | 3' primer | 5'-CTGCTTGCTGATCCACATCT-3' (SEQ ID NO: 8) | 1152 | |
| | probe | 5'-ATCATTGCTCCTCCTGAGCG-3' (SEQ ID NO: 9) | 1057 | |
| ANXA3 | 5' primer | 5'-GAAACATCTGGTGACTTCCG-3' (SEQ ID NO: 10) | 748 | 103 |
| | 3' primer | 5'-TCTGGGCATCTTGTTTGG-3' (SEQ ID NO: 11) | 850 | |
| | probe | 5'-TTGACTTTGGCAGATGGCAGA-3' (SEQ ID NO: 12) | 778 | |
| | 5' primer | 5'-GGAACAAACGAAGATGCCTTG-3' (SEQ ID NO: 13) | 628 | 137 |
| | 3' primer | 5'-AAGTCACCAGATGTTTCGGA-3' (SEQ ID NO: 14) | 764 | |
| | probe | 5'-ATCTTAACTACCAGGACAAGCAGGCA-3' (SEQ ID NO: 15) | 655 | |
| | 5' primer | 5'-CTACCAGGACAAGCAGGCAA-3' (SEQ ID NO: 16) | 662 | 138 |
| | 3' primer | 5'-TTCTGCCATCTGCCAAAGT-3' (SEQ ID NO: 17) | 799 | |
| | probe | 5'-TCCGAAACATCTGGTGACTTCC-3' (SEQ ID NO: 18) | 745 | |
| CLEC4D | 5' primer | 5'-CCATTTAACCCACGCAGAG-3' (SEQ ID NO: 19) | 673 | 101 |
| | 3' primer | 5'-CAGGCCCATTTATCTTGGTT-3' (SEQ ID NO: 20) | 773 | |
| | probe | 5'-CTGGCATAAGAATGAACCCGACA-3' (SEQ ID NO: 21) | 696 | |
| | 5' primer | 5'-TCCGAAACATCTGGTGACTTCC-3' (SEQ ID NO: 22) | 406 | 118 |
| | 3' primer | 5'-TCCTTTCACTCTCAGCCCAC-3' (SEQ ID NO: 23) | 523 | |
| | probe | 5'-ATGACCATCAGCACGGAAGC-3' (SEQ ID NO: 24) | 550 | |
| | 5' primer | 5'-GGGCTGAGAGTGAAAGGAAC-3' (SEQ ID NO: 25) | 506 | 149 |
| | 3' primer | 5'-CCACTGACCTTTGGCATTC-3' (SEQ ID NO: 26) | 654 | |
| | probe | 5'-ATGACCATCAGCACGGAAGC-3' (SEQ ID NO: 27) | 550 | |
| IL2RB | 5' primer | 5'-AAATCTCCCAAGCCTCCCA-3' (SEQ ID NO: 28) | 588 | 127 |
| | 3' primer | 5'-AGGCAGATCCATTCCTGCT-3' (SEQ ID NO: 29) | 714 | |
| | probe | 5'-TTGAAAGACACCTGGAGTTCG-3' (SEQ ID NO: 30) | 612 | |
| | 5' primer | 5'-GACCCACAGATGCAACATAAG-3' (SEQ ID NO: 31) | 562 | 137 |
| | 3' primer | 5'-GCTTCTGCTTGAGAGTCAGC-3' (SEQ ID NO: 32) | 698 | |
| | probe | 5'-AAATCTCCCAAGCCTCCCAC-3' (SEQ ID NO: 33) | 588 | |
| | 5' primer | 5'-TGGAGACCCACAGATGCAA-3' (SEQ ID NO: 34) | 558 | 141 |
| | 3' primer | 5'-GCTTCTGCTTGAGAGTCAGC-3' (SEQ ID NO: 35) | 698 | |
| | probe | 5'-AAATCTCCCAAGCCTCCCAC-3' (SEQ ID NO: 36) | 588 | |
| LMNB1 | 5' primer | 5'-GGAGTGGTTGTTGAGGAAGAA-3' (SEQ ID NO: 37) | 2051 | 151 |
| | 3' primer | 5'-CTGAGAAGGCTCTGCACTGTA-3' (SEQ ID NO: 38) | 2201 | |
| | probe | 5'-AACCCCAAGAGCATCCAATAG-3' (SEQ ID NO: 39) | 2089 | |
| | 5' primer | 5'-CTGGCGAAGATGTGAAGGT-3' (SEQ ID NO: 40) | 1935 | 135 |
| | 3' primer | 5'-CTTCCTCAACAACCACTCCA-3' (SEQ ID NO: 41) | 2069 | |

TABLE 19-continued

PCR primers and matching polynucleotides of labeled probes for quantitative PCR analysis.

| Gene encoding amplified cDNA | Assay reagent | Nucleic acid sequences of PCR primers and matching polynucleotides comprised in labeled probes | Primer/ probe position | Amplicon size (bp) |
|---|---|---|---|---|
| | probe | 5'-AATTCTCAGGGAGAGGAGGTTG-3' (SEQ ID NO: 42) | 1964 | |
| | 5' primer | 5'-AGGCGAAGAAGAGAGGTTGAAG-3' (SEQ ID NO: 43) | 1513 | 103 |
| | 3' primer | 5'-CCGCTTTCCTCTAGTTGTACG-3' (SEQ ID NO: 44) | 1615 | |
| | probe | 5'-TGTCTCCAAGCCCTTCTTCC-3' (SEQ ID NO: 45) | 1536 | |
| PRRG4 | 5' primer | 5'-ATGCGGGAGAAGAAGTGTTTAC-3' (SEQ ID NO: 46) | 341 | 153 |
| | 3' primer | 5'-CTCTGGCTTCCTCATAATTGC-3' (SEQ ID NO: 47) | 493 | |
| | probe | 5'-CTCTTCACTCCCGGCAACCTAGAA-3' (SEQ ID NO: 48) | 427 | |
| | 5' primer | 5'-TGCTGCTGGAGTATTTTTGG-3' (SEQ ID NO: 49) | 618 | 130 |
| | 3' primer | 5'-AATGATGGAGGGAGTGTGC-3' (SEQ ID NO: 50) | 747 | |
| | probe | 5'-AACATCCATGCTCTTCAGCC-3' (SEQ ID NO: 51) | 693 | |
| | 5' primer | 5'-ACTCCCGGCAACCTAGAAAG-3' (SEQ ID NO: 52) | 433 | 176 |
| | 3' primer | 5'-GTCAGAAGGCCCATAACATCTA-3' (SEQ ID NO: 53) | 608 | |
| | probe | 5'-AACGATTGCATTTTGGCAGG-3' (SEQ ID NO: 54) | 517 | |
| TNFAIP6 | 5' primer | 5'-GCCTATTGCTACAACCCACA-3' (SEQ ID NO: 55) | 448 | 84 |
| | 3' primer | 5'-TGGGAAGCCTGGAGATTTA-3' (SEQ ID NO: 56) | 531 | |
| | probe | 5'-AAGGAGTGTGGTGGCGTCTTTAC-3' (SEQ ID NO: 57) | 472 | |
| | 5' primer | 5'-CAGGTTGCTTGGCTGATTATG-3' (SEQ ID NO: 58) | 632 | 172 |
| | 3' primer | 5'-TTGATTTGGAAACCTCCAGC-3' (SEQ ID NO: 59) | 803 | |
| | probe | 5'-TGGCTTTGTGGGAAGATACTGTGG-3' (SEQ ID NO: 60) | 684 | |
| | 5' primer | 5'-CATTAGACTCAAGTATGGTCAGCG-3' (SEQ ID NO: 61) | 567 | 142 |
| | 3' primer | 5'-TCCACAGTATCTTCCCACAAAG-3' (SEQ ID NO: 62) | 708 | |
| | probe | 5'-CAGGTTGCTTGGCTGATTATGT-3' (SEQ ID NO: 63) | 632 | |
| VNN1 | 5' primer | 5'-TGACAGGAAGTGGCATCTAT-3' (SEQ ID NO: 64) | 835 | 147 |
| | 3' primer | 5'-TACTGCTGGCATAGGAAGTC-3' (SEQ ID NO: 65) | 981 | |
| | probe | 5'-AGAAGAGGGAAAACTCCTCCTCTCG-3' (SEQ ID NO: 66) | 896 | |
| | 5' primer | 5'-CTGGAGAATTTCAGGTGTCA-3' (SEQ ID NO: 67) | 1360 | 111 |
| | 3' primer | 5'-ATGCCCAGTCCTTCTCATAC-3' (SEQ ID NO: 68) | 1470 | |
| | probe | 5'-ACTGACGGACGCTTGTTTAGTCTGA-3' (SEQ ID NO: 69) | 1380 | |
| | 5' primer | 5'-GTATTCCCAACAGCTTGGAT-3' (SEQ ID NO: 70) | 711 | 144 |
| | 3' primer | 5'-ATAGATGCCACTTCCTGTCA-3' (SEQ ID NO: 71) | 854 | |
| | probe | 5'-CATGAGGGTCAATTTCCTTGCATC-3' (SEQ ID NO: 72) | 785 | |

Determining the level of RNA encoded by the marker gene of the invention as a ratio to a housekeeping gene may be effected in any one of various ways routinely employed in the art for determining a ratio of a level of RNA encoded by one gene to a level of RNA encoded by a housekeeping gene, such as ACTB.

In one aspect of the method, determining the level of RNA encoded by the gene of the invention as a ratio to the housekeeping gene is effected via duplex quantitative reverse transcriptase-PCR analysis of RNA encoded by the gene and of RNA encoded by the housekeeping gene in a sample of the invention. Such "duplex quantitative reverse transcriptase PCR analysis" refers to quantitative reverse transcriptase-PCR analysis where DNA complementary to RNA encoded by the gene of the invention and DNA complementary to RNA encoded by the housekeeping gene are co-amplified in the same sample/reaction mixture.

DNA complementary to RNA encoded by the housekeeping gene may be amplified via quantitative reverse transcriptase-PCR analysis using any one of various suitable primers.

In one aspect, the primers may be selected so as to include a primer having a nucleotide sequence which is complementary to a region of a target cDNA template, where the region spans a splice junction joining a pair of exons. It will be appreciated that such a primer can be used to facilitate amplification of DNA complementary to messenger RNA, i.e. mature spliced RNA.

In one aspect of the method, where the housekeeping gene is ACTB, the primers used to amplify DNA complementary to RNA encoded by the housekeeping gene may include a primer having a nucleotide sequence identified as SEQ ID NO: 1, a primer having a nucleotide sequence identified as SEQ ID NO: 2, or both primers.

In another aspect of the method, the level of RNA encoded by the housekeeping gene in blood of the test subject is determined via quantitative reverse transcriptase-PCR analysis, using a labeled probe which comprises a polynucleotide capable of hybridizing to a sense or antisense strand of the amplification product of the DNA complementary to RNA encoded by the housekeeping gene.

In one aspect of the method where the housekeeping gene is ACTB and where the level of RNA encoded by the housekeeping gene in blood of the test subject is determined via quantitative reverse transcriptase-PCR analysis using a primer having a nucleotide sequence identified as SEQ ID NO: 1, and a primer having a nucleotide sequence identified as SEQ ID NO: 2, and a labeled probe, the probe comprises a polynucleotide having a nucleic acid sequence identified as SEQ ID NO: 3.

As is demonstrated in Example 2 of the Examples section which follows, the method of the invention can be practiced by determining the level of RNA encoded by any one of the marker genes ANXA3, CLEC4D, IL2RB, LMNB1, PRRG4, TNFAIP6 and VNN1 as a ratio to a level of RNA encoded by ACTB in blood of a subject of the invention, where the level is determined via duplex quantitative reverse transcriptase-PCR analysis using a primer having a nucleotide sequence identified as SEQ ID NO: 1, a primer having a nucleotide sequence identified as SEQ ID NO: 2, and a labeled probe which comprises a polynucleotide having a nucleic acid sequence identified as SEQ ID NO: 3.

Determining the level of RNA encoded by ANXA3, CLEC4D, LMNB1, PRRG4, TNFAIP6 or VNN1 as a ratio to IL2RB may be effected in any one of various ways.

In one aspect of the method, determining the level of ANXA3, CLEC4D, LMNB1, PRRG4, TNFAIP6 or VNN1 as a ratio to a level of RNA encoded by IL2RB in a sample of the invention is effected via duplex quantitative reverse transcriptase-PCR analysis of RNA encoded by ANXA3, CLEC4D, LMNB1, PRRG4, TNFAIP6 or VNN1 and of RNA encoded by IL2RB in the sample. Such "duplex quantitative reverse transcriptase PCR analysis" refers to quantitative reverse transcriptase-PCR analysis where DNA complementary to RNA encoded by ANXA3, CLEC4D, LMNB1, PRRG4, TNFAIP6 or VNN1 and DNA complementary to RNA encoded by IL2RB are co-amplified in the same sample/reaction mixture.

As described above, following the step of obtaining the test data, the method of the invention comprises the step of determining the probability that the test data corresponds to the positive control data and not to the negative control data.

It will be appreciated that the probability that the test subject does not have any colorectal pathology as opposed to having colorectal cancer can be readily determined from the probability that the test subject has colorectal cancer as opposed to not having colorectal cancer. For example, when expressing the probability that the test subject has colorectal cancer as a percentage probability, the probability that the test subject does not have any colorectal pathology as opposed to having colorectal cancer corresponds to 100 percent minus the probability that the test subject does not have any colorectal pathology as opposed to having colorectal cancer.

Determining the probability that the test data corresponds to the positive control data and not to the negative control data may be effected in any one of various ways known to the ordinarily skilled artisan for determining the probability that a gene expression profile of a test subject corresponds to a gene expression profile of subjects having a pathology and not to a gene expression profile of subjects not having the pathology, where the gene expression profiles of the subjects having the pathology and the subjects not having the pathology are significantly different.

In one aspect of the method, determining the probability that the test data corresponds to the positive control data and not to the negative control data is effected by applying to the test data a mathematical model derived from the positive control data and from the negative control data.

Various suitable mathematical models which are well known in the art of medical diagnosis using disease markers may be employed to classify a test subject as more likely to have colorectal cancer than to not have colorectal cancer, to determine a probability that a test subject is likely to have colorectal cancer as opposed to not having colorectal cancer, or to diagnose a test subject as having colorectal cancer according to the teachings of the invention. Generally these mathematical models can be unsupervised methods performing a clustering whilst supervised methods are more suited to classification of datasets. (refer, for example, to: Dreiseitl S, Ohno-Machado L. Logistic regression and artificial neural network classification models: a methodology review. J Biomed Inform. 2002 October-December; 35(5-6):352-9; Pepe M S. The Statistical Evaluation of Medical Tests for Classification and Prediction. Oxford, England: Oxford University Press; 2003; Dupont W D. Statistical Modeling for Biomedical Researchers. Cambridge, England: Cambridge University Press; 2002; Pampel F C. Logistic regression: A Primer. Publication #07-132, Sage Publications: Thousand Oaks, Calif. 2000; King E N, Ryan T P. A preliminary investigation of maximum likelihood logistic regression versus exact logistic regression. Am Statistician 2002; 56:163-170; Metz C E. Basic principles of ROC analysis. Semin Nucl Med 1978; 8:283-98; Swets J A. Measuring the accuracy of diagnostic systems. Science 1988; 240:1285-93; Zweig M H, Campbell G. Receiver-operating characteristic (ROC) plots: a fundamental evaluation tool in clinical medicine. Clin Chem 1993; 39:561-77; Witten I H, Frank Eibe. Data Mining: Practical Machine Learning Tools and Techniques (second edition). Morgan Kaufman 2005; Deutsch J M. Evolutionary algorithms for finding optimal gene sets in microarray prediction. Bioinformatics 2003; 19:45-52; Niels Landwehr, Mark Hall and Eibe Frank (2003) Logistic Model Trees. pp 241-252 in Machine Learning: ECML 2003: 14th European Conference on Machine Learning, Cavtat-Dubrovnik, Croatia, Sep. 22-26, 2003, Proceedings. Publisher: Springer-Verlag GmbH, ISSN: 0302-9743). Examples of such mathematical models, related to learning machine, include: Random Forests methods, logistic regression methods, neural network methods, k-means methods, principal component analysis methods, nearest neighbour classifier analysis methods, linear discriminant analysis, methods, quadratic discriminant analysis methods, support vector machine methods, decision tree methods, genetic algorithm methods, classifier optimization using bagging methods, classifier optimization using boosting methods, classifier optimization using the Random Subspace methods, projection pursuit methods, genetic programming and weighted voting methods.

In one aspect of the invention, the model used is a logistic regression model. As is described in the Examples section below, logistic regression models can be used according to the method of the invention to determine the probability a test subject has colorectal cancer as opposed to not having any colorectal pathology. Logistic regression models may also be referred to in the art as "logistic models", and "logit models".

Any one of various particular cases of logistic regression models may be used, for any given set of genes of the invention, for determining the probability that the test data corresponds to the positive control data and not to the negative control data.

In one aspect of the method, determining the probability that the test data corresponds to the positive control data and not to the negative control data is effected by using one or more of the logistic regression models disclosed in Example 2, Example 3 and Example 6.

It will be appreciated that a computer may be used for determining the probability that the test subject has colorectal cancer using a mathematical model, according to the method of the invention.

One of skill in the art will know of suitable mathematical formulas for generating a value indicating whether the level of RNA encoded by the gene in blood of the test subject is higher or lower than the level of RNA encoded by the gene in blood of human control subjects not having colorectal cancer.

For example, a suitable formula, is one which generates a value representing the ratio of the level of RNA encoded by the gene in blood of the test subject to the level of RNA encoded by the gene in blood of human control subjects not having colorectal cancer. A ratio of greater than 1 indicates that the level of RNA encoded by the gene in blood of the test subject is higher than the level of RNA encoded by the gene in blood of human control subjects not having colorectal cancer, and a ratio of less than 1 indicates that the level of RNA encoded by the gene in blood of the test subject is lower than the level of RNA encoded by the gene in blood of human control subjects not having colorectal cancer. A formula for generating such a ratio value may have the form:

Value=[level of RNA encoded by the gene in blood of the test subject]/[level of RNA encoded by the gene in blood of human control subjects not having colorectal cancer]

Alternately, a suitable formula is one which subtracts the level of RNA encoded by the gene in blood of human control subjects not having colorectal cancer from the level of RNA encoded by the gene in blood of the test subject, to generate a value representing the difference between the level of RNA encoded by the gene in blood of the test subject from the level of RNA encoded by the gene in blood of human control subjects not having colorectal cancer. A difference having a positive value indicates that the level of RNA encoded by the gene in blood of the test subject is higher than the level of RNA encoded by the gene in blood of human control subjects not having colorectal cancer, and a difference having a negative value indicates that the level of RNA encoded by the gene in blood of the test subject is lower than the level of RNA encoded by the gene in blood of human control subjects not having colorectal cancer. A formula for generating such a difference value may have the form:

Value=[level of RNA encoded by the gene in blood of the test subject]−[level of RNA encoded by the gene in blood of human control subjects not having colorectal cancer]

Thus, according to another aspect of the invention there is provided a computer-based method of determining the probability that a test subject has colorectal cancer as opposed to not having colorectal cancer. The method is effected by causing a computer to apply to the test data a mathematical model according to the invention, and to output the probability, to thereby enable a determination of the probability that the test subject has colorectal cancer as opposed to not having colorectal cancer.

Application of computers for determining a probability that a test subject has a disease as opposed to not having the disease, so as to enable the method of the invention, is routinely practiced in the art using computer systems, and optionally computer-readable media, routinely used in the art.

Thus, according to a further aspect of the invention there is provided a computer system for providing the probability that the test subject has colorectal cancer as opposed to not having colorectal cancer. The computer system comprises a processor; and a memory configured with instructions that cause the processor to provide a user with the probability, where the instructions comprise applying a mathematical model of the invention to test data of the invention, to thereby determine the probability that the test subject has colorectal cancer as opposed to not having colorectal cancer.

The instructions may be provided to the computer in any one of various ways routinely employed in the art. In one aspect, the instructions are provided to the computer using a computer-readable medium.

Thus, according to yet another aspect of the invention there is provided a computer-readable medium having instructions stored thereon that are operable when executed by a computer for applying a mathematical model of the invention to test data of the invention from, thereby determine the probability that a test subject has colorectal cancer as opposed to not having colorectal cancer.

As described above, following the step of obtaining the test data, the method of classifying of the invention comprises the step of comparing test data representing a level of RNA encoded by a marker gene of the invention to negative control data representing a level of RNA encoded by the gene in subjects not having any colorectal pathology, and determining the fold-change between the levels.

It will be appreciated that a computer may be used for comparing test data representing a level of RNA encoded by a marker gene of the invention to negative control data representing a level of RNA encoded by the gene in subjects not having any colorectal pathology, and determining the fold-change between the levels, according to methods of the invention.

Thus, according to another aspect of the invention there is provided a computer-based method of classifying a human test subject as more likely to have colorectal cancer than to not have colorectal cancer. The method is effected by using a computer to apply to test data from a test subject according to the invention, and to negative control data representing a level of RNA encoded by the gene in blood of human control subjects not having colorectal cancer, a mathematical formula for generating a value indicating whether the level of RNA encoded by the gene in blood of the test subject is higher, for ANXA3, CLEC4D, LMNB1, PRRG4, TNFAIP6 and VNN1, or lower, for IL2RB, than the level of RNA encoded by the gene in blood of human control subjects not having colorectal cancer. For ANXA3, CLEC4D, LMNB1, PRRG4, TNFAIP6 and VNN1, an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer, and where, for IL2RB, an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer.

Application of computers for provide a classification of a test subject as more likely to have a disease than to not have the disease, so as to enable the method of the invention, is routinely practiced in the art using computer systems, and optionally computer-readable media, routinely used in the art.

Thus, according to a further aspect of the invention there is provided a computer system for providing a classification that a test subject is more likely to have colorectal cancer than to not have colorectal cancer. The computer system comprises a processor; and a memory configured with instructions that cause the processor to provide a user with the classification, where the instructions comprise causing the processor to apply to test data, and to negative control data representing a level of RNA encoded by the gene in blood of human control subjects not having colorectal cancer, a mathematical formula for generating a value representing a fold-change between the level of RNA encoded by the gene in blood of the test subject and the level of RNA encoded by the gene in blood of human control subjects not having colorectal cancer where, for ANXA3, CLEC4D, LMNB1, PRRG4, TNFAIP6 and VNN1, a value indicating that the level of RNA encoded by the gene in blood of the test subject is higher, for example within a range of suitable fold-changes taught herein, than the level of RNA encoded by the gene in blood of human control subjects not having colorectal cancer classifies the test subject as more likely to have colorectal cancer than to not have colorectal cancer, and where, for IL2RB, a value indicating that the level of RNA encoded by the gene in blood of the test subject is lower, for example within a range of suitable fold-changes disclosed herein, than the level of RNA encoded by the gene in blood of human control subjects not having colorectal cancer classifies the test subject as more likely to have colorectal cancer than to not have colorectal cancer.

The instructions may be provided to the computer in any one of various ways routinely employed in the art. In one aspect, the instructions are provided to the computer using a computer-readable medium.

Thus, according to yet another aspect of the invention there is provided a computer-readable medium having instructions stored thereon that are operable when executed by a computer for applying to test data and to negative control data representing a level of RNA encoded by a marker gene of the invention in blood of human control subjects not having colorectal cancer, a mathematical formula for generating a value representing the fold-change between the level of RNA encoded by the gene in blood of the test subject and the level of RNA encoded by the gene in blood of human control subjects not having colorectal cancer, where, for ANXA3, CLEC4D, LMNB1, PRRG4, TNFAIP6 and VNN1, a value indicating that the level of RNA encoded by the gene in blood of the test subject is higher, for example, within a suitable range of fold-changes disclosed herein, than the level of RNA encoded by the gene in blood of human control subjects not having colorectal cancer classifies the test subject as more likely to have colorectal cancer than to not have colorectal cancer, and where, for IL2RB, a value indicating that the level of RNA encoded by the gene in blood of the test subject is lower, for example, within a suitable range of fold-changes disclosed herein, than the level of RNA encoded by the gene in blood of human control subjects not having colorectal cancer classifies the test subject as more likely to have colorectal cancer than to not have colorectal cancer.

Thus, according to still yet another aspect of the invention there is provided a computer-readable medium having instructions stored thereon that are operable when executed by a computer for applying, to test data representing a level of RNA encoded by the gene in blood of a human test subject, and to negative control data representing a level of RNA encoded by the gene in blood of human control subjects not having colorectal cancer, a mathematical formula for generating a value indicating, for ANXA3, CLEC4D, LMNB1, PRRG4, TNFAIP6 and VNN1, whether the level of RNA encoded by the gene in blood of the test subject is higher than the level of RNA encoded by the gene in blood of human control subjects not having colorectal cancer, and, for IL2RB, whether the level of RNA encoded by the gene in blood of the test subject is lower than the level of RNA encoded by the gene in blood of human control subjects not having colorectal cancer, where, for ANXA3, CLEC4D, LMNB1, PRRG4, TNFAIP6 and VNN1, an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer, and where, for IL2RB, an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer.

An exemplary computer system for practicing certain of the methods described herein is described in FIG. 1.

FIG. 1 shows a schematic of a general-purpose computer system 100 suitable for practicing the methods described herein. The computer system 100, shown as a self-contained unit but not necessarily so limited, comprises at least one data processing unit (CPU) 102, a memory 104, which will typically include both high speed random access memory as well as non-volatile memory (such as one or more magnetic disk drives) but may be simply flash memory, a user interface 108, optionally a disk 110 controlled by a disk controller 112, and at least one optional network or other communication interface card 114 for communicating with other computers as well as other devices. At least the CPU 102, memory 104, user interface 108, disk controller where present, and network interface card, communicate with one another via at least one communication bus 106.

Memory 104 stores procedures and data, typically including: an operating system 140 for providing basic system services; application programs 152 such as user level programs for viewing and manipulating data, evaluating formulae for the purpose of diagnosing a test subject; authoring tools for assisting with the writing of computer programs; a file system 142, a user interface controller 144 for handling communications with a user via user interface 108, and optionally one or more databases 146 for storing data of the invention and other information, optionally a graphics controller 148 for controlling display of data, and optionally a floating point coprocessor 150 dedicated to carrying out mathematical operations. The methods of the invention may also draw upon functions contained in one or more dynamically linked libraries, not shown in FIG. 1, but stored either in Memory 104, or on disk 110, or accessible via network interface connection 114.

User interface 108 may comprise a display 128, a mouse 126, and a keyboard 130. Although shown as separate components in FIG. 1, one or more of these user interface components can be integrated with one another in embodiments such as handheld computers. Display 128 may be a cathode ray tube (CRT), or flat-screen display such as an LCD based on active matrix or TFT embodiments, or may be an electroluminescent display, based on light emitting organic molecules such as conjugated small molecules or polymers. Other embodiments of a user interface not shown in FIG. 1 include, e.g., several buttons on a keypad, a card-reader, a touch-screen with or without a dedicated touching device, a trackpad, a trackball, or a microphone used in conjunction with voice-recognition software, or any combination thereof, or a security-device such as a fingerprint sensor or a retinal scanner that prohibits an unauthorized user from accessing data and programs stored in system 100.

System 100 may also be connected to an output device such as a printer (not shown), either directly through a dedicated printer cable connected to a serial or USB port, or wirelessly, or via a network connection.

The database 146 may instead, optionally, be stored on disk 110 in circumstances where the amount of data in the database is too great to be efficiently stored in memory 104. The database may also instead, or in part, be stored on one or more remote computers that communicate with computer system 100 through network interface connection 114.

The network interface 134 may be a connection to the internet or to a local area network via a cable and modem, or ethernet, firewire, or USB connectivity, or a digital subscriber line. Preferably the computer network connection is wireless, e.g., utilizing CDMA, GSM, or GPRS, or bluetooth, or standards such as 802.11a, 802.11b, or 802.11g.

It would be understood that various embodiments and configurations and distributions of the components of system 10 across different devices and locations are consistent with practice of the methods described herein. For example, a user may use a handheld embodiment that accepts data from a test subject, and transmits that data across a network connection to another device or location where the data is analyzed according to a formulae described herein. A result of such an analysis can be stored at the other location and/or additionally transmitted back to the handheld embodiment. In such a configuration, the act of accepting data from a test subject can include the act of a user inputting the information. The network connection can include a web-based interface to a remote site at, for example, a healthcare provider. Alternatively, system 10 can be a device such as a handheld device that accepts data from the test subject, analyzes the data, such as by inputting the data into a formula as further described herein, and generating a result that is displayed to the user. The result can then be, optionally, transmitted back to a remote location via a network interface such as a wireless interface. System 100 may further be configured to permit a user to transmit by e-mail results of an analysis directly to some other party, such as a healthcare provider, or a diagnostic facility, or a patient.

In one aspect of the invention there is provided a method of determining whether a subject is at an increased risk of having colorectal cancer relative to the general population. The method comprises obtaining a test biological sample of blood from the subject; for each of a set of genes selected from the group consisting of ANXA3, CLEC4D, LMNB1, PRRG4, TNFAIP6 and VNN1, determining the amount of RNA encoded by the gene in the test biological sample; comparing the determined amount of RNA for each these genes with the amount in one or more control biological samples of blood; and concluding or determining that the subject is at increased risk, average risk or decreased risk of having colorectal cancer relative to the general population if the amount of RNA encoded by each gene in the test biological sample is higher than in the control biological samples for genes ANXA3, CLEC4D, LMNB1, PRRG4, TNFAIP6 and VNN1, and lower for IL2RB.

A test subject would be considered as being at "increased risk" of having or developing colorectal cancer if the amount of RNA encoded by ANXA3, CLEC4D, LMNB1, PRRG4, TNFAIP6 and/or VNN1 present in the test biological sample is higher than that seen in the control samples to an approximate extent (plus or minus 10%) seen in the working examples herein. A test subject would be considered as being at "increased risk" of having or developing colorectal cancer if the amount of RNA encoded by IL2RB present in the test biological sample is lower than that seen in the control samples to an approximate extent (plus or minus 10%) seen in the working examples herein.

A combination of marker genes of the invention, such as ANXA3, CLEC4D, LMNB1, PRRG4, VNN1, and IL2RB, can be used together with the known CRC prevalence rate to determine useful thresholds for stratifying the probability of having colorectal cancer in an average risk population. Using the combined training/blind set (IL2RB duplex) described in the Examples, an increased probability threshold can be selected to identify a sub-population with a colorectal cancer occurrence rate of 1.5%, a 3-fold increase over the base disease prevalence rate; this threshold reflects the same relative risk associated with having a first degree relative with colorectal cancer. A decreased probability threshold reflecting a sensitivity for colorectal cancer detection of, for example, 80%, 75%, 70%, 65%, can be selected to identify a lower-than-average probability sub-population. This approach can be used to stratify patients into an increased probability group, a decreased probability, and an average probability group.

One of ordinary skill in the art will be able to determine directly from the literature, or will be able to calculate from available statistical data, a suitable prevalence rate of colorectal cancer for practicing embodiments of the invention. For example, the prevalence rate for colorectal cancer in the average risk population over 50 years of age has been determined to be 0.7% (see for example Imperiale T F. et al., 2004. Colorectal Cancer Study Group. Fecal DNA versus fecal occult blood for colorectal-cancer screening in an average-risk population. New Engl J Med 351:2704-14).

It will be appreciated that components for practicing quantitative PCR according to the method of the invention may be assembled in a kit.

Thus, according to still another aspect of the invention there is provided a kit. The kit comprises packaging and contains, for each gene of a set of two or more of the following target genes of the invention: ACTB, ANXA3, CLEC4D, IL2RB, LMNB1, PRRG4, TNFAIP6 and VNN1; a primer set capable of generating an amplification product of DNA complementary to RNA encoded, in a human subject, only by the gene.

In various aspects of the kit of the invention, the set of genes may be any combination of two or more of the target genes of the invention, as described hereinabove and in the Examples section, below.

In one aspect of the invention, the kit further contains two or more of the following components: a thermostable polymerase, a reverse transcriptase, deoxynucleotide triphosphates, nucleotide triphosphates and enzyme buffer.

In another aspect of the invention, the kit further contains at least one labeled probe capable of selectively hybridizing to either a sense or an antisense strand of the amplification product.

In yet another aspect of the invention, the kit further contains a computer-readable medium of the invention.

In one aspect, the kit is identified in print in or on the packaging as being for determining a probability that a test subject has colorectal cancer, for example, a probability that a test subject has colorectal cancer as opposed to not having colorectal cancer.

In another aspect, the kit is identified in print in or on the packaging as being for classifying a test subject as being more likely to have colorectal cancer than to not have colorectal cancer, and/or as being more likely to not have colorectal cancer than to have colorectal cancer.

In a further aspect, the kit is identified in print in or on the packaging as being for determining whether a test subject is at an increased risk of having colorectal cancer relative to the general population.

In various aspects of the kit of the invention, the set of genes may be any combination of two or more of the target genes of the invention.

Sets of genes of the invention which consist of two or more of ACTB, ANXA3, CLEC4D, IL2RB, LMNB1, PRRG4, TNFAIP6 and VNN1 include: ACTB, ANXA3, CLEC4D, IL2RB, LMNB1, PRRG4, TNFAIP6, VNN1; ACTB, ANXA3, CLEC4D, IL2RB, LMNB1, PRRG4, VNN1; ACTB, ANXA3, CLEC4D, IL2RB, PRRG4; ACTB, ANXA3, CLEC4D, IL2RB, LMNB1, PRRG4; ACTB, ANXA3, CLEC4D, IL2RB, PRRG4, VNN1; ACTB, ANXA3, IL2RB, LMNB1, PRRG4, VNN1; ACTB, ANXA3, CLEC4D, IL2RB, PRRG4, TNFAIP6; ACTB, ANXA3, IL2RB, LMNB1, PRRG4, TNFAIP6; ACTB, ANXA3, CLEC4D, IL2RB, LMNB1, PRRG4, TNFAIP6; ACTB, ANXA3, CLEC4D, IL2RB, PRRG4, TNFAIP6, VNN1; ACTB, ANXA3, IL2RB, LMNB1, PRRG4, TNFAIP6, VNN1; ACTB, ANXA3, IL2RB, LMNB1, PRRG4; ACTB, IL2RB, PRRG4, VNN1; ACTB, ANXA3, IL2RB, PRRG4, VNN1; ACTB, CLEC4D, IL2RB, PRRG4, VNN1; ACTB, IL2RB, LMNB1, PRRG4, VNN1; ACTB, CLEC4D, IL2RB, LMNB1, PRRG4, VNN1; ACTB, ANXA3, IL2RB, PRRG4, TNFAIP6; ACTB, IL2RB, PRRG4, TNFAIP6, VNN1; ACTB, ANXA3, IL2RB; ACTB, IL2RB, PRRG4, TNFAIP6, VNN1; ACTB, CLEC4D, IL2RB; ACTB, IL2RB, LMNB1, PRRG4, TNFAIP6, VNN1; ACTB, CLEC4D, IL2RB, PRRG4, TNFAIP6, VNN1; ACTB, ANXA3, IL2RB, LMNB1; ACTB, CLEC4D, IL2RB, LMNB1, PRRG4, TNFAIP6, VNN1; ACTB, CLEC4D, IL2RB, LMNB1, PRRG4, VNN1; LMNB1, PRRG4, TNFAIP6, VNN1; ACTB, IL2RB, PRRG4; ACTB, ANXA3, IL2RB, PRRG4; ACTB, CLEC4D, IL2RB, PRRG4; ACTB, IL2RB, LMNB1, PRRG4; ACTB, CLEC4D, IL2RB, LMNB1, PRRG4; ACTB, IL2RB, PRRG4, TNFAIP6; ACTB, CLEC4D, IL2RB, PRRG4, TNFAIP6; ACTB, IL2RB, LMNB1, PRRG4, TNFAIP6; ACTB, CLEC4D, IL2RB, LMNB1, PRRG4, TNFAIP6; ACTB, ANXA3, IL2RB, VNN1; ACTB, ANXA3, CLEC4D, IL2RB, VNN1; ACTB, ANXA3, IL2RB, LMNB1, VNN1; ACTB, ANXA3, CLEC4D, IL2RB, LMNB1, VNN1; ACTB, ANXA3, CLEC4D, LMNB1, PRRG4, VNN1; ACTB, ANXA3, IL2RB, TNFAIP6, VNN1; ACTB, ANXA3, CLEC4D, IL2RB, TNFAIP6, VNN1; ACTB, ANXA3, IL2RB, LMNB1, TNFAIP6, VNN1; ACTB, ANXA3, CLEC4D, IL2RB, LMNB1, TNFAIP6, VNN1; ACTB, ANXA3, CLEC4D, LMNB1, PRRG4, TNFAIP6, VNN1; ACTB, ANXA3, CLEC4D, IL2RB; ACTB, ANXA3, CLEC4D, IL2RB; ACTB, ANXA3, IL2RB, LMNB1; ACTB, ANXA3, CLEC4D, IL2RB, LMNB1; ACTB, ANXA3, CLEC4D, LMNB1, PRRG4; ACTB, CLEC4D, IL2RB, LMNB1, VNN1; ACTB, ANXA3, IL2RB, TNFAIP6; ACTB, ANXA3, CLEC4D, IL2RB, TNFAIP6; ACTB, ANXA3, IL2RB, LMNB1, TNFAIP6; ACTB, ANXA3, CLEC4D, IL2RB, LMNB1, TNFAIP6; ACTB, ANXA3, CLEC4D, LMNB1, PRRG4, TNFAIP6; ACTB, IL2RB, LMNB1, TNFAIP6, VNN1; ACTB, CLEC4D, IL2RB, LMNB1, TNFAIP6, VNN1; ACTB, IL2RB, LMNB1, VNN1; ACTB, ANXA3, LMNB1, PRRG4, VNN1; ACTB, ANXA3, LMNB1, PRRG4, TNFAIP6, VNN1; ACTB, ANXA3, CLEC4D, PRRG4; ACTB, ANXA3, LMNB1, PRRG4; ACTB, CLEC4D, IL2RB, VNN1; ACTB, ANXA3, CLEC4D, PRRG4, VNN1; ACTB, IL2RB, LMNB1, TNFAIP6; ACTB, CLEC4D, IL2RB, LMNB1, TNFAIP6; ACTB, ANXA3, CLEC4D, PRRG4, TNFAIP6; ACTB, ANXA3, LMNB1, PRRG4, TNFAIP6; ACTB, IL2RB, TNFAIP6, VNN1; ACTB, ANXA3, CLEC4D, PRRG4, TNFAIP6, VNN1; ACTB, ANXA3, CLEC4D, PRRG4, TNFAIP6, VNN1; ACTB, IL2RB, LMNB1; ACTB, CLEC4D, IL2RB, LMNB1; ACTB, IL2RB, VNN1; ACTB, ANXA3, CLEC4D; ACTB, ANXA3, LMNB1; ACTB, ANXA3, VNN1; ACTB, ANXA3, TNFAIP6; ACTB, ANXA3, CLEC4D, TNFAIP6; ACTB, IL2RB, TNFAIP6; ACTB, CLEC4D, IL2RB, TNFAIP6; ACTB, ANXA3, LMNB1, TNFAIP6; ACTB, ANXA3, TNFAIP6, VNN1; ACTB, CLEC4D, IL2RB; ACTB, PRRG4, VNN1; ACTB, CLEC4D, PRRG4, VNN1; ACTB, LMNB1, PRRG4, VNN1; ACTB, CLEC4D, LMNB1, PRRG4, VNN1; ACTB, PRRG4, TNFAIP6, VNN1; ACTB, CLEC4D, PRRG4, TNFAIP6, VNN1; ACTB, LMNB1, PRRG4, TNFAIP6, VNN1; ACTB, CLEC4D, LMNB1, PRRG4, TNFAIP6, VNN1; ACTB, PRRG4; ACTB, CLEC4D, PRRG4; ACTB, LMNB1, PRRG4; ACTB, CLEC4D, LMNB1, PRRG4; ACTB, PRRG4, TNFAIP6; ACTB, CLEC4D, PRRG4, TNFAIP6; ACTB, LMNB1, PRRG4, TNFAIP6; ACTB, CLEC4D, LMNB1, PRRG4, TNFAIP6; ACTB, LMNB1, TNFAIP6, VNN1; ACTB, CLEC4D, VNN1; ACTB, LMNB1, VNN1; ACTB, CLEC4D, LMNB1, VNN1; ACTB, LMNB1, TNFAIP6; ACTB, LMNB1, TNFAIP6; ACTB, TNFAIP6, VNN1; ACTB, CLEC4D, TNFAIP6, VNN1; ACTB, CLEC4D, LMNB1, TNFAIP6, VNN1; ACTB, LMNB1; ACTB, CLEC4D, LMNB1; ACTB, VNN1; ACTB, CLEC4D, TNFAIP6; ACTB, TNFAIP6; ACTB, CLEC4D; and ACTB, IL2RB.

In one aspect of the kit of the invention, the set of one or more genes consists of a housekeeping gene such as ACTB, and one or more of the colorectal cancer marker genes: ANXA3, CLEC4D, IL2RB, LMNB1, PRRG4, TNFAIP6 and VNN1.

In one aspect of the kit of the invention, the set of one or more genes consists of ACTB and ANXA3.

In one aspect of the kit of the invention, the set of one or more genes consists of ACTB and CLEC4D.

In one aspect of the kit of the invention, the set of one or more genes consists of ACTB and IL2RB.

In one aspect of the kit of the invention, the set of one or more genes consists of ACTB and LMNB1.

In one aspect of the kit of the invention, the set of one or more genes consists of ACTB and PRRG4.

In one aspect of the kit of the invention, the set of one or more genes consists of ACTB and TNFAIP6.

In one aspect of the kit of the invention, the set of one or more genes consists of ACTB and VNN1.

In another aspect of the kit of the invention, the set of one or more genes consists of IL2RB, and one or more of the colorectal cancer marker genes: ANXA3, CLEC4D, LMNB1, PRRG4, TNFAIP6 and VNN1.

In one aspect of the kit of the invention, the set of one or more genes consists of IL2RB and ANXA3.

In one aspect of the kit of the invention, the set of one or more genes consists of IL2RB and CLEC4D.

In one aspect of the kit of the invention, the set of one or more genes consists of IL2RB and LMNB1.

In one aspect of the kit of the invention, the set of one or more genes consists of IL2RB and PRRG4.

In one aspect of the kit of the invention, the set of one or more genes consists of IL2RB and TNFAIP6.

In one aspect of the kit of the invention, the set of one or more genes consists of IL2RB and VNN1.

In one aspect of the invention, the kit contains a primer having a nucleotide sequence identified as SEQ ID NO: 1, and a primer having a nucleotide sequence identified as SEQ ID NO: 2.

In one aspect of the invention, the kit contains a primer having a nucleotide sequence identified as SEQ ID NO: 1, and a primer having a nucleotide sequence identified as SEQ ID NO: 2 and the kit further contains a labeled probe which comprises a polynucleotide having a nucleic acid sequence identified as SEQ ID NO: 3.

In one aspect of the invention, the kit contains a primer having a nucleotide sequence identified as SEQ ID NO: 10, and a primer having a nucleotide sequence identified as SEQ ID NO: 11.

In one aspect of the invention, the kit contains a primer having a nucleotide sequence identified as SEQ ID NO: 10, and a primer having a nucleotide sequence identified as SEQ ID NO: 11, and the kit further contains a labeled probe which comprises a polynucleotide having a nucleic acid sequence identified as SEQ ID NO: 12.

In one aspect of the invention, the kit contains a primer having a nucleotide sequence identified as SEQ ID NO: 19, and a primer having a nucleotide sequence identified as SEQ ID NO: 20.

In one aspect of the invention, the kit contains a primer having a nucleotide sequence identified as SEQ ID NO: 19, and a primer having a nucleotide sequence identified as SEQ ID NO: 20 and the kit further contains a labeled probe which comprises a polynucleotide having a nucleic acid sequence identified as SEQ ID NO: 21.

In one aspect of the invention, for example, the kit contains a primer having a nucleotide sequence identified as SEQ ID NO: 28, and a primer having a nucleotide sequence identified as SEQ ID NO: 29.

In one aspect of the invention, for example, the kit contains a primer having a nucleotide sequence identified as SEQ ID NO: 28, and a primer having a nucleotide sequence identified as SEQ ID NO: 29 and the kit further contains a labeled probe which comprises a polynucleotide having a nucleic acid sequence identified as SEQ ID NO: 30.

In one aspect of the invention, the kit contains a primer having a nucleotide sequence identified as SEQ ID NO: 37, and a primer having a nucleotide sequence identified as SEQ ID NO: 38.

In one aspect of the invention, the kit contains a primer having a nucleotide sequence identified as SEQ ID NO: 37, and a primer having a nucleotide sequence identified as SEQ ID NO: 38 and the kit further contains a labeled probe which comprises a polynucleotide having a nucleic acid sequence identified as SEQ ID NO: 39.

In one aspect of the invention, the kit contains a primer having a nucleotide sequence identified as SEQ ID NO: 46, and a primer having a nucleotide sequence identified as SEQ ID NO: 47.

In one aspect of the invention, the kit contains a primer having a nucleotide sequence identified as SEQ ID NO: 46, and a primer having a nucleotide sequence identified as SEQ ID NO: 47, and the kit further contains a labeled probe which comprises a polynucleotide having a nucleic acid sequence identified as SEQ ID NO: 48.

In one aspect of the invention, the kit contains a primer having a nucleotide sequence identified as SEQ ID NO: 55, and a primer having a nucleotide sequence identified as SEQ ID NO: 56.

In one aspect of the invention, the kit contains a primer having a nucleotide sequence identified as SEQ ID NO: 55, and a primer having a nucleotide sequence identified as SEQ ID NO: 56 and the kit further contains a labeled probe which comprises a polynucleotide having a nucleic acid sequence identified as SEQ ID NO: 57.

Further, non-limiting, specific aspects of the invention include the following:

One aspect of the invention disclosed herein is a method of determining a probability that a human test subject has colorectal cancer as opposed to not having colorectal cancer, the method comprising: the steps of (a) determining a level of RNA encoded by a ANXA3 gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a method of determining a probability that a human test subject has colorectal cancer as opposed to not having colorectal cancer, the method comprising the steps of (a) determining a level of RNA encoded by a CLEC4D gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a method of determining a probability that a human test subject has colorectal cancer as opposed to not having colorectal cancer, the method comprising the steps of (a) determining a level of RNA encoded by a IL2RB gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a method of determining a probability that a human test subject has colorectal cancer as opposed to not having colorectal cancer, the method comprising the steps of: (a) determining a level of RNA encoded by a LMNB1 gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a method of determining a probability that a human test subject has colorectal cancer as opposed to not having colorectal cancer, the method comprising the steps of: (a) determining a level of RNA encoded by a PRRG4 gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a method of determining a probability that a human test subject has colorectal cancer as opposed to not having colorectal cancer, the method comprising the steps of: (a) determining a level of RNA encoded by a TNFAIP6 gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a method of determining a probability that a human test subject has colorectal cancer as opposed to not having colorectal cancer, the method comprising the steps of: (a) determining a level of RNA encoded by a VNN1 gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, where the probability that the test data corresponds to the positive control data and not to the negative control data represents the probability that the test subject has colorectal cancer as opposed to not having colorectal cancer.

An embodiment of aspects of the invention disclosed herein includes that the determining of the level of RNA encoded by the gene in blood of the test subject be effected by determining the level of RNA encoded by the gene in a blood sample isolated from the test subject. An embodiment of aspects of the invention disclosed herein includes the further step of determining the levels of RNA encoded by the gene in blood of a population of human subjects having colorectal cancer, thereby providing the positive control data representing the levels of RNA encoded by the gene in blood of human control subjects having colorectal cancer, and determining levels of RNA encoded by the gene in blood of a population of human subjects not having colorectal cancer, thereby providing the negative control data representing the levels of RNA encoded by the gene in blood of human control subjects not having colorectal cancer. An embodiment of aspects of the invention disclosed herein includes that the level of RNA encoded by the gene in blood of the test subject is determined via quantitative reverse transcriptase-polymerase chain reaction analysis. An embodiment of aspects of the invention disclosed herein includes that the level of RNA encoded by the gene in blood of the test subject and the levels of RNA encoded by the gene in blood of the control subjects are determined via the same method. An embodiment of aspects of the invention disclosed herein includes that the determining of the probability that the test data corresponds to the positive control data and not to the negative control data is effected by applying to the test data a mathematical model derived from the positive control data and from the negative control data, and where the mathematical model is for determining the probability that data representing a level of RNA encoded by the gene corresponds to the positive control data and not to the negative control data. An embodiment of aspects of the invention disclosed herein includes that the level of RNA encoded by the gene in blood of the test subject is determined as a ratio to a level of RNA encoded by ACTB in blood of the test subject. An aspect of this latter embodiment includes that the level of RNA encoded by the gene in blood of the test subject and the level of RNA encoded by ACTB in blood of the test subject are determined via duplex quantitative reverse transcriptase-polymerase chain reaction analysis of RNA encoded by the gene and of RNA encoded by ACTB. An embodiment of aspects of the invention disclosed herein includes that the level of RNA encoded by the gene in blood of the test subject is determined as a ratio to a level of RNA encoded by IL2RB in blood of the test subject. An aspect of this latter embodiment includes that the level of RNA encoded by the gene in blood of the test subject and the level of RNA encoded by IL2RB in blood of the test subject are determined via duplex quantitative reverse transcriptase-polymerase chain reaction analysis of RNA encoded by the gene and of RNA encoded by IL2RB.

An aspect of the invention disclosed herein is a computer-based method of determining a probability that a human test subject has colorectal cancer as opposed to not having colorectal cancer, from test data representing a level of RNA encoded by a ANXA3 gene in blood of the test subject, the method comprising computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, where the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a computer-based method of determining a probability that a human test subject has colorectal cancer as opposed to not having colorectal cancer, from test data representing a level of RNA encoded by a ANXA3 gene in blood of the test subject, the method comprising computer-implemented steps of: inputting, to a computer, test data representing a level of RNA encoded by a CLEC4D gene in blood of the test subject; and causing the computer to apply to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, where the mathematical model is for determining a probability that data representing a level of RNA encoded by the gene corresponds to the positive control data and not to the negative control data; and (b) outputting the probability that data representing a level of RNA encoded by the gene corresponds to the negative control data, where the probability that the test data corresponds to the positive control data and not to the negative control data represents the probability that the test subject has colorectal cancer as opposed to not having colorectal cancer. Another aspect of the invention disclosed herein is a computer-based method of determining a probability that a human test subject has colorectal cancer as opposed to not having colorectal cancer, from test data representing a level of RNA encoded by a ANXA3 gene in blood of the test subject, the method comprising computer-implemented steps of: inputting, to a computer, test data representing a level of RNA encoded by a IL2RB gene in blood of the test subject; and causing the computer to apply to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, where the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a computer-based method of determining a probability that a human test subject has colorectal cancer as opposed to not having colorectal cancer, from test data representing a level of RNA encoded by a ANXA3 gene in blood of the test subject, the method comprising computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, where the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a computer-based method of determining a probability that a human test subject has colorectal cancer as opposed to not having colorectal cancer, from test data representing a level of RNA encoded by a ANXA3 gene in blood of the test subject, the method comprising computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, where the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a computer-based method of determining a probability that a human test subject has colorectal cancer as opposed to not having colorectal cancer, from test data representing a level of RNA encoded by a ANXA3 gene in blood of the test subject, the method comprising computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, where the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, where the probability that the test data corresponds to the positive control data and not to the negative control data represents the probability that the test subject has colorectal cancer as opposed to not having colorectal cancer. Another aspect of the invention disclosed herein is a computer-based method of determining a probability that a human test subject has colorectal cancer as opposed to not having colorectal cancer, from test data representing a level of RNA encoded by a ANXA3 gene in blood of the test subject, the method comprising computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, where the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, where the probability that the test data corresponds to the positive control data and not to the negative control data represents the probability that the test subject has colorectal cancer as opposed to not having colorectal cancer.

An embodiment of the invention's computer based methods includes where the level of RNA encoded by the gene in blood of the test subject is determined via quantitative reverse transcriptase-polymerase chain reaction analysis. An embodiment of computer based methods of the invention includes where the level of RNA encoded by the gene in blood of the test subject and the levels of RNA encoded by the gene in blood of the control subjects are determined via the same method. An embodiment of each of computer based methods of the invention includes where the level of RNA encoded by the gene in blood of the test subject is determined as a ratio to a level of RNA encoded by ACTB in blood of the test subject. An embodiment of computer based methods of the invention includes where the level of RNA encoded by the gene in blood of the test subject and the level of RNA encoded by ACTB in blood of the test subject are determined via duplex quantitative reverse transcriptase-polymerase chain reaction analysis of RNA encoded by the gene and of RNA encoded by ACTB. An embodiment of each of the computer based methods of the invention includes where the level of RNA encoded by the gene in blood of the test subject is determined as a ratio to a level of RNA encoded by IL2RB in blood of the test subject. In a further embodiment the level of RNA encoded by the gene in blood of the test subject and the level of RNA encoded by IL2RB in blood of the test subject are determined via duplex quantitative reverse transcriptase-polymerase chain reaction analysis of RNA encoded by the gene and of RNA encoded by IL2RB.

Another aspect of the invention disclosed herein is a method of determining a probability that a human test subject has colorectal cancer as opposed to not having colorectal cancer, the method comprising, for each gene of a set of one or more genes selected from the group consisting of ANXA3, CLEC4D, IL2RB, LMNB1, PRRG4, TNFAIP6 and VNN1: comprising the steps of: (a) determining a level of RNA encoded by the gene in blood of the test subject, thereby generating test data; (b) providing positive control data representing levels of RNA encoded by the gene in blood of human control subjects having colorectal cancer, and providing negative control data representing levels of RNA encoded by the gene in blood of human control subjects not having colorectal cancer; and (c) determining a probability that the test data corresponds to the positive control data and not to the negative control data, where the probability that the test data corresponds to the positive control data and not to the negative control data represents the probability that the test subject has colorectal cancer as opposed to not having colorectal cancer. An embodiment of this aspect of the invention disclosed herein is where the determining of the level of RNA encoded by the gene in blood of the test subject is effected by determining the level of RNA encoded by the gene in a blood sample isolated from the test subject. An embodiment of this aspect of the invention disclosed herein further comprises determining levels of RNA encoded by the gene in blood of a population of human subjects having colorectal cancer, thereby providing the positive control data representing the levels of RNA encoded by the gene in blood of human control subjects having colorectal cancer, and determining levels of RNA encoded by the gene in blood of a population of human subjects not having colorectal cancer, thereby providing the negative control data representing the levels of RNA encoded by the gene in blood of human control subjects not having colorectal cancer. An embodiment of this aspect of the invention disclosed herein is where the level of RNA encoded by the gene in blood of the test subject is determined via quantitative reverse transcriptase-polymerase chain reaction analysis. An embodiment of this aspect of the invention disclosed herein is where the level of RNA encoded by the gene in blood of the test subject and the levels of RNA encoded by the gene in blood of the control subjects are determined via the same method. An embodiment of this aspect of the invention disclosed herein is where the determining of the probability that the test data corresponds to the positive control data and not to the negative control data is effected by applying to the test data a mathematical model derived from the positive control data and from the negative control data, and where the mathematical model is for determining the probability that data representing a level of RNA encoded by the gene corresponds to the positive control data and not to the negative control data. An embodiment of this aspect of the invention disclosed herein is where the level of RNA encoded by the gene in blood of the test subject is determined as a ratio to a level of RNA encoded by ACTB in blood of the test subject. In a further embodiment, the level of RNA encoded by the gene in blood of the test subject and the level of RNA encoded by ACTB in blood of the test subject are determined via duplex quantitative reverse transcriptase-polymerase chain reaction analysis of RNA encoded by the gene and of RNA encoded by ACTB. An embodiment of this aspect of the invention disclosed herein is where the set of one or more genes is a set of one or more genes selected from the group consisting of ANXA3, CLEC4D, LMNB1, PRRG4, TNFAIP6 and VNN1, and where the level of RNA encoded by the gene in blood of the test subject is determined as a ratio to a level of RNA encoded by IL2RB in blood of the test subject. In a further embodiment, the level of RNA encoded by the gene in blood of the test subject and the level of RNA encoded by IL2RB in blood of the test subject are determined via duplex quantitative reverse transcriptase-polymerase chain reaction analysis of RNA encoded by the gene and of RNA encoded by IL2RB.

Another aspect of the invention disclosed herein is a computer-based method of determining a probability that a human test subject has colorectal cancer as opposed to not having colorectal cancer, from test data representing a level of RNA encoded by the gene in blood of the test subject, the method comprising, for each gene of a set of one or more genes selected from the group consisting of ANXA3, CLEC4D, IL2RB, LMNB1, PRRG4, TNFAIP6 and VNN1, computer-implemented steps of: (a) applying to the test data a mathematical model derived from positive control data representing levels of RNA encoded by the gene in blood of human control subjects having colorectal cancer, and from negative control data representing levels of RNA encoded by the gene in blood of human control subjects not having colorectal cancer, where the mathematical model is for determining a probability that data representing a level of RNA encoded by the gene corresponds to the positive control data and not to the negative control data; and (b) outputting the probability that data representing a level of RNA encoded by the gene corresponds to the positive control data and not to the negative control data, where the probability that the test data corresponds to the positive control data and not to the negative control data represents the probability that the test subject has colorectal cancer as opposed to not having colorectal cancer. In an embodiment of this aspect of the invention disclosed herein is where the level of RNA encoded by the gene in blood of the test subject is determined via quantitative reverse transcriptase-polymerase chain reaction analysis. In an embodiment of this aspect of the invention disclosed herein is where the level of RNA encoded by the gene in blood of the test subject and the levels of RNA encoded by the gene in blood of the control subjects are determined via the same method. In an embodiment of this aspect of the invention disclosed herein is where the level of RNA encoded by the gene in blood of the test subject is determined as a ratio to a level of RNA encoded by ACTB in blood of the test subject. In a further embodiment of this aspect of the invention disclosed herein is where the level of RNA encoded by the gene in blood of the test subject and the level of RNA encoded by ACTB in blood of the test subject are determined via duplex quantitative reverse transcriptase-polymerase chain reaction analysis of RNA encoded by the gene and of RNA encoded by ACTB. In an embodiment of this aspect of the invention disclosed herein is where the set of one or more genes is a set of one or more genes selected from the group consisting of ANXA3, CLEC4D, LMNB1, PRRG4, TNFAIP6 and VNN1, and where the level of RNA encoded by the gene in blood of the test subject is determined as a ratio to a level of RNA encoded by IL2RB in blood of the test subject. In a further embodiment of this aspect of the invention disclosed herein, the level of RNA encoded by the gene in blood of the test subject and the level of RNA encoded by IL2RB in blood of the test subject are determined via duplex quantitative reverse transcriptase-polymerase chain reaction analysis of RNA encoded by the gene and of RNA encoded by IL2RB. In an embodiment of this aspect of the invention disclosed herein is where the set of one or more genes consists of PRRG4. In an embodiment of this aspect of the invention disclosed herein is where the set of one or more genes consists of IL2RB and PRRG4.

Another aspect of the invention disclosed herein is a kit comprising packaging and containing, for each gene of a set of two or more genes selected from the group consisting of ACTB, ANXA3, CLEC4D, IL2RB, LMNB1, PRRG4, TNFAIP6 and VNN1, a primer set capable of generating an amplification product of DNA complementary to RNA encoded, in a human subject, only by the gene. An embodiment of this aspect of the invention disclosed herein is where the kit further contains two or more components selected from the group consisting of a thermostable polymerase, a reverse transcriptase, deoxynucleotide triphosphates, nucleotide triphosphates and enzyme buffer. An embodiment of this aspect of the invention disclosed herein is where the kit further contains at least one labelled probe capable of selectively hybridizing to either a sense or an antisense strand of the amplification product. An embodiment of this aspect of the invention disclosed herein is where the kit further contains a computer-readable medium having instructions stored thereon that are operable when executed by a computer for applying a mathematical model to test data representing a level of RNA encoded by the gene in blood of a human test subject, where the mathematical model is derived from positive control data representing levels of RNA encoded by the gene in blood of human control subjects having colorectal cancer, and from negative control data representing levels of RNA encoded by the gene in blood of human control subjects not having colorectal cancer, where the mathematical model is for determining a probability that data representing a level of RNA encoded by the gene corresponds to the positive control data and not to the negative control data, and where the probability that the test data corresponds to the positive control data and not to the negative control data represents the probability that the test subject has colorectal cancer as opposed to not having colorectal cancer. An embodiment of this aspect of the invention disclosed herein is where the set of one or more genes of the kit consists of ACTB and one or more genes selected from the group consisting of ANXA3, CLEC4D, IL2RB, LMNB1, PRRG4, TNFAIP6 and VNN1. An embodiment of this aspect of the invention disclosed herein is where the set of one or more genes of one or more genes of the kit consists of ACTB and ANXA3. An embodiment of this aspect of the invention disclosed herein is where the set of one or more genes of one or more genes of the kit consists of ACTB and CLEC4D. An embodiment of this aspect of the invention disclosed herein is where the set of one or more genes of one or more genes of the kit consists of ACTB and IL2RB. An embodiment of this aspect of the invention disclosed herein is where the set of one or more genes of one or more genes of the kit consists of ACTB and LMNB1. An embodiment of this aspect of the invention disclosed herein is where the set of one or more genes of one or more genes of the kit consists of ACTB and PRRG4. An embodiment of this aspect of the invention disclosed herein is where the set of one or more genes of one or more genes of the kit consists of ACTB and TNFAIP6. An embodiment of this aspect of the invention disclosed herein is where the set of one or more genes of one or more genes of the kit consists of ACTB and VNN1. An embodiment of this aspect of the invention disclosed herein is where the set of one or more genes of one or more genes of the kit consists of IL2RB and one or more genes selected from the group consisting of ANXA3, CLEC4D, LMNB1, PRRG4, TNFAIP6 and VNN1. An embodiment of this aspect of the invention disclosed herein is where the set of one or more genes of one or more genes of the kit consists of IL2RB and ANXA3. An embodiment of this aspect of the invention disclosed herein is where the set of one or more genes of one or more genes of the kit consists of \ IL2RB and CLEC4D. An embodiment of this aspect of the invention disclosed herein is where the set of one or more genes of one or more genes of the kit consists of IL2RB and LMNB1. An embodiment of this aspect of the invention disclosed herein is where the set of one or more genes of one or more genes of the kit consists of IL2RB and PRRG4. An embodiment of this aspect of the invention disclosed herein is where the set of one or more genes of one or more genes of the kit consists of IL2RB and TNFAIP6. An embodiment of this aspect of the invention disclosed herein is where the set of one or more genes of one or more genes of the kit consists of IL2RB and VNN1.

Another aspect of the invention disclosed herein is a method of classifying a human test subject as more likely to have colorectal cancer than to not have colorectal cancer, the method comprising: (a) determining a level of RNA encoded by a ANXA3 gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, where an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer. Another aspect of the invention disclosed herein is a method of classifying a human test subject as more likely to have colorectal cancer than to not have colorectal cancer, the method comprising: (a) determining a level of RNA encoded by a CLEC4D gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, where an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer. Another aspect of the invention disclosed herein is a method of classifying a human test subject as more likely to have colorectal cancer than to not have colorectal cancer, the method comprising: (a) determining a level of RNA encoded by a IL2RB gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, where an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer. Another aspect of the invention disclosed herein is a method of classifying a human test subject as more likely to have colorectal cancer than to not have colorectal cancer, the method comprising: (a) determining a level of RNA encoded by a LMNB1 gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, where an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer. Another aspect of the invention disclosed herein is a method of classifying a human test subject as more likely to have colorectal cancer than to not have colorectal cancer, the method comprising: (a) determining a level of RNA encoded by a PRRG4 gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, where an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer. Another aspect of the invention disclosed herein is a method of classifying a human test subject as more likely to have colorectal cancer than to not have colorectal cancer, the method comprising: (a) determining a level of RNA encoded by a TNFAIP6 gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, where an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer. Another aspect of the invention disclosed herein is a method of classifying a human test subject as more likely to have colorectal cancer than to not have colorectal cancer, the method comprising: (a) determining a level of RNA encoded by a VNN1 gene in blood of the test subject, thereby generating test data; (b) providing negative control data representing a level of RNA encoded by the gene in blood of human control subjects not having colorectal cancer; and (c) applying to the test data and to the negative control data a mathematical formula for generating a value indicating whether the level of RNA encoded by the gene in blood of the test subject is higher than the level of RNA encoded by the gene in blood of human control subjects not having colorectal cancer, where an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer.

An embodiment of the methods of classifying a human test subject as more likely to have colorectal cancer than to not have colorectal cancer of the invention includes determining of the level of RNA encoded by the gene in blood of the test subject is effected by determining the level of RNA encoded by the gene in a blood sample isolated from the test subject. An embodiment of the invention's methods of classifying a human test subject as more likely to have colorectal cancer than to not have colorectal cancer of the invention includes further determining levels of RNA encoded by the gene in blood of a population of human subjects not having colorectal cancer, thereby providing the negative control data representing the levels of RNA encoded by the gene in blood of human control subjects not having colorectal cancer. An embodiment of the invention's methods of classifying a human test subject as more likely to have colorectal cancer than to not have colorectal cancer of the invention includes where the level of RNA encoded by the gene in blood of the test subject is determined via quantitative reverse transcriptase-polymerase chain reaction analysis. An embodiment of the invention's methods of classifying a human test subject as more likely to have colorectal cancer than to not have colorectal cancer of the invention includes where the level of RNA encoded by the gene in blood of the test subject and the levels of RNA encoded by the gene in blood of the control subjects are determined via the same method. An embodiment of the invention's methods of classifying a human test subject as more likely to have colorectal cancer than to not have colorectal cancer of the invention includes where the level of RNA encoded by the gene in blood of the test subject is determined as a ratio to a level of RNA encoded by ACTB in blood of the test subject. In an aspect of this embodiment, the level of RNA encoded by the gene in blood of the test subject and the level of RNA encoded by ACTB in blood of the test subject are determined via duplex quantitative reverse transcriptase-polymerase chain reaction analysis of RNA encoded by the gene and of RNA encoded by ACTB. An embodiment of the invention's methods of classifying a human test subject as more likely to have colorectal cancer than to not have colorectal cancer includes where the level of RNA encoded by the gene in blood of the test subject is determined as a ratio to a level of RNA encoded by IL2RB in blood of the test subject, and/or where the level of RNA encoded by the gene in blood of the test subject and the level of RNA encoded by IL2RB in blood of the test subject are determined via duplex quantitative reverse transcriptase-polymerase chain reaction analysis of RNA encoded by the gene and of RNA encoded by IL2RB.

Another aspect of the invention disclosed herein is a computer-based method of classifying a human test subject as more likely to have colorectal cancer than to not have colorectal cancer, the method comprising computer-implemented steps of: (a) applying to test data representing a level of RNA encoded by a ANXA3 gene in blood of the test subject and to negative control data representing a level of RNA encoded by the gene in blood of human control subjects not having colorectal cancer a mathematical formula for generating a value indicating whether the level of RNA encoded by the gene in blood of the test subject is higher than the level of RNA encoded by the gene in blood of human control subjects not having colorectal cancer; and (b) outputting the value, where an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer. Another aspect of the invention disclosed herein is a computer-based method of classifying a human test subject as more likely to have colorectal cancer than to not have colorectal cancer, the method comprising computer-implemented steps of: (a) applying to test data representing a level of RNA encoded by a CLEC4D gene in blood of the test subject and to negative control data representing a level of RNA encoded by the gene in blood of human control subjects not having colorectal cancer a mathematical formula for generating a value indicating whether the level of RNA encoded by the gene in blood of the test subject is higher than the level of RNA encoded by the gene in blood of human control subjects not having colorectal cancer; and (b) outputting the value, where an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer. Another aspect of the invention disclosed herein is a computer-based method of classifying a human test subject as more likely to have colorectal cancer than to not have colorectal cancer, the method comprising computer-implemented steps of: (a) applying to test data representing a level of RNA encoded by a IL2RB gene in blood of the test subject and to negative control data representing a level of RNA encoded by the gene in blood of human control subjects not having colorectal cancer a mathematical formula for generating a value indicating whether the level of RNA encoded by the gene in blood of the test subject is higher than the level of RNA encoded by the gene in blood of human control subjects not having colorectal cancer; and (b) outputting the value, where an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer. Another aspect of the invention disclosed herein is a computer-based method of classifying a human test subject as more likely to have colorectal cancer than to not have colorectal cancer, the method comprising computer-implemented steps of: (a) applying to test data representing a level of RNA encoded by a LMNB1 gene in blood of the test subject and to negative control data representing a level of RNA encoded by the gene in blood of human control subjects not having colorectal cancer a mathematical formula for generating a value indicating whether the level of RNA encoded by the gene in blood of the test subject is higher than the level of RNA encoded by the gene in blood of human control subjects not having colorectal cancer; and (b) outputting the value, where an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer. Another aspect of the invention disclosed herein is a computer-based method of classifying a human test subject as more likely to have colorectal cancer than to not have colorectal cancer, the method comprising computer-implemented steps of: (a) applying to test data representing a level of RNA encoded by a PRRG4 gene in blood of the test subject and to negative control data representing a level of RNA encoded by the gene in blood of human control subjects not having colorectal cancer a mathematical formula for generating a value indicating whether the level of RNA encoded by the gene in blood of the test subject is higher than the level of RNA encoded by the gene in blood of human control subjects not having colorectal cancer; and (b) outputting the value, where an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer. Another aspect of the invention disclosed herein is a computer-based method of classifying a human test subject as more likely to have colorectal cancer than to not have colorectal cancer, the method comprising computer-implemented steps of: (a) applying to test data representing a level of RNA encoded by a TNFAIP6 gene in blood of the test subject and to negative control data representing a level of RNA encoded by the gene in blood of human control subjects not having colorectal cancer a mathematical formula for generating a value indicating whether the level of RNA encoded by the gene in blood of the test subject is higher than the level of RNA encoded by the gene in blood of human control subjects not having colorectal cancer; and (b) outputting the value, where an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer. Another aspect of the invention disclosed herein is a computer-based method of classifying a human test subject as more likely to have colorectal cancer than to not have colorectal cancer, the method comprising computer-implemented steps of: (a) applying to test data representing a level of RNA encoded by a VNN1 gene in blood of the test subject and to negative control data representing a level of RNA encoded by the gene in blood of human control subjects not having colorectal cancer a mathematical formula for generating a value indicating whether the level of RNA encoded by the gene in blood of the test subject is higher than the level of RNA encoded by the gene in blood of human control subjects not having colorectal cancer; and (b) outputting the value, where an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer.

An embodiment of the invention's computer-based methods of classifying a human test subject as more likely to have colorectal cancer than to not have colorectal cancer, includes where the level of RNA encoded by the gene in blood of the test subject is determined via quantitative reverse transcriptase-polymerase chain reaction analysis. An embodiment of the invention's computer-based methods of classifying a human test subject as more likely to have colorectal cancer than to not have colorectal cancer, includes where the level of RNA encoded by the gene in blood of the test subject and the levels of RNA encoded by the gene in blood of the control subjects are determined via the same method. An embodiment of the invention's computer-based methods of classifying a human test subject as more likely to have colorectal cancer than to not have colorectal cancer, includes where the level of RNA encoded by the gene in blood of the test subject is determined as a ratio to a level of RNA encoded by ACTB in blood of the test subject. An aspect of this embodiment includes where the level of RNA encoded by the gene in blood of the test subject and the level of RNA encoded by ACTB in blood of the test subject are determined via duplex quantitative reverse transcriptase-polymerase chain reaction analysis of RNA encoded by the gene and of RNA encoded by ACTB. An embodiment of the invention's computer-based methods of classifying a human test subject as more likely to have colorectal cancer than to not have colorectal cancer, includes where the level of RNA encoded by the gene in blood of the test subject is determined as a ratio to a level of RNA encoded by IL2RB in blood of the test subject. An aspect of this embodiment includes where the level of RNA encoded by the gene in blood of the test subject and the level of RNA encoded by IL2RB in blood of the test subject are determined via duplex quantitative reverse transcriptase-polymerase chain reaction analysis of RNA encoded by the gene and of RNA encoded by IL2RB.

Another aspect of the invention disclosed herein is a method of classifying a human test subject as more likely to have colorectal cancer than to not have colorectal cancer, the method comprising, for each gene of a set of one or more genes selected from the group consisting of ANXA3, CLEC4D, IL2RB, LMNB1, PRRG4, TNFAIP6 and VNN1: (a) determining a level of RNA encoded by the gene in blood of the test subject, thereby generating test data; (b) providing negative control data representing levels of RNA encoded by the gene in blood of human control subjects not having colorectal cancer; and (c) applying to the test data and to the negative control data a mathematical formula for generating a value indicating, for ANXA3, CLEC4D, LMNB1, PRRG4, TNFAIP6 and VNN1, whether the level of RNA encoded by the gene in blood of the test subject is higher than the level of RNA encoded by the gene in blood of human control subjects not having colorectal cancer, and indicating, for IL2RB, whether the level of RNA encoded by the gene in blood of the test subject is lower than the level of RNA encoded by the gene in blood of human control subjects not having colorectal cancer, where, for ANXA3, CLEC4D, LMNB1, PRRG4, TNFAIP6 and VNN1, an indication by the value that the level of RNA encoded by the gene in blood of the test subject is higher than the level of RNA encoded by the gene in blood of human control subjects not having colorectal cancer classifies the test subject as more likely to have colorectal cancer than to not have colorectal cancer, and where, for IL2RB, an indication by the value that the level of RNA encoded by the gene in blood of the test subject is lower than the level of RNA encoded by the gene in blood of human control subjects not having colorectal cancer classifies the test subject as more likely to have colorectal cancer than to not have colorectal cancer. An embodiment of this aspect includes determining of the level of RNA encoded by the gene in blood of the test subject is effected by determining the level of RNA encoded by the gene in a blood sample isolated from the test subject. Another embodiment of this aspect includes further comprising determining levels of RNA encoded by the gene in blood of a population of human subjects having colorectal cancer, thereby providing the positive control data representing the levels of RNA encoded by the gene in blood of human control subjects having colorectal cancer, and determining levels of RNA encoded by the gene in blood of a population of human subjects not having colorectal cancer, thereby providing the negative control data representing the levels of RNA encoded by the gene in blood of human control subjects not having colorectal cancer. Anther embodiment of this aspect includes where the level of RNA encoded by the gene in blood of the test subject is determined via quantitative reverse transcriptase-polymerase chain reaction analysis. An embodiment of this aspect includes where the level of RNA encoded by the gene in blood of the test subject and the levels of RNA encoded by the gene in blood of the control subjects are determined via the same method. An embodiment of this aspect includes where the level of RNA encoded by the gene in blood of the test subject is determined as a ratio to a level of RNA encoded by ACTB in blood of the test subject. An further embodiment includes where the level of RNA encoded by the gene in blood of the test subject and the level of RNA encoded by ACTB in blood of the test subject are determined via duplex quantitative reverse transcriptase-polymerase chain reaction analysis of RNA encoded by the gene and of RNA encoded by ACTB. An embodiment of this aspect includes where the set of one or more genes is a set of one or more genes selected from the group consisting of ANXA3, CLEC4D, LMNB1, PRRG4, TNFAIP6 and VNN1, and where the level of RNA encoded by the gene in blood of the test subject is determined as a ratio to a level of RNA encoded by IL2RB in blood of the test subject. An embodiment of this aspect includes where the level of RNA encoded by the gene in blood of the test subject and the level of RNA encoded by IL2RB in blood of the test subject are determined via duplex quantitative reverse transcriptase-polymerase chain reaction analysis of RNA encoded by the gene and of RNA encoded by IL2RB.

Another aspect of the invention disclosed herein is a computer-based method of classifying a human test subject as more likely to have colorectal cancer than to not have colorectal cancer, the method comprising, for each gene of a set of one or more genes selected from the group consisting of ANXA3, CLEC4D, IL2RB, LMNB1, PRRG4, TNFAIP6 and VNN1, computer-implemented steps of: (a) applying to test data representing a level of RNA encoded by the gene in blood of the test subject and to negative control data representing a level of RNA encoded by the gene in blood of human control subjects not having colorectal cancer, a formula for calculating a value indicating, for ANXA3, CLEC4D, LMNB1, PRRG4, TNFAIP6 and VNN1, whether the level of RNA encoded by the gene in blood of the test subject is higher than the level of RNA encoded by the gene in blood of human control subjects not having colorectal cancer, and indicating, for IL2RB, whether the level of RNA encoded by the gene in blood of the test subject is lower than the level of RNA encoded by the gene in blood of human control subjects not having colorectal cancer, where, for ANXA3, CLEC4D, LMNB1, PRRG4, TNFAIP6 and VNN1, an indication that the level of RNA encoded by the gene in blood of the test subject is higher than the level of RNA encoded by the gene in blood of human control subjects not having colorectal cancer classifies the test subject as more likely to have colorectal cancer than to not have colorectal cancer, and where, for IL2RB, an indication that the level of RNA encoded by the gene in blood of the test subject is lower than the level of RNA encoded by the gene in blood of human control subjects not having colorectal cancer classifies the test subject as more likely to have colorectal cancer than to not have colorectal cancer. An embodiment of this aspect of the invention disclosed herein includes where the level of RNA encoded by the gene in blood of the test subject is determined via quantitative reverse transcriptase-polymerase chain reaction analysis. Another embodiment of this aspect of the invention disclosed herein includes where the level of RNA encoded by the gene in blood of the test subject and the levels of RNA encoded by the gene in blood of the control subjects are determined via the same method. Another embodiment of this aspect of the invention disclosed herein includes where the level of RNA encoded by the gene in blood of the test subject is determined as a ratio to a level of RNA encoded by ACTB in blood of the test subject. In a further embodiment of this embodiment of the invention as disclosed herein is where the level of RNA encoded by the gene in blood of the test subject and the level of RNA encoded by ACTB in blood of the test subject are determined via duplex quantitative reverse transcriptase-polymerase chain reaction analysis of RNA encoded by the gene and of RNA encoded by ACTB. Another embodiment of this aspect of the invention disclosed herein includes where the set of one or more genes is a set of one or more genes selected from the group consisting of ANXA3, CLEC4D, LMNB1, PRRG4, TNFAIP6 and VNN1, and where the level of RNA encoded by the gene in blood of the test subject is determined as a ratio to a level of RNA encoded by IL2RB in blood of the test subject. In a further embodiment of this embodiment of the invention as disclosed herein, the level of RNA encoded by the gene in blood of the test subject and the level of RNA encoded by IL2RB in blood of the test subject are determined via duplex quantitative reverse transcriptase-polymerase chain reaction analysis of RNA encoded by the gene and of RNA encoded by IL2RB. In a further embodiment of this embodiment of the invention as disclosed herein, the set of one or more genes consists of PRRG4. In a further embodiment of this embodiment of the invention as disclosed herein, the set of one or more genes consists of IL2RB and PRRG4.

Another aspect of the invention disclosed herein is a kit comprising packaging and containing, for each gene of a set of two or more genes selected from the group consisting of ACTB, ANXA3, CLEC4D, IL2RB, LMNB1, PRRG4, TNFAIP6 and VNN1, a primer set capable of generating an amplification product of DNA complementary to RNA encoded, in a human subject, only by the gene. In an embodiment of this aspect of the invention disclosed herein, the kit further containing two or more components selected from the group consisting of a thermostable polymerase, a reverse transcriptase, deoxynucleotide triphosphates, nucleotide triphosphates and enzyme buffer. In another embodiment of this aspect of the invention disclosed herein, the kit further contains at least one labelled probe capable of selectively hybridizing to either a sense or an antisense strand of the amplification product. In another embodiment of this aspect of the invention disclosed herein, the set of one or more genes of the kit consists of ACTB and one or more genes selected from the group consisting of ANXA3, CLEC4D, IL2RB, LMNB1, PRRG4, TNFAIP6 and VNN1. In another embodiment of this aspect of the invention disclosed herein, the set of one or more genes of the kit consists of ACTB and ANXA3. In another embodiment of this aspect of the invention disclosed herein, the set of one or more genes of the kit consists of ACTB and CLEC4D. In another embodiment of this aspect of the invention disclosed herein, the set of one or more genes of the kit consists of ACTB and IL2RB. In another embodiment of this aspect of the invention disclosed herein, the set of one or more genes of the kit consists of ACTB and LMNB1. In another embodiment of this aspect of the invention disclosed herein, the set of one or more genes of the kit consists of ACTB and PRRG4. In another embodiment of this aspect of the invention disclosed herein, the set of one or more genes of the kit consists of ACTB and TNFAIP6. In another embodiment of this aspect of the invention disclosed herein, the set of one or more genes of the kit consists of ACTB and VNN1. In another embodiment of this aspect of the invention disclosed herein, the set of one or more genes of the kit consists of IL2RB and one or more genes selected from the group consisting of ANXA3, CLEC4D, LMNB1, PRRG4, TNFAIP6 and VNN1. In another embodiment of this aspect of the invention disclosed herein, the set of one or more genes of the kit consists IL2RB and ANXA3. In another embodiment of this aspect of the invention disclosed herein, the set of one or more genes of the kit consists of IL2RB and CLEC4D. In another embodiment of this aspect of the invention disclosed herein, the set of one or more genes of the kit consists of IL2RB and LMNB1. In another embodiment of this aspect of the invention disclosed herein, the set of one or more genes of the kit consists of IL2RB and PRRG4. In another embodiment of this aspect of the invention disclosed herein, the set of one or more genes of the kit consists of IL2RB and TNFAIP6. In another embodiment of this aspect of the invention disclosed herein, the set of one or more genes of the kit consists of IL2RB and VNN1.

Another aspect of the invention disclosed herein is a method of determining whether a test subject is at an increased risk of having colorectal cancer relative to the general population, comprising: (a) obtaining a test sample of blood from the subject; and (i) determining a level of RNA encoded by a annexin A3 (ANXA3) gene in the test sample of blood, (ii) comparing the level of RNA encoded by ANXA3 as determined in step (i) with a level of the RNA encoded by the gene in control samples of blood; and (b) concluding that the subject is at an increased risk of having colorectal cancer relative to the general population if the level of RNA encoded by the gene in the test sample of blood is higher than in the control samples of blood. Another aspect of the invention disclosed herein is a method of determining whether a test subject is at an increased risk of having colorectal cancer relative to the general population, comprising: (a) obtaining a test sample of blood from the subject; and (i) determining a level of RNA encoded by a C-type lectin domain family 4, member D (CLEC4D) gene in the test sample of blood, (ii) comparing the level of RNA encoded by the gene as determined in step (i) with the level of the RNA encoded by the gene in control samples of blood; and (b) concluding that the subject is at an increased risk of having colorectal cancer relative to the general population if the level of RNA encoded by the gene in the test sample of blood is higher than in the control samples of blood. Another aspect of the invention disclosed herein is a method of determining whether a test subject is at an increased risk of having colorectal cancer relative to the general population, comprising: (a) obtaining a test sample of blood from the subject; and (i) determining a level of RNA encoded by a interleukin 2 receptor, beta (IL2RB) gene in the test sample of blood, (ii) comparing the level of RNA encoded by the gene as determined in step (i) with the level of the RNA encoded by the gene in control samples of blood; and (b) concluding that the subject is at an increased risk of having colorectal cancer relative to the general population if the level of RNA encoded by the gene in the test sample of blood is lower than in the control samples of blood. Another aspect of the invention disclosed herein is a method of determining whether a test subject is at an increased risk of having colorectal cancer relative to the general population, comprising: (a) obtaining a test sample of blood from the subject; and (i) determining a level of RNA encoded by a lamin B1 (LMNB1) gene in the test sample of blood, (ii) comparing the level of RNA encoded by the gene as determined in step (i) with the level of the RNA encoded by the gene in control samples of blood; and (b) concluding that the subject is at an increased risk of having colorectal cancer relative to the general population if the level of RNA encoded by the gene in the test sample of blood is higher than in the control samples of blood. Another aspect of the invention disclosed herein is a method of determining whether a test subject is at an increased risk of having colorectal cancer relative to the general population, comprising: (a) obtaining a test sample of blood from the subject; and (i) determining a level of RNA encoded by a proline rich Gla (G carboxyglutamic acid) 4 (transmembrane) (PRRG4) gene in the test sample of blood, (ii) comparing the level of RNA encoded by the gene as determined in step (i) with the level of the RNA encoded by the gene in control samples of blood; and (b) concluding that the subject is at an increased risk of having colorectal cancer relative to the general population if the level of RNA encoded by the gene in the test sample of blood is higher than in the control samples of blood. Another aspect of the invention disclosed herein is a method of determining whether a test subject is at an increased risk of having colorectal cancer relative to the general population, comprising: (a) obtaining a test sample of blood from the subject; and (i) determining a level of RNA encoded by a tumor necrosis factor, alpha induced protein 6 gene (TNFAIP6) in the test sample of blood, (ii) comparing the level of RNA encoded by the gene as determined in step (i) with the level of the RNA encoded by the gene in control samples of blood; and (b) concluding that the subject is at an increased risk of having colorectal cancer relative to the general population if the level of RNA encoded by the gene in the test sample of blood is higher than in the control samples of blood. Another aspect of the invention disclosed herein is a method of determining whether a test subject is at an increased risk of having colorectal cancer relative to the general population, comprising: (a) obtaining a test sample of blood from the subject; and (i) determining a level of RNA encoded by a vanin 1 (VNN1) gene in the test sample of blood, (ii) comparing the level of RNA encoded by the gene as determined in step (i) with the level of the RNA encoded by the gene in control samples of blood; and (b) concluding that the subject is at an increased risk of having colorectal cancer relative to the general population if the level of RNA encoded by the gene in the test sample of blood is higher than in the control samples of blood. In an embodiment of any one of these eight aspects these methods of determining whether a test subject is at an increased risk of having colorectal cancer relative to the general population, the control samples are from individuals who have been diagnosed as not having colorectal cancer.

Another aspect of the invention disclosed herein is a method of determining whether a test subject is at an increased risk of having colorectal cancer relative to the general population, comprising: (a) obtaining a test sample of blood from the subject; and for each gene of a set of genes selected from the group consisting of: ANXA3, CLEC4D, IL2RB, LMNB1, PRRG4, TNFAIP6 and VNN1, (i) determining a level of RNA encoded by the gene in the test sample of blood, thereby generating test data; and (ii) applying to the test data and to control data representing a level of RNA encoded by the gene in one or more control samples of blood a mathematical formula for generating a value indicating, for ANXA3, CLEC4D, LMNB1, PRRG4, TNFAIP6 and VNN1, whether the level of RNA encoded by the gene in the test sample of blood is higher than in the control samples of blood, and, for IL2RB, whether the level of RNA encoded by the gene in the test sample of blood is lower than in the control samples of blood; and (b) concluding that the subject is at an increased risk of having colorectal cancer relative to the general population if, for ANXA3, CLEC4D, LMNB1, PRRG4, TNFAIP6 and VNN1, the value indicates that the level of RNA encoded by the gene in the test sample of blood is higher than in the control samples of blood, and concluding that the subject is at an increased risk of having colorectal cancer relative to the general population if, for IL2RB, the value indicates that the level of RNA encoded by the gene in the test sample of blood is lower than in the control samples of blood. Another aspect of the invention disclosed herein is an isolated composition comprising a blood sample from a test subject and a nucleic acid molecule selected from one or more of the group consisting of RNA encoded by an ANXA3 gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of CLEC4D, IL2RB, LMNB1, PRRG4, TNFAIP6 and VNN1, cDNA complementary to the RNA of the group of genes, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising a blood sample from a test subject and a nucleic acid molecule selected from one or more of the group consisting of RNA encoded by a CLEC4D gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, IL2RB, LMNB1, PRRG4, TNFAIP6 and VNN1, cDNA complementary to the RNA of the group of genes, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising a blood sample from a test subject and a nucleic acid molecule selected from one or more of the group consisting of RNA encoded by a IL2RB gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, CLEC4D, LMNB1, PRRG4, TNFAIP6 and VNN1, cDNA complementary to the RNA of the group of genes, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising a blood sample from a test subject and a nucleic acid molecule selected from one or more of the group consisting of RNA encoded by a LMNB1 gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, CLEC4D, IL2RB, PRRG4, TNFAIP6 and VNN1, cDNA complementary to the RNA of the group of genes, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising a blood sample from a test subject and a nucleic acid molecule selected from one or more of the group consisting of RNA encoded by a PRRG4 gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises nucleic acid molecule selected from one or more of the group consisting of RNA encoded by one or more genes selected from the group of genes consisting of ANXA3, CLEC4D, IL2RB, LMNB1, TNFAIP6 and VNN1, cDNA complementary to the RNA of the group of genes, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising a blood sample from a test subject and a nucleic acid molecule selected from one or more of the group consisting of RNA encoded by a TNFAIP6 gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, CLEC4D, IL2RB, LMNB1, PRRG4, and VNN1, cDNA complementary to the RNA of the group of genes, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising a blood sample from a test subject and a nucleic acid molecule selected from one or more of the group consisting of RNA encoded by a VNN1 gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, CLEC4D, IL2RB, LMNB1, PRRG4, and TNFAIP6, cDNA complementary to the RNA of the group of genes, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes.

Another aspect of the invention disclosed herein is an isolated composition comprising an isolated nucleic acid molecule of a blood sample from a test subject, where the nucleic acid molecule is selected from one or more of the group consisting of RNA encoded by an ANXA3 gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of CLEC4D, IL2RB, LMNB1, PRRG4, TNFAIP6 and VNN1, cDNA complementary to the RNA of the group of genes or the complement thereof, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising an isolated nucleic acid molecule of a blood sample from a test subject, where the nucleic acid molecule is selected from one or more of the group consisting of RNA encoded by an CLEC4D gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, IL2RB, LMNB1, PRRG4, TNFAIP6 and VNN1, cDNA complementary to the RNA of the group of genes or the complement thereof, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising an isolated nucleic acid molecule of a blood sample from a test subject, where the nucleic acid molecule is selected from one or more of the group consisting of RNA encoded by an IL2RB gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, CLEC4D, LMNB1, PRRG4, TNFAIP6 and VNN1, cDNA complementary to the RNA of the group of genes or the complement thereof, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising an isolated nucleic acid molecule of a blood sample from a test subject, where the nucleic acid molecule is selected from one or more of the group consisting of RNA encoded by an LMNB1 gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, CLEC4D, IL2RB, PRRG4, TNFAIP6 and VNN1, cDNA complementary to the RNA of the group of genes or the complement thereof, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising an isolated nucleic acid molecule of a blood sample from a test subject, where the nucleic acid molecule is selected from one or more of the group consisting of RNA encoded by a PRRG4 gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, CLEC4D, IL2RB, LMNB1, TNFAIP6 and VNN1, cDNA complementary to the RNA of the group of genes or the complement thereof, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. Another aspect of the invention disclosed herein is an isolated composition comprising an isolated nucleic acid molecule of a blood sample from a test subject, where the nucleic acid molecule is selected from one or more of the group consisting of RNA encoded by a TNFAIP6 gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, CLEC4D, IL2RB, LMNB1, PRRG4, and VNN1, cDNA complementary to the RNA of the group of genes or the complement thereof, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes. An isolated composition comprising a blood sample from a test subject and a nucleic acid molecule selected from one or more of the group consisting of RNA encoded by a VNN1 gene, cDNA complementary to the RNA, an oligonucleotide which specifically hybridizes to the cDNA or the RNA under stringent conditions, a primer set capable of generating an amplification product of the cDNA complementary to RNA, and an amplification product of the cDNA. One embodiment of this composition further comprises a nucleic acid molecule selected from one or more of the group consisting of RNA encoded by one or more genes selected from the group of genes consisting of ANXA3, CLEC4D, IL2RB, LMNB1, PRRG4, and TNFAIP6, cDNA complementary to the RNA of the group of genes or the complement thereof, an oligonucleotide which specifically hybridizes to the cDNA complementary to the RNA of the group of genes or to the RNA of the group of genes under stringent conditions, a primer set capable of generating an amplification product of the cDNA complementary to RNA of the group of genes, and an amplification product of the cDNA of the RNA of the group of genes.

Another aspect of the invention disclosed herein is a primer set comprising a first primer, where the first primer is one of a set of primers capable of generating an amplification product of cDNA complementary to RNA of encoded by an ANXA3 gene, and a second primer, where the second primer is one of a set of primers capable of generating an amplification product of cDNA complementary to RNA of encoded by a VNN1 gene, or composition thereof. Another aspect of the invention disclosed herein is a primer set comprising a first primer, where the first primer is one of a set of primers capable of generating an amplification product of cDNA complementary to RNA of encoded by an ANXA3 gene, and a second primer, where the second primer is one of a set of primers capable of generating an amplification product of cDNA complementary to RNA of encoded by a TNFAIP6 gene, or composition thereof. Another aspect of the invention disclosed herein is a primer set comprising a first primer, where the first primer is one of a set of primers capable of generating an amplification product of cDNA complementary to RNA of encoded by an ANXA3 gene, and a second primer, where the second primer is one of a set of primers capable of generating an amplification product of cDNA complementary to RNA of encoded by a PRRG4 gene, or composition thereof. Another aspect of the invention disclosed herein is a primer set comprising a first primer, where the first primer is one of a set of primers capable of generating an amplification product of cDNA complementary to RNA of encoded by an ANXA3 gene, and a second primer, where the second primer is one of a set of primers capable of generating an amplification product of cDNA complementary to RNA of encoded by a PRRG4 gene, or composition thereof. Another aspect of the invention disclosed herein is a primer set comprising a first primer, where the first primer is one of a set of primers capable of generating an amplification product of cDNA complementary to RNA of encoded by an ANXA3 gene, and a second primer, where the second primer is one of a set of primers capable of generating an amplification product of cDNA complementary to RNA of encoded by a LMNB1 gene, or composition thereof. Another aspect of the invention disclosed herein is a primer set comprising a first primer, where the first primer is one of a set of primers capable of generating an amplification product of cDNA complementary to RNA of encoded by an ANXA3 gene, and a second primer, where the second primer is one of a set of primers capable of generating an amplification product of cDNA complementary to RNA of encoded by an IL2RB gene, or composition thereof. Another aspect of the invention disclosed herein is a primer set comprising a first primer, where the first primer is one of a set of primers capable of generating an amplification product of cDNA complementary to RNA of encoded by an ANXA3 gene, and a second primer, where the second primer is one of a set of primers capable of generating an amplification product of cDNA complementary to RNA of encoded by a CLEC4D gene, or composition thereof. Another aspect of the invention disclosed herein is a primer set comprising a first primer, where the first primer is one of a set of primers capable of generating an amplification product of cDNA complementary to RNA of encoded by an CLEC4D gene, and a second primer, where the second primer is one of a set of primers capable of generating an amplification product of cDNA complementary to RNA of encoded by a VNN1 gene, or composition thereof. Another aspect of the invention disclosed herein is a primer set comprising a first primer, where the first primer is one of a set of primers capable of generating an amplification product of cDNA complementary to RNA of encoded by an CLEC4D gene, and a second primer, where the second primer is one of a set of primers capable of generating an amplification product of cDNA complementary to RNA of encoded by a TNFAIP6 gene, or composition thereof. Another aspect of the invention disclosed herein is a primer set comprising a first primer, where the first primer is one of a set of primers capable of generating an amplification product of cDNA complementary to RNA of encoded by an CLEC4D gene, and a second primer, where the second primer is one of a set of primers capable of generating an amplification product of cDNA complementary to RNA of encoded by a PRRG4 gene, or composition thereof. Another aspect of the invention disclosed herein is a primer set comprising a first primer, where the first primer is one of a set of primers capable of generating an amplification product of cDNA complementary to RNA of encoded by an CLEC4D gene, and a second primer, where the second primer is one of a set of primers capable of generating an amplification product of cDNA complementary to RNA of encoded by a PRRG4 gene, or composition thereof. Another aspect of the invention disclosed herein is a primer set comprising a first primer, where the first primer is one of a set of primers capable of generating an amplification product of cDNA complementary to RNA of encoded by an CLEC4D gene, and a second primer, where the second primer is one of a set of primers capable of generating an amplification product of cDNA complementary to RNA of encoded by a LMNB1 gene, or composition thereof. Another aspect of the invention disclosed herein is a primer set comprising a first primer, where the first primer is one of a set of primers capable of generating an amplification product of cDNA complementary to RNA of encoded by an CLEC4D gene, and a second primer, where the second primer is one of a set of primers capable of generating an amplification product of cDNA complementary to RNA of encoded by an IL2RB gene, or composition thereof. Another aspect of the invention disclosed herein is a primer set comprising a first primer, where the first primer is one of a set of primers capable of generating an amplification product of cDNA complementary to RNA of encoded by an IL2RB gene, and a second primer, where the second primer is one of a set of primers capable of generating an amplification product of cDNA complementary to RNA of encoded by a TNFAIP6 gene, or composition thereof. Another aspect of the invention disclosed herein is a primer set comprising a first primer, where the first primer is one of a set of primers capable of generating an amplification product of cDNA complementary to RNA of encoded by an IL2RB gene, and a second primer, where the second primer is one of a set of primers capable of generating an amplification product of cDNA complementary to RNA of encoded by a PRRG4 gene, or composition thereof. Another aspect of the invention disclosed herein is a primer set comprising a first primer, where the first primer is one of a set of primers capable of generating an amplification product of cDNA complementary to RNA of encoded by an IL2RB gene, and a second primer, where the second primer is one of a set of primers capable of generating an amplification product of cDNA complementary to RNA of encoded by a LMNB1 gene, or composition thereof. Another aspect of the invention disclosed herein is a primer set comprising a first primer, where the first primer is one of a set of primers capable of generating an amplification product of cDNA complementary to RNA of encoded by an IL2RB gene, and a second primer, where the second primer is one of a set of primers capable of generating an amplification product of cDNA complementary to RNA of encoded by a VNN1 gene, or composition thereof. Another aspect of the invention disclosed herein is a primer set comprising a first primer, where the first primer is one of a set of primers capable of generating an amplification product of cDNA complementary to RNA of encoded by a LMNB1 gene, and a second primer, where the second primer is one of a set of primers capable of generating an amplification product of cDNA complementary to RNA of encoded by a PRRG4 gene, or composition thereof. Another aspect of the invention disclosed herein is a primer set comprising a first primer, where the first primer is one of a set of primers capable of generating an amplification product of cDNA complementary to RNA of encoded by a LMNB1 gene, and a second primer, where the second primer is one of a set of primers capable of generating an amplification product of cDNA complementary to RNA of encoded by a TNFAIP6 gene, or composition thereof. Another aspect of the invention disclosed herein is a primer set comprising a first primer, where the first primer is one of a set of primers capable of generating an amplification product of cDNA complementary to RNA of encoded by an LMNB1 gene, and a second primer, where the second primer is one of a set of primers capable of generating an amplification product of cDNA complementary to RNA of encoded by a VNN1 gene, or composition thereof. Another aspect of the invention disclosed herein is a primer set comprising a first primer, where the first primer is one of a set of primers capable of generating an amplification product of cDNA complementary to RNA of encoded by a PRRG4 gene, and a second primer, where the second primer is one of a set of primers capable of generating an amplification product of cDNA complementary to RNA of encoded by a VNN1 gene, or composition thereof. Another aspect of the invention disclosed herein is a primer set comprising a first primer, where the first primer is one of a set of primers capable of generating an amplification product of cDNA complementary to RNA of encoded by a PRRG4 gene, and a second primer, where the second primer is one of a set of primers capable of generating an amplification product of cDNA complementary to RNA of encoded by a TNFAIP6 gene, or composition thereof. Another aspect of the invention disclosed herein is a primer set comprising a first primer, where the first primer is one of a set of primers capable of generating an amplification product of cDNA complementary to RNA of encoded by a VNN1 gene, and a second primer, where the second primer is one of a set of primers capable of generating an amplification product of cDNA complementary to RNA of encoded by a TNFAIP6 gene, or composition thereof.

Another aspect of the invention disclosed herein is test system comprising: a) two or more blood samples where each blood sample is from a different test subject, and b) an isolated nucleic acid molecule of each the blood sample from a test subject, where the nucleic acid molecule is selected from one or more of the group consisting of RNA encoded by an ANXA3 gene, cDNA complementary to the RNA, an oligonucleotide which specifically hybridizes to the cDNA or complement thereof, or the RNA under stringent conditions, a primer set capable of generating an amplification product of the cDNA complementary to RNA, and an amplification product of the cDNA. Another aspect of the invention disclosed herein is a test system comprising: a) two or more blood samples where each blood sample is from a different test subject, and b) an isolated nucleic acid molecule of each the blood sample from a test subject, where the nucleic acid molecule is selected from one or more of the group consisting of RNA encoded by a CLEC4D, gene, cDNA complementary to the RNA, an oligonucleotide which specifically hybridizes to the cDNA or complement thereof, or the RNA under stringent conditions, a primer set capable of generating an amplification product of the cDNA complementary to RNA, and an amplification product of the cDNA Another aspect of the invention disclosed herein is a test system comprising: a) two or more blood samples where each blood sample is from a different test subject, and b) an isolated nucleic acid molecule of each the blood sample from a test subject, where the nucleic acid molecule is selected from one or more of the group consisting of RNA encoded by an IL2RB gene, cDNA complementary to the RNA, an oligonucleotide which specifically hybridizes to the cDNA or complement thereof, or the RNA under stringent conditions, a primer set capable of generating an amplification product of the cDNA complementary to RNA, and an amplification product of the cDNA. Another aspect of the invention disclosed herein is a test system comprising: a) two or more blood samples where each blood sample is from a different test subject, and b) an isolated nucleic acid molecule of each the blood sample from a test subject, where the nucleic acid molecule is selected from one or more of the group consisting of RNA encoded by an LMNB1 gene, cDNA complementary to the RNA, an oligonucleotide which specifically hybridizes to the cDNA or complement thereof, or the RNA under stringent conditions, a primer set capable of generating an amplification product of the cDNA complementary to RNA, and an amplification product of the cDNA. Another aspect of the invention disclosed herein is a test system comprising: a) two or more blood samples where each blood sample is from a different test subject, and b) an isolated nucleic acid molecule of each the blood sample from a test subject, where the nucleic acid molecule is selected from one or more of the group consisting of RNA encoded by a PRRG4 gene, cDNA complementary to the RNA, an oligonucleotide which specifically hybridizes to the cDNA or complement thereof, or the RNA under stringent conditions, a primer set capable of generating an amplification product of the cDNA complementary to RNA, and an amplification product of the cDNA. Another aspect of the invention disclosed herein is a test system comprising: a) two or more blood samples where each blood sample is from a different test subject, and b) an isolated nucleic acid molecule of each the blood sample from a test subject, where the nucleic acid molecule is selected from one or more of the group consisting of RNA encoded by a TNFAIP6 gene, cDNA complementary to the RNA, an oligonucleotide which specifically hybridizes to the cDNA or complement thereof, or the RNA under stringent conditions, a primer set capable of generating an amplification product of the cDNA complementary to RNA, and an amplification product of the cDNA. Another aspect of the invention disclosed herein is a test system comprising: a) two or more blood samples where each blood sample is from a different test subject, and b) an isolated nucleic acid molecule of each the blood sample from a test subject, where the nucleic acid molecule is selected from one or more of the group consisting of RNA encoded by a VNN1 gene, cDNA complementary to the RNA, an oligonucleotide which specifically hybridizes to the cDNA or complement thereof, or the RNA under stringent conditions, a primer set capable of generating an amplification product of the cDNA complementary to RNA, and an amplification product of the cDNA. An embodiment of any of the test systems described in this paragraph includes where the test subject is being screened for colorectal cancer.

The following non-limiting examples are illustrative of the invention:

EXAMPLES

Example 1

General Materials and Methods

Introduction:
The following materials and methods describe experiments performed to demonstrate that analysis of blood for levels of RNA encoded by genes surprisingly identified by the present inventors as colorectal cancer marker genes in blood via array hybridization analysis using an Affymetrix U133Plus 2.0 GeneChip oligonucleotide array (Affymetrix; Santa Clara, Calif.) (data not shown), can also serve as blood markers for diagnosing colorectal cancer via quantitative reverse-transcriptase PCR analysis.

Blood Sample Collection:
Samples of 2.5 ml whole blood were collected into PAXgene Blood RNA Tubes (PreAnalytiX) from human subjects not having any colorectal pathology and from human subjects having colorectal cancer. Samples were obtained from subjects enrolled in colorectal cancer studies conducted by GeneNews Corp. and collaborating institutions. Blood samples from subjects having colorectal cancer were collected prior to tumor resection, and cancer stage and histology were determined by institutional pathologists. Blood samples from subjects not having any colorectal pathology were collected from subjects presenting for endoscopy screening. Informed consent was obtained according to the research protocols approved by the research ethical boards of the institutions involved. Experimental group sample pairs were selected with an effort to match gender, age, body mass index (BMI), ethnicity and medical history. Samples were divided into training and test sets.

RNA Isolation:
A sample of 2.5 ml whole blood was collected into PAXgene Blood RNA tubes (PreAnalytiX) and processed in accordance with the instructions of the PAXgene Blood RNA Kit protocol. In brief, after storing the blood in the PAXgene tube for at least 2 hours, the blood sample was centrifuged and the supernatant discarded. To the remaining sample, 350 microliters of the supplied Buffer B R1 was added, and the sample was pipetted into the spin column and centrifuged, washed and finally eluted as isolated RNA and stored.

Reverse Transcription:
Reverse transcription of blood sample-derived RNA into single-stranded complementary DNA was performed using the High Capacity cDNA Reverse Transcription Kit from (Applied Biosystems; Foster City, Calif.; Product number 4368814), according to the manufacturer's instructions. Specifically, 1 microgram of isolated RNA was incubated with reverse transcriptase buffer, dNTPs, random primers and reverse transcriptase and incubated at 25° C. for 10 minutes and subsequently at 37° C. for two hours.

Quantitative Real Time RT-PCR:

Quantitative real-time PCR analysis to measure levels of RNA encoded by the genes listed in Table 1 was performed on cDNA samples using the QuantiTect™ Probe RT-PCR system (Qiagen; Valencia, Calif.; Product No. 204345), using the primers listed in Table 2 for amplification of cDNA template corresponding to the indicated gene, and TaqMan dual labeled probes comprising the polynucleotides listed in Table 3 for measuring levels of amplicon corresponding to the indicated gene. The TaqMan probe and primers were ordered from Applied Biosystems Assays-On-Demand, or from IDT (Integrated DNA Technologies, Coralville, Iowa), or from Biosearch Technologies (Novato, Calif.). Amplicon levels were measured in real time using a RealTime PCR System 7500 instrument (Applied Biosystems). Specifically, 20 nanograms of cDNA resulting from reverse transcription was added to the QuantiTect Probe PCR Master Mix as provided and no adjustments were made for magnesium concentration. Uracil-N-Glycosylase was not added. Both forward primer and reverse primer (Table 1) specific to the target genes were added to a concentration of 5 micromolar, and the resultant 25 microliter reaction volume was incubated as follows: 50 degrees centigrade for 2 minutes, followed by 95 degrees centigrade for 15 minutes, followed by 40 cycles of: [94 degrees centigrade for 15 seconds, followed by 55 degrees centigrade for 35 seconds, followed by 72 degrees centigrade for 30 seconds]. Amplification data was collected during each of the 40 incubations at 55 degrees centigrade. All quantitative reverse transcriptase-PCR analyses were performed as duplex amplifications of a target gene and a reference gene (either ACTB or IL2RB, as indicated) in the same reaction mixture. Serial dilution measurements for target and duplex partner genes were assayed, to ensure that the values were within linear range and that the amplification efficiencies were approximately equal. Examination via polyacrylamide gel electrophoresis provided confirmation of specific PCR amplification and the lack of primer-dimer formation in each reaction well.

TABLE 1

Genes encoding target RNAs for determining colorectal cancer probability versus absence of colorectal pathology.

| Gene Symbol | GenBank Accession | Gene Description |
|---|---|---|
| ACTB | NM_001101 | beta-actin |
| ANXA3 | NM_005139 | annexin A3 |
| CLEC4D | NM_080387 | C-type lectin domain family 4, member D |
| IL2RB | NM_000878 | interleukin 2 receptor, beta |
| LMNB1 | NM_005573 | lamin B1 |
| PRRG4 | NM_024081 | proline rich Gla (G-carboxyglutamic acid) 4 (transmembrane) |
| TNFAIP6 | NM_007115 | tumor necrosis factor, alpha-induced protein 6 |
| VNN1 | NM_004666 | vanin 1 |

TABLE 2

Primers used for quantitative PCR analysis.

| Gene encoding amplified cDNA | Primer | Primer pair sequences | Primer position | Amplicon size (bp) |
|---|---|---|---|---|
| ACTB | 5' | 5'-CACCACACCTTCTACAATGAGCTG-3' (SEQ ID NO: 1) | 259 | 158 |
| | 3' | 5'-ACAGCCTGGATAGCAACGTACA-3' (SEQ ID NO: 2) | 416 | |
| ANXA3 | 5' | 5'-GAAACATCTGGTGACTTCCG-3' (SEQ ID NO: 10) | 748 | 103 |
| | 3' | 5'-TCTGGGCATCTTGTTTGG-3' (SEQ ID NO: 11) | 850 | |
| CLEC4D | 5' | 5'-CCATTTAACCCACGCAGAG-3' (SEQ ID NO: 19) | 673 | 101 |
| | 3' | 5'-CAGGCCCATTTATCTTGGTT-3' (SEQ ID NO: 20) | 773 | |
| IL2RB | 5' | 5'-AAATCTCCCAAGCCTCCCA-3' (SEQ ID NO: 28) | 588 | 127 |
| | 3' | 5'-AGGCAGATCCATTCCTGCT-3' (SEQ ID NO: 29) | 714 | |
| LMNB1 | 5' | 5'-GGAGTGGTTGTTGAGGAAGAA-3' (SEQ ID NO: 37) | 2051 | 151 |
| | 3' | 5'-CTGAGAAGGCTCTGCACTGTA-3' (SEQ ID NO: 38) | 2201 | |
| PRRG4 | 5' | 5'-ATGCGGGAGAAGAAGTGTTTAC-3' (SEQ ID NO: 46) | 341 | 153 |
| | 3' | 5'-CTCTGGCTTCCTCATAATTGC-3' (SEQ ID NO: 47) | 493 | |
| TNFAIP6 | 5' | 5'-GCCTATTGCTACAACCCACA-3' (SEQ ID NO: 55) | 448 | 84 |
| | 3' | 5'-TGGGAAGCCTGGAGATTTA-3' (SEQ ID NO: 56) | 531 | |
| VNN1 | 5' | 5'-TGACAGGAAGTGGCATCTAT-3' (SEQ ID NO: 64) | 835 | 147 |
| | 3' | 5'-TACTGCTGGCATAGGAAGTC-3' (SEQ ID NO: 65) | 981 | |

TABLE 3

TaqMan ® probes used for quantitative PCR analysis.

| Gene encoding amplicon | Taqman probe base sequence | Probe position |
|---|---|---|
| ACTB | 5'-AACCGCGAGAAGATGACCCAGATCAT-3' (SEQ ID NO: 3) | 343 |
| ANXA3 | 5'-TTGACTTTGGCAGATGGCAGA-3' (SEQ ID NO: 12) | 778 |
| CLEC4D | 5'-CTGGCATAAGAATGAACCCGACA-3' (SEQ ID NO: 21) | 696 |
| IL2RB | 5'-TTGAAAGACACCTGGAGTTCG-3' (SEQ ID NO: 30) | 612 |
| LMNB1 | 5'-AACCCCAAGAGCATCCAATAG-3' (SEQ ID NO: 39) | 2089 |
| PRRG4 | 5'-CTCTTCACTCCCGGCAACCTAGAA-3' (SEQ ID NO: 48) | 427 |
| TNFAIP6 | 5'-AAGGAGTGTGGTGGCGTCTTTAC-3' (SEQ ID NO: 57) | 472 |
| VNN1 | 5'-AGAAGAGGGAAAACTCCTCCTCTCG-3' (SEQ ID NO: 66) | 896 |

Determination of Observed Range of Fold-Changes in Levels of RNA Encoded by Marker Genes in Blood of Subjects Having Colorectal Cancer Relative to Subjects not Having any Colorectal Pathology:

For each of the sample training and sample test sets, average fold-change in levels of RNA encoded by marker genes, normalized to either ACTB or IL2RB, were calculated as the ratio of average levels of RNA encoded by marker genes in blood of subjects having colorectal cancer to average levels of RNA encoded by marker genes in blood of subjects not having any colorectal pathology. The statistical significance of the fold-changes were confirmed by a p-value of less than 0.05. Maximum observed directional fold-changes in normalized levels of RNA encoded by marker genes found to be higher in blood of subjects having colorectal cancer than in blood of subjects not having any colorectal pathology were further calculated, for each marker gene, as the ratio of the highest level observed in any single sample from a subject having colorectal cancer to the average level in subjects not having any colorectal pathology. Similarly, maximum observed directional fold-changes in normalized levels of RNA encoded by marker genes found to be lower in blood of subjects having colorectal cancer than in blood of subjects not having any colorectal pathology were further calculated, for each marker gene, as the ratio of the lowest level observed in any single sample from a subject having colorectal cancer to the average level in subjects not having any colorectal pathology. In this way, observed ranges of fold-changes, ranging from average fold-change to maximal observed directional fold-change, in levels of RNA encoded by marker genes in blood of subjects having colorectal cancer relative to subjects not having any colorectal pathology were determined.

Formulation of Mathematical Models for Determining Probability of Colorectal Cancer Versus Absence of Colorectal Pathology:

Logistic regression was used to formulate mathematical models for determining the probability that a test subject has colorectal cancer as opposed to not having any colorectal pathology. Levels of RNA encoded by colorectal cancer marker genes and of reference genes determined via duplex quantitative reverse transcriptase PCR in blood of positive and negative control subjects were analyzed via logistic regression so as to generate models having the general form:

$$P=\{1+e^{\wedge}-[K_0+K_1L_1+K_2L_2+K_3L_3\ldots+K_nL_n]\}^{\wedge}-1,$$

where P is the probability that a test subject has colorectal cancer as opposed to not having any colorectal pathology; $K_0$ is a constant; $K_1$ is a coefficient specific to a first marker gene; $L_1$ is a ratio of a level of RNA encoded by the first gene to a level of RNA encoded by a reference gene in blood of the test subject; $K_2$ is a coefficient specific to a second marker gene; $L_2$ is a ratio of a level of RNA encoded by the second gene to a level of RNA encoded by the reference gene in blood of the test subject; $K_3$ is a coefficient specific to a third marker gene; $L_3$ is a ratio of a level of RNA encoded by the third gene to a level of RNA encoded by the reference gene in blood of the test subject; $K_n$ is a coefficient specific to an nth marker gene; and $L_n$ is a ratio of a level of RNA encoded by the nth gene to a level of RNA encoded by the reference gene in blood of the test subject. The ratio of the level of RNA encoded by a marker gene to the level of RNA encoded by a reference gene was calculated as the change ($\Delta$Ct) in the cycle number (Ct) at which the increase in fluorescence is exponential between the marker gene and the reference gene according to the equation: $\Delta$Ct=Ct (marker gene)–Ct (reference gene). The caret symbol "^" is used herein to denote that a value preceding the caret is raised to a power corresponding to the value following the caret.

Example 2

Measurement of Blood Levels of RNA Encoded by any Combination of ANXA3, CLEC4D, IL2RB, LMNB1, PRRG4, TNFAIP6 and/or VNN1 can be Used to Determine a Probability that a Test Subject has Colorectal Cancer as Opposed to not Having any Colorectal Pathology Materials and Methods:
Refer to "General materials and methods", above.
Experimental Results:
Sample Training Set:
Discovery of Significantly Different Levels of RNA Encoded by ANXA3, CLEC4D, IL2RB, LMNB1, PRRG4, TNFAIP6 and VNN1 and in Blood of Subjects Having Colorectal Cancer Relative to Subjects not Having any Colorectal Pathology:

Quantitative reverse transcriptase PCR analysis of gene expression in a training set of blood samples from 117 subjects having colorectal cancer and 130 subjects not having any colorectal pathology, using the housekeeping gene ACTB as duplex partner for normalization of gene expression levels was performed. The normalized RNA levels measured are shown in Table 4.

TABLE 4

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by ACTB. Levels shown correspond to ΔCt.

| Sample ID | Group | ANXA3 | CLEC4D | IL2RB | LMNB1 | PRRG4 | TNFAIP6 | VNN1 |
|---|---|---|---|---|---|---|---|---|
| CD0011pax | 0 | 6.523 | 7.755 | 5.195 | 7.310 | 7.860 | 8.501 | 8.991 |
| CD0012pax | 0 | 7.878 | 8.595 | 5.250 | 7.525 | 8.183 | 8.439 | 9.878 |
| CD0030pax | 0 | 6.411 | 6.420 | 4.173 | 6.220 | 6.973 | 5.901 | 7.101 |
| CD0063pax | 0 | 7.103 | 8.545 | 4.203 | 7.165 | 7.795 | 8.499 | 8.628 |
| CD0077pax | 0 | 4.808 | 6.185 | 5.098 | 5.405 | 6.710 | 6.524 | 6.533 |
| CD0078pax | 0 | 5.946 | 7.000 | 3.553 | 5.820 | 5.570 | 7.476 | 6.488 |
| CD0085pax | 0 | 5.543 | 7.700 | 5.003 | 6.210 | 7.460 | 8.149 | 6.678 |
| CD0117pax | 0 | 6.021 | 8.170 | 4.463 | 5.685 | 8.020 | 8.166 | 6.573 |
| CD0146pax | 0 | 5.396 | 6.335 | 4.468 | 5.320 | 5.735 | 6.691 | 6.253 |
| CD0167pax | 0 | 3.501 | 4.893 | 4.480 | 4.978 | 5.590 | 6.469 | 5.173 |
| CD0249pax | 0 | 4.443 | 4.855 | 4.878 | 4.803 | 6.043 | 5.556 | 6.471 |
| CD0279pax | 0 | 5.503 | 7.095 | 4.270 | 5.395 | 6.098 | 6.694 | 7.043 |
| CD0286pax | 0 | 4.791 | 6.928 | 4.350 | 5.383 | 5.960 | 5.714 | 5.598 |
| CD0297pax | 0 | 5.861 | 6.670 | 5.083 | 6.565 | 6.405 | 6.186 | 7.118 |
| CD0323pax | 0 | 6.966 | 7.773 | 4.645 | 5.723 | 7.470 | 8.149 | 8.738 |
| CD0445pax | 0 | 6.458 | 7.420 | 4.448 | 6.103 | 6.448 | 7.216 | 7.411 |
| CD0463pax | 0 | 4.391 | 6.485 | 4.203 | 5.605 | 6.583 | 6.161 | 7.036 |
| CD0491pax | 0 | 5.093 | 6.370 | 4.928 | 6.123 | 6.978 | 7.171 | 6.511 |
| CD0496pax | 0 | 6.058 | 8.270 | 4.670 | 6.355 | 7.783 | 6.434 | 6.623 |
| CD0501pax | 0 | 6.326 | 7.725 | 4.613 | 6.270 | 7.215 | 8.581 | 6.978 |
| CD0504pax | 0 | 4.023 | 5.060 | 4.858 | 5.920 | 7.530 | 5.289 | 6.113 |
| CD0573pax | 0 | 6.791 | 6.140 | 4.248 | 6.160 | 6.713 | 7.646 | 7.286 |
| CD0578pax | 0 | 6.328 | 6.670 | 4.128 | 5.128 | 6.033 | 6.411 | 7.081 |
| CD0620pax | 0 | 2.361 | 3.628 | 6.120 | 3.873 | 6.120 | 5.274 | 5.613 |
| CD0639pax | 0 | 5.611 | 7.013 | 4.980 | 6.258 | 5.630 | 6.689 | 7.528 |
| CD0645pax | 0 | 4.596 | 5.868 | 5.190 | 4.908 | 5.475 | 6.099 | 5.608 |
| CD0679pax | 0 | 5.611 | 7.808 | 5.070 | 5.633 | 6.150 | 7.974 | 7.748 |
| CD0685pax | 0 | 5.796 | 8.150 | 4.358 | 6.050 | 7.155 | 7.606 | 6.673 |
| CD0716pax | 0 | 6.961 | 8.193 | 4.090 | 5.648 | 5.750 | 6.669 | 7.388 |
| CD0749pax | 0 | 5.208 | 6.970 | 4.520 | 5.565 | 6.430 | 7.176 | 6.316 |
| CD0760pax | 0 | 2.868 | 5.020 | 5.603 | 3.605 | 5.790 | 4.679 | 5.663 |
| CD0811pax | 0 | 7.188 | 8.065 | 3.275 | 6.500 | 7.305 | 6.021 | 6.141 |
| CD0846pax | 0 | 4.626 | 6.488 | 4.730 | 5.308 | 5.645 | 4.864 | 7.813 |
| CD0848pax | 0 | 5.113 | 6.235 | 3.380 | 5.915 | 6.388 | 6.409 | 7.263 |
| CD0924pax | 0 | 5.731 | 6.370 | 5.238 | 6.095 | 6.248 | 5.791 | 6.131 |
| CD1066pax | 0 | 5.346 | 5.900 | 4.903 | 5.990 | 6.868 | 7.466 | 6.211 |
| CD1073pax | 0 | 5.681 | 5.813 | 5.150 | 5.858 | 6.350 | 6.674 | 6.663 |
| CD1075pax | 0 | 5.128 | 7.010 | 4.535 | 6.075 | 8.228 | 7.264 | 6.563 |
| CD1089pax | 0 | 5.081 | 7.225 | 5.733 | 5.550 | 6.395 | 6.546 | 6.668 |
| CD1116pax | 0 | 4.188 | 5.500 | 5.023 | 5.295 | 6.180 | 5.764 | 6.378 |
| CD1120pax | 0 | 3.663 | 5.495 | 5.203 | 4.780 | 6.555 | 6.864 | 5.118 |
| CD1198pax | 0 | 5.398 | 6.210 | 4.155 | 6.055 | 6.095 | 6.086 | 5.881 |
| PB1179pax | 0 | 6.401 | 7.293 | 4.700 | 6.563 | 7.080 | 8.169 | 7.418 |
| PB1277pax | 0 | 6.403 | 7.520 | 4.860 | 6.260 | 7.185 | 7.586 | 6.351 |
| PB1301pax | 0 | 4.733 | 6.200 | 6.268 | 5.608 | 6.863 | 5.891 | 5.531 |
| PB1315pax | 0 | 3.898 | 6.165 | 5.438 | 4.998 | 6.008 | 5.206 | 7.161 |
| PB1345pax | 0 | 5.246 | 6.280 | 4.598 | 6.410 | 6.775 | 6.051 | 7.663 |
| PB1518pax | 0 | 6.806 | 7.803 | 5.055 | 5.818 | 7.230 | 7.134 | 7.328 |
| PB1520pax | 0 | 4.283 | 5.560 | 3.250 | 4.660 | 3.793 | 5.214 | 6.108 |
| PB1574pax | 0 | 7.538 | 8.685 | 5.583 | 7.453 | 7.483 | 7.166 | 8.226 |
| PB1783pax | 0 | 8.056 | 9.095 | 5.453 | 7.650 | 8.535 | 9.011 | 8.448 |
| PB1799pax | 0 | 7.338 | 8.760 | 5.765 | 7.435 | 8.855 | 9.181 | 7.801 |
| PB1811pax | 0 | 6.848 | 8.115 | 5.080 | 7.140 | 8.390 | 7.416 | 7.471 |
| PB1830pax | 0 | 5.788 | 7.385 | 5.923 | 6.440 | 6.870 | 7.444 | 9.253 |
| PB1833pax | 0 | 5.943 | 7.620 | 5.488 | 6.615 | 7.620 | 6.829 | 8.098 |
| PB1843pax | 0 | 7.218 | 7.870 | 5.780 | 6.770 | 8.338 | 5.739 | 8.708 |
| PB1851pax | 0 | 7.468 | 8.045 | 6.050 | 7.795 | 8.325 | 10.181 | 9.261 |
| PB1919pax | 0 | 8.271 | 9.525 | 5.233 | 7.165 | 8.975 | 9.051 | 9.108 |
| PB1922pax | 0 | 6.788 | 8.280 | 6.028 | 7.363 | 8.348 | 9.281 | 8.306 |
| PB1924pax | 0 | 7.748 | 8.655 | 6.758 | 7.628 | 8.303 | 8.816 | 9.401 |
| PB1937pax | 0 | 7.178 | 9.085 | 5.118 | 7.665 | 9.740 | 8.754 | 8.798 |
| PB1964pax | 0 | 5.491 | 7.820 | 4.463 | 6.065 | 7.843 | 7.726 | 8.496 |
| PB2027pax | 0 | 5.463 | 6.525 | 5.150 | 6.300 | 7.360 | 7.401 | 7.546 |
| PB2029pax | 0 | 5.793 | 7.060 | 5.050 | 6.375 | 6.973 | 7.624 | 7.758 |
| PB2073pax | 0 | 6.021 | 6.335 | 4.873 | 6.290 | 7.933 | 6.991 | 6.846 |
| PB2086pax | 0 | 5.048 | 5.665 | 4.208 | 5.098 | 6.453 | 5.286 | 5.991 |
| PB2099pax | 0 | 4.808 | 5.360 | 5.388 | 5.910 | 6.680 | 5.604 | 7.003 |
| PB2100pax | 0 | 6.353 | 6.960 | 4.465 | 6.085 | 7.625 | 7.351 | 6.826 |
| PB2132pax | 0 | 5.693 | 7.235 | 4.438 | 5.745 | 6.995 | 7.649 | 7.518 |
| PB2168pax | 0 | 6.776 | 7.593 | 4.605 | 6.168 | 7.125 | 8.284 | 6.993 |

TABLE 4-continued

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by ACTB. Levels shown correspond to ΔCt.

| Sample ID | Group | Gene | | | | | | |
|---|---|---|---|---|---|---|---|---|
| | | ANXA3 | CLEC4D | IL2RB | LMNB1 | PRRG4 | TNFAIP6 | VNN1 |
| PB2192pax | 0 | 6.701 | 7.845 | 5.483 | 6.230 | 6.965 | 7.751 | 8.378 |
| PB2196pax | 0 | 6.061 | 7.655 | 4.573 | 6.195 | 7.985 | 7.781 | 6.668 |
| PB2200pax | 0 | 6.706 | 7.640 | 5.158 | 6.025 | 7.103 | 6.826 | 6.276 |
| PB2213pax | 0 | 6.898 | 7.435 | 4.773 | 6.380 | 6.630 | 8.614 | 7.448 |
| PB2224pax | 0 | 4.841 | 5.385 | 4.743 | 5.210 | 6.448 | 7.546 | 6.851 |
| PB2228pax | 0 | 6.511 | 6.915 | 3.953 | 6.450 | 7.373 | 8.906 | 8.086 |
| PB2229pax | 0 | 5.771 | 6.440 | 5.588 | 6.030 | 5.865 | 7.091 | 6.528 |
| PB2277pax | 0 | 6.348 | 6.685 | 4.290 | 5.705 | 5.930 | 5.986 | 7.351 |
| PB2297pax | 0 | 5.886 | 6.785 | 4.703 | 5.835 | 6.533 | 6.451 | 5.696 |
| PB2312pax | 0 | 5.533 | 6.530 | 3.773 | 6.098 | 5.978 | 6.651 | 6.746 |
| PB2398pax | 0 | 4.711 | 5.390 | 5.033 | 5.440 | 5.748 | 5.136 | 7.111 |
| PB2409pax | 0 | 5.946 | 7.195 | 4.933 | 5.835 | 6.950 | 6.811 | 7.683 |
| PB2414pax | 0 | 7.843 | 7.790 | 3.955 | 6.380 | 7.745 | 9.026 | 7.101 |
| PB2467pax | 0 | 5.773 | 6.935 | 4.260 | 5.955 | 6.525 | 7.596 | 6.756 |
| PB2473pax | 0 | 6.818 | 8.275 | 5.530 | 7.375 | 8.405 | 7.586 | 8.561 |
| PB2512pax | 0 | 5.603 | 7.355 | 4.340 | 6.215 | 6.345 | 6.926 | 7.511 |
| PB2568pax | 0 | 5.326 | 5.850 | 5.303 | 5.710 | 7.178 | 7.561 | 7.331 |
| PB2571pax | 0 | 5.561 | 5.995 | 4.523 | 6.060 | 6.173 | 7.396 | 7.791 |
| PB2603pax | 0 | 5.778 | 6.480 | 3.953 | 5.903 | 6.313 | 7.021 | 5.986 |
| PB2624pax | 0 | 5.383 | 5.465 | 3.948 | 5.498 | 6.838 | 6.146 | 6.741 |
| PB2824pax | 0 | 5.781 | 6.748 | 4.675 | 5.758 | 6.830 | 7.154 | 7.223 |
| PB2880pax | 0 | 5.906 | 6.090 | 4.728 | 6.160 | 5.218 | 7.361 | 7.386 |
| PB3088pax | 0 | 6.601 | 6.760 | 3.858 | 5.725 | 6.395 | 8.456 | 7.378 |
| RC0882pax | 0 | 5.043 | 6.540 | 4.533 | 5.708 | 6.083 | 7.351 | 7.151 |
| RC0888pax | 0 | 4.726 | 5.740 | 4.948 | 5.330 | 6.775 | 6.516 | 6.168 |
| RC0968pax | 0 | 3.238 | 3.590 | 4.008 | 4.303 | 6.118 | 4.716 | 7.086 |
| RC2114pax | 0 | 4.473 | 5.900 | 4.768 | 5.168 | 6.028 | 5.216 | 7.446 |
| RC2238pax | 0 | 7.318 | 8.785 | 5.878 | 7.175 | 8.665 | 9.209 | 9.903 |
| RC2681pax | 0 | 6.331 | 7.515 | 5.623 | 6.995 | 7.833 | 6.471 | 7.536 |
| RC2703pax | 0 | 8.093 | 8.360 | 5.973 | 7.053 | 8.253 | 7.801 | 8.091 |
| RC2749pax | 0 | 6.448 | 8.695 | 5.895 | 7.205 | 7.905 | 7.726 | 8.666 |
| RC2750pax | 0 | 5.578 | 6.650 | 6.753 | 6.428 | 7.993 | 7.761 | 7.111 |
| RC2756pax | 0 | 7.478 | 8.135 | 5.340 | 7.095 | 8.420 | 7.781 | 8.671 |
| RC2771pax | 0 | 5.848 | 8.345 | 6.240 | 6.440 | 7.648 | 8.449 | 9.303 |
| RC2790pax | 0 | 8.086 | 9.228 | 6.880 | 7.573 | 8.475 | 8.679 | 8.948 |
| RC2792pax | 0 | 7.956 | 8.058 | 5.850 | 7.068 | 8.320 | 9.219 | 8.448 |
| RC2808pax | 0 | 6.556 | 8.790 | 5.233 | 6.605 | 7.815 | 7.096 | 7.653 |
| RC2822pax | 0 | 7.921 | 9.163 | 6.255 | 7.193 | 8.075 | 10.284 | 7.718 |
| RC2834pax | 0 | 6.588 | 8.535 | 6.520 | 6.810 | 7.920 | 9.946 | 9.651 |
| RC2871pax | 0 | 5.443 | 6.530 | 4.563 | 6.280 | 7.165 | 7.479 | 8.158 |
| RC2879pax | 0 | 6.266 | 8.105 | 5.978 | 6.620 | 8.465 | 7.971 | 7.298 |
| RC2892pax | 0 | 6.086 | 7.423 | 5.185 | 6.163 | 7.185 | 8.559 | 7.748 |
| RC2895pax | 0 | 6.148 | 6.900 | 4.378 | 6.270 | 7.450 | 6.109 | 7.473 |
| RC2921pax | 0 | 6.846 | 7.623 | 4.720 | 6.758 | 7.520 | 7.954 | 8.073 |
| RC2958pax | 0 | 6.581 | 6.735 | 4.863 | 6.185 | 6.638 | 5.851 | 7.616 |
| RC3022pax | 0 | 6.401 | 6.660 | 4.888 | 6.685 | 7.925 | 7.776 | 6.578 |
| RC3112pax | 0 | 6.938 | 8.095 | 5.408 | 6.435 | 7.475 | 8.629 | 7.713 |
| RC3146pax | 0 | 6.018 | 6.655 | 5.340 | 5.905 | 6.855 | 7.491 | 7.451 |
| RC3184pax | 0 | 6.998 | 7.910 | 4.398 | 6.370 | 7.395 | 7.329 | 7.598 |
| RC3232pax | 0 | 5.021 | 6.460 | 5.003 | 5.030 | 7.008 | 4.941 | 8.671 |
| RC3324pax | 0 | 5.158 | 6.220 | 5.203 | 5.055 | 6.935 | 6.869 | 5.713 |
| RC3327pax | 0 | 5.238 | 5.225 | 4.708 | 5.313 | 5.253 | 6.381 | 7.541 |
| RC3334pax | 0 | 5.953 | 7.670 | 4.710 | 6.135 | 6.850 | 6.816 | 8.081 |
| RC3355pax | 0 | 5.871 | 7.253 | 5.620 | 5.358 | 6.325 | 7.699 | 6.648 |
| RC3380pax | 0 | 5.418 | 6.395 | 5.363 | 5.453 | 6.423 | 6.786 | 6.481 |
| RC3392pax | 0 | 6.378 | 8.025 | 4.445 | 6.170 | 7.265 | 8.546 | 7.756 |
| RC3413pax | 0 | 6.176 | 7.940 | 4.768 | 6.100 | 6.545 | 7.051 | 8.858 |
| RC3421pax | 0 | 5.661 | 5.515 | 5.088 | 5.900 | 6.483 | 5.191 | 5.961 |
| RC3468pax | 0 | 5.831 | 5.890 | 5.443 | 5.905 | 6.523 | 7.171 | 6.636 |
| RC3498pax | 0 | 5.553 | 5.515 | 5.593 | 6.145 | 7.200 | 7.484 | 6.468 |
| CD0157pax | 1 | 6.223 | 6.530 | 4.198 | 6.115 | 6.930 | 7.654 | 8.168 |
| CD0164pax | 1 | 4.726 | 5.395 | 4.083 | 5.660 | 10.733 | 7.791 | 6.696 |
| CD0256pax | 1 | 4.833 | 6.295 | 4.735 | 6.045 | 6.785 | 7.141 | 6.911 |
| CD0322pax | 1 | 5.153 | 7.050 | 6.308 | 5.820 | 7.325 | 7.239 | 8.603 |
| CD0356pax | 1 | 5.243 | 5.555 | 6.038 | 5.925 | 6.580 | 6.239 | 5.823 |
| CD0371pax | 1 | 5.643 | 7.110 | 5.073 | 6.045 | 6.245 | 6.394 | 5.968 |
| CD0629pax | 1 | 4.453 | 5.995 | 4.503 | 5.555 | 7.380 | 5.114 | 6.563 |
| CD1050pax | 1 | 6.238 | 5.930 | 4.943 | 6.150 | 7.105 | 6.969 | 7.243 |
| MH0001pax | 1 | 7.266 | 8.375 | 5.103 | 7.770 | 8.568 | 9.266 | 8.706 |
| MH0009pax | 1 | 6.078 | 7.150 | 5.990 | 6.325 | 7.185 | 6.131 | 6.426 |

TABLE 4-continued

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by ACTB. Levels shown correspond to ΔCt.

| | | Gene | | | | | | |
|---|---|---|---|---|---|---|---|---|
| Sample ID | Group | ANXA3 | CLEC4D | IL2RB | LMNB1 | PRRG4 | TNFAIP6 | VNN1 |
| MH0011pax | 1 | 2.393 | 4.420 | 8.808 | 4.258 | 6.888 | 3.846 | 5.756 |
| MH0012pax | 1 | 4.673 | 6.965 | 5.368 | 5.970 | 7.680 | 6.659 | 7.043 |
| MH0014pax | 1 | 6.266 | 8.155 | 5.003 | 6.395 | 6.995 | 9.436 | 7.983 |
| MH0016pax | 1 | 5.408 | 6.770 | 6.225 | 6.050 | 6.635 | 6.181 | 6.561 |
| MH0017pax | 1 | 6.071 | 8.290 | 5.323 | 6.710 | 6.750 | 8.231 | 8.433 |
| MH0018pax | 1 | 6.856 | 7.175 | 5.093 | 6.250 | 7.358 | 8.451 | 6.791 |
| MH0021pax | 1 | 6.948 | 6.675 | 5.263 | 5.483 | 6.398 | 8.236 | 8.111 |
| MH0022pax | 1 | 6.471 | 7.508 | 5.280 | 6.228 | 7.030 | 7.344 | 7.548 |
| MH0024pax | 1 | 5.016 | 5.640 | 4.488 | 5.340 | 5.793 | 5.211 | 6.241 |
| MH0026pax | 1 | 4.351 | 6.775 | 5.558 | 5.440 | 6.840 | 5.861 | 6.028 |
| MH0028pax | 1 | 6.183 | 6.815 | 5.818 | 5.918 | 5.883 | 5.986 | 6.176 |
| MH0029pax | 1 | 5.388 | 6.360 | 5.015 | 6.255 | 5.925 | 6.846 | 6.831 |
| MH0035pax | 1 | 6.111 | 8.575 | 4.708 | 6.645 | 7.460 | 7.051 | 7.638 |
| MH0037pax | 1 | 5.441 | 7.063 | 5.375 | 5.578 | 6.325 | 7.089 | 7.948 |
| MH0038pax | 1 | 7.206 | 7.463 | 5.020 | 6.748 | 7.635 | 8.089 | 8.113 |
| MH0039pax | 1 | 4.036 | 5.113 | 5.110 | 5.298 | 5.110 | 5.394 | 6.383 |
| MH0042pax | 1 | 4.643 | 5.560 | 4.425 | 5.900 | 5.785 | 4.876 | 5.901 |
| MH0050pax | 1 | 3.763 | 6.495 | 4.908 | 4.718 | 5.698 | 6.641 | 7.721 |
| MH0051pax | 1 | 4.941 | 5.693 | 6.225 | 5.818 | 4.795 | 4.044 | 6.338 |
| PB1829pax | 1 | 7.363 | 9.380 | 6.678 | 7.073 | 7.428 | 8.841 | 9.241 |
| PB1842pax | 1 | 7.483 | 8.295 | 6.188 | 7.488 | 7.173 | 8.786 | 8.011 |
| PB1872pax | 1 | 7.051 | 8.525 | 6.318 | 7.410 | 7.175 | 8.486 | 7.533 |
| PB2857pax | 1 | 4.268 | 6.600 | 4.810 | 5.300 | 6.470 | 5.266 | 6.976 |
| RC2919pax | 1 | 7.106 | 7.488 | 4.420 | 6.463 | 8.350 | 8.399 | 9.318 |
| RC3062pax | 1 | 5.006 | 6.200 | 4.513 | 5.195 | 6.340 | 5.271 | 5.538 |
| RC3277pax | 1 | 5.068 | 6.360 | 4.770 | 5.360 | 6.205 | 5.701 | 6.136 |
| RC3297pax | 1 | 5.748 | 6.970 | 4.728 | 5.843 | 6.493 | 8.451 | 7.206 |
| RC3445pax | 1 | 5.503 | 6.560 | 5.290 | 6.295 | 6.560 | 6.711 | 7.021 |
| RC3467pax | 1 | 6.893 | 8.640 | 3.945 | 6.670 | 7.040 | 8.251 | 7.771 |
| CC0003pax | 1 | 4.281 | 5.963 | 5.500 | 4.608 | 5.205 | 7.009 | 4.853 |
| DC0001pax | 1 | 5.713 | 5.580 | 5.378 | 5.868 | 6.408 | 6.201 | 6.541 |
| DC0002pax | 1 | 6.323 | 6.125 | 5.423 | 6.380 | 6.410 | 7.374 | 7.273 |
| DS0003pax | 1 | 4.816 | 6.663 | 6.615 | 5.248 | 7.380 | 6.849 | 6.398 |
| FC0005pax | 1 | 5.953 | 6.735 | 5.618 | 6.605 | 6.980 | 6.649 | 8.698 |
| FC0011pax | 1 | 6.458 | 7.550 | 7.063 | 6.915 | 7.950 | 8.539 | 8.338 |
| FC0012pax | 1 | 3.868 | 6.850 | 7.138 | 5.285 | 6.375 | 6.849 | 7.063 |
| JGA0001pax | 1 | 5.426 | 6.250 | 7.448 | 6.125 | 8.173 | 6.586 | 7.096 |
| JGA0008pax | 1 | 5.448 | 7.600 | 6.018 | 6.793 | 7.403 | 7.366 | 7.841 |
| JH0002pax | 1 | 6.108 | 7.335 | 5.633 | 6.725 | 6.950 | 7.484 | 7.128 |
| JH0003pax | 1 | 6.053 | 6.635 | 5.090 | 5.905 | 6.145 | 5.701 | 7.081 |
| JH0004pax | 1 | 5.373 | 5.985 | 5.265 | 5.935 | 6.570 | 7.371 | 6.961 |
| JH0005pax | 1 | 5.341 | 6.565 | 5.008 | 5.780 | 6.688 | 7.356 | 7.091 |
| JH0006pax | 1 | 4.771 | 5.840 | 5.073 | 5.525 | 6.198 | 6.731 | 5.551 |
| JH0007pax | 1 | 2.956 | 3.035 | 5.353 | 4.815 | 6.483 | 5.661 | 4.916 |
| JH0008pax | 1 | 5.876 | 8.435 | 5.173 | 6.265 | 7.573 | 7.811 | 6.711 |
| JH0009pax | 1 | 4.101 | 3.770 | 4.793 | 5.540 | 5.293 | 4.636 | 5.876 |
| JH0010pax | 1 | 5.026 | 5.810 | 4.958 | 6.105 | 7.018 | 6.046 | 5.526 |
| JH0012pax | 1 | 4.981 | 5.435 | 4.718 | 5.965 | 6.318 | 5.801 | 6.511 |
| JH0013pax | 1 | 5.501 | 6.610 | 5.268 | 5.905 | 7.048 | 8.861 | 7.191 |
| JH0014pax | 1 | 5.053 | 5.235 | 4.253 | 4.735 | 4.860 | 6.259 | 7.488 |
| JH0016pax | 1 | 5.596 | 6.390 | 4.438 | 5.980 | 6.338 | 5.566 | 6.191 |
| JH0018pax | 1 | 4.401 | 5.770 | 5.248 | 5.765 | 6.348 | 5.696 | 6.446 |
| JH0019pax | 1 | 5.751 | 6.775 | 5.468 | 6.055 | 6.693 | 5.926 | 6.656 |
| JH0020pax | 1 | 5.001 | 7.450 | 4.563 | 5.875 | 5.618 | 5.756 | 6.706 |
| JH0021pax | 1 | 5.726 | 7.650 | 6.058 | 5.730 | 6.105 | 6.611 | 6.808 |
| JH0023pax | 1 | 4.696 | 6.805 | 3.873 | 5.020 | 6.960 | 5.951 | 6.968 |
| JH0024pax | 1 | 6.008 | 7.895 | 5.113 | 6.865 | 7.620 | 9.099 | 8.698 |
| JH0025pax | 1 | 4.796 | 5.780 | 5.398 | 5.150 | 5.225 | 5.626 | 6.423 |
| JH0026pax | 1 | 4.491 | 6.940 | 5.363 | 5.800 | 6.725 | 7.646 | 7.493 |
| JH0027pax | 1 | 3.111 | 4.720 | 6.498 | 4.280 | 5.225 | 4.486 | 5.288 |
| JH0028pax | 1 | 4.416 | 5.680 | 3.858 | 5.395 | 5.820 | 7.196 | 6.378 |
| JH0029pax | 1 | 4.176 | 5.950 | 5.063 | 5.055 | 5.850 | 4.971 | 6.963 |
| JH0031pax | 1 | 5.371 | 7.385 | 5.613 | 6.040 | 6.595 | 7.096 | 7.213 |
| JH0032pax | 1 | 7.326 | 8.430 | 4.933 | 6.075 | 6.925 | 8.231 | 8.408 |
| JH0033pax | 1 | 5.258 | 8.160 | 5.380 | 5.560 | 6.455 | 8.126 | 6.181 |
| JH0034pax | 1 | 4.061 | 6.560 | 4.468 | 5.725 | 6.135 | 6.721 | 6.703 |
| JH0035pax | 1 | 4.051 | 6.625 | 3.703 | 4.690 | 4.400 | 6.551 | 5.523 |
| JH0036pax | 1 | 5.348 | 6.260 | 4.608 | 5.480 | 6.030 | 6.904 | 6.618 |
| JH0038pax | 1 | 4.538 | 6.195 | 4.878 | 5.025 | 5.945 | 7.049 | 5.673 |
| JH0039pax | 1 | 5.458 | 6.595 | 4.165 | 5.525 | 6.950 | 8.691 | 5.141 |

TABLE 4-continued

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by ACTB. Levels shown correspond to ΔCt.

| Sample ID | Group | Gene | | | | | | |
|---|---|---|---|---|---|---|---|---|
| | | ANXA3 | CLEC4D | IL2RB | LMNB1 | PRRG4 | TNFAIP6 | VNN1 |
| JH0040pax | 1 | 5.458 | 6.555 | 4.773 | 6.140 | 6.580 | 6.144 | 6.658 |
| JH0041pax | 1 | 6.038 | 7.940 | 5.033 | 6.335 | 6.760 | 7.489 | 7.178 |
| JH0042pax | 1 | 3.191 | 4.985 | 5.398 | 4.500 | 5.978 | 4.401 | 4.221 |
| JH0043pax | 1 | 5.263 | 6.670 | 6.073 | 6.110 | 5.955 | 5.779 | 9.668 |
| JH0046pax | 1 | 5.161 | 5.360 | 4.448 | 5.885 | 5.808 | 5.951 | 5.811 |
| JH0047pax | 1 | 4.396 | 6.385 | 4.078 | 5.625 | 6.828 | 6.501 | 6.836 |
| JH0051pax | 1 | 4.881 | 6.370 | 5.158 | 5.290 | 5.130 | 5.676 | 5.388 |
| JH0052pax | 1 | 5.066 | 7.240 | 5.528 | 5.510 | 5.625 | 5.616 | 5.703 |
| JH0053pax | 1 | 4.653 | 6.375 | 5.483 | 5.258 | 6.578 | 5.701 | 6.571 |
| JH0057pax | 1 | 4.201 | 7.330 | 4.208 | 4.755 | 6.140 | 6.661 | 5.968 |
| JH0059pax | 1 | 3.698 | 4.950 | 4.243 | 4.478 | 4.668 | 4.896 | 5.166 |
| JH0060pax | 1 | 4.733 | 6.230 | 5.303 | 5.833 | 6.448 | 6.646 | 6.861 |
| JH0061pax | 1 | 5.063 | 7.300 | 4.298 | 5.063 | 6.208 | 8.041 | 5.466 |
| JH0063pax | 1 | 4.923 | 6.845 | 4.748 | 5.433 | 5.178 | 6.021 | 7.756 |
| JH0065pax | 1 | 3.263 | 5.220 | 5.660 | 4.510 | 5.355 | 4.816 | 4.301 |
| JH0066pax | 1 | 5.703 | 7.575 | 6.638 | 5.988 | 5.818 | 5.851 | 6.791 |
| JH0068pax | 1 | 5.536 | 6.448 | 4.895 | 5.473 | 5.925 | 7.239 | 7.708 |
| JH0069pax | 1 | 3.723 | 5.435 | 4.460 | 4.800 | 4.955 | 4.436 | 4.061 |
| JH0071pax | 1 | 3.748 | 4.580 | 6.050 | 4.785 | 5.850 | 5.096 | 6.261 |
| JH0072pax | 1 | 5.863 | 6.185 | 5.185 | 6.015 | 6.035 | 7.306 | 6.386 |
| JH0077pax | 1 | 4.473 | 5.810 | 5.193 | 5.635 | 6.020 | 5.959 | 7.278 |
| JH0078pax | 1 | 5.591 | 5.693 | 3.685 | 5.818 | 4.875 | 5.419 | 5.778 |
| JH0080pax | 1 | 2.903 | 4.470 | 5.033 | 4.158 | 5.093 | 3.921 | 6.031 |
| JH0082pax | 1 | 4.611 | 5.398 | 4.800 | 5.108 | 5.465 | 5.364 | 6.683 |
| JH0083pax | 1 | 3.903 | 6.445 | 5.398 | 5.333 | 4.473 | 6.006 | 6.606 |
| JH0086pax | 1 | 5.633 | 5.850 | 5.063 | 5.288 | 4.978 | 5.936 | 7.021 |
| JH0092pax | 1 | 5.241 | 8.328 | 5.350 | 6.113 | 6.540 | 6.349 | 7.663 |
| MIP0004pax | 1 | 3.201 | 3.098 | 5.340 | 3.873 | 4.510 | 4.459 | 2.743 |
| MP0013Apax | 1 | 7.028 | 9.300 | 6.195 | 7.105 | 8.385 | 8.561 | 7.406 |
| MP0014Bpax | 1 | 6.418 | 8.420 | 6.623 | 6.633 | 8.008 | 8.746 | 7.586 |
| MP0018Apax | 1 | 6.003 | 7.900 | 7.005 | 6.740 | 6.635 | 7.146 | 6.281 |
| MP0019Bpax | 1 | 6.283 | 7.090 | 6.653 | 6.528 | 7.058 | 6.696 | 8.656 |
| MP0024pax | 1 | 5.436 | 7.823 | 6.375 | 6.383 | 7.655 | 8.939 | 8.013 |
| NK2001pax | 1 | 5.061 | 6.843 | 6.230 | 5.613 | 4.680 | 6.349 | 7.873 |
| NK2002pax | 1 | 5.516 | 5.903 | 5.210 | 5.568 | 5.585 | 6.809 | 6.753 |
| NK2003pax | 1 | 4.986 | 6.388 | 5.590 | 5.588 | 6.345 | 7.404 | 5.723 |
| NK2004pax | 1 | 4.626 | 6.648 | 5.435 | 5.048 | 4.945 | 6.319 | 5.318 |

Surprisingly, analysis of the data showed that RNA encoded by ANXA3, CLEC4D, LMNB1, PRRG4, TNFAIP6 and VNN1 is present on average at a significantly higher level (p-value less than 0.05) in blood of subjects having colorectal cancer relative to subjects having no colorectal pathology, and that RNA encoded by IL2RB is present on average at a significantly lower level (p-value less than 0.05) in blood of subjects having colorectal cancer relative to subjects having no colorectal pathology (Table 5). The ranges of fold-change in the levels of RNA encoded by these genes normalized to levels of RNA encoded by ACTB in blood of the training set subjects having colorectal cancer relative to the training set subjects not having any colorectal pathology are shown in Table 5.

TABLE 5

Sample training set ranges of fold-changes in levels of RNA encoded by ANXA3, CLEC4D, IL2RB, LMNB1, PRRG4, TNFAIP6 and VNN1 normalized to levels of RNA encoded by ACTB in blood of subjects having colorectal cancer relative to subjects not having any colorectal pathology.

| | Gene | | | | | | |
|---|---|---|---|---|---|---|---|
| | ANXA3 | CLEC4D | IL2RB | LMNB1 | PRRG4 | TNFAIP6 | VNN1 |
| Average normalized RNA level in subjects having colorectal cancer (ΔCt) | 5.21 | 6.58 | 5.28 | 5.76 | 6.41 | 6.64 | 6.77 |
| Average normalized RNA level in subjects not having any colorectal pathology (ΔCt) | 5.92 | 7.02 | 4.95 | 6.09 | 7.00 | 17.19 | 7.31 |
| Average RNA level fold-change | 1.63 | 1.36 | 0.80 | 1.26 | 1.51 | 1.46 | 1.45 |

TABLE 5-continued

Sample training set ranges of fold-changes in levels of RNA encoded by ANXA3, CLEC4D, IL2RB, LMNB1, PRRG4, TNFAIP6 and VNN1 normalized to levels of RNA encoded by ACTB in blood of subjects having colorectal cancer relative to subjects not having any colorectal pathology.

| | Gene | | | | | | |
|---|---|---|---|---|---|---|---|
| | ANXA3 | CLEC4D | IL2RB | LMNB1 | PRRG4 | TNFAIP6 | VNN1 |
| p-value for average RNA level fold-change | 5.0E−07 | 2.6E−03 | 1.1E−03 | 5.4E−04 | 2.3E−06 | 7.0E−04 | 1.4E−04 |
| Maximum observed RNA level directional fold-change | 11.53 | 15.86 | 0.07 | 4.66 | 6.07 | 10.12 | 23.63 |

As can be seen in Table 5, a test subject having a blood level of RNA encoded by ANXA3 which is 1.6 to 11.5 fold higher than the average level of RNA encoded by this gene in blood of subjects not having any colorectal pathology is more likely to have colorectal cancer than to not have any colorectal pathology.

As can be seen in Table 5, a test subject having a blood level of RNA encoded by CLEC4D which is 1.4 to 15.9 fold higher than the average level of RNA encoded by this gene in blood of subjects not having any colorectal pathology is more likely to have colorectal cancer than to not have any colorectal pathology.

As can be seen in Table 5, a test subject having a blood level of RNA encoded by LMNB1 which is 1.3 to 4.7 fold higher than the average level of RNA encoded by this gene in blood of subjects not having any colorectal pathology is more likely to have colorectal cancer than to not have any colorectal pathology.

As can be seen in Table 5, a test subject having a blood level of RNA encoded by PRRG4 which is 1.5 to 6.1 fold higher than the average level of RNA encoded by this gene in blood of subjects not having any colorectal pathology is more likely to have colorectal cancer than to not have any colorectal pathology.

As can be seen in Table 5, a test subject having a blood level of RNA encoded by TNFAIP6 which is 1.46 to 10.12 fold higher than the average level of RNA encoded by this gene in blood of subjects not having any colorectal pathology is more likely to have colorectal cancer than to not have any colorectal pathology.

As can be seen in Table 5, a test subject having a blood level of RNA encoded by VNN1 which is 1.45 to 23.63 fold higher than the average level of RNA encoded by this gene in blood of subjects not having any colorectal pathology is more likely to have colorectal cancer than to not have any colorectal pathology.

As can be seen in Table 5, a test subject having a blood level of RNA encoded by IL2RB which is 0.8 to 0.1 fold that of the average level of RNA encoded by this gene in blood of subjects not having any colorectal pathology is more likely to have colorectal cancer than to not have any colorectal pathology.

Generation of Logistic Regression Models for Determining the Probability that a Test Subject has Colorectal Cancer Versus not Having any Colorectal Pathology Via Measurement of Levels of RNA Encoded by ANXA3, CLEC4D, IL2RB, LMNB1, PRRG4, TNFAIP6 and VNN1 Normalized to Levels of RNA Encoded by ACTB:

Linear regression analysis of levels of RNA encoded by ANXA3, CLEC4D, IL2RB, LMNB1, PRRG4, TNFAIP6 and VNN1 surprisingly showed that logistic regression models based on blood expression levels of all 127 possible combinations of one or more of these genes determined in the sample training set could be generated, for discriminating, with a receiver-operating characteristic (ROC) area under the curve (AUC) of at least 0.61, between subjects having colorectal cancer and subjects not having any colorectal pathology. Examples of these logistic regression models are shown in Table 6. A model based on ANXA3, CLEC4D, IL2RB, LMNB1, PRRG4, TNFAIP6 and VNN1 (Table 6, Model #1) was surprisingly found to enable discrimination with a ROC AUC of 0.79 between subjects having colorectal cancer and subjects not having any colorectal pathology.

By way of example, Model #1 of Table 6 corresponds to:

$$P=\{1+e^{\wedge}-[0.684+(-0.916)(L_{ANXA3})+(0.353)(L_{CLEC4D})+(0.871)(L_{IL2RB})+(0.907)(L_{LMNB1})+(-0.968)(L_{PRRG4})+(0.154)(L_{TNFAIP6})+(-0.355)(L_{VNN1})]\}^{\wedge}-1,$$

where P is the probability that a test subject has colorectal cancer as opposed to not having any colorectal pathology, $L_{ANXA3}$ is a ratio of a level of RNA encoded by ANXA3 to a level of RNA encoded by ACTB in blood of the test subject, $L_{CLEC4D}$ is a ratio of a level of RNA encoded by CLEC4D to a level of RNA encoded by ACTB in blood of the test subject, $L_{IL2RB}$ is a ratio of a level of RNA encoded by IL2RB to a level of RNA encoded by ACTB in blood of the test subject, $L_{LMNB1}$ is a ratio of a level of RNA encoded by LMNB1 to a level of RNA encoded by ACTB in blood of the test subject, $L_{PRRG4}$ is a ratio of a level of RNA encoded by PRRG4 to a level of RNA encoded by ACTB in blood of the test subject, $L_{TNFAIP6}$ is a ratio of a level of RNA encoded by TNFAIP6 to a level of RNA encoded by ACTB in blood of the test subject, and $L_{VNN1}$ is a ratio of a level of RNA encoded by VNN1 to a level of RNA encoded by ACTB in blood of the test subject.

Further by way of example, Model #104 of Table 6 corresponds to:

$$P=\{1+e^{\wedge}-[4.311+(-0.659)(L_{PRRG4})]\}^{\wedge}-1,$$

where P is the probability that a test subject has colorectal cancer as opposed to not having any colorectal pathology, and $L_{PRRG4}$ is a ratio of a level of RNA encoded by PRRG4 to a level of RNA encoded by ACTB in blood of the test subject.

TABLE 6

Logistic regression models based on blood expression levels of any possible combination of one or more of ANXA3, CLEC4D, IL2RB, LMNB1, PRRG4, TNFAIP6 and VNN1 for determining the probability that a test subject has colorectal cancer as opposed to not having colorectal cancer.

| Logistic regression model # | No. of genes in model | ROC AUC Training Set | ROC AUC Blind Test Set | Constant ($K_0$) | Gene-specific regression coefficient ($K_n$) | | | | | | |
|---|---|---|---|---|---|---|---|---|---|---|---|
| | | | | | ANXA3 | CLEC4D | IL2RB | LMNB1 | PRRG4 | TNFAIP6 | VNN1 |
| 1 | 7 | 0.79 | 0.79 | 0.684 | −0.916 | 0.353 | 0.871 | 0.907 | −0.968 | 0.154 | −0.355 |
| 2 | 6 | 0.79 | 0.79 | 0.743 | −0.859 | 0.402 | 0.870 | 0.893 | −0.916 | — | −0.341 |
| 3 | 4 | 0.78 | 0.78 | 1.321 | −0.614 | 0.358 | 0.898 | — | −0.749 | — | — |
| 4 | 5 | 0.78 | 0.79 | 0.343 | −0.907 | 0.322 | 0.829 | 0.737 | −0.925 | — | — |
| 5 | 5 | 0.78 | 0.78 | 1.814 | −0.527 | 0.424 | 0.943 | — | −0.715 | — | −0.267 |
| 6 | 5 | 0.78 | 0.82 | 0.830 | −0.641 | — | 0.883 | 0.935 | −0.824 | — | −0.270 |
| 7 | 5 | 0.78 | 0.79 | 1.264 | −0.658 | 0.318 | 0.898 | — | −0.788 | 0.120 | — |
| 8 | 5 | 0.78 | 0.82 | 0.359 | −0.825 | — | 0.845 | 0.794 | −0.927 | 0.189 | — |
| 9 | 6 | 0.78 | 0.80 | 0.282 | −0.953 | 0.280 | 0.829 | 0.740 | −0.965 | 0.123 | — |
| 10 | 6 | 0.78 | 0.78 | 1.772 | −0.575 | 0.380 | 0.944 | — | −0.760 | 0.141 | −0.277 |
| 11 | 6 | 0.78 | 0.82 | 0.727 | −0.768 | — | 0.883 | 0.948 | −0.918 | 0.230 | −0.304 |
| 12 | 4 | 0.77 | 0.82 | 0.477 | −0.716 | — | 0.848 | 0.803 | −0.850 | — | — |
| 13 | 3 | 0.77 | 0.80 | 1.969 | — | — | 1.001 | — | −0.752 | — | −0.305 |
| 14 | 4 | 0.77 | 0.81 | 1.950 | −0.280 | — | 0.966 | — | −0.610 | — | −0.189 |
| 15 | 4 | 0.77 | 0.78 | 1.915 | — | 0.161 | 1.009 | — | −0.840 | — | −0.374 |
| 16 | 4 | 0.77 | 0.80 | 1.686 | — | — | 0.995 | 0.238 | −0.855 | — | −0.363 |
| 17 | 5 | 0.77 | 0.79 | 1.748 | — | 0.130 | 1.005 | 0.147 | −0.887 | — | −0.397 |
| 18 | 4 | 0.77 | 0.82 | 1.436 | −0.487 | — | 0.925 | — | −0.731 | 0.195 | — |
| 19 | 4 | 0.77 | 0.80 | 1.934 | — | — | 1.008 | — | −0.808 | 0.084 | −0.334 |
| 20 | 5 | 0.77 | 0.81 | 1.861 | −0.398 | — | 0.965 | — | −0.697 | 0.223 | −0.218 |
| 21 | 5 | 0.77 | 0.79 | 1.907 | — | 0.147 | 1.011 | — | −0.852 | 0.029 | −0.378 |
| 22 | 5 | 0.77 | 0.79 | 1.697 | — | — | 1.001 | 0.207 | −0.880 | 0.058 | −0.376 |
| 23 | 6 | 0.77 | 0.79 | 1.748 | — | 0.121 | 1.006 | 0.142 | −0.894 | 0.021 | −0.399 |
| 24 | 2 | 0.76 | 0.79 | 1.225 | — | — | 0.957 | — | −0.928 | — | — |
| 25 | 3 | 0.76 | 0.81 | 1.570 | −0.371 | — | 0.930 | — | −0.649 | — | — |
| 26 | 3 | 0.76 | 0.79 | 1.233 | — | −0.006 | 0.957 | — | −0.924 | — | — |
| 27 | 3 | 0.76 | 0.79 | 1.328 | — | — | 0.960 | −0.058 | −0.894 | — | — |
| 28 | 4 | 0.76 | 0.79 | 1.332 | — | 0.015 | 0.960 | −0.072 | −0.898 | — | — |
| 29 | 3 | 0.76 | 0.79 | 1.249 | — | — | 0.956 | — | −0.912 | −0.019 | — |
| 30 | 4 | 0.76 | 0.79 | 1.244 | — | 0.006 | 0.956 | — | −0.914 | −0.022 | — |
| 31 | 4 | 0.76 | 0.79 | 1.328 | — | — | 0.959 | −0.052 | −0.890 | −0.009 | — |
| 32 | 5 | 0.76 | 0.79 | 1.333 | — | 0.022 | 0.960 | −0.067 | −0.893 | −0.016 | — |
| 33 | 3 | 0.75 | 0.80 | 0.744 | −0.544 | — | 0.820 | — | — | — | −0.282 |
| 34 | 4 | 0.75 | 0.78 | 0.536 | −0.717 | 0.252 | 0.784 | — | — | — | −0.333 |
| 35 | 4 | 0.75 | 0.80 | 0.324 | −0.670 | — | 0.780 | 0.260 | — | — | −0.313 |
| 36 | 5 | 0.75 | 0.78 | 0.241 | −0.798 | 0.236 | 0.757 | 0.189 | — | — | −0.353 |
| 37 | 5 | 0.75 | 0.75 | 2.890 | −1.124 | 0.436 | — | 1.167 | −0.723 | — | −0.254 |
| 38 | 4 | 0.75 | 0.80 | 0.701 | −0.567 | — | 0.818 | — | — | 0.033 | −0.288 |
| 39 | 5 | 0.75 | 0.78 | 0.571 | −0.702 | 0.266 | 0.785 | — | — | −0.036 | −0.330 |
| 40 | 5 | 0.75 | 0.80 | 0.308 | −0.680 | — | 0.779 | 0.254 | — | 0.019 | −0.316 |
| 41 | 6 | 0.75 | 0.78 | 0.271 | −0.784 | 0.253 | 0.757 | 0.198 | — | −0.043 | −0.349 |
| 42 | 6 | 0.75 | 0.76 | 2.851 | −1.176 | 0.395 | — | 1.177 | −0.767 | 0.134 | −0.266 |
| 43 | 2 | 0.74 | 0.80 | 0.043 | −0.713 | — | 0.751 | — | — | — | — |
| 44 | 3 | 0.74 | 0.79 | −0.169 | −0.843 | 0.160 | 0.721 | — | — | — | — |
| 45 | 3 | 0.74 | 0.80 | −0.101 | −0.755 | — | 0.738 | 0.076 | — | — | — |
| 46 | 4 | 0.74 | 0.79 | −0.190 | −0.848 | 0.159 | 0.719 | 0.011 | — | — | — |
| 47 | 4 | 0.74 | 0.75 | 2.528 | −1.146 | 0.378 | — | 1.036 | −0.741 | — | — |
| 48 | 4 | 0.74 | 0.77 | 1.234 | — | −0.009 | 0.883 | −0.489 | — | — | −0.407 |
| 49 | 3 | 0.74 | 0.80 | 0.070 | −0.701 | — | 0.753 | — | — | −0.015 | — |
| 50 | 4 | 0.74 | 0.78 | −0.082 | −0.811 | 0.189 | 0.723 | — | — | −0.068 | — |
| 51 | 4 | 0.74 | 0.80 | −0.079 | −0.742 | — | 0.738 | 0.084 | — | −0.021 | — |
| 52 | 5 | 0.74 | 0.78 | −0.130 | −0.824 | 0.187 | 0.719 | 0.028 | — | −0.069 | — |
| 53 | 5 | 0.74 | 0.76 | 2.481 | −1.189 | 0.342 | — | 1.038 | −0.778 | 0.110 | — |
| 54 | 4 | 0.74 | 0.77 | 1.245 | — | — | 0.878 | −0.387 | — | −0.120 | −0.382 |
| 55 | 5 | 0.74 | 0.77 | 1.272 | — | 0.059 | 0.877 | −0.424 | — | −0.139 | −0.392 |
| 56 | 3 | 0.73 | 0.77 | 1.238 | — | — | 0.883 | −0.498 | — | — | −0.409 |
| 57 | 4 | 0.73 | 0.80 | 3.012 | −0.891 | — | — | 1.247 | −0.638 | — | −0.182 |
| 58 | 5 | 0.73 | 0.80 | 2.927 | −1.011 | — | — | 1.251 | −0.721 | 0.217 | −0.212 |
| 59 | 3 | 0.72 | 0.73 | 4.212 | −0.733 | 0.451 | — | — | −0.493 | — | — |
| 60 | 3 | 0.72 | 0.80 | 2.728 | −0.930 | — | — | 1.141 | −0.660 | — | — |
| 61 | 3 | 0.72 | 0.77 | 0.438 | — | −0.175 | 0.826 | — | — | — | −0.505 |
| 62 | 4 | 0.72 | 0.73 | 4.547 | −0.690 | 0.489 | — | — | −0.466 | — | −0.144 |
| 63 | 3 | 0.72 | 0.76 | 0.855 | — | — | 0.835 | −0.659 | — | −0.188 | — |
| 64 | 4 | 0.72 | 0.77 | 0.847 | — | −0.031 | 0.836 | −0.636 | — | −0.177 | — |
| 65 | 4 | 0.72 | 0.74 | 4.171 | −0.772 | 0.418 | — | — | −0.527 | 0.104 | — |
| 66 | 4 | 0.72 | 0.80 | 2.614 | −1.040 | — | — | 1.128 | −0.735 | 0.188 | — |
| 67 | 3 | 0.72 | 0.76 | 0.608 | — | — | 0.823 | — | — | −0.217 | −0.482 |
| 68 | 4 | 0.72 | 0.77 | 0.637 | — | −0.049 | 0.828 | — | — | −0.194 | −0.466 |
| 69 | 5 | 0.72 | 0.74 | 4.526 | −0.731 | 0.455 | — | — | −0.504 | 0.117 | −0.154 |

TABLE 6-continued

Logistic regression models based on blood expression levels of any possible combination of one
or more of ANXA3, CLEC4D, IL2RB, LMNB1, PRRG4, TNFAIP6 and VNN1 for determining the probability
that a test subject has colorectal cancer as opposed to not having colorectal cancer.

| Logistic regression model # | No. of genes in model | ROC AUC Training Set | ROC AUC Blind Test Set | Constant ($K_0$) | Gene-specific regression coefficient ($K_n$) | | | | | | |
|---|---|---|---|---|---|---|---|---|---|---|---|
| | | | | | ANXA3 | CLEC4D | IL2RB | LMNB1 | PRRG4 | TNFAIP6 | VNN1 |
| 70 | 2 | 0.71 | 0.76 | 0.786 | — | — | 0.840 | −0.871 | — | — | — |
| 71 | 3 | 0.71 | 0.78 | 0.770 | — | −0.122 | 0.844 | −0.733 | — | — | — |
| 72 | 2 | 0.71 | 0.74 | 0.162 | — | — | 0.799 | — | — | — | −0.616 |
| 73 | 4 | 0.71 | 0.74 | 2.134 | −1.028 | 0.310 | — | 0.571 | — | — | −0.286 |
| 74 | 5 | 0.71 | 0.74 | 2.164 | −1.014 | 0.327 | — | 0.580 | — | −0.044 | −0.282 |
| 75 | 3 | 0.70 | 0.75 | 1.725 | −1.054 | 0.242 | — | 0.404 | — | — | — |
| 76 | 2 | 0.70 | 0.80 | 4.710 | −0.417 | — | — | — | −0.372 | — | — |
| 77 | 3 | 0.70 | 0.73 | 3.283 | −0.791 | 0.371 | — | — | — | — | −0.214 |
| 78 | 3 | 0.70 | 0.79 | 2.309 | −0.868 | — | — | 0.682 | — | — | −0.231 |
| 79 | 3 | 0.70 | 0.80 | 4.842 | −0.393 | — | — | — | −0.360 | — | −0.050 |
| 80 | 4 | 0.70 | 0.75 | 1.785 | −1.031 | 0.269 | — | 0.421 | — | −0.069 | — |
| 81 | 3 | 0.70 | 0.80 | 4.558 | −0.539 | — | — | — | −0.455 | 0.200 | — |
| 82 | 4 | 0.70 | 0.73 | 3.305 | −0.783 | 0.378 | — | — | — | −0.020 | −0.211 |
| 83 | 4 | 0.70 | 0.79 | 2.279 | −0.886 | — | — | 0.671 | — | 0.034 | −0.237 |
| 84 | 4 | 0.70 | 0.81 | 4.759 | −0.506 | — | — | — | −0.440 | 0.211 | −0.079 |
| 85 | 1 | 0.69 | 0.79 | 3.324 | −0.616 | — | — | — | — | — | — |
| 86 | 2 | 0.69 | 0.74 | 2.681 | −0.868 | 0.301 | — | — | — | — | — |
| 87 | 2 | 0.69 | 0.79 | 1.931 | −0.919 | — | — | 0.520 | — | — | — |
| 88 | 2 | 0.69 | 0.79 | 3.768 | −0.536 | — | — | — | — | — | −0.126 |
| 89 | 2 | 0.69 | 0.79 | 3.214 | −0.654 | — | — | — | — | 0.047 | — |
| 90 | 3 | 0.69 | 0.73 | 2.748 | −0.847 | 0.321 | — | — | — | −0.046 | — |
| 91 | 2 | 0.69 | 0.73 | −0.674 | — | — | 0.701 | — | — | −0.435 | — |
| 92 | 3 | 0.69 | 0.76 | −0.326 | — | −0.240 | 0.745 | — | — | −0.281 | — |
| 93 | 3 | 0.69 | 0.79 | 1.931 | −0.919 | — | — | 0.520 | — | 0.000 | — |
| 94 | 3 | 0.69 | 0.80 | 3.648 | −0.587 | — | — | — | — | 0.075 | −0.143 |
| 95 | 2 | 0.68 | 0.75 | −0.764 | — | −0.455 | 0.736 | — | — | — | — |
| 96 | 2 | 0.68 | 0.78 | 4.977 | — | — | — | — | −0.524 | — | −0.223 |
| 97 | 3 | 0.68 | 0.76 | 4.939 | — | 0.113 | — | — | −0.579 | — | −0.275 |
| 98 | 3 | 0.68 | 0.77 | 4.670 | — | — | — | 0.238 | −0.620 | — | −0.289 |
| 99 | 4 | 0.68 | 0.76 | 4.716 | — | 0.067 | — | 0.185 | −0.631 | — | −0.304 |
| 100 | 3 | 0.68 | 0.78 | 4.975 | — | — | — | — | −0.531 | 0.012 | −0.228 |
| 101 | 4 | 0.68 | 0.76 | 4.941 | — | 0.134 | — | — | −0.564 | −0.042 | −0.268 |
| 102 | 4 | 0.68 | 0.77 | 4.655 | — | — | — | 0.255 | −0.610 | −0.028 | −0.283 |
| 103 | 5 | 0.68 | 0.76 | 4.702 | — | 0.091 | — | 0.200 | −0.615 | −0.055 | −0.299 |
| 104 | 1 | 0.67 | 0.76 | 4.311 | — | — | — | — | −0.659 | — | — |
| 105 | 2 | 0.67 | 0.77 | 4.327 | — | −0.010 | — | — | −0.652 | — | — |
| 106 | 2 | 0.67 | 0.76 | 4.314 | — | — | — | −0.001 | −0.658 | — | — |
| 107 | 3 | 0.67 | 0.77 | 4.309 | — | −0.014 | — | 0.012 | −0.656 | — | — |
| 108 | 2 | 0.67 | 0.77 | 4.391 | — | — | — | — | −0.607 | −0.062 | — |
| 109 | 3 | 0.67 | 0.76 | 4.356 | — | 0.035 | — | — | −0.619 | −0.079 | — |
| 110 | 3 | 0.67 | 0.76 | 4.292 | — | — | — | 0.056 | −0.629 | −0.074 | — |
| 111 | 4 | 0.67 | 0.76 | 4.299 | — | 0.024 | — | 0.038 | −0.630 | −0.082 | — |
| 112 | 3 | 0.65 | 0.74 | 3.919 | — | — | — | −0.142 | — | −0.152 | −0.303 |
| 113 | 2 | 0.64 | 0.74 | 3.402 | — | −0.105 | — | — | — | — | −0.397 |
| 114 | 2 | 0.64 | 0.75 | 3.927 | — | — | — | −0.277 | — | — | −0.340 |
| 115 | 3 | 0.64 | 0.75 | 3.922 | — | −0.010 | — | −0.268 | — | — | −0.337 |
| 116 | 2 | 0.64 | 0.73 | 3.528 | — | — | — | −0.373 | — | −0.206 | — |
| 117 | 3 | 0.64 | 0.73 | 3.528 | — | — | — | −0.373 | — | −0.206 | — |
| 118 | 2 | 0.64 | 0.73 | 3.628 | — | — | — | — | — | −0.189 | −0.345 |
| 119 | 3 | 0.64 | 0.73 | 3.610 | — | 0.020 | — | — | — | −0.199 | −0.352 |
| 120 | 4 | 0.64 | 0.73 | 3.951 | — | 0.071 | — | −0.188 | — | −0.174 | −0.316 |
| 121 | 1 | 0.63 | 0.75 | 3.466 | — | — | — | −0.603 | — | — | — |
| 122 | 2 | 0.63 | 0.78 | 3.457 | — | −0.104 | — | −0.482 | — | — | — |
| 123 | 1 | 0.63 | 0.71 | 3.191 | — | — | — | — | — | — | −0.468 |
| 124 | 2 | 0.63 | 0.74 | 2.657 | — | −0.133 | — | — | — | −0.269 | — |
| 125 | 1 | 0.62 | 0.69 | 2.363 | — | — | — | — | — | −0.357 | — |
| 126 | 1 | 0.61 | 0.73 | 2.197 | — | −0.338 | — | — | — | — | — |
| 127 | 1 | 0.61 | 0.64 | −2.973 | — | — | 0.561 | — | — | — | — |

ROC AUC values for the models are shown for the sample training set used to generate the models, as well as for an independent blind sample test set used to test the models. The models, listed in order of decreasing ROC AUC value for the training set, are based on expression levels determined via quantitative reverse transcriptase-PCR analysis using ACTB as duplex partner for normalization. The form of these models is: $P = \{1 + e^{-[K_0 + K_1L_1 + K_2L_2 + K_3L_3 \ldots + K_nL_n]}\}^{-1}$, where P is the probability that a test subject has colorectal cancer as opposed to not having any colorectal pathology; $K_0$ is a constant; $K_1$ is a coefficient specific to a first gene; $L_1$ is a ratio of a level of RNA encoded by the first gene to a level of RNA encoded by ACTB in blood of the test subject; $K_2$ is a coefficient specific to a second gene; $L_2$ is a ratio of a level of RNA encoded by the second gene to a level of RNA encoded by ACTB in blood of the test subject; $K_3$ is a coefficient specific to a third gene; $L_3$ is a ratio of a level of RNA encoded by the third gene to a level of RNA encoded by ACTB in blood of the test subject; $K_n$ is a coefficient specific to an nth gene; and $L_n$ is a ratio of a level of RNA encoded by the nth gene to a level of RNA encoded by ACTB in blood of the test subject. No regression coefficients are specified for genes which are not included in the gene combination (indicated by "—") on which a given logistic regression model is based.

Blind Sample Test Set:

Quantitative RT-PCR analysis of gene expression in an independent blind test set of blood samples from 76 subjects having colorectal cancer and 77 subjects not having any colorectal pathology was performed as described above for the training set. The normalized RNA levels measured are shown in Table 7.

TABLE 7

Sample test set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by ACTB. Levels shown correspond to ΔCt.

| Sample ID | Group | ANXA3 | CLEC4D | IL2RB | LMNB1 | PRRG4 | TNFAIP6 | VNN1 |
|---|---|---|---|---|---|---|---|---|
| CD0214pax | 0 | 5.56 | 6.17 | 4.50 | 6.44 | 7.07 | 5.78 | 6.69 |
| CD0242pax | 0 | 5.87 | 7.32 | 4.54 | 5.43 | 5.19 | 5.87 | 7.38 |
| RC2897pax | 0 | 6.67 | 8.37 | 5.49 | 5.95 | 7.18 | 7.80 | 7.96 |
| CD0670pax | 0 | 7.79 | 5.80 | 3.25 | 6.35 | 7.10 | 8.40 | 7.80 |
| CD1401pax | 0 | 5.84 | 6.39 | 5.42 | 5.85 | 7.30 | 6.55 | 7.12 |
| PB2924pax | 0 | 5.56 | 7.17 | 4.12 | 5.97 | 6.51 | 5.90 | 7.12 |
| CD0482pax | 0 | 7.65 | 8.34 | 3.43 | 6.91 | 7.02 | 8.94 | 8.48 |
| PB1275pax | 0 | 5.26 | 6.13 | 5.18 | 5.54 | 7.09 | 5.89 | 8.78 |
| CD0148pax | 0 | 5.90 | 7.83 | 3.98 | 5.95 | 7.60 | 7.35 | 7.20 |
| CD0122pax | 0 | 6.55 | 8.40 | 5.02 | 6.38 | 7.07 | 7.96 | 8.83 |
| PB2272pax | 0 | 7.30 | 8.30 | 3.95 | 6.57 | 7.42 | 9.42 | 7.49 |
| CD1708pax | 0 | 6.28 | 9.11 | 4.07 | 5.74 | 6.01 | 7.48 | 7.13 |
| CD0354pax | 0 | 6.55 | 8.20 | 4.93 | 6.30 | 8.06 | 8.28 | 7.81 |
| PB2634pax | 0 | 5.76 | 7.74 | 5.28 | 6.80 | 7.20 | 9.18 | 7.39 |
| CD0204pax | 0 | 5.90 | 6.53 | 4.83 | 5.56 | 6.25 | 7.29 | 6.87 |
| PB1336pax | 0 | 7.60 | 9.00 | 6.87 | 6.99 | 7.13 | 8.92 | 9.71 |
| RC2699pax | 0 | 7.72 | 9.42 | 6.03 | 7.12 | 7.99 | 8.67 | 8.57 |
| CD1278pax | 0 | 5.95 | 7.57 | 4.20 | 5.72 | 6.31 | 6.83 | 7.36 |
| PB2062pax | 0 | 7.31 | 7.76 | 4.31 | 6.50 | 7.29 | 8.38 | 7.78 |
| PB2464pax | 0 | 5.95 | 8.33 | 4.73 | 5.52 | 5.52 | 6.39 | 8.43 |
| CD0053pax | 0 | 6.17 | 7.90 | 4.09 | 6.56 | 7.18 | 8.25 | 7.44 |
| CD0192pax | 0 | 5.49 | 7.60 | 4.19 | 5.66 | 7.38 | 5.48 | 6.03 |
| CD0244pax | 0 | 6.32 | 7.31 | 5.26 | 6.21 | 7.56 | 7.63 | 6.89 |
| CD0833pax | 0 | 5.52 | 8.65 | 4.72 | 5.55 | 6.33 | 6.60 | 5.47 |
| CD1719pax | 0 | 6.19 | 7.94 | 5.40 | 5.93 | 6.39 | 6.50 | 7.51 |
| CD0036pax | 0 | 5.20 | 5.95 | 4.60 | 4.95 | 4.51 | 5.99 | 5.82 |
| PB2015pax | 0 | 6.62 | 7.13 | 3.85 | 5.99 | 7.62 | 8.53 | 7.13 |
| PB0662pax | 0 | 6.09 | 7.17 | 5.33 | 6.49 | 7.40 | 7.43 | 6.60 |
| PB2024pax | 0 | 6.16 | 6.10 | 4.49 | 5.94 | 6.86 | 8.23 | 7.44 |
| RC2565pax | 0 | 6.63 | 8.81 | 5.94 | 6.33 | 8.38 | 7.11 | 8.75 |
| CD1561pax | 0 | 7.29 | 6.78 | 4.73 | 6.48 | 7.49 | 8.18 | 8.21 |
| CD1728pax | 0 | 7.13 | 6.89 | 4.30 | 6.52 | 7.76 | 7.08 | 8.63 |
| CD0238pax | 0 | 5.47 | 7.06 | 4.85 | 6.10 | 7.13 | 7.38 | 7.14 |
| PB2342pax | 0 |  | 7.65 | 4.19 | 6.21 | 7.29 | 8.02 | 8.00 |
| CD0800pax | 0 | 7.42 | 8.19 | 3.99 | 6.61 | 7.78 | 8.79 | 8.44 |
| CD0437pax | 0 | 4.74 | 5.92 | 5.05 | 4.90 | 5.58 | 6.27 | 6.17 |
| RC3214pax | 0 | 6.35 | 8.13 | 4.96 | 6.22 | 7.02 | 8.19 | 7.01 |
| CD1487pax | 0 | 5.24 | 7.83 | 4.51 | 5.99 | 7.26 | 7.36 | 6.48 |
| PB1763pax | 0 | 7.83 | 9.12 | 5.21 | 7.40 | 8.78 | 9.20 | 8.37 |
| CD0580pax | 0 | 5.14 | 5.72 | 3.17 | 4.54 | 4.78 | 6.28 | 5.28 |
| CD0840pax | 0 | 4.94 | 6.63 | 4.96 | 5.38 | 5.60 | 6.63 | 6.10 |
| PB2757pax | 0 | 5.32 | 7.54 | 4.98 | 5.51 | 6.48 | 6.77 | 8.12 |
| PB2184pax | 0 | 5.11 | 7.34 | 5.73 | 5.68 | 6.63 | 6.30 | 8.26 |
| PB2179pax | 0 | 5.57 | 6.84 | 4.80 | 5.59 | 5.75 | 5.74 | 6.56 |
| PB1324pax | 0 | 4.77 | 9.26 | 4.24 | 5.57 | 6.78 | 7.16 | 7.37 |
| CD0237pax | 0 | 6.46 | 8.06 | 5.42 | 5.89 | 6.89 | 7.51 | 7.26 |
| CD1329pax | 0 | 6.03 | 6.72 | 4.93 | 5.93 | 6.06 | 7.37 | 7.38 |
| PB2005pax | 0 | 7.51 | 7.37 | 4.66 | 6.41 | 7.63 | 9.46 | 8.15 |
| PB3227pax | 0 | 5.08 | 6.46 | 4.44 | 5.74 | 6.46 | 7.62 | 7.51 |
| PB3163pax | 0 | 4.51 | 6.23 | 4.17 | 5.32 | 6.10 | 7.12 | 6.54 |
| PB3481pax | 0 | 5.66 | 7.99 | 5.16 | 5.95 | 8.33 | 6.48 | 8.26 |
| CD1320pax | 0 | 4.16 | 5.93 | 4.79 | 4.60 | 5.55 | 5.10 | 6.16 |
| RC3191pax | 0 | 7.15 | 7.64 | 4.92 | 6.94 | 7.20 | 8.20 | 8.30 |
| CD0583pax | 0 | 4.29 | 7.00 | 4.44 | 4.16 | 3.96 | 8.82 | 3.97 |
| PB3032pax | 0 | 5.12 | 6.51 | 5.09 | 5.96 | 6.08 | 6.91 | 7.87 |
| CD0367pax | 0 | 5.75 | 6.68 | 4.34 | 5.49 | 6.25 | 7.12 | 7.06 |
| PB2889pax | 0 | 6.03 | 8.25 | 4.75 | 6.39 | 7.27 | 7.04 | 7.68 |
| PB3524pax | 0 | 6.66 | 6.73 | 5.40 | 6.83 | 7.72 | 6.07 | 7.38 |
| RC2986pax | 0 | 6.90 | 7.96 | 5.36 | 6.14 | 7.22 | 8.87 | 7.75 |
| CD1428pax | 0 | 6.64 | 9.25 | 3.67 | 5.82 | 7.04 | 7.12 | 6.09 |
| RC2236pax | 0 | 6.82 | 6.87 | 5.24 | 6.21 | 7.41 | 7.27 | 8.02 |
| PB1918pax | 0 | 8.72 | 7.41 | 5.20 | 7.28 | 8.29 | 10.44 | 9.02 |
| CD0277pax | 0 | 6.42 | 8.60 | 5.37 | 6.63 | 7.61 | 8.57 | 7.04 |
| CD0667pax | 0 | 5.15 | 6.09 | 5.57 | 5.26 | 6.33 | 6.27 | 6.41 |
| CD1741pax | 0 | 5.46 | 6.18 | 5.57 | 5.76 | 6.50 | 7.24 | 7.18 |
| PB1973pax | 0 | 8.07 | 9.15 | 4.68 | 7.12 | 8.89 | 9.13 | 10.01 |

TABLE 7-continued

Sample test set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by ACTB. Levels shown correspond to ΔCt.

| Sample ID | Group | ANXA3 | CLEC4D | IL2RB | LMNB1 | PRRG4 | TNFAIP6 | VNN1 |
|---|---|---|---|---|---|---|---|---|
| PB1222pax | 0 | 5.80 | 7.45 | 5.57 | 5.95 | 5.81 | 6.15 | 7.61 |
| RC2683pax | 0 | 8.25 | 9.29 | 5.83 | 6.98 | 8.07 | 9.46 | 9.66 |
| PB3200pax | 0 | 5.00 | 6.73 | 4.23 | 5.42 | 6.59 | 6.31 | 7.35 |
| PB2130pax | 0 | 6.31 | 7.61 | 4.91 | 5.50 | 5.79 | 6.48 | 6.81 |
| PB3097pax | 0 | 6.33 | 3.94 | 5.77 | 6.08 | 6.72 | 7.78 | 7.51 |
| CD0571pax | 0 | 5.28 | 6.04 | 3.76 | 5.54 | 6.60 | 6.99 | 5.82 |
| CD0676pax | 0 | 5.50 | 6.68 | 5.78 | 5.79 | 5.91 | 6.91 | 7.18 |
| PB1514pax | 0 | 7.57 | 5.96 | 5.35 | 7.38 | 8.09 | 7.63 | 8.37 |
| CD0547pax | 0 | 4.62 | 7.13 | 6.05 | 5.85 | 7.44 | 6.70 | 6.88 |
| CD1068pax | 0 | 5.79 | 6.49 | 4.84 | 6.23 | 7.14 | 8.55 | 6.32 |
| CD0715pax | 0 | 2.97 | 4.03 | 4.74 | 4.51 | 4.94 | 5.38 | 6.46 |
| JH0130pax | 1 | 5.32 | 5.90 | 6.01 | 5.47 | 5.77 | 5.93 | 6.90 |
| MH0079pax | 1 | 6.41 | 6.17 | 5.06 | 6.19 | 6.42 | 6.61 | 7.57 |
| MH0082pax | 1 | 7.06 | 4.93 | 5.26 | 6.82 | 6.74 | 8.27 | 7.32 |
| AN0013pax | 1 | 4.94 | 7.96 | 3.89 | 5.60 | 5.49 | 7.86 | 7.95 |
| NK2005pax | 1 | 4.20 | 5.83 | 5.59 | 5.08 | 5.65 | 4.02 | 6.98 |
| CD1111pax | 1 | 6.62 | 6.64 | 4.17 | 6.17 | 7.32 | 7.62 | 7.72 |
| JH0105pax | 1 | 5.31 | 7.29 | 4.84 | 5.39 | 5.34 | 7.13 | 8.28 |
| MIP1007pax | 1 | 3.42 | 7.30 | 4.89 | 4.27 | 6.00 | 5.13 | 3.62 |
| DC0011pax | 1 | 4.33 | 5.63 | 4.17 | 5.45 | 5.74 | 6.41 | 7.06 |
| MH0073pax | 1 | 4.68 | 6.28 | 5.84 | 4.57 | 5.52 | 6.41 | 5.86 |
| DC0003pax | 1 | 6.24 | 7.65 | 5.02 | 6.05 | 6.64 | 7.05 | 8.46 |
| DC1002pax | 1 | 4.62 | 4.35 | 5.41 | 5.26 | 6.40 | 7.24 | 6.90 |
| JH0096pax | 1 | 3.45 | 5.49 | 5.18 | 4.79 | 5.74 | 3.34 | 7.61 |
| KW0002pax | 1 | 4.26 | 6.89 | 4.62 | 4.71 | 4.76 | 5.78 | 6.53 |
| JH0120pax | 1 | 5.89 | 4.91 | 5.53 | 6.38 | 5.56 | 8.45 | 6.44 |
| MIP1008pax | 1 | 4.84 | 7.74 | 5.47 | 5.41 | 5.63 | 5.36 | 6.93 |
| MIP0002pax | 1 | 3.76 | 6.96 | 5.63 | 4.85 | 6.55 | 5.74 | 6.87 |
| MIP1011pax | 1 | 4.70 | 6.28 | 5.12 | 4.63 | 4.60 | 5.68 | 4.55 |
| MH0074pax | 1 | 5.11 | 5.73 | 5.75 | 5.68 | 6.74 | 7.59 | 6.00 |
| DC0008pax | 1 | 4.97 | 6.33 | 4.16 | 5.44 | 4.95 | 6.54 | 5.87 |
| AN4014pax | 1 | 3.93 | 5.76 | 4.25 | 4.58 | 5.76 | 5.20 | 7.74 |
| DC0012pax | 1 | 4.25 | 6.07 | 5.15 | 5.08 | 7.00 | 4.86 | 6.37 |
| MIP2002pax | 1 | 5.54 | 5.71 | 4.26 | 5.54 | 5.77 | 6.57 | 6.33 |
| NK1005pax | 1 | 5.76 | 8.79 | 5.22 | 7.02 | 7.38 | 8.60 | 7.55 |
| MIP0007pax | 1 | 2.91 | 3.55 | 6.69 | 3.21 | 4.38 | 3.48 | 4.85 |
| JH0118pax | 1 | 5.72 | 7.53 | 4.77 | 5.56 | 5.85 | 6.56 | 6.04 |
| JH0089pax | 1 | 5.11 | 7.30 | 4.99 | 5.68 | 5.58 | 6.54 | 7.38 |
| MH0057pax | 1 | 5.80 | 6.60 | 6.01 | 6.35 | 6.36 | 7.44 | 6.44 |
| DC0005pax | 1 | 5.98 | 7.66 | 4.72 | 6.38 | 6.39 | 7.47 | 7.19 |
| MH0067pax | 1 | 4.75 | 6.06 | 6.11 | 4.96 | 5.30 | 6.78 | 5.54 |
| JH0085pax | 1 | 5.19 | 6.48 | 5.92 | 5.99 | 5.76 | 6.65 | 7.12 |
| JH0127pax | 1 | 5.48 | 6.43 | 5.18 | 6.13 | 7.59 | 6.63 | 7.04 |
| MIP1013pax | 1 | 4.86 | 5.89 | 4.56 | 5.29 | 5.21 | 5.89 | 6.51 |
| JH0126pax | 1 | 4.21 | 7.08 | 5.35 | 5.68 | 5.40 | 5.50 | 7.07 |
| AN4013pax | 1 | 5.15 | 5.66 | 4.15 | 5.19 | 5.38 | 5.94 | 6.91 |
| MH0053pax | 1 | 7.07 | 8.10 | 4.16 | 6.42 | 5.83 | 8.33 | 7.84 |
| JH0115pax | 1 | 3.82 | 7.54 | 5.74 | 4.75 | 6.03 | 6.27 | 7.36 |
| CC0004pax | 1 | 3.83 | 5.81 | 4.59 | 4.67 | 5.46 | 5.50 | 5.84 |
| JH0091pax | 1 | 5.26 | 5.92 | 4.74 | 5.31 | 7.34 | 6.70 | 6.91 |
| NK1004pax | 1 | 5.76 | 7.32 | 6.16 | 5.78 | 6.58 | 7.99 | 7.77 |
| NK1008pax | 1 | 4.70 | 7.52 | 5.56 | 5.57 | 6.80 | 6.58 | 7.52 |
| MIP2006pax | 1 | 4.25 | 6.38 | 4.28 | 4.74 | 5.69 | 5.36 | 5.38 |
| AN0020pax | 1 | 4.12 | 6.61 | 5.57 | 4.81 | 4.61 | 4.45 | 6.07 |
| JH0117pax | 1 | 3.36 | 8.59 | 4.90 | 4.29 | 4.99 | 5.12 | 5.76 |
| JH0100pax | 1 | 5.54 | 6.69 | 4.86 | 5.66 | 6.57 | 7.23 | 7.26 |
| MH0066pax | 1 | 5.12 | 5.25 | 6.28 | 5.59 | 6.61 | 6.27 | 6.13 |
| NK2009pax | 1 | 5.30 | 5.93 | 4.95 | 5.76 | 5.27 | 7.71 | 5.77 |
| NK2008pax | 1 | 4.14 | 5.57 | 5.88 | 4.93 | 5.45 | 6.59 | 5.66 |
| PB3067-2pax | 1 | 5.84 | 8.25 | 4.70 | 6.20 | 6.51 | 7.78 | 6.81 |
| NK1003pax | 1 | 4.41 | 6.99 | 5.48 | 5.30 | 6.08 | 6.48 | 7.13 |
| MIP1009pax | 1 | 3.22 | 8.02 | 6.45 | 4.25 | 5.14 | 5.47 | 5.21 |
| DC2006pax | 1 | 6.06 | 5.91 | 4.81 | 5.88 | 6.05 | 7.24 | 7.34 |
| JH0131pax | 1 | 5.19 | 6.71 | 4.98 | 5.21 | 5.15 | 4.75 | 6.43 |
| DC0015pax | 1 | 4.95 | 6.98 | 5.01 | 5.46 | 6.53 | 6.02 | 6.17 |
| AN0001pax | 1 | 4.36 | 6.54 | 5.97 | 5.60 | 5.83 | 6.72 | 7.13 |
| JH0111pax | 1 | 5.04 | 6.83 | 4.22 | 5.09 | 6.96 | 7.14 | 5.78 |
| MIP0005pax | 1 | 3.74 | 5.56 | 5.98 | 4.46 | 5.80 | 5.74 | 5.33 |
| MH0065pax | 1 | 4.50 | 5.37 | 5.63 | 5.51 | 6.30 | 6.09 | 5.82 |
| JH0136pax | 1 | 3.39 | 4.63 | 6.12 | 4.86 | 5.19 | 7.76 | 4.59 |
| CD1351pax | 1 | 6.86 | 7.94 | 5.55 | 6.06 | 6.52 | 8.46 | 7.62 |

TABLE 7-continued

Sample test set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by ACTB. Levels shown correspond to ΔCt.

| Sample ID | Group | ANXA3 | CLEC4D | IL2RB | LMNB1 | PRRG4 | TNFAIP6 | VNN1 |
|---|---|---|---|---|---|---|---|---|
| MH0075pax | 1 | 6.05 | 7.17 | 5.57 | 5.77 | 6.75 | 7.32 | 7.27 |
| MH0078pax | 1 | 4.60 | 6.70 | 5.49 | 5.26 | 4.21 | 5.25 | 7.54 |
| MH0068pax | 1 | 7.58 | 5.49 | 4.48 | 6.43 | 7.14 | 8.00 | 6.36 |
| MIP2003pax | 1 | 4.24 | 5.60 | 4.30 | 4.93 | 6.05 | 6.85 | 5.97 |
| NK2015pax | 1 | 5.42 | 5.52 | 5.54 | 6.08 | 6.40 | 8.40 | 8.09 |
| MH0070pax | 1 | 5.40 | 7.11 | 4.66 | 5.74 | 6.55 | 7.09 | 7.08 |
| JH0093pax | 1 | 5.22 | 7.62 | 4.66 | 5.29 | 5.39 | 7.00 | 7.15 |
| JH0135pax | 1 | 4.40 | 4.64 | 5.52 | 4.62 | 5.38 | 4.31 | 4.62 |
| CD1571pax | 1 | 5.45 | 6.48 | 4.41 | 5.65 | 7.26 | 7.88 | 7.17 |
| MH0061pax | 1 | 4.99 | 5.15 | 5.47 | 5.72 | 6.73 | 7.65 | 7.76 |
| NK2007pax | 1 | 5.98 | 7.25 | 5.17 | 5.76 | 7.02 | 7.32 | 6.38 |
| JH0132pax | 1 | 5.29 | 7.18 | 5.29 | 5.76 | 6.96 | 6.66 | 6.83 |
| MH0062pax | 1 | 4.40 | 6.01 | 4.86 | 5.42 | 5.50 | 6.26 | 6.45 |
| JH0114pax | 1 | 4.78 | 6.93 | 7.12 | 5.58 | 7.50 | 5.62 | 5.26 |
| CD1260pax | 1 | 5.28 | 5.92 | 5.24 | 5.73 | 5.86 | 7.18 | 7.37 |
| JH0022pax | 1 | 5.00 | 5.94 | 4.73 | 5.49 | 6.17 | 5.66 | 6.80 |

Analysis of the test set results confirmed the surprising finding based on the training set that ANXA3, CLEC4D, IL2RB, LMNB1, PRRG4, TNFAIP6 and VNN1 each express RNA on average at a significantly higher level (p-value less than 0.05) in blood of subjects having colorectal cancer relative to subjects having no colorectal pathology, and that IL2RB expresses RNA on average at a significantly lower level (p-value less than 0.05) in blood of subjects having colorectal cancer relative to subjects having no colorectal pathology (Table 8). The ranges of fold-change in the levels of RNA encoded by ANXA3, CLEC4D, IL2RB, LMNB1, PRRG4, TNFAIP6 and VNN1 normalized to levels of RNA encoded by ACTB in blood of the test set subjects having colorectal cancer relative to the test set subjects not having any colorectal pathology are also shown in Table 8.

As can be seen in Table 8, a test subject having a blood level of RNA encoded by ANXA3 which is 2.2 to 9.1 fold higher than the average level of RNA encoded by this gene in blood of subjects not having any colorectal pathology is more likely to have colorectal cancer than to not have any colorectal pathology.

As can be seen in Table 8, a test subject having a blood level of RNA encoded by CLEC4D which is 1.8 to 13.7 fold higher than the average level of RNA encoded by this gene in blood of subjects not having any colorectal pathology is more likely to have colorectal cancer than to not have any colorectal pathology.

As can be seen in Table 8, a test subject having a blood level of RNA encoded by LMNB1 which is 1.5 to 7.0 fold higher than the average level of RNA encoded by this gene in blood of subjects not having any colorectal pathology is more likely to have colorectal cancer than to not have any colorectal pathology.

TABLE 8

Sample test set ranges of fold-change in levels of RNA encoded by ANXA3, CLEC4D, IL2RB, LMNB1, PRRG4, TNFAIP6, VNN1 normalized to levels of RNA encoded by ACTB in blood of subjects having colorectal cancer relative to subjects not having any colorectal pathology.

| | ANXA3 | CLEC4D | IL2RB | LMNB1 | PRRG4 | TNFAIP6 | VNN1 |
|---|---|---|---|---|---|---|---|
| Average normalized RNA level in subjects having colorectal cancer (ΔCt) | 4.98 | 6.45 | 5.18 | 5.42 | 6.01 | 6.51 | 6.63 |
| Average normalized RNA level in subjects not having any colorectal pathology (ΔCt) | 6.10 | 7.32 | 4.83 | 6.01 | 6.86 | 7.41 | 7.40 |
| Average RNA level fold-change | 2.17 | 1.82 | 0.78 | 1.50 | 1.80 | 1.87 | 1.70 |
| p-value for average RNA level fold-change | 1.7E−10 | 1.9E−06 | 1.4E−03 | 1.3E−07 | 1.6E−08 | 3.8E−06 | 4.4E−06 |
| Maximum observed RNA level directional fold-change | 9.13 | 13.66 | 0.20 | 6.98 | 6.26 | 16.78 | 13.78 |

As can be seen in Table 8, a test subject having a blood level of RNA encoded by PRRG4 which is 1.8 to 6.3 fold higher than the average level of RNA encoded by this gene in blood of subjects not having any colorectal pathology is more likely to have colorectal cancer than to not have any colorectal pathology.

As can be seen in Table 8, a test subject having a blood level of RNA encoded by TNFAIP6 which is 1.9 to 16.8 fold higher than the average level of RNA encoded by this gene in blood of subjects not having any colorectal pathology is more likely to have colorectal cancer than to not have any colorectal pathology.

As can be seen in Table 8, a test subject having a blood level of RNA encoded by VNN1 which is 1.7 to 13.8 fold higher than the average level of RNA encoded by this gene in blood of subjects not having any colorectal pathology is more likely to have colorectal cancer than to not have any colorectal pathology.

As can be seen in Table 8, a test subject having a blood level of RNA encoded by IL2RB which is 0.8 to 0.2 fold that of the average level of RNA encoded by this gene in blood of subjects not having any colorectal pathology is more likely to have colorectal cancer than to not have any colorectal pathology.

Furthermore, the test set results confirmed the surprising finding based on the training set that logistic regression models based on blood expression levels for any of the 127 possible combinations of one or more of ANXA3, CLEC4D, IL2RB, LMNB1, PRRG4, TNFAIP6 and VNN1, each of which normalized against expression levels of ACTB, can be used to discriminate, with a ROC AUC of at least 0.64 (Table 6), between subjects having colorectal cancer and subjects not having any colorectal pathology. As such, the novel logistic regression models listed in Table 6 can be used to determine the probability that a test subject has colorectal cancer as opposed to not having any colorectal pathology, based on blood levels of expression of ANXA3, CLEC4D, IL2RB, LMNB1, PRRG4, TNFAIP6 and/or VNN1.

Example 3

Measurement of Blood Levels of RNA Encoded by any Combination of ANXA3, CLEC4D, LMNB1, PRRG4, TNFAIP6 and/or VNN1 Relative to the Level of RNA Encoded by IL2RB can be Used to Determine the Probability that a Test Subject has Colorectal Cancer as Opposed to not Having any Colorectal Pathology Materials and Methods:
Refer to "General materials and methods", above.
Experimental Results:
Sample Training Set:
Discovery of Significantly Different Levels of RNA Encoded by ANXA3, CLEC4D, LMNB1, PRRG4, VNN1, TNFAIP6 Normalized to IL2RB in Blood of Subjects Having Colorectal Cancer Relative to Subjects not Having any Colorectal Pathology:

Quantitative reverse transcriptase-PCR analysis of gene expression in a training set of blood samples from 116 subjects having colorectal cancer and 127 subjects not having any colorectal pathology, using IL2RB as duplex partner for normalization of gene expression levels was performed. The normalized RNA levels measured are shown in Table 9

TABLE 9

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

|  |  | Gene | | | | | |
| --- | --- | --- | --- | --- | --- | --- | --- |
| Sample ID | Group | ANXA3 | CLEC4D | LMNB1 | PRRG4 | TNFAIP6 | VNN1 |
| CD0011pax | 0 | 0.8303 | 1.3467 | 1.2008 | 0.8909 | 2.1665 | 2.6036 |
| CD0012pax | 0 | 1.2503 | 1.4917 | 0.8258 | 0.9309 | 1.9115 | 2.9086 |
| CD0030pax | 0 | 1.2878 | 1.2957 | 0.7182 | 1.1632 | 0.7535 | 1.7757 |
| CD0063pax | 0 | 2.4078 | 3.0807 | 1.6332 | 1.8532 | 3.4685 | 3.0157 |
| CD0077pax | 0 | −0.0047 | 1.2417 | 0.7058 | 0.7009 | 0.8465 | 1.7436 |
| CD0078pax | 0 | 1.6928 | 2.4057 | 0.9432 | 0.9332 | 2.6735 | 1.4807 |
| CD0085pax | 0 | 0.4428 | 1.5007 | 0.4032 | 0.8232 | 2.4335 | 0.4457 |
| CD0117pax | 0 | 0.6028 | 2.2057 | 0.7632 | 2.0182 | 2.2585 | 0.6557 |
| CD0146pax | 0 | 0.0353 | 0.7117 | 0.6708 | 0.1659 | 1.3215 | 0.7236 |
| CD0167pax | 0 | −1.3147 | −0.1483 | 0.0358 | 0.2609 | 1.3315 | 0.0786 |
| CD0249pax | 0 | −0.7797 | −0.6233 | −0.8142 | 0.0609 | −0.0085 | 0.2486 |
| CD0279pax | 0 | 0.8278 | 1.9907 | 0.7632 | 0.7382 | 1.6185 | 1.4957 |
| CD0286pax | 0 | 0.0753 | 1.5217 | 0.7058 | 0.6659 | 0.7215 | 0.7286 |
| CD0297pax | 0 | −0.1797 | 0.2867 | 0.1958 | −0.3291 | 0.0665 | 0.4836 |
| CD0323pax | 0 | 1.7303 | 1.6817 | 0.5408 | 1.2359 | 2.2865 | 3.0636 |
| CD0445pax | 0 | 0.9878 | 1.2107 | 0.6682 | 0.6932 | 1.8085 | 1.6907 |
| CD0463pax | 0 | −0.3647 | 1.2267 | 0.3058 | 0.5559 | 1.2365 | 1.0136 |
| CD0491pax | 0 | −0.3972 | 0.3507 | 0.4482 | 0.7032 | 1.1785 | 0.2907 |
| CD0496pax | 0 | 0.8753 | 2.4167 | 0.6958 | 1.4509 | 1.0515 | 0.6436 |
| CD0501pax | 0 | 0.8753 | 1.7517 | 0.9558 | 0.9109 | 2.7615 | 1.0986 |
| CD0504pax | 0 | −0.4947 | 0.2367 | 0.2358 | 1.0209 | 0.3715 | 0.7936 |
| CD0573pax | 0 | 1.9978 | 1.3107 | 0.9582 | 0.9982 | 2.4435 | 1.9357 |
| CD0578pax | 0 | 1.6103 | 1.7317 | 0.6408 | 0.6259 | 1.6865 | 1.7136 |
| CD0639pax | 0 | 0.1028 | 0.6657 | 0.6232 | −0.2618 | 0.9985 | 1.5857 |
| CD0645pax | 0 | −0.8347 | −0.1883 | −0.4342 | −0.4441 | 0.4965 | 0.0986 |
| CD0679pax | 0 | 0.4703 | 1.7767 | 0.6658 | 0.5659 | 1.9465 | 2.2636 |
| CD0685pax | 0 | 0.8753 | 2.3317 | 0.8008 | 1.3759 | 2.1915 | 1.4836 |
| CD0716pax | 0 | 1.9978 | 2.4057 | 0.9182 | 0.4432 | 1.5835 | 2.0457 |
| CD0749pax | 0 | 0.3303 | 1.3717 | 0.4058 | 0.5509 | 2.0465 | 1.0336 |
| CD0760pax | 0 | −2.5747 | −1.3583 | −1.9442 | −1.1491 | −1.2335 | −0.8714 |

TABLE 9-continued

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| Sample ID | Group | ANXA3 | CLEC4D | LMNB1 | PRRG4 | TNFAIP6 | VNN1 |
|---|---|---|---|---|---|---|---|
| CD0811pax | 0 | 2.2353 | 2.8417 | 1.1858 | 1.3609 | 1.3865 | 1.3286 |
| CD0846pax | 0 | −0.6522 | 0.3407 | −0.6418 | −0.3468 | −0.6315 | 1.5657 |
| CD0848pax | 0 | 0.7278 | 1.2057 | 0.9832 | 1.0232 | 1.5785 | 1.8307 |
| CD0924pax | 0 | 0.1428 | 0.5357 | −0.0768 | −0.4418 | 0.2935 | −0.0793 |
| CD1066pax | 0 | 0.1753 | 0.6667 | 0.2658 | 0.2059 | 1.9715 | 0.5786 |
| CD1073pax | 0 | 0.1053 | −0.0633 | −0.0092 | −0.1341 | 0.8015 | 1.0886 |
| CD1075pax | 0 | −0.3322 | 0.4757 | −0.0118 | 1.1582 | 1.2385 | 0.1957 |
| CD1089pax | 0 | −1.1072 | 0.1657 | −0.7818 | −0.5318 | 0.1935 | −0.1193 |
| CD1116pax | 0 | −0.2072 | −0.0543 | −0.2818 | 0.2982 | 1.4885 | 0.4107 |
| CD1120pax | 0 | −0.8872 | 0.0357 | −0.5868 | 0.2032 | 1.1885 | −0.2443 |
| CD1198pax | 0 | 0.5253 | 0.5317 | 0.7908 | 0.7509 | 0.7915 | 0.9786 |
| PB1179pax | 0 | 1.0003 | 1.0617 | 0.8808 | 0.9909 | 2.4315 | 1.2286 |
| PB1277pax | 0 | 0.8803 | 1.4817 | 0.4258 | 0.9859 | 1.5765 | 0.8286 |
| PB1301pax | 0 | −1.7247 | −0.9183 | −0.9092 | −0.5091 | −0.6985 | −1.2864 |
| PB1315pax | 0 | −1.5572 | 0.2257 | −0.6218 | −0.3118 | −0.2015 | 0.9007 |
| PB1345pax | 0 | 0.1953 | 0.6617 | 0.7508 | 1.0459 | 0.3615 | 2.0236 |
| PB1518pax | 0 | 1.2653 | 1.6967 | 0.2058 | 0.8359 | 1.3565 | 1.3036 |
| PB1520pax | 0 | 1.0953 | 2.0267 | 0.9708 | 0.0109 | 1.6565 | 2.2236 |
| PB1574pax | 0 | 1.0753 | 1.5467 | 0.8008 | 0.6109 | 1.0465 | 1.1836 |
| PB1783pax | 0 | 1.5978 | 1.7007 | 1.1982 | 1.2632 | 2.1135 | 1.5907 |
| PB1799pax | 0 | 0.6978 | 1.0157 | 0.5282 | 1.0632 | 2.0785 | 0.5957 |
| PB1811pax | 0 | 0.8628 | 1.4057 | 0.8232 | 1.2632 | 1.3685 | 0.9507 |
| PB1830pax | 0 | 0.1428 | 0.6807 | 0.2532 | 0.1182 | 0.8985 | 2.3407 |
| PB1833pax | 0 | 0.2028 | 1.1407 | 0.4782 | 0.5532 | 0.9385 | 1.5457 |
| PB1843pax | 0 | 0.5553 | 0.4717 | 0.0708 | 0.5909 | −0.5285 | 1.1486 |
| PB1851pax | 0 | 0.4428 | 0.1007 | 0.2632 | 0.3232 | 2.7035 | 1.6007 |
| PB1919pax | 0 | 1.4703 | 2.1067 | 0.8108 | 1.7959 | 2.1365 | 2.5086 |
| PB1922pax | 0 | 0.3103 | 1.1867 | 0.4258 | 1.3759 | 2.1215 | 0.9986 |
| PB1924pax | 0 | 0.2428 | 0.5357 | 0.1632 | 0.3632 | 1.1535 | 1.2357 |
| PB1937pax | 0 | 1.3128 | 2.1057 | 1.0982 | 2.9132 | 2.4835 | 2.2007 |
| PB1964pax | 0 | 0.4828 | 2.6207 | 0.7382 | 1.5332 | 2.4035 | 2.7507 |
| PB2027pax | 0 | −0.1422 | 0.3857 | 0.1582 | 0.3182 | 1.1835 | 1.5807 |
| PB2029pax | 0 | 0.1953 | 0.5917 | 0.0708 | −0.0391 | 1.8615 | 0.7336 |
| PB2073pax | 0 | 0.4478 | 0.9057 | 0.4382 | 1.6632 | 1.5085 | 0.9257 |
| PB2086pax | 0 | 0.1153 | 0.1817 | 0.3108 | 0.8409 | 0.3215 | 0.5386 |
| PB2099pax | 0 | −0.4622 | −0.5993 | −0.1568 | 0.0732 | −0.1265 | 0.1057 |
| PB2100pax | 0 | 1.1628 | 1.1057 | 0.6532 | 1.5482 | 2.1385 | 1.1507 |
| PB2132pax | 0 | 0.5503 | 1.1517 | 0.3558 | 0.6109 | 2.1315 | 1.4536 |
| PB2168pax | 0 | 1.3278 | 1.5357 | 0.8482 | 1.1682 | 2.3435 | 1.3307 |
| PB2192pax | 0 | 0.3153 | 0.8967 | 0.3308 | −0.0291 | 1.2515 | 1.9286 |
| PB2196pax | 0 | 0.8328 | 1.6107 | 0.7932 | 1.4432 | 2.0535 | 1.2107 |
| PB2200pax | 0 | 1.1028 | 1.4807 | 0.3732 | 0.4432 | 0.9635 | 0.5757 |
| PB2213pax | 0 | 2.1753 | 2.2717 | 1.1658 | 0.9009 | 3.1465 | 1.9736 |
| PB2224pax | 0 | −0.2772 | 0.6207 | 0.0482 | 0.3582 | 2.1235 | 1.2607 |
| PB2228pax | 0 | 1.7703 | 2.1017 | 1.3658 | 1.6859 | 3.6965 | 2.7186 |
| PB2229pax | 0 | −0.2047 | −0.3183 | −0.0542 | −0.9241 | 0.5615 | −0.1764 |
| PB2277pax | 0 | 1.3578 | 0.8507 | 0.6332 | 0.3582 | 1.0785 | 1.7457 |
| PB2297pax | 0 | 0.4178 | 1.1507 | 0.1282 | 0.0332 | 0.9235 | −0.3343 |
| PB2312pax | 0 | 1.3628 | 2.0057 | 1.4132 | 0.9632 | 2.0885 | 2.0357 |
| PB2398pax | 0 | −0.5822 | 0.1007 | −0.2868 | −0.7518 | −0.1865 | 1.3307 |
| PB2409pax | 0 | 0.1153 | 0.6817 | 0.3008 | 0.3359 | 1.0115 | 1.5036 |
| PB2414pax | 0 | 2.7128 | 2.3707 | 1.2132 | 2.1832 | 3.6985 | 1.9707 |
| PB2467pax | 0 | 0.7478 | 1.1457 | 0.5482 | 0.6382 | 2.2385 | 1.3607 |
| PB2473pax | 0 | 0.3828 | 0.8857 | 0.4432 | 1.0932 | 0.9185 | 1.8407 |
| PB2512pax | 0 | 0.7003 | 1.7267 | 0.8458 | 0.4709 | 1.8115 | 2.0136 |
| PB2568pax | 0 | −0.4772 | 0.0157 | −0.3718 | 0.4132 | 1.2435 | 1.0857 |
| PB2571pax | 0 | 0.3003 | 1.0017 | 0.5558 | 0.2609 | 1.8915 | 1.9336 |
| PB2603pax | 0 | 1.0128 | 1.4757 | 1.1082 | 1.1632 | 2.3335 | 0.7457 |
| PB2624pax | 0 | 0.4403 | 0.5167 | 0.7208 | 1.3259 | 1.3865 | 1.2286 |
| PB2824pax | 0 | 0.5178 | 0.9907 | 0.4582 | 1.0132 | 1.8135 | 1.3207 |
| PB2880pax | 0 | 1.0403 | 1.0617 | 0.6208 | −0.2491 | 1.8615 | 1.5586 |
| PB3088pax | 0 | 1.6503 | 1.7517 | 1.3208 | 1.1359 | 3.4165 | 2.3786 |
| RC0882pax | 0 | 0.2728 | 1.4507 | 0.6582 | 0.7682 | 2.0985 | 1.8007 |
| RC0888pax | 0 | −0.7872 | −0.3193 | −0.2118 | 0.2932 | 0.7835 | 0.2957 |
| RC0968pax | 0 | −0.8522 | −0.6493 | 0.0182 | 1.4382 | 0.7835 | 2.1457 |
| RC2114pax | 0 | −0.4722 | 0.7557 | 0.0282 | 0.4132 | 0.1335 | 1.9357 |
| RC2238pax | 0 | 0.9528 | 1.8557 | 0.5982 | 1.5182 | 2.4435 | 2.8857 |
| RC2681pax | 0 | 0.3278 | 1.1957 | 0.4582 | 0.5532 | 0.7435 | 0.9507 |
| RC2703pax | 0 | 1.6403 | 1.8317 | 0.7658 | 1.1959 | 1.1615 | 1.1436 |
| RC2749pax | 0 | 0.3978 | 1.1407 | 0.3632 | 0.4682 | 1.6635 | 1.5157 |
| RC2750pax | 0 | −1.7872 | −1.2393 | −1.0418 | −0.3118 | −0.1115 | −0.6943 |

TABLE 9-continued

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| RC2756pax | 0 | 1.3803 | 0.9167 | 0.5508 | 1.0009 | 1.6415 | 1.9636 |
| RC2771pax | 0 | −0.9547 | 0.3567 | −0.6792 | −0.3341 | 1.1965 | 1.4536 |
| RC2790pax | 0 | 0.8953 | 0.9817 | 0.4808 | 0.7259 | 1.0815 | 1.3536 |
| RC2792pax | 0 | 1.2903 | 0.8667 | 0.8058 | 1.4559 | 1.9415 | 1.5836 |
| RC2808pax | 0 | 0.7953 | 1.9117 | 0.7558 | 1.0009 | 1.1715 | 1.4036 |
| RC2822pax | 0 | 0.7728 | 1.2607 | 0.3282 | 0.5932 | 2.5785 | 0.5807 |
| RC2834pax | 0 | −0.6247 | 0.2917 | −0.5742 | 0.9309 | 2.0765 | 0.9236 |
| RC2871pax | 0 | 0.9028 | 1.4107 | 1.1032 | 1.5332 | 2.6485 | 2.6307 |
| RC2879pax | 0 | −0.2047 | 0.3867 | −0.0342 | 0.8509 | 0.6315 | 0.5086 |
| RC2892pax | 0 | −0.0022 | 0.5557 | −0.0968 | 0.7032 | 2.0385 | 1.1857 |
| RC2895pax | 0 | 1.7178 | 1.9857 | 1.2632 | 1.3682 | 1.4435 | 2.0557 |
| RC2921pax | 0 | 1.3153 | 1.2967 | 1.0058 | 1.3709 | 2.0315 | 2.0886 |
| RC2958pax | 0 | 1.0553 | 1.1017 | 0.4958 | 0.1409 | 0.4965 | 1.4836 |
| RC3022pax | 0 | 0.3028 | 0.3007 | 0.3582 | 1.0432 | 1.7635 | 0.4707 |
| RC3112pax | 0 | 1.2553 | 1.4667 | 0.5908 | 0.5759 | 2.5515 | 1.3286 |
| RC3146pax | 0 | −0.1572 | −0.2793 | −0.4918 | 0.1432 | 1.0235 | 0.8307 |
| RC3184pax | 0 | 2.1353 | 2.5967 | 1.0758 | 1.3559 | 2.2865 | 2.2336 |
| RC3232pax | 0 | −0.3747 | 0.5667 | −0.5942 | 0.5309 | −0.4385 | 2.3786 |
| RC3324pax | 0 | 0.2128 | 0.8557 | 0.0082 | 0.3282 | 1.3985 | −0.0693 |
| RC3327pax | 0 | 0.2003 | −0.1333 | −0.0292 | −0.2491 | 1.2315 | 1.8086 |
| RC3355pax | 0 | 0.0328 | 0.5657 | −0.2668 | −0.0418 | 1.2935 | 0.4857 |
| RC3380pax | 0 | −0.4372 | 0.4907 | −0.3518 | −0.0318 | 0.5235 | 0.0757 |
| RC3413pax | 0 | 0.6028 | 1.1907 | 0.4532 | 0.0182 | 0.8435 | 2.3907 |
| RC3421pax | 0 | −0.0047 | 0.2917 | −0.0142 | 0.1409 | −0.0735 | −0.0964 |
| RC3468pax | 0 | −0.1022 | −0.0143 | −0.0618 | −0.3368 | 1.1485 | 0.2907 |
| RC3498pax | 0 | 0.0353 | −0.2633 | −0.1892 | 0.2909 | 1.2415 | 0.2486 |
| CC0003pax | 1 | −1.4122 | −0.3593 | −0.9318 | −0.6468 | 0.8435 | −0.8893 |
| CD0157pax | 1 | 1.5153 | 1.5517 | 1.1308 | 1.3209 | 3.0715 | 2.8186 |
| CD0164pax | 1 | −0.0247 | 0.4667 | 0.6758 | 1.0059 | 2.5315 | 1.2886 |
| CD0256pax | 1 | −0.6322 | 0.0807 | 0.0032 | 0.0382 | 0.8935 | 1.1557 |
| CD0322pax | 1 | −1.1572 | −0.4693 | −0.8368 | −0.2818 | 0.5435 | 1.0507 |
| CD0356pax | 1 | −0.6772 | −1.1393 | −0.7718 | −0.8668 | −0.2215 | −1.1643 |
| CD0371pax | 1 | 0.1028 | 0.9607 | −0.1918 | −0.3018 | 0.8385 | −0.2843 |
| CD0629pax | 1 | −0.0772 | 0.5407 | 0.5382 | 1.3882 | 0.2885 | 1.2507 |
| CD1050pax | 1 | 0.8153 | 0.1417 | 0.2208 | 0.7559 | 1.3815 | 1.0836 |
| DC0001pax | 1 | 0.1353 | −0.4183 | 0.1208 | −0.0941 | 0.3065 | 0.0936 |
| DC0002pax | 1 | 0.9878 | 0.2857 | 0.3632 | −0.1718 | 1.7035 | 0.9057 |
| DS0003pax | 1 | −1.8347 | −0.7183 | −1.5192 | −1.5591 | −0.3485 | 0.6886 |
| FC0005pax | 1 | 0.0928 | 0.1507 | 0.2682 | 0.1732 | 0.4235 | 1.8157 |
| FC0011pax | 1 | −0.4572 | −0.0793 | −0.1118 | −0.2318 | 0.8635 | 0.2707 |
| FC0012pax | 1 | −2.5847 | −0.4033 | −1.3792 | −1.2541 | −0.2885 | −0.3614 |
| JGA0001pax | 1 | −2.3247 | −1.6483 | −1.5592 | −0.7241 | −1.2535 | −1.1814 |
| JGA0008pax | 1 | −0.6772 | 1.0357 | 0.5732 | 0.0932 | 0.8485 | 0.7057 |
| JH0002pax | 1 | 0.5453 | 0.9667 | 0.5608 | 0.4459 | 1.4065 | 0.7586 |
| JH0003pax | 1 | 0.2853 | 0.1667 | −0.2292 | −0.3941 | −0.1385 | 1.0886 |
| JH0004pax | 1 | −0.1747 | −0.1733 | −0.3592 | −0.5591 | 1.1515 | 0.6686 |
| JH0005pax | 1 | 0.0928 | 1.2207 | 0.0682 | 0.1482 | 1.5735 | 1.1757 |
| JH0006pax | 1 | −0.6397 | 0.0667 | −0.2692 | −0.2741 | 0.8715 | −0.3114 |
| JH0007pax | 1 | −2.6372 | −2.2043 | −1.6168 | −0.5018 | −0.0865 | −1.2993 |
| JH0008pax | 1 | 0.5453 | 2.4167 | 0.2208 | 0.8859 | 2.1315 | 0.6336 |
| JH0009pax | 1 | −0.8522 | −0.7793 | −0.0968 | −0.6668 | −0.1815 | 0.4507 |
| JH0010pax | 1 | −0.3847 | 0.6517 | 0.2208 | 0.3059 | 0.6365 | −0.2664 |
| JH0012pax | 1 | −0.1072 | 0.3857 | 0.2882 | 0.0432 | 0.6685 | 0.9807 |
| JH0013pax | 1 | −0.3022 | 0.2007 | −0.3118 | −0.0568 | 2.0485 | 0.8357 |
| JH0014pax | 1 | 1.1828 | 1.2107 | 0.3182 | −0.0418 | 2.0485 | 2.5207 |
| JH0016pax | 1 | 0.5053 | 0.9167 | 0.6658 | 0.2659 | 0.4715 | 0.8636 |
| JH0018pax | 1 | −1.1972 | −0.1493 | −0.4268 | −0.4318 | −0.1465 | 0.3207 |
| JH0019pax | 1 | 0.1153 | 0.6267 | 0.0558 | −0.2091 | 0.1565 | 0.1936 |
| JH0020pax | 1 | 0.2728 | 2.0207 | 0.7332 | −0.1518 | 0.7585 | 1.3107 |
| JH0021pax | 1 | −0.8297 | 0.7867 | −0.3992 | −0.8541 | 0.2615 | 0.0586 |
| JH0023pax | 1 | −0.2272 | 1.3307 | 0.5182 | 1.6882 | 1.2985 | 1.9507 |
| JH0024pax | 1 | 1.0653 | 2.5467 | 1.2508 | 1.4159 | 3.3465 | 2.9786 |
| JH0025pax | 1 | −0.7847 | −0.3833 | −0.4292 | −0.8891 | −0.2435 | 0.5136 |
| JH0026pax | 1 | −1.1522 | 0.5857 | −0.0418 | −0.3468 | 1.1035 | 1.1507 |
| JH0027pax | 1 | −3.3947 | −2.5983 | −2.3842 | −2.0791 | −2.3435 | −1.8814 |
| JH0028pax | 1 | 0.3253 | 1.0967 | 0.9908 | 0.7459 | 2.5415 | 1.4586 |
| JH0029pax | 1 | −1.3522 | −0.6093 | −0.5918 | −0.7818 | −0.5615 | 0.5557 |
| JH0031pax | 1 | −0.7297 | 0.2817 | −0.2092 | −0.2791 | 0.5615 | 0.5136 |
| JH0032pax | 1 | 1.5478 | 1.7557 | 0.4532 | 0.3732 | 1.7785 | 1.8307 |
| JH0033pax | 1 | −0.8797 | 1.0817 | −0.4242 | −0.6141 | 1.3865 | −0.1914 |
| JH0034pax | 1 | −0.5397 | 1.0667 | 0.4908 | 0.3909 | 1.5465 | 1.5186 |

TABLE 9-continued

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| JH0035pax | 1 | −0.3222 | 1.3857 | 0.2782 | −0.3268 | 1.9385 | 0.8207 |
| JH0036pax | 1 | 0.8128 | 1.0107 | 0.4032 | 0.2182 | 1.9235 | 1.1757 |
| JH0038pax | 1 | 0.3103 | 1.5367 | 0.2258 | 0.4109 | 2.1215 | 0.8386 |
| JH0039pax | 1 | 0.5278 | 0.6207 | 0.5032 | 1.1232 | 3.1135 | 0.0857 |
| JH0040pax | 1 | 0.4353 | 0.8117 | 0.5508 | 0.3259 | 1.2465 | 0.8636 |
| JH0041pax | 1 | 0.7303 | 1.7117 | 0.4508 | 0.2759 | 1.9565 | 1.0436 |
| JH0042pax | 1 | −2.2922 | −0.6293 | −1.2268 | −0.7568 | −1.0515 | −1.7443 |
| JH0043pax | 1 | −0.8022 | −0.1993 | −0.2918 | −0.9318 | −0.3015 | −0.2393 |
| JH0046pax | 1 | −0.0447 | 0.0567 | 0.6408 | −0.2541 | 0.8965 | 0.0336 |
| JH0047pax | 1 | 0.1728 | 1.9907 | 0.6082 | 1.2782 | 1.6085 | 2.0757 |
| JH0051pax | 1 | −0.9647 | −0.1533 | −0.3892 | −1.0491 | −0.2135 | −0.4064 |
| JH0052pax | 1 | −0.6597 | 0.3067 | −0.4442 | −0.9141 | −0.4585 | −0.7914 |
| JH0053pax | 1 | −0.9522 | −0.1693 | −0.5918 | −0.0318 | −0.2515 | 0.1107 |
| JH0057pax | 1 | −0.1872 | 1.9757 | 0.1432 | 0.6682 | 1.4335 | 1.2057 |
| JH0059pax | 1 | −0.7897 | 0.0717 | −0.3442 | −0.3241 | 0.3215 | 0.1136 |
| JH0060pax | 1 | −1.0122 | 0.1207 | −0.2818 | 0.0482 | 0.3385 | 0.3557 |
| JH0061pax | 1 | 0.7803 | 2.5567 | 0.5558 | 1.0309 | 3.2565 | 0.3136 |
| JH0063pax | 1 | −0.2197 | 1.0467 | 0.2458 | −0.4141 | 0.8115 | 2.0486 |
| JH0065pax | 1 | −2.7497 | −1.4333 | −2.0542 | −2.8691 | −1.5035 | −0.4814 |
| JH0066pax | 1 | −1.1972 | −0.0343 | −0.8418 | −1.6318 | −1.0715 | −0.4643 |
| JH0068pax | 1 | 0.3653 | 0.8867 | 0.7108 | 0.4809 | 1.7165 | 2.1986 |
| JH0069pax | 1 | −0.6447 | 0.3967 | −0.0892 | −0.1791 | −0.0735 | −0.4014 |
| JH0071pax | 1 | −2.3272 | −2.1943 | −1.6968 | −1.0318 | −1.2715 | −0.3743 |
| JH0072pax | 1 | −0.1197 | −0.7533 | −0.0892 | −0.6741 | 1.1515 | 0.0586 |
| JH0077pax | 1 | −0.3022 | 0.2957 | 0.0882 | −0.0368 | 0.4435 | 1.6307 |
| JH0078pax | 1 | 1.2953 | 1.2767 | 1.2058 | 0.2609 | 1.2165 | 1.2786 |
| JH0080pax | 1 | −2.1122 | −1.1393 | −1.0418 | −0.7568 | −1.5315 | 0.3507 |
| JH0082pax | 1 | −0.6722 | −0.5393 | −0.0518 | −0.2368 | −0.3065 | 1.0857 |
| JH0083pax | 1 | −1.3997 | −0.0133 | −0.3542 | −1.2991 | 0.3115 | 0.7236 |
| JH0086pax | 1 | 0.2553 | 0.1667 | 0.0158 | −0.7941 | 0.4015 | 1.1086 |
| JH0092pax | 1 | −0.2647 | 1.6167 | 0.2158 | 0.2559 | 0.1565 | 1.3386 |
| MH0001pax | 1 | 1.1653 | 1.7717 | 1.0908 | 1.1159 | 2.8015 | 1.9086 |
| MH0009pax | 1 | −0.4972 | −0.0193 | −0.7268 | −0.5768 | −0.3015 | −0.3493 |
| MH0012pax | 1 | −0.1347 | 1.0017 | 0.3658 | 0.8559 | 0.9765 | 0.9186 |
| MH0014pax | 1 | 0.8278 | 1.4457 | 0.8482 | 0.5432 | 3.0535 | 1.8007 |
| MH0016pax | 1 | −1.1672 | −0.8793 | −0.9168 | −1.2168 | −0.4165 | −0.7243 |
| MH0017pax | 1 | 0.3403 | 1.4267 | 0.5658 | −0.0241 | 1.7565 | 2.0536 |
| MH0018pax | 1 | 1.2128 | 0.7657 | 0.3232 | 0.3682 | 2.1235 | 0.7057 |
| MH0021pax | 1 | 0.8103 | 0.2517 | −0.3192 | 0.0709 | 1.6865 | 1.7086 |
| MH0022pax | 1 | 0.6903 | 1.3667 | 0.6308 | 0.5459 | 1.2515 | 1.4236 |
| MH0024pax | 1 | 0.2228 | 0.4757 | −0.0568 | −0.1768 | 0.0635 | 0.9057 |
| MH0026pax | 1 | −1.2897 | 0.0417 | −0.4392 | 0.1059 | −0.3935 | −0.1914 |
| MH0028pax | 1 | −0.0272 | 0.3557 | −0.1068 | −0.8368 | −0.0765 | −0.0493 |
| MH0029pax | 1 | −0.0697 | 0.0167 | 0.0658 | −0.6641 | 1.0215 | 0.3536 |
| MH0035pax | 1 | 0.6603 | 2.0217 | 0.9458 | 0.7759 | 1.0965 | 1.4036 |
| MH0037pax | 1 | −0.1697 | 1.0717 | −0.0342 | 0.1309 | 1.1665 | 1.6186 |
| MH0038pax | 1 | 1.7453 | 1.5967 | 1.3108 | 1.4609 | 2.2365 | 2.3736 |
| MH0039pax | 1 | −1.1922 | −0.3093 | −0.1218 | −0.5718 | −0.0965 | 0.5557 |
| MH0042pax | 1 | −0.1522 | 0.0657 | 0.2332 | −0.1318 | −0.0815 | 0.9357 |
| MH0050pax | 1 | −1.4222 | 0.5507 | −0.6818 | −0.3468 | 0.8885 | 1.6307 |
| MH0051pax | 1 | −1.2197 | −1.0683 | −0.7092 | −1.6041 | −2.1735 | −0.1814 |
| MIP0004pax | 1 | −2.1722 | −2.1793 | −1.4118 | −1.1218 | −0.9865 | −2.2593 |
| MP0013Apax | 1 | 0.4028 | 1.2307 | 0.0782 | 0.2282 | 1.4535 | 0.1557 |
| MP0014Bpax | 1 | −0.4347 | 0.6117 | −0.5542 | −0.0441 | 1.2765 | −0.1964 |
| MP0018Apax | 1 | −1.0022 | −0.4193 | −0.9668 | −1.5668 | −0.3165 | −1.4293 |
| MP0019Bpax | 1 | −0.6222 | −0.2993 | −0.3768 | −0.6268 | −0.3465 | 0.8757 |
| MP0024pax | 1 | −1.2597 | −0.2333 | −0.4542 | 0.1409 | 1.3465 | 0.7386 |
| NK2001pax | 1 | −0.8347 | −0.1233 | −0.6992 | −1.5741 | −0.0785 | 1.1036 |
| NK2002pax | 1 | 0.0203 | −0.0183 | 0.1908 | −0.4741 | 0.8115 | 0.9786 |
| NK2003pax | 1 | −0.7372 | 0.0407 | −0.3218 | −0.2868 | 1.2085 | −0.1993 |
| NK2004pax | 1 | −0.9022 | 0.3107 | −0.5118 | −0.9568 | 0.5285 | −0.3843 |
| PB1829pax | 1 | 0.3378 | 1.5057 | 0.0682 | 0.0782 | 1.5485 | 1.7407 |
| PB1842pax | 1 | 1.0953 | 1.3467 | 0.8708 | 0.2009 | 2.3265 | 0.9536 |
| PB1872pax | 1 | 0.3928 | 0.6507 | 0.5682 | −0.5068 | 1.2035 | 0.1807 |
| PB2857pax | 1 | −0.9422 | 0.5057 | −0.3968 | 0.2982 | −0.2165 | 0.8657 |
| RC2919pax | 1 | 2.0678 | 2.0357 | 1.6382 | 3.0282 | 2.8985 | 3.9757 |
| RC3062pax | 1 | 0.1453 | 0.5917 | 0.1408 | 0.3759 | 0.1365 | 0.3386 |
| RC3277pax | 1 | −0.1122 | 0.1707 | −0.0568 | −0.0168 | 0.7285 | 0.2457 |
| RC3297pax | 1 | 0.2078 | 0.9457 | 0.4032 | 0.5332 | 2.7135 | 0.9807 |

TABLE 9-continued

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| RC3445pax | 1 | −0.8497 | −0.1233 | −0.3442 | −0.7391 | 0.6765 | 0.3086 |
| RC3467pax | 1 | 2.0928 | 2.9557 | 1.5782 | 1.4332 | 2.8485 | 2.8457 |

Surprisingly, analysis of the data showed that RNA encoded by ANXA3, CLEC4D, LMNB1, PRRG4, TNFAIP6 and VNN1 is present on average at a significantly higher level (p-value less than 0.05) in blood of subjects having colorectal cancer relative to subjects having no colorectal pathology (Table 10). The ranges of fold-change in the levels of RNA encoded by these genes normalized to levels of RNA encoded by IL2RB in blood of the training set subjects having colorectal cancer relative to the training set subjects not having any colorectal pathology are shown in Table 10.

RNA encoded by IL2RB, which is 1.3 to 11.5 fold higher than the average level of RNA encoded by this gene in blood of subjects not having any colorectal pathology is more likely to have colorectal cancer than to not have any colorectal pathology.

As can be seen in Table 10, a test subject having a blood level of RNA encoded by TNFAIP6, normalized to a level of RNA encoded by IL2RB, which is 1.5 to 13.6 fold higher than the average level of RNA encoded by this gene in blood

TABLE 10

Sample training set ranges of fold-change in levels of RNA encoded by ANXA3, CLEC4D, LMNB1, PRRG4, TNFAIP6 and VNN1 normalized to levels of RNA encoded by IL2RB in blood of subjects having colorectal cancer relative to subjects not having any colorectal pathology.

| | Gene | | | | | |
|---|---|---|---|---|---|---|
| | ANXA3 | CLEC4D | LMNB1 | PRRG4 | TNFAIP6 | VNN1 |
| Average normalized RNA level in subjects having colorectal cancer (ΔCt) | −0.30 | 0.42 | −0.05 | −0.12 | 0.79 | 0.66 |
| Average normalized RNA level in subjects not having any colorectal pathology (ΔCt) | 0.46 | 0.99 | 0.39 | 0.65 | 1.42 | 1.25 |
| Average RNA level fold-change | 1.69 | 1.48 | 1.55 | 1.35 | 1.55 | 1.35 |
| p-value for average RNA level fold-change | 5.5E−09 | 5.5E−06 | 6.4E−07 | 2.5E−13 | 6.0E−06 | 2.7E−06 |
| Maximum observed RNA level directional fold-change | 14.43 | 12.01 | 6.83 | 11.46 | 13.58 | 11.36 |

As can be seen in Table 10, a test subject having a blood level of RNA encoded by ANXA3, normalized to a level of RNA encoded by IL2RB, which is 1.7 to 14.4 fold higher than the average level of RNA encoded by this gene in blood of subjects not having any colorectal pathology is more likely to have colorectal cancer than to not have any colorectal pathology.

As can be seen in Table 10, a test subject having a blood level of RNA encoded by CLEC4D, normalized to a level of RNA encoded by IL2RB, which is 1.5 to 12.0 fold higher than the average level of RNA encoded by this gene in blood of subjects not having any colorectal pathology is more likely to have colorectal cancer than to not have any colorectal pathology.

As can be seen in Table 10, a test subject having a blood level of RNA encoded by LMNB1, normalized to a level of RNA encoded by IL2RB, which is 1.5 to 6.8 fold higher than the average level of RNA encoded by this gene in blood of subjects not having any colorectal pathology is more likely to have colorectal cancer than to not have any colorectal pathology.

As can be seen in Table 10, a test subject having a blood level of RNA encoded by PRRG4, normalized to a level of RNA encoded by IL2RB, which is 1.3 to 11.5 fold higher than the average level of RNA encoded by this gene in blood of subjects not having any colorectal pathology is more likely to have colorectal cancer than to not have any colorectal pathology.

As can be seen in Table 10, a test subject having a blood level of RNA encoded by VNN1, normalized to a level of RNA encoded by IL2RB, which is 1.3 to 11.4 fold higher than the average level of RNA encoded by this gene in blood of subjects not having any colorectal pathology is more likely to have colorectal cancer than to not have any colorectal pathology.

Generation of Logistic Regression Models for Determining the Probability that a Test Subject has Colorectal Cancer Versus not Having any Colorectal Pathology Via Measurement of Levels of RNA Encoded by ANXA3, CLEC4D, LMNB1, PRRG4, TNFAIP6 and VNN1 Normalized to Levels of RNA Encoded by IL2RB:

Linear regression analysis of levels of RNA encoded by ANXA3, CLEC4D, LMNB1, PRRG4, TNFAIP6 and VNN1 normalized to IL2RB surprisingly showed that logistic regression models could be generated, based on blood expression levels normalized to IL2RB for all 63 possible combinations of one or more of these genes, for discriminating, with a ROC AUC of at least 0.67, between subjects having colorectal cancer and subjects not having any colorectal pathology. Examples of these logistic regression models are shown in Table 11. A logistic regression model based on ANXA3, CLEC4D, LMNB1, PRRG4, TNFAIP6 and VNN1 (Table 11, Model #128) was surprisingly found to enable discrimination between subjects having colorectal cancer and subjects not having any colorectal pathology with a ROC AUC of 0.80.

By way of example, Model #128 of Table 11 corresponds to:

$$P = \{1 + e^{\wedge} - [(-0.196) + (-1.042)(L_{ANXA3}) + (0.393)(L_{CLEC4D}) + (1.272)(L_{LMNB1}) + (-1.837)(L_{PRRG4}) + (0.289)(L_{TNFAIP6}) + (-0.153)(L_{VNN1})]\}^{\wedge} - 1,$$

where P is the probability that a test subject has colorectal cancer as opposed to not having any colorectal pathology, where $L_{ANXA3}$ is a ratio of a level of RNA encoded by ANXA3 to a level of RNA encoded by IL2RB in blood of the test subject, $L_{CLEC4D}$ is a ratio of a level of RNA encoded by CLEC4D to a level of RNA encoded by IL2RB in blood of the test subject, $L_{LMNB1}$ is a ratio of a level of RNA encoded by LMNB1 to a level of RNA encoded by IL2RB in blood of the test subject, $L_{PRRG4}$ is a ratio of a level of RNA encoded by PRRG4 to a level of RNA encoded by IL2RB in blood of the test subject, $L_{TNFAIP6}$ is a ratio of a level of RNA encoded by TNFAIP6 to a level of RNA encoded by IL2RB in blood of the test subject, and $L_{VNN1}$ is a ratio of a level of RNA encoded by VNN1 to a level of RNA encoded by IL2RB in blood of the test subject.

Further by way of example, Model #157 of Table 11 corresponds to:

$$P = \{1 + e^{\wedge} - [0.288 + (-1.392)(L_{PRRG4})]\}^{\wedge} - 1,$$

where P is the probability that a test subject has colorectal cancer as opposed to not having any colorectal pathology, and $L_{PRRG4}$ is a ratio of a level of RNA encoded by PRRG4 to a level of RNA encoded by IL2RB in blood of the test subject.

TABLE 11

Logistic regression models based on blood expression levels for any possible combination of one or more of ANXA3, CLEC4D, LMNB1, PRRG4, TNFAIP6 and VNN1, normalized to IL2RB expression levels for determining the probability that a test subject has colorectal cancer as opposed to not having colorectal cancer.

| Logistic Regression Model # | No. of genes in Model | ROC AUC Training Set | ROC AUC Test Set | Constant ($K_0$) | Gene-specific regression coefficient ($K_n$) | | | | | |
|---|---|---|---|---|---|---|---|---|---|---|
| | | | | | ANXA3 | CLEC4D | LMNB1 | PRRG4 | TNFAIP6 | VNN1 |
| 128 | 6 | 0.80 | 0.78 | −0.196 | −1.042 | 0.393 | 1.272 | −1.837 | 0.289 | −0.153 |
| 129 | 5 | 0.80 | 0.79 | −0.298 | −1.058 | 0.366 | 1.187 | −1.854 | 0.285 | — |
| 130 | 5 | 0.80 | 0.79 | 0.034 | −0.945 | 0.456 | 1.300 | −1.715 | — | −0.146 |
| 131 | 5 | 0.79 | 0.78 | −0.070 | −0.937 | — | 1.469 | −1.774 | 0.336 | −0.115 |
| 132 | 4 | 0.79 | 0.79 | −0.065 | −0.961 | 0.428 | 1.221 | −1.733 | — | — |
| 133 | 4 | 0.79 | 0.78 | −0.154 | −0.955 | — | 1.394 | −1.790 | 0.330 | — |
| 134 | 5 | 0.79 | 0.78 | −0.305 | −0.630 | 0.575 | — | −1.632 | 0.311 | −0.049 |
| 135 | 4 | 0.79 | 0.78 | 0.229 | −0.799 | — | 1.537 | −1.620 | — | −0.097 |
| 136 | 4 | 0.79 | 0.79 | −0.337 | −0.645 | 0.562 | — | −1.642 | 0.309 | — |
| 137 | 4 | 0.79 | 0.78 | −0.058 | −0.516 | 0.645 | — | −1.493 | — | −0.041 |
| 138 | 5 | 0.79 | 0.76 | 0.239 | — | 0.173 | 0.355 | −1.782 | 0.144 | −0.210 |
| 139 | 3 | 0.79 | 0.78 | 0.153 | −0.817 | — | 1.474 | −1.637 | — | — |
| 140 | 3 | 0.79 | 0.79 | −0.085 | −0.528 | 0.634 | — | −1.503 | — | — |
| 141 | 4 | 0.79 | 0.76 | 0.128 | — | 0.280 | — | −1.707 | 0.174 | −0.162 |
| 142 | 4 | 0.79 | 0.76 | 0.337 | — | 0.216 | 0.413 | −1.721 | — | −0.203 |
| 143 | 3 | 0.79 | 0.77 | 0.229 | — | 0.355 | — | −1.615 | — | −0.144 |
| 144 | 4 | 0.79 | 0.76 | 0.279 | — | — | 0.492 | −1.757 | 0.172 | −0.189 |
| 145 | 4 | 0.78 | 0.76 | 0.109 | — | 0.128 | 0.225 | −1.802 | 0.134 | — |
| 146 | 3 | 0.78 | 0.76 | 0.053 | — | 0.209 | — | −1.747 | 0.157 | — |
| 147 | 3 | 0.78 | 0.76 | 0.416 | — | — | 0.607 | −1.673 | — | −0.173 |
| 148 | 3 | 0.78 | 0.76 | 0.206 | — | 0.169 | 0.285 | −1.745 | — | — |
| 149 | 3 | 0.78 | 0.76 | 0.150 | — | — | 0.339 | −1.781 | 0.156 | — |
| 150 | 2 | 0.78 | 0.77 | 0.153 | — | 0.285 | — | −1.659 | — | — |
| 151 | 2 | 0.78 | 0.76 | 0.284 | — | — | 0.457 | −1.703 | — | — |
| 152 | 3 | 0.78 | 0.76 | 0.123 | — | — | — | −1.591 | 0.257 | −0.078 |
| 153 | 3 | 0.78 | 0.77 | −0.102 | −0.352 | — | — | −1.463 | 0.390 | — |
| 154 | 4 | 0.78 | 0.77 | −0.130 | −0.368 | — | — | −1.474 | 0.388 | 0.037 |
| 155 | 2 | 0.78 | 0.76 | 0.082 | — | — | — | −1.630 | 0.237 | — |
| 156 | 3 | 0.77 | 0.77 | 0.216 | −0.179 | — | — | −1.276 | — | 0.061 |
| 157 | 1 | 0.77 | 0.76 | 0.288 | — | — | — | −1.392 | — | — |
| 158 | 2 | 0.77 | 0.77 | 0.267 | −0.150 | — | — | −1.256 | — | — |
| 159 | 2 | 0.77 | 0.76 | 0.296 | — | — | — | −1.384 | — | −0.011 |
| 160 | 5 | 0.73 | 0.75 | 0.162 | −0.907 | 0.153 | 0.321 | — | −0.073 | −0.270 |
| 161 | 4 | 0.73 | 0.75 | 0.108 | −0.930 | 0.130 | 0.296 | — | — | −0.273 |
| 162 | 3 | 0.73 | 0.76 | 0.086 | −0.818 | 0.185 | — | — | — | −0.243 |
| 163 | 4 | 0.73 | 0.76 | 0.125 | −0.793 | 0.206 | — | — | −0.055 | −0.238 |
| 164 | 4 | 0.72 | 0.75 | 0.208 | −0.868 | — | 0.406 | — | −0.046 | −0.254 |
| 165 | 3 | 0.72 | 0.75 | 0.167 | −0.888 | — | 0.380 | — | — | −0.258 |
| 166 | 2 | 0.72 | 0.75 | 0.171 | −0.698 | — | — | — | — | −0.204 |
| 167 | 3 | 0.72 | 0.75 | 0.179 | −0.691 | — | — | — | −0.009 | −0.203 |
| 168 | 3 | 0.72 | 0.76 | −0.021 | −0.870 | 0.134 | — | — | −0.077 | — |
| 169 | 4 | 0.72 | 0.76 | −0.012 | −0.929 | 0.103 | 0.155 | — | −0.087 | — |
| 170 | 2 | 0.72 | 0.77 | −0.080 | −0.907 | 0.102 | — | — | — | — |
| 171 | 1 | 0.72 | 0.76 | −0.014 | −0.827 | — | — | — | — | — |

TABLE 11-continued

Logistic regression models based on blood expression levels for any possible
combination of one or more of ANXA3, CLEC4D, LMNB1, PRRG4, TNFAIP6 and VNN1,
normalized to IL2RB expression levels for determining the probability that a
test subject has colorectal cancer as opposed to not having colorectal cancer.

| Logistic Regression Model # | No. of genes in Model | ROC AUC Training Set | ROC AUC Test Set | Constant ($K_0$) | Gene-specific regression coefficient ($K_n$) ANXA3 | CLEC4D | LMNB1 | PRRG4 | TNFAIP6 | VNN1 |
|---|---|---|---|---|---|---|---|---|---|---|
| 172 | 2 | 0.72 | 0.76 | 0.031 | −0.793 | — | — | — | −0.043 | — |
| 173 | 3 | 0.72 | 0.76 | −0.079 | −0.957 | 0.074 | 0.122 | — | — | — |
| 174 | 2 | 0.72 | 0.76 | −0.039 | −0.932 | — | 0.178 | — | — | — |
| 175 | 3 | 0.72 | 0.76 | 0.026 | −0.902 | — | 0.221 | — | −0.068 | — |
| 176 | 3 | 0.71 | 0.72 | 0.514 | — | — | −0.502 | — | −0.191 | −0.309 |
| 177 | 4 | 0.71 | 0.72 | 0.519 | — | −0.024 | −0.482 | — | −0.186 | −0.306 |
| 178 | 3 | 0.70 | 0.72 | 0.398 | — | −0.097 | −0.604 | — | — | −0.319 |
| 179 | 2 | 0.70 | 0.73 | 0.361 | — | — | −0.706 | — | — | −0.333 |
| 180 | 2 | 0.70 | 0.70 | 0.727 | — | — | — | — | −0.345 | −0.451 |
| 181 | 3 | 0.70 | 0.71 | 0.701 | — | −0.192 | — | — | −0.256 | −0.383 |
| 182 | 2 | 0.70 | 0.73 | 0.306 | — | — | −0.769 | — | −0.227 | — |
| 183 | 3 | 0.69 | 0.73 | 0.331 | — | −0.085 | −0.690 | — | −0.208 | — |
| 184 | 1 | 0.69 | 0.73 | 0.102 | — | — | −1.041 | — | — | — |
| 185 | 2 | 0.69 | 0.70 | 0.589 | — | −0.367 | — | — | — | −0.433 |
| 186 | 2 | 0.69 | 0.73 | 0.186 | — | −0.170 | −0.838 | — | — | — |
| 187 | 1 | 0.68 | 0.69 | 0.552 | — | — | — | — | — | −0.671 |
| 188 | 2 | 0.68 | 0.72 | 0.548 | — | −0.379 | — | — | −0.331 | — |
| 189 | 1 | 0.67 | 0.70 | 0.549 | — | — | — | — | −0.576 | — |
| 190 | 1 | 0.67 | 0.71 | 0.371 | — | −0.649 | — | — | — | — |

ROC AUC values for the models are shown for the sample training set used to generate the models, as well as for an independent blind sample test set used to test the models. The models, listed in order of decreasing ROC AUC value for the training set, are based on expression levels determined via quantitative reverse transcriptase-PCR analysis using IL2RB as duplex partner for normalization. The form of these models is: $P = \{1 + e^{-[K_0 + K_1L_1 + K_2L_2 + K_3L_3 \ldots + K_nL_n]}\}^{-1}$, where P is the probability that a test subject has colorectal cancer as opposed to not having any colorectal pathology; $K_0$ is a constant; $K_1$ is a coefficient specific to a first gene; $L_1$ is a ratio of a level of RNA encoded by the first gene in blood to a level of RNA encoded by IL2RB in blood; $K_2$ is a coefficient specific to a second gene; $L_2$ is a ratio of a level of RNA encoded by the second gene in blood to a level of RNA encoded by IL2RB in blood; $K_3$ is a coefficient specific to a third gene; $L_3$ is a ratio of a level of RNA encoded by the third gene in blood to a level of RNA encoded by IL2RB in blood; $K_n$ is a coefficient specific to an nth gene; and $L_n$ is a ratio of a level of RNA encoded by the nth gene in blood to a level of RNA encoded by IL2RB in blood. No regression coefficients are specified for genes which are not included in the gene combination (indicated by "—") on which a given logistic regression model is based.

Blind Sample Test Set:

Quantitative reverse transcriptase-PCR analysis of expression of ANXA3, CLEC4D, LMNB1, PRRG4, TNFAIP6 and VNN1 in an independent test set of blood samples from 165 subjects having colorectal cancer and 171 subjects not having any colorectal pathology was performed as described above for the training set. The normalized RNA levels measured are shown in Table 12.

TABLE 12

Sample test set levels of RNA encoded by ANXA3, CLEC4D, LMNB1, PRRG4,
TNFAIP6 and VNN1 in blood of subjects having colorectal cancer (Group
1) and subjects not having any colorectal pathology (Group 0), normalized
to levels of RNA encoded by IL2RB. Levels shown correspond to ΔCt.

| Sample ID | Group | Gene ANXA3 | CLEC4D | LMNB1 | PRRG4 | TNFAIP6 | VNN1 |
|---|---|---|---|---|---|---|---|
| CD0036pax | 0 | −0.0922 | −0.0443 | −0.1868 | −1.0168 | 0.5035 | −0.0543 |
| CD0053pax | 0 | 1.1828 | 2.1407 | 1.5032 | 1.3032 | 2.9135 | 1.5907 |
| CD0092pax | 0 | 1.2028 | 0.9057 | 0.8232 | 0.6032 | 1.6285 | 0.2907 |
| CD0108pax | 0 | −0.0522 | −0.1893 | 0.2582 | −0.1318 | 0.3385 | 0.2757 |
| CD0122pax | 0 | 0.5628 | 1.2857 | 0.5582 | 0.6382 | 2.0485 | 1.9357 |
| CD0148pax | 0 | 0.6778 | 2.0057 | 0.6732 | 1.4432 | 2.0335 | 1.5607 |
| CD0192pax | 0 | 0.6878 | 0.8157 | 0.7682 | 1.5882 | 0.7085 | 0.8907 |
| CD0204pax | 0 | 0.1978 | 0.6907 | 0.0782 | −0.1418 | 1.0185 | 0.9557 |
| CD0214pax | 0 | 0.4478 | 0.1557 | 1.1682 | 1.1932 | 0.6235 | 0.6157 |
| CD0237pax | 0 | 0.3828 | 0.8707 | −0.0168 | 0.0582 | 1.1685 | 0.8007 |
| CD0238pax | 0 | 0.2428 | 0.8957 | 0.3982 | 1.0232 | 1.5385 | 0.9657 |
| CD0242pax | 0 | 0.9528 | 1.3957 | 0.5082 | −0.3818 | 0.9685 | 1.0307 |
| CD0244pax | 0 | 0.4928 | 0.3507 | 0.4182 | 0.8982 | 1.4535 | −0.0493 |
| CD0277pax | 0 | 0.1453 | 1.7617 | 0.2358 | 0.4909 | 1.8265 | 0.1486 |
| CD0282pax | 0 | −0.1572 | 0.2207 | −0.2118 | 0.0632 | 0.7585 | −1.2243 |
| CD0295pax | 0 | 0.1578 | 0.7957 | 0.5482 | 0.5332 | 1.1735 | 0.1907 |
| CD0354pax | 0 | 0.5178 | 0.9557 | 0.2432 | 1.0732 | 1.6235 | 1.0307 |
| CD0367pax | 0 | 0.7778 | 0.6857 | 0.5232 | 0.3432 | 1.8935 | 0.8457 |
| CD0369pax | 0 | 1.0328 | 2.1057 | 0.9982 | 1.9532 | 2.1885 | 1.7607 |
| CD0398pax | 0 | 2.1128 | 2.2157 | 1.6682 | 2.0432 | 3.7635 | 3.1407 |
| CD0409pax | 0 | −0.2272 | 0.7757 | 0.0282 | 0.7082 | 0.5735 | 1.2357 |

TABLE 12-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| Sample ID | Group | ANXA3 | CLEC4D | LMNB1 | PRRG4 | TNFAIP6 | VNN1 |
|---|---|---|---|---|---|---|---|
| CD0419pax | 0 | 0.2503 | 0.9617 | 0.5758 | 0.3759 | 2.1815 | −0.3114 |
| CD0432pax | 0 | 0.3628 | 0.5607 | 0.2532 | 0.0282 | 2.0485 | 0.4407 |
| CD0437pax | 0 | −0.8872 | −0.1793 | −0.6918 | −0.7768 | 0.4635 | −0.1593 |
| CD0472pax | 0 | −2.1022 | −0.4543 | −1.0718 | −0.6968 | 0.0235 | −0.4243 |
| CD0482pax | 0 | 3.2778 | 3.4857 | 2.2282 | 2.2532 | 4.6085 | 3.4507 |
| CD0484pax | 0 | 0.2778 | 1.1907 | 0.3932 | 1.3182 | 1.7635 | 0.4107 |
| CD0507pax | 0 | 1.4228 | 1.0757 | 1.0982 | 0.4282 | 2.4985 | 1.5357 |
| CD0547pax | 0 | −1.6622 | −0.1543 | −0.5068 | 0.0632 | 0.1035 | −0.3643 |
| CD0571pax | 0 | 0.9378 | 1.2407 | 1.0382 | 1.8282 | 2.3535 | 0.5757 |
| CD0580pax | 0 | 1.2978 | 1.6557 | 0.5582 | 0.4382 | 2.3585 | 1.2807 |
| CD0583pax | 0 | −0.4472 | −0.9493 | −0.4968 | −0.5218 | 0.7935 | −0.6093 |
| CD0603pax | 0 | 0.6928 | 0.5507 | 0.1582 | −0.0818 | 1.4135 | 1.2457 |
| CD0604pax | 0 | 0.0028 | 0.6557 | −0.1218 | −0.1268 | 1.6635 | −0.1443 |
| CD0619pax | 0 | −0.3072 | 0.2557 | 0.1532 | 0.5182 | 0.3285 | 0.8407 |
| CD0637pax | 0 | 0.3428 | 0.0357 | −0.0618 | 0.3132 | 0.8935 | 0.6657 |
| CD0667pax | 0 | −0.5672 | −0.4993 | −0.5168 | −0.1568 | 0.0235 | −0.2643 |
| CD0670pax | 0 | 3.0478 | 2.9307 | 1.7582 | 1.5882 | 3.3985 | 2.6957 |
| CD0676pax | 0 | −0.7022 | −0.6343 | −0.5518 | −1.0468 | 0.2485 | 0.0357 |
| CD0687pax | 0 | 1.4528 | 2.5807 | 1.6032 | 1.9382 | 1.9035 | 2.4357 |
| CD0715pax | 0 | −2.1372 | −1.5893 | −1.0468 | −0.7768 | −0.3665 | 0.4757 |
| CD0721pax | 0 | 0.1778 | 1.1807 | 0.0382 | 0.0582 | 1.1935 | 0.7607 |
| CD0726pax | 0 | −0.2472 | −0.2193 | 0.0432 | −0.0318 | 0.8985 | −1.1393 |
| CD0743pax | 0 | 0.4178 | −0.4243 | 0.2032 | 0.2782 | 1.6735 | −0.0243 |
| CD0786pax | 0 | 0.6678 | 1.0807 | 0.6132 | 0.9682 | 1.8735 | 1.0607 |
| CD0800pax | 0 | 2.6478 | 2.7757 | 1.9282 | 2.4682 | 3.8585 | 3.0107 |
| CD0829pax | 0 | −0.0722 | 0.4757 | 0.2082 | −0.3318 | 0.5785 | 0.7957 |
| CD0833pax | 0 | 0.1378 | −0.3693 | 0.0982 | 0.5032 | 0.8185 | −0.2293 |
| CD0840pax | 0 | −0.5072 | 0.4157 | −0.2018 | −0.5618 | 0.6035 | 0.1307 |
| CD0843pax | 0 | 0.2853 | −0.1433 | −0.2192 | −0.5291 | 0.3415 | 0.2136 |
| CD0937pax | 0 | 1.2178 | 0.8507 | 0.9632 | 1.4432 | 2.6285 | 1.8457 |
| CD1001pax | 0 | 0.7553 | 0.8367 | 0.2758 | −0.3541 | 2.7865 | 0.9686 |
| CD1032pax | 0 | −3.0422 | −2.3193 | −0.7918 | −0.7218 | −1.1065 | 0.0557 |
| CD1068pax | 0 | −0.1722 | −0.0343 | 0.1382 | 0.5532 | 2.0935 | −0.2243 |
| CD1134pax | 0 | 0.4253 | 1.2867 | 0.2608 | 0.4409 | 1.3565 | 1.9236 |
| CD1269pax | 0 | 0.0378 | 1.3507 | 0.1732 | −0.2218 | 1.1735 | 1.1007 |
| CD1270pax | 0 | 0.8328 | 0.8557 | 0.6482 | 0.3532 | 1.4535 | 1.4157 |
| CD1271pax | 0 | 1.6778 | 2.4257 | 1.2282 | 0.6282 | 0.9885 | 1.8207 |
| CD1278pax | 0 | 0.2578 | 1.0757 | 0.5232 | 0.1582 | 1.2685 | 1.3507 |
| CD1285pax | 0 | 0.6903 | 0.3917 | 0.8458 | 0.3609 | 2.7765 | 0.8986 |
| CD1313pax | 0 | 1.7278 | 1.3757 | 0.8182 | 1.0282 | 2.8285 | 0.6057 |
| CD1320pax | 0 | −0.8972 | 0.2757 | −0.6068 | −0.0668 | 0.1335 | 0.7907 |
| CD1329pax | 0 | 0.1903 | −0.0983 | 0.2308 | −0.3091 | 1.1115 | 0.8936 |
| CD1349pax | 0 | −0.1622 | 0.5757 | −0.3668 | −0.9268 | 0.3935 | 0.5807 |
| CD1401pax | 0 | −0.0397 | −0.2933 | −0.2492 | 0.2409 | 0.2715 | 0.2036 |
| CD1428pax | 0 | 2.0228 | 2.1257 | 1.1632 | 2.0382 | 2.5385 | 1.4807 |
| CD1438pax | 0 | −0.1572 | 0.3757 | −0.1418 | 0.3782 | 0.6935 | −0.1493 |
| CD1441pax | 0 | −0.6972 | 0.3307 | 0.0582 | 0.1132 | 0.7235 | −0.3693 |
| CD1458pax | 0 | 0.2328 | 0.2407 | 0.9082 | 0.7332 | 1.8935 | 0.5707 |
| CD1487pax | 0 | 0.2378 | 1.9757 | 0.9582 | 1.6032 | 1.9785 | 0.5407 |
| CD1559pax | 0 | −0.0022 | 0.8557 | 0.1632 | 0.3532 | 1.8685 | 1.0657 |
| CD1561pax | 0 | 1.1728 | 0.7557 | 0.6132 | 0.5432 | 1.8635 | 1.9307 |
| CD1567pax | 0 | 0.6928 | 1.4807 | 0.4982 | 1.2232 | 1.6035 | 1.2807 |
| CD1627pax | 0 | −1.0072 | −0.6693 | −0.1868 | 0.2632 | −0.4965 | −0.2743 |
| CD1708pax | 0 | 1.3903 | 1.8417 | 1.1458 | 0.6909 | 2.4365 | 1.8636 |
| CD1719pax | 0 | −0.4022 | 0.0407 | −0.3068 | −0.7568 | 0.1285 | 0.4657 |
| CD1728pax | 0 | 1.8578 | 2.0957 | 1.2732 | 2.0332 | 1.9635 | 3.0907 |
| CD1741pax | 0 | −0.4922 | −0.5493 | −0.1868 | −0.4618 | 1.0035 | 0.3257 |
| PB0662pax | 0 | 0.0003 | 0.3867 | 0.6908 | 0.6809 | 1.2815 | −0.1464 |
| PB0701pax | 0 | 0.8803 | 1.5017 | 1.2058 | 2.1159 | 1.6765 | 3.1036 |
| PB0790pax | 0 | 0.4253 | 0.2867 | 0.5158 | 0.5459 | 0.1665 | −0.2414 |
| PB1222pax | 0 | −0.0272 | 0.4407 | 0.2932 | −0.6868 | −0.0465 | 0.8957 |
| PB1260pax | 0 | −1.3447 | −1.3983 | −0.3742 | −1.2441 | −0.6585 | −0.5814 |
| PB1275pax | 0 | −0.7447 | 0.3767 | −0.3092 | 0.2359 | −0.1835 | 2.1786 |
| PB1324pax | 0 | −0.1597 | 0.5667 | 0.4508 | 1.1109 | 1.7015 | 1.8886 |
| PB1336pax | 0 | 0.4853 | 0.6817 | 0.2158 | −0.5991 | 1.1365 | 1.5136 |
| PB1446pax | 0 | −0.9897 | −0.0133 | −0.1992 | 0.0159 | 0.7765 | 1.0086 |
| PB1514pax | 0 | −1.2222 | −0.2093 | −0.3418 | −0.4868 | 0.8185 | −0.0293 |
| PB1540pax | 0 | −0.7672 | −0.2493 | −0.2668 | −0.0068 | 0.5185 | 0.8157 |
| PB1700pax | 0 | 0.5403 | 0.7517 | 0.5258 | 0.8759 | 1.3265 | 0.8836 |
| PB1763pax | 0 | 2.0953 | 2.5067 | 1.7958 | 2.6409 | 3.0115 | 1.9736 |
| PB1785pax | 0 | 0.9903 | 1.6717 | 0.6008 | 1.4309 | 1.3415 | 0.9486 |

TABLE 12-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| PB1871pax | 0 | 0.4853 | 0.3717 | 0.2008 | 0.3059 | 1.3365 | 1.4286 |
| PB1918pax | 0 | 2.6678 | 2.3457 | 1.4632 | 1.7882 | 3.8835 | 2.6107 |
| PB1944pax | 0 | 0.0028 | −0.4843 | 0.4432 | 0.7482 | 0.5435 | 1.3507 |
| PB1952pax | 0 | 1.9703 | 1.9167 | 0.5508 | 1.8859 | 2.9865 | 2.0386 |
| PB1973pax | 0 | 2.7753 | 2.8667 | 1.9308 | 3.1009 | 3.7065 | 3.7736 |
| PB1984pax | 0 | −2.2397 | −1.7683 | −1.8492 | −1.7341 | −1.4835 | −1.3114 |
| PB2005pax | 0 | 1.4803 | 1.5917 | 0.8408 | 1.1159 | 3.3915 | 1.8386 |
| PB2015pax | 0 | 2.4703 | 1.9567 | 2.0908 | 3.2409 | 4.2865 | 2.5086 |
| PB2024pax | 0 | 0.8053 | 1.3967 | 0.8908 | 1.1359 | 2.6515 | 2.2286 |
| PB2041pax | 0 | −0.5647 | 0.7517 | −0.0692 | 0.1909 | 1.7565 | 0.1836 |
| PB2062pax | 0 | 2.4703 | 2.4517 | 1.7908 | 2.2809 | 3.3065 | 2.6786 |
| PB2084pax | 0 | 1.3553 | 1.0517 | 0.6808 | 1.5959 | 2.3965 | 1.4886 |
| PB2130pax | 0 | 0.4353 | 0.6717 | 0.0408 | −0.1091 | 0.6315 | 0.6436 |
| PB2179pax | 0 | 0.6453 | 1.5017 | 0.5358 | 0.3559 | 0.7115 | 0.8686 |
| PB2184pax | 0 | −0.8047 | −0.1983 | −0.3292 | 0.0859 | 0.2715 | 1.4886 |
| PB2258pax | 0 | −0.0397 | −0.9183 | −0.5042 | −0.4191 | 0.8415 | −1.1164 |
| PB2272pax | 0 | 2.2653 | 2.2717 | 1.6408 | 1.7259 | 4.0015 | 1.8136 |
| PB2342pax | 0 | 2.9678 | 2.7557 | 1.1682 | 1.6732 | 2.4335 | 2.7607 |
| PB2464pax | 0 | 1.0003 | 1.6717 | 0.8458 | 0.4759 | 1.4465 | 3.2686 |
| PB2516pax | 0 | 0.1603 | 0.8067 | 0.4858 | 0.2109 | 0.6065 | 1.9036 |
| PB2564pax | 0 | 0.1253 | 1.3217 | 0.0258 | 0.3009 | 0.5815 | 0.7836 |
| PB2634pax | 0 | 0.0153 | 1.1567 | 0.8958 | 0.7009 | 2.5465 | 0.5586 |
| PB2682pax | 0 | −1.2297 | −0.1383 | −0.5242 | −1.4441 | 0.0415 | −0.0114 |
| PB2709pax | 0 | 1.2978 | 1.7457 | 1.3832 | 1.9982 | 2.2535 | 1.3107 |
| PB2711pax | 0 | −0.8797 | −1.1033 | −0.3892 | −0.8391 | 0.5215 | 0.4736 |
| PB2757pax | 0 | 0.5353 | 1.6117 | 0.8508 | 0.6659 | 1.5865 | 1.9836 |
| PB2809pax | 0 | −0.1722 | 0.9957 | 0.0032 | −0.1768 | 0.6335 | 0.9057 |
| PB2842pax | 0 | −0.5547 | 0.3867 | −0.3492 | 0.0209 | −0.2585 | 0.3486 |
| PB2875pax | 0 | −0.0497 | 1.2967 | 0.3958 | 0.3959 | 1.2365 | 1.1736 |
| PB2889pax | 0 | 0.6453 | 1.9717 | 1.0808 | 1.4209 | 1.4015 | 1.5286 |
| PB2909pax | 0 | −0.1372 | −1.0543 | −0.4368 | −0.7268 | 0.2735 | −0.3993 |
| PB2924pax | 0 | 0.7803 | 1.5167 | 1.1858 | 1.2159 | 1.3115 | 1.2786 |
| PB2927pax | 0 | 2.1453 | 0.8717 | 0.7158 | 0.1309 | 1.5815 | 2.1286 |
| PB2931pax | 0 | 0.2203 | −0.3283 | −0.8242 | −0.8241 | 1.8315 | −0.3664 |
| PB2951pax | 0 | −0.0897 | −1.6683 | −1.0792 | −0.2891 | −0.3035 | −0.9164 |
| PB2974pax | 0 | −0.2547 | 0.8417 | 0.1958 | 0.2259 | 1.0515 | 2.2086 |
| PB2978pax | 0 | 3.1253 | 3.2667 | 2.2458 | 2.4059 | 3.7165 | 2.9886 |
| PB2988pax | 0 | −1.5847 | −1.3333 | −0.7892 | −1.1941 | −0.2435 | −0.3764 |
| PB3014pax | 0 | 1.3953 | 1.9017 | 1.2458 | 0.7959 | 2.3615 | 2.5236 |
| PB3021pax | 0 | 0.3053 | 2.1667 | 0.4108 | 0.9459 | 0.9015 | 0.7786 |
| PB3032pax | 0 | −0.1547 | 0.4867 | 0.6658 | 0.0409 | 1.5065 | 1.1036 |
| PB3163pax | 0 | 0.3003 | 1.4117 | 0.5908 | 1.1459 | 2.4115 | 1.7336 |
| PB3193pax | 0 | −0.0047 | 0.3717 | 0.0058 | 0.4559 | 1.1065 | 0.7036 |
| PB3200pax | 0 | 0.2653 | 1.0967 | 0.8608 | 1.0859 | 1.4265 | 1.5786 |
| PB3226pax | 0 | 0.3203 | 0.9467 | 0.4658 | 0.6709 | 1.9165 | 1.1536 |
| PB3227pax | 0 | −0.0147 | 0.7317 | 0.4658 | 0.6559 | 2.0115 | 1.3936 |
| PB3361pax | 0 | −0.8197 | −0.1133 | −0.5592 | −0.9891 | 0.8715 | −0.6564 |
| PB3439pax | 0 | −1.2272 | −1.8643 | −1.1768 | −1.2568 | −0.9015 | −1.7543 |
| PB3445pax | 0 | 1.6203 | 2.4017 | 1.5208 | 2.2859 | 2.7265 | 2.2836 |
| PB3481pax | 0 | −0.0397 | 0.9167 | 0.3308 | 1.1359 | 0.5015 | 1.3636 |
| PB3513pax | 0 | −0.0347 | −0.2133 | −0.5142 | −0.6891 | 0.8765 | −0.9214 |
| PB3524pax | 0 | 0.2103 | −0.5733 | 0.1758 | 0.1859 | 1.2865 | 0.8486 |
| PB3533pax | 0 | −0.3047 | −0.7483 | −0.2442 | −0.0641 | 1.0465 | −0.2664 |
| PB3568pax | 0 | 1.3153 | 1.4267 | 0.9858 | 1.0159 | 1.8915 | 0.8386 |
| PB3582pax | 0 | 1.4703 | 2.3517 | 1.7258 | 1.8509 | 3.3165 | 2.4236 |
| PB3594pax | 0 | 1.0753 | 1.2267 | 0.6958 | 1.2059 | 2.4615 | 1.2786 |
| PB3806pax | 0 | −1.7122 | 0.1507 | −0.6168 | −0.1418 | −0.2615 | −0.3843 |
| PB3828pax | 0 | −0.8197 | 0.3417 | −0.2942 | −0.6091 | −0.2085 | 0.4136 |
| PB3863pax | 0 | 1.9153 | 1.8567 | 1.5808 | 1.4659 | 2.7065 | 2.5436 |
| PB3877pax | 0 | 2.1003 | 2.3217 | 1.6458 | 1.3909 | 3.4115 | 2.2186 |
| RC2112pax | 0 | 1.0653 | 2.1567 | 1.3008 | 1.7109 | 1.6115 | 2.0886 |
| RC2236pax | 0 | 1.1903 | 1.2017 | 1.0508 | 1.2159 | 1.5165 | 2.2136 |
| RC2239pax | 0 | −0.2897 | 1.0767 | 1.0608 | 1.3759 | 0.5315 | 1.6386 |
| RC2252pax | 0 | 2.5353 | 1.9417 | 1.4658 | 1.9359 | 1.9515 | 2.7336 |
| RC2338pax | 0 | 1.1953 | 2.1167 | 1.1358 | 1.0609 | 2.2215 | 2.0636 |
| RC2565pax | 0 | 0.0753 | 1.1417 | 0.0458 | 1.2659 | 0.5465 | 2.0486 |
| RC2615pax | 0 | −0.4847 | 0.1417 | 0.3558 | 0.5509 | 0.2765 | 1.1436 |
| RC2699pax | 0 | 1.1453 | 1.5167 | 0.8658 | 0.6759 | 1.7615 | 1.5636 |
| RC2716pax | 0 | 0.2703 | 0.4317 | 0.7308 | 1.1609 | 2.2865 | 0.9336 |
| RC2728pax | 0 | −0.1697 | 1.2267 | 0.8108 | 0.5209 | 1.1265 | 0.4386 |
| RC2768pax | 0 | 1.2553 | 1.6867 | 0.9908 | 1.5259 | 1.8865 | 2.7936 |

TABLE 12-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| Sample ID | Group | Gene | | | | | |
|---|---|---|---|---|---|---|---|
| | | ANXA3 | CLEC4D | LMNB1 | PRRG4 | TNFAIP6 | VNN1 |
| RC2782pax | 0 | 2.7703 | 3.4667 | 2.2058 | 2.3409 | 5.0215 | 2.7836 |
| RC2869pax | 0 | 1.3178 | 1.1907 | 0.7582 | 1.3432 | 2.3085 | 2.1657 |
| RC2897pax | 0 | 0.1853 | 0.7067 | −0.0642 | 0.3409 | 1.1865 | 1.0436 |
| RC2986pax | 0 | 0.8953 | 0.9867 | 0.3458 | 0.4359 | 2.5115 | 1.4186 |
| RC3191pax | 0 | 1.4403 | 2.2267 | 1.2558 | 1.0409 | 1.9615 | 2.2036 |
| RC3214pax | 0 | 0.7903 | 1.6817 | 0.8258 | 0.8409 | 2.5365 | 1.1586 |
| RC3379pax | 0 | 1.3003 | 1.7467 | 1.0158 | 1.0509 | 2.4615 | 0.5686 |
| RC3420pax | 0 | 0.9153 | 1.0217 | 0.9258 | 1.6209 | 2.5815 | 0.4436 |
| AN0001pax | 1 | −2.1122 | −1.1143 | −1.0218 | −1.6018 | −0.1515 | −0.4493 |
| AN0003pax | 1 | −3.9172 | −2.1693 | −2.9568 | −1.2268 | −2.2065 | −2.5393 |
| AN0007pax | 1 | −3.0572 | −1.7593 | −2.1818 | −3.1218 | −2.5615 | −1.0493 |
| AN0009pax | 1 | −0.3772 | 0.6607 | 0.0832 | −0.0718 | 1.9985 | 1.0707 |
| AN0012pax | 1 | 0.5478 | 1.1207 | 0.3632 | −0.0868 | 1.6385 | 1.6507 |
| AN0013pax | 1 | 0.2178 | 2.0007 | 0.9732 | 0.1332 | 2.7685 | 2.1157 |
| AN0020pax | 1 | −1.8472 | −0.4843 | −1.1768 | −1.7718 | −1.3165 | −0.3293 |
| AN4011pax | 1 | −0.0972 | 0.8507 | 0.9782 | 0.5082 | 2.1785 | 0.9257 |
| AN4012pax | 1 | 1.6828 | 1.2857 | 1.1782 | 1.2582 | 2.7935 | 2.4957 |
| AN4013pax | 1 | 0.7928 | 2.0057 | 0.8132 | 0.6482 | 1.6385 | 1.8907 |
| AN4014pax | 1 | −1.0472 | 0.2207 | −0.1918 | 0.1232 | 0.4685 | 1.9757 |
| AN4017pax | 1 | 1.0003 | 1.3817 | 0.3358 | 0.2709 | 0.4565 | 1.2836 |
| BE3001pax | 1 | −1.4472 | 0.2507 | −0.3068 | −0.6768 | −0.8115 | 0.8657 |
| CC0001pax | 1 | −0.2222 | 0.1107 | −0.1668 | −0.0168 | 1.2635 | 0.7907 |
| CC0002pax | 1 | −0.5572 | −0.8993 | −0.6118 | −1.9568 | −0.2715 | 0.0957 |
| CC0004pax | 1 | −1.2622 | −1.0993 | −0.4268 | −0.1268 | 0.5335 | 0.6457 |
| CC0005pax | 1 | 0.8628 | 1.2457 | 0.6532 | 0.9132 | 1.8285 | 0.4607 |
| CC0006pax | 1 | 0.3128 | 0.4957 | 0.2332 | 0.5682 | 1.7235 | 2.2507 |
| CC0007pax | 1 | −1.5122 | 0.0857 | −0.2318 | 0.0032 | −0.1365 | 0.3407 |
| CC2001pax | 1 | −0.6672 | 1.0957 | −0.0268 | 0.1382 | 0.9435 | 0.7757 |
| CC2002pax | 1 | −0.6022 | −0.9543 | −0.6518 | −1.5068 | −0.2315 | −0.3993 |
| CD1111pax | 1 | 1.5528 | 0.9857 | 1.1082 | 1.6382 | 2.0285 | 2.2057 |
| CD1260pax | 1 | −0.4922 | −0.5393 | 0.0532 | −0.5368 | 1.1035 | 0.7257 |
| CD1351pax | 1 | 0.3978 | 0.4007 | −0.0268 | −0.3368 | 1.6485 | 0.5707 |
| CD1571pax | 1 | 0.6253 | 0.7717 | 0.9908 | 1.7909 | 2.5465 | 1.3386 |
| CD1690pax | 1 | 0.4278 | 0.5007 | 0.4682 | 0.5232 | 1.3985 | −0.1993 |
| DC0003pax | 1 | 0.3378 | 0.8707 | 0.1182 | 0.0432 | 0.8135 | 1.8807 |
| DC0005pax | 1 | 0.6328 | 1.6957 | 0.6782 | 0.4432 | 1.5635 | 1.7007 |
| DC0008pax | 1 | 0.3628 | 0.7757 | 0.4632 | −0.3718 | 1.6735 | 0.2907 |
| DC0011pax | 1 | −0.1322 | 0.4157 | 0.5532 | 0.5082 | 1.5035 | 1.6757 |
| DC0012pax | 1 | −1.2222 | −0.4443 | −0.6868 | 0.3132 | −1.1115 | −0.2343 |
| DC1002pax | 1 | −1.2322 | −0.7593 | −0.3968 | −0.3968 | 0.5535 | 0.3907 |
| DC2005pax | 1 | −2.3922 | −1.8993 | −1.9468 | −0.6968 | −1.5515 | −0.4343 |
| DC2006pax | 1 | 0.1778 | 0.4107 | 0.1982 | −0.6518 | 1.0185 | 0.8557 |
| DC3003pax | 1 | −0.2272 | 0.9507 | 0.1682 | −0.4168 | 1.5985 | 1.8207 |
| DC5006Apax | 1 | −0.0922 | 0.2057 | 0.2232 | −0.3768 | −0.1115 | 0.2157 |
| DC5008Apax | 1 | −0.5972 | −0.1043 | −0.7018 | −0.5168 | 0.8335 | 1.1557 |
| DES1001pax | 1 | −1.8422 | −0.8843 | −1.1918 | −1.4518 | 0.8185 | −0.4143 |
| DES1002pax | 1 | −0.6822 | −0.8993 | −0.0418 | −0.5318 | 1.1235 | −0.7943 |
| JH0022pax | 1 | 0.0828 | 0.5507 | 0.4282 | 0.5332 | 0.5935 | 1.0307 |
| JH0076pax | 1 | −0.4872 | −0.7793 | −0.2418 | −1.6768 | −0.1715 | 0.1407 |
| JH0085pax | 1 | −1.0822 | −0.6293 | −0.4668 | −1.2268 | −0.0365 | −0.0193 |
| JH0089pax | 1 | −0.1597 | 1.0267 | −0.1642 | −0.5691 | 0.7915 | 1.1336 |
| JH0090pax | 1 | −0.7322 | −1.0293 | −0.4218 | −0.0518 | 0.0435 | 0.4657 |
| JH0091pax | 1 | 0.1353 | 0.2617 | 0.2708 | 1.2709 | 1.2965 | 1.1536 |
| JH0093pax | 1 | 0.2428 | 1.4557 | 0.4232 | −0.5368 | 1.5685 | 0.9107 |
| JH0096pax | 1 | −2.0347 | −0.6183 | −1.4842 | −0.6891 | −2.2235 | 0.8736 |
| JH0097pax | 1 | −0.4422 | −0.5293 | −0.0218 | −0.7968 | 0.4985 | −0.7193 |
| JH0100pax | 1 | 0.3803 | 1.2117 | 0.4858 | 0.6959 | 1.7015 | 1.0036 |
| JH0101pax | 1 | 0.8128 | 0.4507 | 0.6232 | 0.3482 | 1.6835 | 0.5857 |
| JH0105pax | 1 | 0.3878 | 1.1657 | 0.3682 | −0.5768 | 1.7485 | 2.0007 |
| JH0106pax | 1 | −0.6497 | −0.2083 | 0.0308 | −0.1191 | 0.8115 | 1.1536 |
| JH0108pax | 1 | −0.0772 | 0.6557 | 0.3282 | −0.0768 | 0.8485 | 1.1157 |
| JH0109pax | 1 | 0.9803 | 1.9517 | 0.7158 | 0.2559 | 1.7615 | 2.2986 |
| JH0110pax | 1 | −0.5072 | 0.2307 | −0.1668 | −0.6018 | −0.3515 | 0.7807 |
| JH0111pax | 1 | 0.7503 | 1.7717 | 0.4808 | 1.8809 | 2.4715 | 1.1486 |
| JH0113pax | 1 | −0.3047 | 0.5867 | 0.3308 | −0.8441 | 0.5715 | 0.1886 |
| JH0114pax | 1 | −2.0472 | −1.6493 | −1.3618 | −0.6518 | −1.7715 | −2.1743 |
| JH0116pax | 1 | −0.2772 | 1.1207 | 0.2182 | 0.6082 | 0.7885 | 0.7457 |
| JH0117pax | 1 | −1.6972 | −0.6243 | −1.0418 | −0.8018 | −0.1765 | 0.4257 |
| JH0118pax | 1 | 0.3503 | −0.0433 | 0.5258 | −0.0441 | 1.1065 | 0.4236 |
| JH0120pax | 1 | −0.3797 | 0.2467 | −0.0792 | −1.2341 | 1.4265 | 0.0686 |
| JH0123pax | 1 | −1.8597 | −0.9733 | −0.7492 | −0.5891 | −0.8185 | −1.2464 |

TABLE 12-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| JH0126pax | 1 | −1.7822 | −0.3243 | −0.7168 | −1.3618 | −0.6665 | 0.2307 |
| JH0127pax | 1 | −0.3897 | 1.0367 | 0.4308 | 0.7759 | 0.6415 | 0.6086 |
| JH0129pax | 1 | 0.3903 | 1.2817 | 0.6808 | 1.0259 | 2.6865 | 1.8886 |
| JH0130pax | 1 | −0.9022 | −0.3543 | −0.7818 | −0.9818 | −0.4465 | 0.2657 |
| JH0131pax | 1 | −0.4922 | −0.5243 | −0.5968 | −1.3968 | −0.8715 | 0.2057 |
| JH0132pax | 1 | −0.3897 | 0.1117 | −0.0742 | 0.3959 | 0.4615 | 0.1436 |
| JH0135pax | 1 | −1.3622 | −1.6143 | −1.2368 | −1.1018 | −1.2465 | −1.4743 |
| JH0136pax | 1 | −2.6172 | −1.9043 | −1.3118 | −1.4768 | −1.1965 | −2.0743 |
| JH0137pax | 1 | −0.1372 | 0.9407 | −0.3768 | −0.6168 | 0.7685 | 0.5507 |
| JH0138pax | 1 | −0.5622 | 0.1957 | 0.0532 | −0.3068 | 0.2285 | 0.2757 |
| JH0139pax | 1 | −0.7247 | −0.6583 | −0.5792 | −1.1191 | −0.4935 | −0.8464 |
| JH0142pax | 1 | −0.4547 | 0.7017 | 0.3608 | 0.4459 | 0.7815 | −0.1964 |
| JH0144pax | 1 | 0.3128 | 2.3157 | 0.8682 | −0.1368 | 2.0135 | 1.2707 |
| JH0147pax | 1 | 0.3778 | 1.4257 | 0.4532 | 0.5232 | 2.9535 | 0.7407 |
| JH0149pax | 1 | 0.5528 | 1.2407 | 0.3682 | 0.1432 | 2.5535 | 0.9357 |
| KW0002pax | 1 | −0.4072 | 0.4307 | −0.1868 | −0.4968 | 0.6785 | 1.3907 |
| KW0003pax | 1 | 0.0253 | 1.3217 | 0.7908 | −0.0691 | 0.1415 | 3.0886 |
| MH0053pax | 1 | 2.2253 | 2.3967 | 1.2558 | 0.6209 | 3.2815 | 2.1886 |
| MH0057pax | 1 | −0.6947 | −0.5333 | −0.4792 | −0.5041 | 0.5915 | −0.5264 |
| MH0059pax | 1 | −2.8497 | −2.1083 | −2.1892 | −1.5691 | −0.3235 | −1.1764 |
| MH0062pax | 1 | −0.9697 | −0.1633 | −0.0592 | −0.4891 | 0.5065 | 0.3186 |
| MH0065pax | 1 | −1.7097 | −1.6233 | −0.8042 | −0.9491 | −0.6235 | −1.1314 |
| MH0066pax | 1 | −1.4297 | −0.9733 | −1.0642 | −0.8041 | −0.5235 | −0.9314 |
| MH0068pax | 1 | 2.4828 | 2.4407 | 1.7882 | 1.6982 | 3.0035 | 1.0707 |
| MH0070pax | 1 | 0.1703 | 0.8467 | 0.5808 | 0.3859 | 1.4015 | 1.1036 |
| MH0073pax | 1 | −1.5622 | −0.8493 | −1.3868 | −1.4018 | −0.1715 | −0.7993 |
| MH0074pax | 1 | −1.0422 | −1.1393 | −0.6218 | −0.6218 | 0.7535 | −1.2193 |
| MH0076pax | 1 | 0.2653 | 1.8167 | 0.0658 | −0.4241 | 2.0165 | 2.0386 |
| MH0077pax | 1 | −0.2772 | 0.3357 | −0.2418 | −0.6218 | 0.2935 | 0.4157 |
| MH0078pax | 1 | −1.2497 | −0.0583 | −0.6992 | −1.7091 | −0.7685 | 1.0236 |
| MH0079pax | 1 | 0.6153 | 0.7767 | 0.5608 | −0.0241 | 0.6065 | 1.1786 |
| MH0080pax | 1 | −0.1597 | 0.2867 | 0.5258 | 0.3709 | 1.5765 | 0.6186 |
| MH0081pax | 1 | 0.1403 | 1.2367 | 0.1658 | −1.1941 | 1.7615 | 0.7686 |
| MH0082pax | 1 | 0.8203 | 1.4817 | 0.4558 | −0.1441 | 1.6365 | 0.7336 |
| MH0083pax | 1 | 1.5778 | 1.7007 | 0.9332 | 1.2532 | 2.2185 | 1.6807 |
| MH0087pax | 1 | −0.9922 | 0.9707 | −0.0668 | 0.5032 | 1.4985 | 0.6507 |
| MH0088pax | 1 | −0.2172 | 0.8457 | 0.3582 | −0.1868 | 0.8535 | 0.5157 |
| MH0089pax | 1 | −2.2197 | −1.5133 | −1.0292 | −1.5141 | −0.8685 | −0.3364 |
| MH0090pax | 1 | −0.9247 | 0.3217 | −0.2792 | −0.6841 | 0.0065 | −0.4964 |
| MH0095pax | 1 | −2.1147 | −1.5633 | −1.4142 | −1.8041 | −1.0985 | −0.9514 |
| MIP0002pax | 1 | −1.8047 | −0.3533 | −0.6842 | −0.1141 | −0.0685 | 0.4836 |
| MIP0003pax | 1 | 0.0778 | 0.1157 | −0.1818 | 0.0282 | 0.7585 | −0.1643 |
| MIP0005pax | 1 | −2.2797 | −1.3883 | −1.6292 | −1.1741 | −0.8035 | −1.7414 |
| MIP0008pax | 1 | 0.5053 | 0.8367 | 0.0008 | −0.2191 | 1.8415 | 0.7086 |
| MIP0009pax | 1 | −1.3122 | −1.1793 | −1.2268 | −1.4768 | −0.6215 | −1.0043 |
| MIP1007pax | 1 | −1.1547 | −0.4633 | −0.4792 | 0.1859 | 0.2515 | −1.4864 |
| MIP1009pax | 1 | −2.9997 | −1.6083 | −2.0442 | −1.4391 | −0.7485 | −1.1164 |
| MIP1011pax | 1 | −0.6497 | −0.7283 | −0.8992 | −1.0491 | 0.3015 | −0.8914 |
| MIP1013pax | 1 | −0.0222 | 0.8707 | 0.0282 | 0.0432 | 0.7335 | 1.4007 |
| MIP2002pax | 1 | 0.8603 | 1.4317 | 0.7358 | 0.4159 | 1.6165 | 1.3386 |
| MIP2003pax | 1 | −0.2947 | 0.3567 | 0.2508 | 0.6959 | 1.8515 | 0.8486 |
| MIP2006pax | 1 | −0.3622 | 0.7457 | 0.0432 | 0.5432 | 0.8035 | 0.3157 |
| MIP3003pax | 1 | −2.5772 | −1.5843 | −2.1418 | −1.4368 | −1.7415 | −1.3193 |
| MIP3004pax | 1 | −0.9222 | −0.5393 | −0.4618 | −0.3918 | 0.6435 | −0.6943 |
| NK1001pax | 1 | 0.4828 | 1.0657 | 0.0782 | 0.1832 | 1.9635 | 0.9307 |
| NK1003pax | 1 | −0.9747 | 0.1017 | −0.1192 | −0.3691 | 0.4365 | 0.4536 |
| NK1004pax | 1 | −0.7947 | −0.5133 | −0.4642 | −0.8441 | 0.6715 | 0.0186 |
| NK1005pax | 1 | −0.1597 | 1.5217 | 0.4809 | 0.4809 | 2.0815 | 0.9936 |
| NK1008pax | 1 | −1.6222 | 0.1407 | −0.5918 | −0.2818 | −0.0215 | 0.2257 |
| NK1009pax | 1 | 1.6828 | 1.5207 | 0.7182 | 0.4582 | 2.3135 | 1.0907 |
| NK2005pax | 1 | −1.5347 | −0.9483 | −0.6192 | −0.8041 | −1.9435 | −0.0114 |
| NK2006pax | 1 | −1.9272 | −1.2543 | −1.7168 | −1.1568 | −0.7815 | −1.6093 |
| NK2007pax | 1 | 0.1978 | 0.4957 | 0.1282 | 0.6782 | 1.0285 | −0.0693 |
| NK2008pax | 1 | −1.9022 | −1.2193 | −1.0068 | −1.3468 | −0.0615 | −1.4393 |
| NK2009pax | 1 | −0.4097 | 0.3167 | 0.0658 | −0.7691 | 1.5165 | −0.0614 |
| NK2010pax | 1 | −1.1147 | −0.5983 | −0.4692 | −0.8091 | −0.3935 | −0.7364 |
| NK2014pax | 1 | 0.6753 | 1.6317 | 1.0258 | 1.0759 | 2.0515 | 1.1686 |
| NK2015pax | 1 | −0.6222 | 0.6307 | 0.0482 | −0.4318 | 1.6935 | 1.3107 |
| NK2016pax | 1 | −0.4297 | 0.2167 | −0.2092 | 0.0659 | 1.6815 | 0.4936 |
| NK2018pax | 1 | −1.9522 | −1.1093 | −0.8468 | −0.9018 | −0.2715 | −0.9843 |
| NK5008pax | 1 | −1.4522 | −1.6693 | −1.3418 | −1.5618 | 0.4085 | −1.2843 |

TABLE 12-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| OL0003pax | 1 | −1.2897 | −0.5083 | −0.9542 | −0.7241 | −0.1385 | −0.3214 |
| OL0014pax | 1 | −2.3397 | −2.4483 | −1.7342 | −1.7191 | −1.8585 | −1.0564 |
| OL0017pax | 1 | −1.0297 | −1.0083 | −0.6692 | −0.5541 | 0.6465 | 0.3036 |
| OL0026pax | 1 | −2.2947 | −1.4533 | −2.0092 | −1.8291 | −0.6635 | −0.4364 |
| OL0034pax | 1 | −1.3647 | −0.8333 | −1.2992 | −1.7341 | 0.1615 | 0.0536 |
| OL0041pax | 1 | −2.2297 | −1.6183 | −2.1492 | −2.8641 | −1.4835 | −2.1464 |
| OL0043pax | 1 | −0.8772 | −0.6193 | −0.7268 | −1.2568 | 0.0285 | −0.5693 |
| OL0052pax | 1 | −1.3047 | −1.2733 | −0.4242 | −0.5541 | −0.2135 | −0.5464 |
| OL0056pax | 1 | −0.2972 | −0.9943 | −0.0518 | −0.6268 | 1.5235 | 0.6557 |
| OL0057pax | 1 | −0.8447 | −0.4883 | −0.7942 | −0.8191 | −0.1335 | −0.1664 |
| OL0058pax | 1 | −1.1572 | −1.2643 | −1.1518 | −0.9918 | −0.1265 | −1.8993 |
| OL0059pax | 1 | −1.1947 | −0.0983 | −0.5492 | 0.0109 | 0.0115 | 0.0936 |
| OL0060pax | 1 | −1.8622 | −1.6843 | −1.4368 | −2.0668 | −1.6665 | −1.0693 |
| OL0062pax | 1 | 0.3003 | 0.2817 | 0.3108 | 0.0709 | 1.7915 | 1.3986 |
| OL0063pax | 1 | −1.3172 | −0.8843 | −0.8068 | −0.5168 | −0.3665 | −0.7093 |
| OL0064pax | 1 | 0.3203 | 0.9317 | 0.7908 | 0.6409 | 1.8015 | 0.7186 |
| OL0065pax | 1 | 0.4578 | 0.7257 | 0.6832 | 0.6982 | 1.8085 | 0.6357 |
| OL0066pax | 1 | −0.2722 | 0.5757 | −0.0618 | 0.4232 | 0.6785 | 1.0357 |
| OL0068pax | 1 | −1.9622 | −0.7143 | −1.3218 | −1.1918 | −0.5765 | −1.0593 |
| OL0070pax | 1 | −1.3622 | −0.6193 | −1.2868 | −2.0718 | −0.3665 | −1.5243 |
| OL0071pax | 1 | −0.6897 | 0.1217 | −0.3542 | 0.1559 | 0.7515 | 0.8136 |
| OL0072pax | 1 | −1.1047 | −0.4033 | −0.4392 | −1.1791 | 0.2315 | −0.9964 |
| OL0073pax | 1 | −2.6897 | −1.9933 | −1.1642 | −1.1641 | 0.3565 | −0.5114 |
| OL0074pax | 1 | −1.4447 | −0.7883 | −0.9142 | −0.6891 | 1.0865 | −0.1364 |
| OL0075pax | 1 | −0.8322 | −0.0343 | −0.3218 | 0.3782 | 0.8585 | 0.5457 |
| OL0077pax | 1 | −1.0747 | −0.5933 | 0.1708 | 0.3059 | 0.2265 | 0.2036 |
| OL0078pax | 1 | −2.2597 | −1.8983 | −1.1942 | −1.1441 | −0.8135 | −0.9764 |
| OL0079pax | 1 | −1.1797 | −0.7633 | −0.9442 | −1.2641 | −0.8335 | −0.0214 |
| OL0080pax | 1 | −0.0772 | 0.4507 | 0.2882 | 0.3882 | 0.3985 | 0.5357 |
| PB3545pax | 1 | −0.3222 | 1.4657 | 0.0382 | 0.4682 | 1.1435 | 0.6807 |
| PB3890pax | 1 | −0.4397 | −0.2383 | 0.4108 | 0.7759 | 0.1265 | 0.1686 |

The test set results confirmed the surprising finding based on the training set that ANXA3, CLEC4D, LMNB1, PRRG4, TNFAIP6 and VNN1 each express RNA on average at a significantly higher level (p-value less than 0.05) in blood of subjects having colorectal cancer relative to subjects having no colorectal pathology (Table 13). The ranges of fold-change in the levels of RNA encoded by ANXA3, CLEC4D, LMNB1, PRRG4, TNFAIP6 and VNN1 normalized to levels of RNA encoded by IL2RB in blood of the test set subjects having colorectal cancer relative to the test set subjects not having any colorectal pathology are also shown in Table 13.

TABLE 13

Sample test set ranges of fold-changes in levels of RNA encoded by ANXA3, CLEC4D, LMNB1, PRRG4, TNFAIP6 and VNN1 normalized to levels of RNA encoded by IL2RB in blood of subjects having colorectal cancer relative to subjects not having any colorectal pathology.

| | Gene | | | | | |
|---|---|---|---|---|---|---|
| | ANXA3 | CLEC4D | LMNB1 | PRRG4 | TNFAIP6 | VNN1 |
| Average normalized RNA level in subjects having colorectal cancer (ΔCt) | −0.63 | 0.01 | −0.27 | −0.38 | 0.56 | 0.28 |
| Average normalized RNA level in subjects not having any colorectal pathology (ΔCt) | 0.45 | 0.85 | 0.45 | 0.59 | 1.47 | 1.04 |
| Average RNA level fold-change | 2.11 | 1.80 | 1.65 | 1.95 | 1.88 | 1.69 |
| p-value for average RNA level fold-change | 1.2E−17 | 7.3E−12 | 1.5E−15 | 2.5E−19 | 5.4E−12 | 2.6E−10 |
| Maximum observed RNA level directional fold-change | 20.61 | 9.85 | 10.64 | 13.07 | 16.37 | 11.93 |

As can be seen in Table 13, a test subject having a blood level of RNA encoded by ANXA3, normalized to a level of RNA encoded by IL2RB, which is 2.1 to 20.6 fold higher than the average level of RNA encoded by this gene in blood of subjects not having any colorectal pathology is more likely to have colorectal cancer than to not have any colorectal pathology.

As can be seen in Table 13, a test subject having a blood level of RNA encoded by CLEC4D, normalized to a level of RNA encoded by IL2RB, which is 1.8 to 9.85 fold higher than the average level of RNA encoded by this gene in blood of subjects not having any colorectal pathology is more likely to have colorectal cancer than to not have any colorectal pathology.

As can be seen in Table 13, a test subject having a blood level of RNA encoded by LMNB1, normalized to a level of RNA encoded by IL2RB, which is 1.65 to 10.6 fold higher than the average level of RNA encoded by this gene in blood of subjects not having any colorectal pathology is more likely to have colorectal cancer than to not have any colorectal pathology.

As can be seen in Table 13, a test subject having a blood level of RNA encoded by PRRG4, normalized to a level of RNA encoded by IL2RB, which is 1.95 to 13.1 fold higher than the average level of RNA encoded by this gene in blood of subjects not having any colorectal pathology is more likely to have colorectal cancer than to not have any colorectal pathology.

As can be seen in Table 13, a test subject having a blood level of RNA encoded by TNFAIP6, normalized to a level of RNA encoded by IL2RB, which is 1.9 to 16.4 fold higher than the average level of RNA encoded by this gene in blood of subjects not having any colorectal pathology is more likely to have colorectal cancer than to not have any colorectal pathology.

As can be seen in Table 13, a test subject having a blood level of RNA encoded by VNN1, normalized to a level of RNA encoded by IL2RB, which is 1.7 to 11.9 fold higher than the average level of RNA encoded by this gene in blood of subjects not having any colorectal pathology is more likely to have colorectal cancer than to not have any colorectal pathology.

Furthermore, the test set results confirmed the surprising finding based on the training set that logistic regression models based on blood expression levels for any of the 63 possible combinations of one or more of ANXA3, CLEC4D, LMNB1, PRRG4, TNFAIP6 and VNN1, each of which normalized against expression levels of IL2RB, can be used to discriminate, with a ROC AUC of at least 0.66 (Table 11), between subjects having colorectal cancer and subjects not having any colorectal pathology. As such, the novel logistic regression models listed in Table 11 can be used to determine the probability that a test subject has colorectal cancer as opposed to not having any colorectal pathology, based on blood levels of expression of ANXA3, CLEC4D, LMNB1, PRRG4, TNFAIP6 and/or VNN1 normalized to those of IL2RB.

Example 4

Determination of the Probability that a Test Subject has Colorectal Cancer as Opposed to not Having Colorectal Cancer Using Blood Levels of RNA Encoded by the Colorectal Cancer Markers: ANXA3, CLEC4D, IL2RB, LMNB1, PRRG4, TNFAIP6 and VNN1 Normalized to Those of ACTB A blood sample from a test subject is analyzed for levels of RNA encoded by ACTB, ANXA3, CLEC4D, IL2RB, LMNB1, PRRG4, TNFAIP6 and VNN1, as described in Example 1, above, thereby generating test data. Logistic regression model #1 of Table 6 is applied to the test data, thereby providing the probability that the test subject has colorectal cancer as opposed to not having any colorectal pathology.

Example 5

Determination of the Probability that a Test Subject has Colorectal Cancer as Opposed to not Having Colorectal Cancer Using Blood Levels of RNA Encoded by the Colorectal Cancer Markers: ANXA3, CLEC4D, IL2RB, LMNB1, PRRG4, TNFAIP6 and VNN1 Normalized to Those of IL2RB A blood sample from a test subject is analyzed for levels of RNA encoded by ANXA3, CLEC4D, IL2RB, LMNB1, PRRG4, TNFAIP6 and VNN1 as described in Example 1, above, thereby generating test data. Logistic regression model #64 of Table 11 is applied to the test data, thereby providing the probability that the test subject has colorectal cancer as opposed to not having any colorectal pathology.

Example 6

Measurement of Blood Levels of RNA Encoded by a Combination of ANXA3, CLEC4D, LMNB1, PRRG4, TNFAIP6 and VNN1 Relative to the Level of RNA Encoded by IL2RB can be Used to Determine the Probability that a Test Subject has Colorectal Cancer as Opposed to not Having any Colorectal Pathology Materials and Methods:
Refer to "General materials and methods", above.
Experimental Results:
Sample Training Set:

Discovery of Significantly Different Levels of RNA Encoded by ANXA3, CLEC4D, LMNB1, PRRG4, VNN1, TNFAIP6 Normalized to IL2RB in Blood of Subjects Having Colorectal Cancer Relative to Subjects not Having any Colorectal Pathology Quantitative reverse transcriptase-PCR analysis of gene expression in a training set of blood samples from 112 subjects having colorectal cancer and 120 subjects not having any colorectal pathology (subset of samples listed in Table 9 of Example 3, above), using IL2RB as duplex partner for normalization of gene expression levels was performed. The normalized RNA levels measured are shown in Table 14.

TABLE 14

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| CD0011pax | 0 | 1.0600 | 1.5250 | 1.3250 | 1.1000 | 2.3500 | 2.7750 |
| CD0012pax | 0 | 1.3600 | 1.6300 | 0.8600 | 0.8500 | 1.8350 | 2.7300 |
| CD0030pax | 0 | 1.4100 | 1.4500 | 0.9800 | 1.2850 | 1.0250 | 1.9600 |
| CD0063pax | 0 | 2.5700 | 3.3050 | 1.7550 | 1.9950 | 3.6000 | 3.2500 |
| CD0077pax | 0 | −0.2350 | 0.7700 | 0.1500 | 0.3000 | 0.3900 | 1.1650 |
| CD0078pax | 0 | 1.5150 | 2.2800 | 0.7550 | 0.6750 | 2.6250 | 1.3750 |
| CD0085pax | 0 | 0.5750 | 1.6050 | 0.6450 | 0.9450 | 2.5450 | 0.7200 |
| CD0117pax | 0 | 0.9750 | 2.3900 | 0.9250 | 2.0600 | 2.4600 | 0.9400 |
| CD0167pax | 0 | −0.9750 | 0.2000 | 0.4600 | 0.6600 | 1.6250 | 0.5800 |
| CD0249pax | 0 | −0.5100 | −0.2750 | −0.5200 | 0.3200 | 0.2750 | 0.6400 |
| CD0286pax | 0 | −0.2850 | 1.0900 | 0.2500 | 0.2050 | 0.3550 | 0.3300 |
| CD0297pax | 0 | 0.0300 | 0.4850 | 0.4700 | −0.0300 | 0.3900 | 1.0050 |
| CD0323pax | 0 | 1.9000 | 1.9500 | 0.8350 | 1.4850 | 2.6400 | 3.4450 |
| CD0445pax | 0 | 0.6600 | 0.8250 | 0.3000 | 0.3750 | 1.4100 | 1.4350 |
| CD0463pax | 0 | −0.0850 | 1.7650 | 0.6000 | 0.8550 | 1.3700 | 1.5650 |
| CD0491pax | 0 | −0.5550 | 0.0650 | 0.1100 | 0.5450 | 0.9000 | 0.2150 |
| CD0496pax | 0 | 1.2050 | 2.8450 | 1.2400 | 1.9200 | 1.4650 | 1.3450 |
| CD0501pax | 0 | 1.1050 | 1.9100 | 1.1100 | 1.0600 | 2.8650 | 1.4900 |
| CD0504pax | 0 | −0.7750 | −0.2850 | −0.1500 | 0.6100 | −0.1950 | 0.3350 |
| CD0573pax | 0 | 1.8100 | 1.2350 | 0.7700 | 0.8300 | 2.2650 | 1.8500 |
| CD0578pax | 0 | 1.8200 | 1.9800 | 0.9550 | 1.0450 | 2.0700 | 2.2950 |
| CD0639pax | 0 | 0.2950 | 0.7900 | 0.7450 | −0.2600 | 1.2000 | 1.7900 |
| CD0645pax | 0 | −1.0950 | −0.6000 | −0.7700 | −0.6250 | −0.0200 | −0.1800 |
| CD0679pax | 0 | 0.2300 | 1.5950 | 0.5200 | 0.3350 | 1.8800 | 1.8750 |
| CD0685pax | 0 | 0.5250 | 1.7300 | 0.4350 | 0.9850 | 1.6850 | 1.0550 |
| CD0716pax | 0 | 1.9900 | 2.4700 | 0.8200 | 0.5250 | 1.4050 | 2.1600 |
| CD0749pax | 0 | 0.1600 | 1.0600 | 0.1200 | 0.3600 | 1.6800 | 0.8350 |
| CD0760pax | 0 | −2.3750 | −1.0500 | −1.7400 | −0.9100 | −0.8100 | −0.6700 |
| CD0811pax | 0 | 1.9250 | 2.3300 | 0.7400 | 0.8900 | 0.9700 | 1.0100 |
| CD0848pax | 0 | 1.0900 | 1.6300 | 1.4050 | 1.3850 | 1.9400 | 2.4750 |
| CD0924pax | 0 | 0.3450 | 0.7500 | 0.2250 | −0.1100 | 0.5050 | 0.3050 |
| CD1066pax | 0 | −0.2050 | 0.0950 | −0.1200 | −0.1750 | 1.3650 | 0.1800 |
| CD1073pax | 0 | 0.3050 | 0.1350 | 0.3150 | 0.9350 | 1.0850 | 0.3400 |
| CD1075pax | 0 | 0.0300 | 0.9000 | 0.4100 | 1.5200 | 1.6000 | 0.8400 |
| CD1089pax | 0 | −1.3250 | −0.2000 | −1.1200 | −0.8700 | −0.1650 | −0.2550 |
| CD1116pax | 0 | −0.3850 | −0.3700 | −0.4500 | 0.0001 | 1.0600 | 0.1750 |
| CD1120pax | 0 | −1.1350 | −0.0400 | −0.7450 | 0.0150 | 1.0100 | −0.5700 |
| CD1198pax | 0 | 0.2950 | 0.4300 | 0.6350 | 0.5200 | 0.7850 | 0.6000 |
| PB1179pax | 0 | 1.2100 | 1.2700 | 1.1550 | 1.2700 | 2.6850 | 1.7300 |
| PB1277pax | 0 | 0.6600 | 1.3300 | 0.2500 | 0.6650 | 1.6000 | 0.5900 |
| PB1301pax | 0 | −2.1150 | −1.4000 | −1.3850 | −1.1000 | −1.2350 | −1.7950 |
| PB1315pax | 0 | −1.3350 | 0.4800 | −0.3200 | −0.1800 | 0.0600 | 1.0750 |
| PB1345pax | 0 | 0.0150 | 0.5500 | 0.5950 | 0.8350 | 0.3650 | 1.9650 |
| PB1520pax | 0 | 0.9250 | 2.0050 | 0.7850 | −0.1800 | 1.4100 | 1.8550 |
| PB1574pax | 0 | 1.2150 | 2.0550 | 1.2150 | 0.9500 | 1.3300 | 1.7150 |
| PB1783pax | 0 | 1.7400 | 1.8450 | 1.3600 | 1.3450 | 2.3150 | 1.8150 |
| PB1799pax | 0 | 0.7800 | 1.1900 | 0.6900 | 1.1150 | 2.3400 | 0.9800 |
| PB1811pax | 0 | 1.0950 | 1.6200 | 1.1050 | 1.4050 | 1.5800 | 1.2650 |
| PB1830pax | 0 | 0.3450 | 0.8850 | 0.5650 | 0.2700 | 1.3300 | 2.4950 |
| PB1833pax | 0 | −0.0150 | 0.7050 | 0.0700 | 0.3150 | 0.5200 | 1.2600 |
| PB1843pax | 0 | 0.8750 | 0.9400 | 0.4750 | 0.8500 | −0.3150 | 1.6500 |
| PB1851pax | 0 | 0.2450 | −0.0450 | 0.1250 | 0.1650 | 2.6550 | 1.3150 |
| PB1919pax | 0 | 1.3100 | 1.8550 | 0.6050 | 1.5350 | 2.0800 | 2.2100 |
| PB1922pax | 0 | −0.1700 | 0.8350 | −0.0700 | 0.8450 | 1.6350 | 0.5700 |
| PB1924pax | 0 | 0.0950 | 0.5700 | −0.0750 | 0.2150 | 1.0050 | 1.3000 |
| PB1937pax | 0 | 1.5250 | 2.5500 | 1.3500 | 3.0050 | 2.7050 | 2.3350 |
| PB1964pax | 0 | 0.6950 | 2.7450 | 1.0200 | 1.6750 | 2.6250 | 3.0550 |
| PB2027pax | 0 | 0.0900 | 0.5100 | 0.3500 | 1.3200 | 1.5250 | 0.7550 |
| PB2029pax | 0 | 0.5250 | 1.0200 | 0.6150 | 0.4300 | 2.2750 | 1.4350 |
| PB2073pax | 0 | 0.6000 | 1.0100 | 0.9000 | 1.8550 | 1.7200 | 1.2800 |
| PB2099pax | 0 | −0.1500 | −0.0950 | 0.1350 | 0.3250 | 0.0950 | 0.6700 |
| PB2100pax | 0 | 1.2350 | 1.3800 | 0.8950 | 1.5600 | 2.3100 | 1.4450 |
| PB2132pax | 0 | 0.5100 | 1.2400 | 0.1700 | 0.5100 | 1.9950 | 1.4750 |
| PB2168pax | 0 | 1.1400 | 1.4600 | 0.6600 | 1.0000 | 2.1650 | 1.2450 |
| PB2192pax | 0 | −0.0050 | 0.4950 | −0.1450 | −0.4800 | 0.8350 | 1.5800 |
| PB2196pax | 0 | 0.8850 | 1.7250 | 0.9850 | 1.9050 | 2.2550 | 1.1350 |
| PB2200pax | 0 | 0.8550 | 1.3850 | 0.2350 | 0.3050 | 0.9050 | 0.4400 |
| PB2213pax | 0 | 1.8550 | 2.0000 | 0.9300 | 0.5300 | 2.9900 | 1.5850 |
| PB2224pax | 0 | −0.3850 | 0.4250 | −0.1400 | 0.1000 | 1.8950 | 0.9750 |
| PB2228pax | 0 | 2.0300 | 2.2200 | 1.8000 | 2.0050 | 4.0300 | 3.0800 |
| PB2229pax | 0 | 0.0050 | −0.0800 | 0.2000 | −0.6150 | 0.9150 | 0.2550 |

TABLE 14-continued

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| PB2277pax | 0 | 1.3400 | 1.0050 | 0.7550 | 0.3700 | 1.3100 | 1.7800 |
| PB2297pax | 0 | 0.2900 | 0.8050 | −0.0900 | −0.0850 | 0.5250 | −0.2800 |
| PB2312pax | 0 | 1.5250 | 2.1700 | 1.6550 | 1.2050 | 2.2900 | 2.1700 |
| PB2398pax | 0 | −0.3800 | 0.2250 | 0.0150 | −0.4700 | 0.1050 | 1.4250 |
| PB2409pax | 0 | 0.3950 | 1.0600 | 0.4950 | 0.5050 | 1.1550 | 1.7350 |
| PB2414pax | 0 | 3.0050 | 2.6050 | 1.4550 | 2.3150 | 3.9600 | 2.1150 |
| PB2467pax | 0 | 0.4800 | 1.0800 | 0.3500 | 0.3600 | 2.1300 | 1.0850 |
| PB2473pax | 0 | 0.2350 | 0.8600 | 0.2850 | 0.8850 | 1.0100 | 1.5950 |
| PB2512pax | 0 | 0.8200 | 1.8950 | 1.1800 | 0.8200 | 2.0650 | 2.3750 |
| PB2568pax | 0 | −0.2950 | 0.1900 | −0.0900 | 0.5850 | 1.4750 | 1.1700 |
| PB2571pax | 0 | 0.5800 | 1.2800 | 0.7500 | 0.4300 | 2.0650 | 2.1050 |
| PB2824pax | 0 | 0.8400 | 1.3650 | 0.8000 | 1.3950 | 2.0150 | 1.7750 |
| PB2880pax | 0 | 1.2500 | 1.4400 | 0.8850 | −0.0600 | 2.2550 | 1.8100 |
| PB3088pax | 0 | 1.3800 | 1.2900 | 0.8550 | 0.6050 | 2.9200 | 2.0800 |
| RC0882pax | 0 | −0.0150 | 1.2350 | 0.2800 | 0.3700 | 1.7700 | 1.6550 |
| RC0888pax | 0 | −1.0450 | −0.4250 | −0.3400 | 0.0550 | 0.4950 | 0.1900 |
| RC0968pax | 0 | −0.6900 | −0.4750 | 0.2700 | 1.5500 | 1.0250 | 2.3500 |
| RC2114pax | 0 | −0.2000 | 0.9600 | 0.3300 | 0.6550 | 0.4550 | 2.0900 |
| RC2238pax | 0 | 1.3450 | 2.0600 | 0.8800 | 1.8300 | 2.7050 | 3.1100 |
| RC2681pax | 0 | 0.1100 | 0.6300 | 0.2200 | 0.2550 | 0.2550 | 0.6550 |
| RC2703pax | 0 | 1.8000 | 2.1000 | 1.0500 | 1.5250 | 1.4250 | 1.5350 |
| RC2749pax | 0 | 0.0900 | 0.7750 | −0.0850 | 0.0500 | 1.2550 | 1.2500 |
| RC2750pax | 0 | −1.5150 | −1.0750 | −0.9000 | −0.2200 | 0.0700 | −0.5400 |
| RC2756pax | 0 | 1.6800 | 1.3850 | 1.0550 | 1.4600 | 1.9450 | 2.5150 |
| RC2771pax | 0 | −0.8450 | 0.4950 | −0.6450 | −0.4150 | 1.1200 | 1.2750 |
| RC2790pax | 0 | 1.0850 | 1.1500 | 0.6150 | 0.8950 | 1.3350 | 1.5650 |
| RC2792pax | 0 | 1.0100 | 0.6250 | 0.6300 | 1.0950 | 1.9150 | 1.3550 |
| RC2808pax | 0 | 0.4850 | 1.4600 | 0.2700 | 0.5100 | 0.6550 | 1.0150 |
| RC2822pax | 0 | 0.4750 | 0.8350 | −0.0900 | 0.3350 | 2.2400 | 0.4750 |
| RC2834pax | 0 | −0.7350 | 0.2100 | −0.6700 | 1.5700 | 2.1300 | −0.3050 |
| RC2871pax | 0 | 0.6150 | 1.1650 | 0.9250 | 1.3150 | 2.4200 | 2.2250 |
| RC2879pax | 0 | −0.4050 | 0.2050 | −0.2400 | 0.5300 | 0.5250 | 0.0900 |
| RC2892pax | 0 | −0.1500 | 0.1200 | −0.4050 | 0.2750 | 1.6700 | 0.9100 |
| RC2895pax | 0 | 1.8700 | 2.2100 | 1.3750 | 1.6500 | 1.5650 | 2.2500 |
| RC2921pax | 0 | 1.2850 | 1.4150 | 0.9900 | 1.4400 | 1.9950 | 2.0900 |
| RC2958pax | 0 | 0.9250 | 1.0000 | 0.2300 | 0.0001 | 0.2700 | 1.2250 |
| RC3022pax | 0 | 0.1450 | −0.0150 | 0.1200 | 0.7850 | 1.3950 | 0.2450 |
| RC3112pax | 0 | 1.0250 | 1.2350 | 0.3150 | 0.2650 | 2.3150 | 0.8700 |
| RC3146pax | 0 | −0.3350 | −0.3450 | −0.6200 | 0.8250 | 0.9650 | −0.3750 |
| RC3184pax | 0 | 2.4850 | 2.8750 | 1.3900 | 1.6250 | 2.5600 | 2.3950 |
| RC3232pax | 0 | −0.2550 | 0.7850 | −0.2900 | 0.6900 | −0.1250 | 2.6700 |
| RC3324pax | 0 | 0.3650 | 1.0800 | 0.1200 | 0.6100 | 1.5200 | 0.1250 |
| RC3327pax | 0 | 0.3600 | 0.0950 | 0.2250 | −0.0500 | 1.4550 | 1.9700 |
| RC3355pax | 0 | −0.1850 | 0.4200 | −0.4950 | −0.3100 | 1.2150 | 0.3400 |
| RC3380pax | 0 | −0.6450 | 0.3950 | −0.5700 | −0.0300 | 0.4950 | −0.2300 |
| RC3413pax | 0 | 0.2750 | 0.8950 | 0.1250 | −0.3400 | 0.5050 | 2.3050 |
| RC3421pax | 0 | 0.3550 | 0.4600 | 0.3900 | 0.4400 | 0.1300 | 0.2750 |
| RC3468pax | 0 | −0.3600 | −0.2800 | −0.4100 | −0.5750 | 0.9000 | 0.0350 |
| RC3498pax | 0 | −0.3150 | −0.7750 | −0.7050 | −0.2900 | 0.7750 | −0.1800 |
| CC0003pax | 1 | −1.2200 | −0.2350 | −0.8100 | −0.6450 | 1.0450 | −0.6850 |
| CD0157pax | 1 | 1.2350 | 1.0300 | 0.7450 | 0.9100 | 2.5050 | 2.3600 |
| CD0164pax | 1 | 0.3150 | 0.8550 | 1.0100 | 1.2550 | 2.7950 | 1.8100 |
| CD0256pax | 1 | −0.4000 | 0.2050 | 0.1950 | 1.0400 | 1.2350 | 0.3300 |
| CD0322pax | 1 | −0.9950 | −0.2450 | −0.7150 | −0.1400 | 0.6750 | 1.2850 |
| CD0356pax | 1 | −0.4950 | −0.8850 | −0.4500 | −0.5650 | −0.1000 | −0.8600 |
| CD0371pax | 1 | 0.2350 | 1.0650 | 0.0500 | −0.1800 | 0.9500 | −0.0100 |
| CD0629pax | 1 | 0.1350 | 0.9850 | 0.7900 | 1.4800 | 0.5100 | 1.3850 |
| CD1050pax | 1 | 1.1750 | 0.3600 | 0.6850 | 1.0250 | 1.7150 | 1.3150 |
| DS0003pax | 1 | −1.6350 | −0.5200 | −1.1950 | −0.4900 | −0.0650 | −0.0600 |
| FC0005pax | 1 | −0.1950 | −0.0950 | 0.0900 | −0.0450 | 0.1950 | 1.4100 |
| FC0011pax | 1 | −0.0650 | 0.1250 | 0.1700 | 0.0800 | 1.1250 | 0.4950 |
| FC0012pax | 1 | −2.2350 | −0.1250 | −1.0650 | −0.9850 | −0.0150 | −0.2000 |
| JGA0001pax | 1 | −2.4550 | −1.7500 | −1.8250 | −0.8650 | −1.4800 | −1.4400 |
| JH0002pax | 1 | 0.3150 | 0.7350 | 0.2850 | 0.1350 | 1.1700 | 0.3000 |
| JH0003pax | 1 | 0.0550 | 0.0650 | −0.3850 | −0.6250 | −0.1450 | 0.7100 |
| JH0004pax | 1 | −0.0550 | −0.0050 | −0.0250 | −0.2100 | 1.4050 | 1.0300 |
| JH0005pax | 1 | 0.2950 | 1.3450 | 0.3700 | 0.4300 | 1.8650 | 1.2700 |
| JH0006pax | 1 | −0.4300 | 0.4450 | −0.0050 | −0.0850 | 1.2650 | −0.0600 |
| JH0007pax | 1 | −2.4350 | −1.9900 | −1.3150 | −0.1700 | 0.1250 | −0.9150 |
| JH0008pax | 1 | 0.9050 | 2.5850 | 0.6250 | 1.1850 | 2.3350 | 1.0050 |
| JH0009pax | 1 | −1.0700 | −1.3450 | −0.3350 | −0.9650 | −0.6700 | 0.1550 |

TABLE 14-continued

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| JH0010pax | 1 | −0.7650 | 0.0800 | −0.1650 | −0.0750 | 0.0300 | −0.6650 |
| JH0012pax | 1 | −0.2150 | 0.1900 | 0.1000 | −0.2150 | 0.4400 | 0.6950 |
| JH0013pax | 1 | −0.1200 | 0.3750 | −0.0300 | 0.1150 | 2.2800 | 0.9200 |
| JH0014pax | 1 | 1.0050 | 0.8950 | 0.1500 | −0.3400 | 1.6200 | 2.2850 |
| JH0016pax | 1 | 0.7850 | 1.1950 | 0.8600 | 0.4350 | 0.6450 | 1.0350 |
| JH0018pax | 1 | −0.9850 | −0.0250 | −0.1450 | −0.2900 | 0.0750 | 0.6250 |
| JH0019pax | 1 | 0.2350 | 0.8450 | 0.3600 | −0.0500 | 0.4700 | 0.4850 |
| JH0020pax | 1 | 0.0150 | 1.7550 | 0.3850 | −0.3900 | 0.5100 | 1.0550 |
| JH0021pax | 1 | −1.1000 | 0.3250 | −0.8650 | −1.3850 | −0.2350 | −0.2400 |
| JH0023pax | 1 | −0.4850 | 1.2250 | 0.3900 | 1.4500 | 1.0100 | 1.8450 |
| JH0024pax | 1 | 0.8350 | 2.0750 | 0.6950 | 1.0150 | 2.8900 | 2.4000 |
| JH0025pax | 1 | −0.9850 | −0.5650 | −0.6350 | −1.2100 | −0.3500 | 0.0950 |
| JH0026pax | 1 | −1.1000 | 0.7000 | 0.1500 | 0.1150 | 1.3050 | 1.0750 |
| JH0027pax | 1 | −3.1650 | −2.4400 | −2.2300 | −1.9300 | −2.2400 | −1.4900 |
| JH0028pax | 1 | 0.5350 | 1.3350 | 1.2450 | 1.0550 | 2.8950 | 1.8900 |
| JH0029pax | 1 | −1.5700 | −0.9750 | −0.9300 | −1.1200 | −0.9200 | 0.4200 |
| JH0031pax | 1 | −1.0400 | −0.1700 | −0.6950 | −0.7700 | 0.0450 | 0.1250 |
| JH0032pax | 1 | 1.3700 | 1.6300 | 0.2650 | 0.1150 | 1.7300 | 1.7250 |
| JH0033pax | 1 | −1.1900 | 0.5700 | −0.8700 | −1.0850 | 0.9700 | −0.5100 |
| JH0034pax | 1 | −0.7000 | 0.8150 | 0.2850 | 0.1300 | 1.4900 | 1.2200 |
| JH0035pax | 1 | 0.0500 | 1.5700 | 0.4400 | −0.2850 | 2.1400 | 1.1050 |
| JH0036pax | 1 | 0.5650 | 0.9350 | 0.2450 | 0.0300 | 1.7450 | 0.8500 |
| JH0038pax | 1 | −0.0100 | 1.2650 | −0.0100 | 0.0400 | 1.9650 | 0.4500 |
| JH0039pax | 1 | 0.2600 | 0.5550 | 0.3050 | 0.8450 | 3.0050 | −0.1900 |
| JH0040pax | 1 | 0.3950 | 0.9000 | 0.3650 | 0.2250 | 1.1100 | 0.8850 |
| JH0041pax | 1 | 0.3800 | 1.2000 | −0.0650 | −0.3050 | 1.4900 | 0.6150 |
| JH0042pax | 1 | −2.4200 | −0.9750 | −1.4450 | −0.8750 | −1.4500 | −1.6900 |
| JH0043pax | 1 | −0.4900 | 0.3050 | 0.0001 | −0.6800 | −0.0800 | 0.3250 |
| JH0046pax | 1 | 0.2350 | 0.5950 | 0.9350 | 0.0450 | 1.0300 | 0.5850 |
| JH0047pax | 1 | 0.3250 | 2.0950 | 1.0700 | 1.4700 | 1.8200 | 2.4300 |
| JH0051pax | 1 | −0.6850 | 0.2250 | −0.1950 | −0.8800 | −0.0700 | −0.1750 |
| JH0052pax | 1 | −0.4500 | 0.5050 | −0.1700 | −0.6150 | −0.1350 | −0.2700 |
| JH0053pax | 1 | −1.2800 | −0.5550 | −0.9600 | −0.3500 | −0.6500 | −0.1450 |
| JH0057pax | 1 | −0.0450 | 2.1200 | 0.3050 | 0.7500 | 1.6350 | 1.4300 |
| JH0059pax | 1 | −0.5200 | 0.4200 | −0.0500 | −0.0650 | 0.6050 | 0.5050 |
| JH0060pax | 1 | −0.7400 | 0.3250 | 0.0200 | 0.2900 | 0.6600 | 0.5100 |
| JH0061pax | 1 | 0.9900 | 2.8050 | 0.8700 | 1.4500 | 3.6400 | 0.8950 |
| JH0063pax | 1 | −0.6100 | 0.5650 | −0.2300 | −1.0050 | 0.2750 | 1.5400 |
| JH0065pax | 1 | −2.8600 | −1.5150 | −2.1500 | −2.2300 | −1.4500 | −1.7100 |
| JH0066pax | 1 | −1.3550 | −0.3200 | −1.1800 | −1.7900 | −1.3500 | −0.5400 |
| JH0068pax | 1 | 0.0050 | 0.4550 | 0.2550 | 0.0200 | 1.3500 | 1.8000 |
| JH0069pax | 1 | −0.8650 | 0.2450 | −0.2650 | −0.5000 | −0.0500 | −0.6400 |
| JH0071pax | 1 | −2.5050 | −2.2600 | −1.8250 | −0.3500 | −1.3300 | −1.5800 |
| JH0072pax | 1 | 0.1100 | −0.5750 | 0.0350 | −0.4650 | 1.3350 | 0.2300 |
| JH0077pax | 1 | −0.1000 | 0.5000 | 0.4000 | 0.1150 | 0.8750 | 1.7850 |
| JH0078pax | 1 | 1.6350 | 1.6250 | 1.6300 | 0.6600 | 1.5100 | 1.7800 |
| JH0080pax | 1 | −2.3200 | −1.2350 | −1.2600 | −1.0250 | −1.5600 | 0.0450 |
| JH0082pax | 1 | −0.9000 | −0.6650 | −0.3200 | −0.5450 | −0.3550 | 0.7200 |
| JH0083pax | 1 | −1.5800 | −0.0750 | −0.5300 | −1.5900 | 0.2450 | 0.2050 |
| JH0086pax | 1 | −0.2250 | −0.1850 | −0.4800 | −1.3250 | −0.0850 | 0.6800 |
| JH0092pax | 1 | −0.5450 | 1.3750 | 0.0400 | −0.1050 | 0.1300 | 1.1100 |
| MH0001pax | 1 | 1.4250 | 1.8900 | 1.5250 | 1.4350 | 3.1350 | 2.2700 |
| MH0009pax | 1 | −0.2050 | 0.2150 | −0.4850 | −0.4450 | −0.0400 | −0.2050 |
| MH0012pax | 1 | 0.0650 | 1.3100 | 0.5700 | 1.0950 | 1.4000 | 1.1200 |
| MH0014pax | 1 | 0.6700 | 1.1300 | 0.6100 | 0.2850 | 2.6850 | 1.5750 |
| MH0016pax | 1 | −1.0950 | −0.6050 | −0.6750 | −1.2050 | −0.2450 | −0.4300 |
| MH0017pax | 1 | −0.0100 | 0.8250 | 0.2000 | −0.4150 | 1.2500 | 1.6250 |
| MH0018pax | 1 | 0.9650 | 0.6700 | 0.1850 | 0.2300 | 2.0650 | 0.5700 |
| MH0021pax | 1 | 0.9700 | 0.4800 | −0.0650 | 0.2700 | 1.9100 | 1.8700 |
| MH0022pax | 1 | 0.2100 | 0.7250 | 0.1150 | 0.1250 | 0.8450 | 1.0950 |
| MH0024pax | 1 | 0.3450 | 0.6300 | 0.2050 | −0.0550 | 0.3350 | 1.0900 |
| MH0028pax | 1 | 0.1350 | 0.5200 | 0.1350 | −0.5950 | 0.1250 | 0.0850 |
| MH0029pax | 1 | 0.2300 | 0.4850 | 0.5700 | −0.2050 | 1.3250 | 0.9050 |
| MH0035pax | 1 | 0.8900 | 2.2000 | 1.2200 | 0.9950 | 1.3300 | 1.9450 |
| MH0037pax | 1 | 0.0001 | 1.3400 | 0.2600 | 0.3800 | 1.5200 | 2.0000 |
| MH0038pax | 1 | 1.5050 | 1.4150 | 1.1650 | 1.2300 | 2.1700 | 1.9850 |
| MH0039pax | 1 | −1.4900 | −0.7350 | −0.5400 | −0.8300 | −0.4350 | 0.4500 |
| MH0042pax | 1 | −0.3500 | −0.0800 | 0.0950 | −0.2900 | −0.1300 | 0.6500 |
| MH0050pax | 1 | −1.2600 | 0.7250 | −0.4300 | −0.2350 | 1.1300 | 1.8350 |
| MH0051pax | 1 | −1.0300 | −0.9000 | −0.5750 | −1.4350 | −1.9200 | 0.0300 |
| MIP0004pax | 1 | −2.3200 | −2.6150 | −1.7200 | −1.5500 | −1.3550 | −2.5350 |

TABLE 14-continued

Sample training set levels of RNA encoded by ANXA3, CLEC4D, IL2RB, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| MP0013Apax | 1 | 0.3150 | 1.0550 | −0.2400 | 0.0200 | 1.2450 | −0.0700 |
| MP0014Bpax | 1 | −0.2950 | 1.1200 | −0.1400 | 0.2950 | 1.5600 | 0.3350 |
| MP0018Apax | 1 | −0.7700 | −0.2050 | −0.6850 | −1.4250 | −0.1050 | −1.1150 |
| MP0019Bpax | 1 | −0.9100 | −0.5150 | −0.7550 | −1.0250 | −0.6750 | 0.7300 |
| MP0024pax | 1 | −1.2900 | −0.1150 | −0.4700 | 0.2100 | 1.3100 | 0.7400 |
| NK2001pax | 1 | −0.6250 | 0.0850 | −0.4250 | −1.2950 | 0.1750 | 1.6050 |
| NK2002pax | 1 | −0.2400 | −0.4300 | −0.1450 | −0.6550 | 0.2950 | 0.7000 |
| NK2003pax | 1 | −0.4150 | 0.4150 | 0.0200 | 0.0950 | 1.4100 | 0.2550 |
| NK2004pax | 1 | −0.9100 | 0.3750 | −0.6100 | −0.8750 | 0.3500 | −0.2700 |
| PB1829pax | 1 | 0.5600 | 1.7600 | 0.3700 | 0.2100 | 1.8100 | 1.9150 |
| PB1842pax | 1 | 1.2550 | 1.6150 | 1.1550 | 0.5300 | 2.5900 | 1.3450 |
| PB1872pax | 1 | 0.0650 | 0.3550 | 0.2400 | −0.8650 | 0.8650 | 0.0950 |
| PB2857pax | 1 | −0.8600 | 0.6800 | −0.2350 | 0.3500 | 0.0450 | 1.2500 |
| RC2919pax | 1 | 1.8500 | 1.8900 | 1.4100 | 2.7600 | 2.8200 | 3.8300 |
| RC3062pax | 1 | −0.1750 | 0.1900 | −0.3350 | −0.0750 | −0.2800 | −0.0100 |
| RC3277pax | 1 | −0.4200 | −0.1950 | −0.5050 | −0.4350 | 0.3200 | −0.0200 |
| RC3297pax | 1 | 0.0600 | 0.9800 | 0.1650 | 0.3850 | 2.5650 | 1.0450 |
| RC3445pax | 1 | −1.0200 | −0.4350 | −0.6300 | −0.9300 | 0.3100 | 0.1100 |
| RC3467pax | 1 | 1.9450 | 2.9300 | 1.4200 | 1.2250 | 2.9400 | 2.6000 |

Surprisingly, analysis of the data showed that RNA encoded by ANXA3, CLEC4D, LMNB1, PRRG4, TNFAIP6 and VNN1 is present on average at a significantly higher level (p-value less than 0.05) in blood of subjects having colorectal cancer relative to subjects having no colorectal pathology (Table 15). The ranges of fold-change in the levels of RNA encoded by these genes normalized to levels of RNA encoded by IL2RB in blood of the training set subjects having colorectal cancer relative to the training set subjects not having any colorectal pathology are shown in Table 15.

TABLE 15

Sample training set ranges of fold-change in levels of RNA encoded by ANXA3, CLEC4D, LMNB1, PRRG4, TNFAIP6 and VNN1 normalized to levels of RNA encoded by IL2RB in blood of subjects having colorectal cancer relative to subjects not having any colorectal pathology.

| | Gene | | | | | |
|---|---|---|---|---|---|---|
| | ANXA3 | CLEC4D | LMNB1 | PRRG4 | TNFAIP6 | VNN1 |
| Average normalized RNA level in subjects having colorectal cancer (ΔCt) | −0.32 | 0.41 | 0.78 | −0.06 | −0.13 | 0.64 |
| Average normalized RNA level in subjects not having any colorectal pathology (ΔCt) | 0.46 | 0.99 | 1.44 | 0.39 | 0.65 | 1.25 |
| Average RNA level fold-change | 1.71 | 1.50 | 1.58 | 1.37 | 1.72 | 1.53 |
| p-value for average RNA level fold-change | 1.1E−08 | 1.0E−05 | 8.8E−06 | 2.3E−06 | 2.8E−12 | 6.3E−06 |
| Maximum observed RNA level directional fold-change | 12.33 | 12.20 | 12.81 | 6.15 | 7.38 | 13.83 |

As can be seen in Table 15, a test subject having a blood level of RNA encoded by ANXA3, normalized to a level of RNA encoded by IL2RB, which is 1.7 to 12.3 fold higher than the average level of RNA encoded by this gene in blood of subjects not having any colorectal pathology is more likely to have colorectal cancer than to not have any colorectal pathology.

As can be seen in Table 15, a test subject having a blood level of RNA encoded by CLEC4D, normalized to a level of RNA encoded by IL2RB, which is 1.5 to 12.2 fold higher than the average level of RNA encoded by this gene in blood of subjects not having any colorectal pathology is more likely to have colorectal cancer than to not have any colorectal pathology.

As can be seen in Table 15, a test subject having a blood level of RNA encoded by LMNB1, normalized to a level of RNA encoded by IL2RB, which is 1.6 to 12.8 fold higher than the average level of RNA encoded by this gene in blood of subjects not having any colorectal pathology is more likely to have colorectal cancer than to not have any colorectal pathology.

As can be seen in Table 15, a test subject having a blood level of RNA encoded by PRRG4, normalized to a level of RNA encoded by IL2RB, which is 1.4 to 6.2 fold higher than the average level of RNA encoded by this gene in blood of subjects not having any colorectal pathology is more likely to have colorectal cancer than to not have any colorectal pathology.

As can be seen in Table 15, a test subject having a blood level of RNA encoded by TNFAIP6, normalized to a level of RNA encoded by IL2RB, which is 1.7 to 7.4 fold higher than the average level of RNA encoded by this gene in blood of subjects not having any colorectal pathology is more likely to have colorectal cancer than to not have any colorectal pathology.

As can be seen in Table 15, a test subject having a blood level of RNA encoded by VNN1, normalized to a level of RNA encoded by IL2RB, which is 1.5 to 13.8 fold higher than the average level of RNA encoded by this gene in blood of subjects not having any colorectal pathology is more likely to have colorectal cancer than to not have any colorectal pathology.

Generation of a Logistic Regression Model (Optimized Relative to the Models Set Forth in Example 3 of the Examples Section, Above) for Determining the Probability that a Test Subject has Colorectal Cancer Versus not Having any Colorectal Pathology Via Measurement of Levels of RNA Encoded by ANXA3, CLEC4D, LMNB1, PRRG4, TNFAIP6 and VNN1 Normalized to Levels of RNA Encoded by IL2RB:

Linear regression analysis of levels of RNA encoded by ANXA3, CLEC4D, LMNB1, PRRG4, TNFAIP6 and VNN1 normalized to IL2RB surprisingly showed that a logistic regression model could be generated, based on blood expression levels normalized to IL2RB for the combination of these 6 genes, for discriminating, with a ROC AUC of 0.80, between subjects having colorectal cancer and subjects not having any colorectal pathology (model #191 shown in Table 16).

The model of Table 16 corresponds to:

$$P=\{1+e^{-[(0.126)+(-1.406)(L_{ANXA3})+(0.399)(L_{CLEC4D})+(1.874)(L_{LMNB1})+(-1.846)(L_{PRRG4})+(0.333)(L_{TNFAIP6})+(-0.277)(L_{VNN1})]}\}^{-1},$$

where P is the probability that a test subject has colorectal cancer as opposed to not having any colorectal pathology, where $L_{ANXA3}$ is a ratio of a level of RNA encoded by ANXA3 to a level of RNA encoded by IL2RB in blood of the test subject, $L_{CLEC4D}$ is a ratio of a level of RNA encoded by CLEC4D to a level of RNA encoded by IL2RB in blood of the test subject, $L_{LMNB1}$ is a ratio of a level of RNA encoded by LMNB1 to a level of RNA encoded by IL2RB in blood of the test subject, $L_{PRRG4}$ is a ratio of a level of RNA encoded by PRRG4 to a level of RNA encoded by IL2RB in blood of the test subject, $L_{TNFAIP6}$ is a ratio of a level of RNA encoded by TNFAIP6 to a level of RNA encoded by IL2RB in blood of the test subject, and $L_{VNN1}$ is a ratio of a level of RNA encoded by VNN1 to a level of RNA encoded by IL2RB in blood of the test subject.

TABLE 16

Logistic regression model based on blood expression levels for the combination of ANXA3, CLEC4D, LMNB1, PRRG4, TNFAIP6 and VNN1, normalized to IL2RB expression levels for determining the probability that a test subject has colorectal cancer as opposed to not having colorectal cancer. The ROC AUC value for the model is shown for the sample training set used to generate the models, as well as for an independent blind sample test set used to test the model.

| Logistic Regression Model # | No. of genes in Model | ROC AUC Training Set | ROC AUC Test Set | Constant ($K_0$) | Gene-specific regression coefficient ($K_n$) | | | | | |
|---|---|---|---|---|---|---|---|---|---|---|
| | | | | | ANXA3 | CLEC4D | LMNB1 | PRRG4 | TNFAIP6 | VNN1 |
| 191 | 6 | 0.80 | 0.80 | 0.126 | −1.406 | 0.399 | 1.874 | −1.846 | 0.333 | −0.277 |

Blind Sample Test Set:

Quantitative reverse transcriptase-PCR analysis of expression of ANXA3, CLEC4D, LMNB1, PRRG4, TNFAIP6 and VNN1 in an independent test set of blood samples from 202 subjects having colorectal cancer and 208 subjects not having any colorectal pathology was performed as described above for the training set (these samples include a subset of the samples listed in Table 12 of Example 3, above, as well as additional samples). The normalized RNA levels measured are shown in Table 17.

TABLE 17

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| PB1952pax | 0 | 2.240 | 2.125 | 0.965 | 2.285 | 3.220 | 2.520 |
| RC3142pax | 0 | 2.795 | 2.380 | 1.225 | 2.040 | 2.675 | 2.500 |
| CD1728pax | 0 | 2.410 | 2.330 | 1.835 | 2.465 | 2.345 | 3.715 |
| PB2015pax | 0 | 2.250 | 1.835 | 2.075 | 3.010 | 4.220 | 2.390 |
| PB1786pax | 0 | 1.210 | 2.530 | 1.085 | 2.310 | 1.555 | 3.185 |

TABLE 17-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| Sample ID | Group | ANXA3 | CLEC4D | LMNB1 | PRRG4 | TNFAIP6 | VNN1 |
|---|---|---|---|---|---|---|---|
| CD0762pax | 0 | 1.215 | 1.260 | 1.140 | 2.360 | 1.925 | 1.730 |
| CD0800pax | 0 | 2.410 | 2.310 | 1.550 | 2.210 | 3.480 | 2.795 |
| PB3267pax | 0 | 1.885 | 2.565 | 1.285 | 2.180 | 2.325 | 2.575 |
| PB2267pax | 0 | 2.160 | 2.890 | 1.505 | 2.215 | 3.085 | 2.895 |
| CD0411pax | 0 | 2.510 | 2.950 | 1.900 | 2.365 | 3.890 | 3.660 |
| CD0211pax | 0 | 1.115 | 2.235 | 1.350 | 2.650 | 2.470 | 2.310 |
| PB1918pax | 0 | 2.450 | 2.080 | 1.145 | 1.590 | 3.675 | 2.435 |
| PB0701pax | 0 | 1.220 | 2.090 | 1.760 | 2.655 | 2.190 | 3.785 |
| PB3445pax | 0 | 1.400 | 1.870 | 1.015 | 1.955 | 2.280 | 2.205 |
| PB1763pax | 0 | 2.035 | 2.435 | 1.720 | 2.490 | 2.975 | 1.785 |
| PB3213pax | 0 | 2.245 | 2.340 | 1.390 | 1.795 | 2.255 | 2.100 |
| CD1424pax | 0 | 1.460 | 1.300 | 1.220 | 1.975 | 2.535 | 2.510 |
| PB2978pax | 0 | 2.945 | 3.175 | 1.990 | 2.175 | 3.680 | 2.840 |
| PB3270pax | 0 | 1.895 | 3.055 | 0.885 | 1.415 | 1.280 | 2.545 |
| RC2030pax | 0 | 1.580 | 2.060 | 1.205 | 1.595 | 1.665 | 4.080 |
| CD0448pax | 0 | 2.195 | 2.955 | 1.800 | 2.400 | 4.090 | 3.800 |
| RC2869pax | 0 | 1.620 | 1.415 | 0.880 | 1.475 | 2.500 | 2.520 |
| PB4296pax | 0 | 1.940 | 2.600 | 1.445 | 1.765 | 2.290 | 3.890 |
| CD0398pax | 0 | 2.425 | 2.560 | 1.970 | 2.265 | 4.015 | 3.515 |
| CD1077pax | 0 | 0.740 | 0.845 | 0.575 | 1.560 | 1.410 | 1.560 |
| PB3805pax | 0 | 2.040 | 1.655 | 1.515 | 1.605 | 1.020 | 1.610 |
| PB1898pax | 0 | 2.075 | 2.445 | 1.180 | 1.800 | 3.165 | 1.410 |
| PB2062pax | 0 | 2.090 | 2.110 | 1.455 | 1.850 | 3.090 | 2.220 |
| CD0937pax | 0 | 1.120 | 0.705 | 0.655 | 1.365 | 2.310 | 1.860 |
| RC2612pax | 0 | 2.725 | 2.685 | 1.810 | 1.830 | 3.395 | 2.535 |
| CD1784pax | 0 | 1.615 | 1.410 | 1.325 | 1.735 | 2.325 | 2.325 |
| PB2984pax | 0 | 1.205 | 2.325 | 0.990 | 1.895 | 2.270 | 2.315 |
| RC2976pax | 0 | −0.045 | 1.445 | −0.305 | 0.685 | −0.305 | 3.570 |
| PB1785pax | 0 | 1.470 | 1.950 | 1.245 | 1.880 | 1.835 | 1.450 |
| CD0691pax | 0 | 1.785 | 2.850 | 1.445 | 2.060 | 2.535 | 1.900 |
| PB2384pax | 0 | 1.700 | 2.440 | 0.915 | 1.380 | 2.500 | 2.405 |
| CD1550pax | 0 | 2.420 | 3.640 | 2.150 | 2.235 | 3.065 | 3.690 |
| CD1540pax | 0 | 1.005 | 0.905 | 0.785 | 1.465 | 1.745 | 0.990 |
| RC2565pax | 0 | −0.125 | 0.690 | −0.330 | 0.735 | 0.200 | 1.790 |
| CD0499pax | 0 | 1.390 | 2.750 | 0.805 | 1.720 | 2.820 | 1.290 |
| RC2174pax | 0 | 0.440 | 1.020 | 0.790 | 1.700 | 1.705 | 2.265 |
| PB3304pax | 0 | 0.550 | 1.270 | 0.520 | 1.760 | 2.765 | 0.835 |
| PB1879pax | 0 | 1.345 | 1.065 | 1.295 | 1.620 | 2.070 | 1.830 |
| PB3808pax | 0 | 1.450 | 1.405 | 1.225 | 1.580 | 2.810 | 2.435 |
| PB4357pax | 0 | 1.065 | 0.195 | 0.295 | 0.690 | 1.245 | 0.360 |
| PB2636pax | 0 | 1.795 | 2.615 | 1.360 | 1.775 | 3.600 | 2.925 |
| PB3440pax | 0 | 1.320 | 1.720 | 1.280 | 1.515 | 0.640 | 1.495 |
| PB2272pax | 0 | 2.225 | 2.130 | 1.335 | 1.475 | 3.785 | 1.805 |
| PB1848pax | 0 | 1.410 | 1.150 | 0.765 | 0.875 | 2.300 | 2.775 |
| RC3420pax | 0 | 1.265 | 1.490 | 1.390 | 2.060 | 2.875 | 0.995 |
| PB2005pax | 0 | 1.800 | 1.830 | 1.045 | 1.285 | 3.465 | 2.250 |
| CD0354pax | 0 | 0.680 | 1.160 | 0.585 | 1.395 | 2.015 | 1.265 |
| CD1945pax | 0 | 1.005 | 1.500 | 0.260 | 0.815 | 2.430 | 2.055 |
| PB4156pax | 0 | 2.005 | 2.405 | 1.435 | 1.370 | 1.995 | 1.990 |
| RC2934pax | 0 | 1.055 | 1.185 | 0.605 | 1.025 | 2.760 | 2.560 |
| PB2214pax | 0 | 1.350 | 1.790 | 0.535 | 0.980 | 2.390 | 1.315 |
| PB3370pax | 0 | 0.965 | 2.430 | 1.125 | 1.795 | 1.985 | 2.235 |
| PB1300-2pax | 0 | 0.885 | 1.535 | 0.425 | 0.960 | 1.765 | 1.860 |
| PB2951pax | 0 | −0.180 | −1.980 | −1.215 | −0.650 | −0.520 | −0.915 |
| PB3356pax | 0 | −0.430 | 1.050 | −0.145 | 1.105 | 0.680 | 1.550 |
| CD0148pax | 0 | 0.740 | 1.890 | 0.515 | 1.255 | 1.835 | 1.665 |
| PB3451pax | 0 | 1.240 | 1.300 | 0.720 | 1.025 | 2.210 | 1.555 |
| CD1409pax | 0 | 0.510 | 0.115 | 0.140 | 0.495 | 0.660 | 1.250 |
| PB3118pax | 0 | 1.480 | 1.615 | 1.415 | 1.375 | 1.195 | 1.855 |
| PB3931pax | 0 | 1.460 | 1.515 | 0.925 | 1.250 | 2.790 | 1.210 |
| CD1163pax | 0 | 1.105 | 2.110 | 1.475 | 2.175 | 3.175 | 1.875 |
| RC2112pax | 0 | 1.255 | 2.285 | 1.555 | 1.830 | 1.825 | 2.530 |
| PB4274pax | 0 | 0.670 | 0.385 | 0.075 | 0.245 | 0.535 | 1.735 |
| CD1028pax | 0 | 1.250 | 2.115 | 0.985 | 1.370 | 2.240 | 1.950 |
| PB4345pax | 0 | 0.680 | 1.445 | 0.895 | 1.320 | 1.125 | 2.145 |
| CD0698pax | 0 | 0.925 | 1.555 | 0.915 | 1.295 | 1.265 | 1.515 |
| PB4066pax | 0 | 0.855 | 0.175 | 0.580 | 0.940 | 1.450 | 0.185 |
| PB4062pax | 0 | 0.720 | 1.380 | 0.455 | 1.305 | 2.385 | 0.300 |
| PB3481pax | 0 | −0.110 | 0.835 | 0.185 | 1.025 | 0.445 | 1.345 |
| CD0252pax | 0 | 1.100 | 0.340 | 0.380 | 0.615 | 2.185 | 0.580 |
| CD0428pax | 0 | 0.480 | 1.090 | 0.225 | 0.815 | 1.420 | 1.465 |

TABLE 17-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| CD0571pax | 0 | 1.060 | 1.425 | 1.430 | 1.960 | 2.575 | 0.890 |
| CD0786pax | 0 | 0.850 | 1.335 | 0.795 | 1.290 | 2.045 | 1.325 |
| PB3863pax | 0 | 1.745 | 1.785 | 1.435 | 1.255 | 2.620 | 2.605 |
| PB2927pax | 0 | 1.955 | 0.820 | 0.520 | −0.140 | 1.515 | 1.890 |
| PB3568pax | 0 | 1.505 | 1.625 | 1.250 | 1.295 | 2.155 | 1.370 |
| RC2839pax | 0 | 0.690 | 1.275 | 0.595 | 0.935 | 1.195 | 1.800 |
| CD1700pax | 0 | 1.095 | 1.520 | 1.160 | 1.250 | 1.480 | 2.020 |
| CD1313pax | 0 | 1.600 | 1.400 | 0.710 | 0.820 | 2.670 | 0.510 |
| PB1700pax | 0 | 0.690 | 1.020 | 0.740 | 1.155 | 1.610 | 1.265 |
| CD0727pax | 0 | 1.515 | 2.780 | 1.015 | 1.245 | 2.130 | 1.450 |
| PB4161pax | 0 | 0.940 | 0.945 | 0.755 | 0.890 | 1.340 | 1.330 |
| CD1583pax | 0 | 0.690 | 0.855 | 0.530 | 0.780 | 1.240 | 1.445 |
| PB3594pax | 0 | 0.885 | 1.175 | 0.500 | 0.935 | 2.395 | 1.040 |
| RC3170pax | 0 | 0.860 | 1.635 | 0.190 | 0.210 | 0.400 | 2.110 |
| CD0553pax | 0 | 2.075 | 3.365 | 1.750 | 1.505 | 2.725 | 3.125 |
| CD0220pax | 0 | 1.080 | 2.120 | 1.110 | 1.210 | 1.380 | 2.345 |
| CD0238pax | 0 | 0.355 | 1.010 | 0.440 | 1.065 | 1.720 | 1.180 |
| CD0409pax | 0 | −0.235 | 0.710 | −0.100 | 0.650 | 0.505 | 1.320 |
| PB3163pax | 0 | 0.530 | 1.630 | 0.885 | 1.515 | 2.675 | 2.245 |
| PB2491pax | 0 | 0.835 | −0.035 | 0.295 | 0.605 | 2.505 | 0.150 |
| PB4377pax | 0 | 0.110 | 0.315 | 0.030 | 0.565 | 1.245 | 1.270 |
| PB4307pax | 0 | 1.845 | 3.790 | 1.730 | 1.775 | 3.650 | 3.665 |
| RC2236pax | 0 | 0.970 | 1.080 | 1.035 | 0.985 | 1.450 | 2.095 |
| RC2716pax | 0 | 0.490 | 0.730 | 0.845 | 1.360 | 2.490 | 1.365 |
| PB2024pax | 0 | 0.815 | 1.375 | 0.785 | 1.075 | 2.445 | 1.850 |
| CD0484pax | 0 | 0.140 | 1.135 | 0.255 | 1.080 | 1.585 | 0.255 |
| RC2897pax | 0 | 0.385 | 1.035 | 0.130 | 0.530 | 1.350 | 1.335 |
| CD0872pax | 0 | 0.580 | −0.005 | 0.490 | 0.585 | 1.435 | 1.005 |
| PB1626pax | 0 | 0.525 | 0.835 | 0.435 | 0.550 | 1.075 | 1.865 |
| CD1974pax | 0 | 0.965 | 1.445 | 0.350 | 0.555 | 2.000 | 0.985 |
| CD1295pax | 0 | 0.560 | 0.450 | 0.425 | 0.560 | 1.575 | 1.570 |
| RC2699pax | 0 | 0.825 | 1.015 | 0.340 | 0.395 | 1.385 | 1.285 |
| RC2986pax | 0 | 1.095 | 1.315 | 0.540 | 0.625 | 2.675 | 1.710 |
| PB1899pax | 0 | −0.230 | 0.420 | −0.365 | 0.095 | 0.270 | 1.625 |
| PB3955pax | 0 | 1.630 | 1.745 | 1.220 | 1.070 | 3.000 | 1.545 |
| PB1230pax | 0 | 0.685 | 1.585 | 0.855 | 0.955 | 0.950 | 1.870 |
| CD1404pax | 0 | −0.045 | 1.190 | 0.225 | 0.740 | 1.330 | 2.630 |
| CD0367pax | 0 | 1.050 | 0.940 | 0.745 | 0.705 | 2.105 | 1.360 |
| PB3226pax | 0 | 0.720 | 1.225 | 0.760 | 1.010 | 2.320 | 1.735 |
| PB3193pax | 0 | 0.475 | 0.650 | 0.650 | 0.905 | 1.600 | 1.205 |
| PB3224pax | 0 | 0.400 | −0.115 | 0.080 | 0.125 | 0.415 | 0.390 |
| PB1871pax | 0 | 0.715 | 0.640 | 0.565 | 0.545 | 1.590 | 1.710 |
| CD1392pax | 0 | 1.055 | 1.540 | 0.860 | 1.030 | 2.995 | 1.720 |
| CD0833pax | 0 | −0.050 | −0.365 | −0.090 | 0.365 | 0.630 | −0.285 |
| CD0386pax | 0 | 1.070 | 2.390 | 1.000 | 1.280 | 3.245 | 2.350 |
| CD1158pax | 0 | 0.335 | 0.270 | 0.110 | 0.065 | 0.185 | 1.405 |
| PB1324pax | 0 | −0.110 | 0.585 | 0.465 | 1.050 | 1.765 | 1.840 |
| CD1455pax | 0 | −0.610 | 0.530 | 0.345 | 1.150 | 0.755 | 1.570 |
| RC2338pax | 0 | 1.395 | 2.355 | 1.590 | 1.460 | 2.515 | 2.445 |
| CD1971pax | 0 | 0.645 | 1.425 | 0.060 | 0.110 | 1.400 | 2.170 |
| CD1048pax | 0 | 0.860 | 2.110 | 1.115 | 1.525 | 2.600 | 1.210 |
| CD0244pax | 0 | 0.285 | 0.305 | 0.260 | 0.670 | 1.395 | −0.095 |
| RC3191pax | 0 | 1.560 | 2.415 | 1.510 | 1.210 | 2.285 | 2.395 |
| PB3582pax | 0 | 1.090 | 1.830 | 1.230 | 1.320 | 2.870 | 1.955 |
| CD0237pax | 0 | 0.595 | 1.085 | 0.245 | 0.400 | 1.400 | 0.985 |
| CD1981pax | 0 | 1.955 | 3.135 | 1.875 | 1.495 | 3.520 | 3.250 |
| CD0603pax | 0 | 1.015 | 1.015 | 0.640 | 0.400 | 1.755 | 1.770 |
| CD1134pax | 0 | 0.795 | 1.655 | 0.815 | 0.790 | 1.850 | 2.475 |
| PB2130pax | 0 | 0.665 | 0.890 | 0.335 | 0.260 | 0.895 | 1.155 |
| PB1275pax | 0 | −0.885 | 0.195 | −0.445 | 0.145 | −0.230 | 2.010 |
| PB2564pax | 0 | 0.385 | 1.960 | 0.460 | 0.810 | 1.055 | 1.265 |
| CD0580pax | 0 | 1.150 | 1.580 | 0.470 | 0.400 | 2.330 | 1.165 |
| PB0768pax | 0 | −0.670 | 0.740 | 0.080 | 0.825 | 0.425 | 1.335 |
| CD0518pax | 0 | 1.575 | 3.770 | 1.750 | 1.775 | 3.120 | 2.440 |
| RC3315pax | 0 | 0.640 | 1.565 | 0.650 | 1.035 | 2.680 | 0.940 |
| CD1270pax | 0 | 0.895 | 1.020 | 0.770 | 0.515 | 1.695 | 1.680 |
| CD1068pax | 0 | 0.380 | 0.200 | 0.700 | 0.985 | 2.475 | 0.400 |
| CD0995pax | 0 | 0.805 | 1.465 | 0.560 | 0.615 | 2.395 | 1.435 |
| CD1438pax | 0 | −0.125 | 0.620 | −0.030 | 0.440 | 0.905 | 0.045 |
| CD1169pax | 0 | 0.270 | 0.295 | 0.470 | 0.500 | 1.845 | 1.430 |
| RC3379pax | 0 | 0.850 | 1.185 | 0.460 | 0.410 | 1.945 | 0.400 |

TABLE 17-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| CD0520pax | 0 | −0.125 | 1.025 | 0.990 | 1.325 | 1.130 | 1.370 |
| PB1718pax | 0 | 0.145 | 1.185 | 0.395 | 0.445 | 0.695 | 1.505 |
| PB2757pax | 0 | 0.555 | 1.690 | 0.995 | 0.915 | 1.750 | 2.335 |
| CD0743pax | 0 | 0.290 | −0.400 | 0.095 | 0.070 | 1.515 | −0.120 |
| CD0667pax | 0 | −0.385 | −0.305 | −0.345 | −0.065 | 0.205 | −0.230 |
| RC3214pax | 0 | 0.940 | 1.860 | 1.200 | 1.140 | 2.730 | 1.620 |
| PB0689pax | 0 | 0.235 | 1.420 | 0.295 | 0.270 | 0.905 | 1.990 |
| CD0911pax | 0 | −0.550 | −0.580 | −0.800 | −0.405 | 0.290 | −0.560 |
| PB2516pax | 0 | 0.310 | 1.075 | 0.700 | 0.490 | 0.890 | 2.285 |
| PB2584pax | 0 | 0.945 | 1.230 | 0.935 | 0.475 | 1.270 | 1.340 |
| CD1487pax | 0 | 0.310 | 2.120 | 1.190 | 1.645 | 2.160 | 0.815 |
| CD0282pax | 0 | 0.165 | 0.685 | 0.270 | 0.545 | 1.100 | −0.700 |
| PB4325pax | 0 | 0.065 | −0.180 | −0.020 | −0.025 | 0.475 | −0.360 |
| RC2652pax | 0 | −1.425 | 0.025 | −0.620 | 0.450 | 0.760 | 0.560 |
| PB2464pax | 0 | 0.620 | 1.330 | 0.510 | 0.045 | 1.230 | 2.810 |
| PB3227pax | 0 | 0.235 | 0.850 | 0.820 | 0.865 | 2.215 | 1.845 |
| CD1559pax | 0 | 0.170 | 1.000 | 0.335 | 0.505 | 2.070 | 1.300 |
| PB4003pax | 0 | 0.070 | 0.655 | 0.170 | 0.215 | 0.880 | 0.690 |
| CD0108pax | 0 | 0.260 | 0.055 | 0.560 | 0.310 | 0.740 | 0.640 |
| PB1758pax | 0 | −0.600 | 0.475 | 0.030 | 0.535 | 0.500 | 0.145 |
| CD0277pax | 0 | 0.605 | 1.980 | 0.800 | 0.940 | 2.250 | 0.720 |
| PB2184pax | 0 | −1.005 | −0.650 | −0.705 | −0.445 | −0.075 | 1.230 |
| CD1683pax | 0 | 0.485 | 1.620 | 0.725 | 0.575 | 1.595 | 1.805 |
| RC2615pax | 0 | −0.655 | 0.070 | 0.210 | 0.340 | 0.190 | 1.205 |
| CD1224pax | 0 | −0.295 | 0.630 | −0.325 | −0.110 | 0.995 | 0.485 |
| CD1458pax | 0 | 0.035 | −0.055 | 0.560 | 0.485 | 1.635 | 0.585 |
| CD0204pax | 0 | 0.380 | 0.885 | 0.250 | −0.050 | 1.200 | 0.990 |
| CD1706pax | 0 | 0.540 | 1.815 | 1.025 | 1.020 | 2.510 | 1.195 |
| CD1542pax | 0 | 0.375 | 0.870 | 0.900 | 0.655 | 1.755 | 1.305 |
| PB2909pax | 0 | −0.345 | −1.240 | −0.675 | −0.915 | −0.075 | −0.645 |
| PB4073pax | 0 | −0.250 | 0.195 | −0.095 | −0.205 | 0.410 | 0.600 |
| CD0604pax | 0 | 0.415 | 1.130 | 0.320 | 0.235 | 2.125 | 0.230 |
| PB3605pax | 0 | −1.120 | −0.290 | −0.695 | −0.340 | 0.305 | 0.660 |
| CD1965pax | 0 | 0.030 | 1.310 | 0.400 | 0.140 | 1.155 | 2.275 |
| CD0432pax | 0 | 0.185 | 0.565 | 0.015 | −0.140 | 1.870 | 0.495 |
| PB1336pax | 0 | 0.695 | 0.780 | 0.320 | −0.470 | 1.310 | 1.805 |
| PB2974pax | 0 | −0.635 | 0.320 | −0.300 | −0.305 | 0.605 | 1.740 |
| PB0662pax | 0 | 0.120 | 0.575 | 0.945 | 0.850 | 1.605 | 0.045 |
| CD1741pax | 0 | −0.310 | −0.335 | 0.015 | −0.160 | 1.205 | 0.850 |
| PB2875pax | 0 | −0.230 | 1.205 | 0.140 | 0.165 | 1.200 | 1.025 |
| CD0419pax | 0 | 0.440 | 1.220 | 0.810 | 0.655 | 2.375 | −0.030 |
| CD1649pax | 0 | 0.925 | 1.565 | 1.000 | 0.130 | 1.550 | 1.630 |
| CD1329pax | 0 | 0.130 | −0.170 | 0.155 | −0.460 | 1.075 | 0.705 |
| CD0466pax | 0 | 0.730 | 1.870 | 0.930 | 0.160 | 1.280 | 1.890 |
| CD0857pax | 0 | −1.460 | −0.755 | −0.560 | −0.360 | −0.670 | 0.255 |
| CD0242pax | 0 | 0.965 | 1.360 | 0.580 | −0.450 | 0.980 | 1.235 |
| PB3513pax | 0 | −0.355 | −0.705 | −0.970 | −1.200 | 0.410 | −1.270 |
| CD0583pax | 0 | −0.605 | −1.045 | −0.595 | −0.740 | 0.765 | −0.705 |
| PB3049pax | 0 | −1.030 | 0.045 | −0.235 | −0.170 | 0.105 | 0.595 |
| PB1446pax | 0 | −1.380 | −0.485 | −0.715 | −0.495 | 0.300 | 0.700 |
| CD1441pax | 0 | −0.565 | 0.485 | 0.230 | 0.175 | 0.995 | 0.055 |
| PB2634pax | 0 | 0.165 | 1.335 | 1.270 | 1.000 | 2.740 | 1.020 |
| CD0547pax | 0 | −1.740 | −0.260 | −0.685 | −0.185 | −0.095 | −0.420 |
| PB2041pax | 0 | −0.655 | 0.440 | −0.205 | −0.170 | 1.540 | 0.185 |
| PB1514pax | 0 | −0.940 | 0.075 | −0.280 | −0.265 | 0.850 | 0.175 |
| PB3032pax | 0 | −0.145 | 0.435 | 0.750 | 0.110 | 1.510 | 1.425 |
| CD0676pax | 0 | −0.730 | −0.640 | −0.610 | −1.085 | 0.300 | 0.100 |
| PB3806pax | 0 | −1.410 | 0.325 | −0.305 | −0.080 | −0.010 | −0.070 |
| CD0472pax | 0 | −1.800 | −0.180 | −0.830 | −0.465 | 0.255 | −0.070 |
| PB1222pax | 0 | −0.165 | 0.415 | 0.325 | −0.795 | −0.035 | 0.860 |
| CD1032pax | 0 | −2.740 | −2.045 | −0.550 | −0.490 | −0.875 | 0.410 |
| JH0111pax | 1 | 1.040 | 1.910 | 0.835 | 2.170 | 2.645 | 1.650 |
| MH0122Bpax | 1 | 0.235 | 1.190 | 0.340 | 1.380 | 0.430 | 3.590 |
| IS3001pax | 1 | 1.925 | 2.145 | 1.030 | 1.300 | 1.885 | 2.880 |
| BE3003pax | 1 | 0.985 | 1.160 | 1.050 | 1.985 | 2.185 | 1.120 |
| MH0083pax | 1 | 1.570 | 1.635 | 0.805 | 1.195 | 2.150 | 1.765 |
| BE1004pax | 1 | 0.085 | 1.050 | 0.730 | 1.825 | 2.040 | 1.790 |
| MH0112Bpax | 1 | 0.960 | 1.720 | 0.810 | 1.325 | 1.975 | 2.055 |
| BE1007pax | 1 | 1.050 | 0.945 | 0.815 | 1.055 | 1.810 | 2.100 |
| MH0031-2pax | 1 | −0.325 | −0.130 | −0.430 | 0.615 | 1.330 | 1.170 |
| MH0112Apax | 1 | 0.925 | 1.760 | 1.025 | 1.500 | 2.025 | 2.220 |

TABLE 17-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| MR4001Apax | 1 | 0.610 | 1.130 | 0.470 | 1.210 | 1.650 | 0.615 |
| NK2011pax | 1 | 1.355 | 2.025 | 1.060 | 1.110 | 2.520 | 3.570 |
| OL0092pax | 1 | 0.790 | 1.555 | 0.670 | 1.160 | 1.585 | 1.650 |
| MIP2007pax | 1 | 1.075 | 1.725 | 0.855 | 1.265 | 2.410 | 1.980 |
| JH0153pax | 1 | 1.085 | 1.470 | 0.610 | 0.580 | 0.495 | 2.085 |
| KW0005pax | 1 | 0.695 | 1.540 | 1.240 | 1.940 | 2.705 | 1.850 |
| JH0054pax | 1 | 0.555 | 1.775 | 0.870 | 1.580 | 1.990 | 1.710 |
| AN4017pax | 1 | 1.190 | 1.630 | 0.590 | 0.510 | 0.620 | 1.665 |
| MP0031Apax | 1 | 1.090 | 1.315 | 0.705 | 0.800 | 1.720 | 1.570 |
| MP0021Bpax | 1 | 0.410 | 0.995 | 0.710 | 1.220 | 1.765 | 1.555 |
| MIP1018Bpax | 1 | 0.600 | 1.535 | 0.490 | 1.020 | 1.720 | 1.115 |
| CC0005pax | 1 | 0.655 | 0.940 | 0.345 | 0.725 | 1.460 | 0.345 |
| NK1009pax | 1 | 1.915 | 1.845 | 1.030 | 0.650 | 2.595 | 1.635 |
| JM0010pax | 1 | 0.130 | 0.610 | 0.670 | 1.075 | 1.260 | 1.775 |
| JH0150pax | 1 | 0.895 | 1.930 | 0.490 | 0.685 | 0.900 | 0.730 |
| IS1004pax | 1 | 1.495 | 2.710 | 1.750 | 1.520 | 2.570 | 3.730 |
| MIP1021Bpax | 1 | 0.600 | 2.605 | 0.860 | 1.455 | 2.305 | 2.180 |
| NK5006pax | 1 | 0.895 | 1.205 | 0.645 | 0.620 | 2.095 | 2.495 |
| MP0032Bpax | 1 | 0.630 | 1.060 | 0.315 | 0.640 | 1.770 | 0.865 |
| BE3012Apax | 1 | −0.830 | −0.545 | −1.045 | −0.330 | −0.330 | 0.700 |
| JH0146pax | 1 | −0.130 | 0.615 | 0.175 | 0.805 | 1.540 | 1.665 |
| NK2007pax | 1 | 0.110 | 0.520 | −0.030 | 0.560 | 0.980 | −0.125 |
| JH0112pax | 1 | 0.500 | 0.910 | 0.265 | 0.530 | 1.635 | 1.090 |
| OL0066pax | 1 | 0.140 | 1.050 | 0.380 | 0.785 | 1.140 | 1.410 |
| DC0012pax | 1 | −1.370 | −0.520 | −0.775 | 0.275 | −1.140 | −0.350 |
| JH0129pax | 1 | 0.580 | 1.530 | 0.935 | 1.265 | 2.850 | 2.270 |
| JH0163pax | 1 | 0.295 | 1.490 | 0.955 | 1.580 | 2.625 | 1.310 |
| FS0005pax | 1 | 0.040 | 0.315 | 0.500 | 0.890 | 1.355 | 0.850 |
| DES1006Apax | 1 | 0.955 | 1.140 | 0.890 | 0.635 | 1.570 | 1.940 |
| MH0030pax | 1 | −0.150 | 0.865 | 0.180 | 0.720 | 0.345 | 0.260 |
| FS0006pax | 1 | 0.100 | 0.195 | 0.585 | 0.825 | 1.165 | 1.025 |
| OL0096pax | 1 | 0.305 | 1.230 | 0.890 | 0.830 | 0.405 | 2.550 |
| MIP2003pax | 1 | −0.045 | 0.665 | 0.295 | 0.835 | 1.865 | 1.060 |
| MH0113Apax | 1 | 0.495 | 0.085 | 0.800 | 0.575 | 1.015 | 1.565 |
| JH0067pax | 1 | 0.230 | 0.940 | 0.100 | 0.355 | 1.180 | 0.980 |
| MH0053pax | 1 | 2.195 | 2.465 | 1.420 | 0.670 | 3.315 | 2.550 |
| MW0001Apax | 1 | 0.345 | 1.160 | 0.540 | 0.680 | 1.290 | 1.545 |
| AN4013pax | 1 | 1.135 | 2.150 | 1.055 | 0.770 | 1.810 | 2.225 |
| WJ0005CSpax | 1 | −0.895 | −0.630 | −1.440 | −0.840 | 0.055 | 0.250 |
| JH0096pax | 1 | −1.745 | −0.480 | −1.130 | −0.400 | −2.050 | 1.375 |
| DC5008Bpax | 1 | 0.045 | 0.855 | 0.140 | 0.300 | 1.415 | 2.280 |
| MIP2002pax | 1 | 1.120 | 1.680 | 1.060 | 0.755 | 2.000 | 1.890 |
| AN0011pax | 1 | 1.110 | 1.075 | 0.125 | −0.780 | 0.320 | 2.935 |
| DES1009Apax | 1 | 0.305 | 0.660 | 0.325 | 0.440 | 0.955 | 0.370 |
| DC0011pax | 1 | 0.150 | 0.700 | 0.615 | 0.730 | 1.535 | 1.880 |
| FC0013pax | 1 | −0.105 | −0.095 | 0.920 | 0.965 | 1.255 | 2.145 |
| OL0075pax | 1 | −0.590 | 0.190 | −0.010 | 0.590 | 1.140 | 0.970 |
| NK2014pax | 1 | 0.485 | 1.240 | 0.650 | 0.745 | 1.705 | 1.100 |
| KW0008pax | 1 | 0.090 | 0.985 | 0.305 | 0.250 | 0.220 | 1.730 |
| OL0080pax | 1 | −0.445 | −0.025 | −0.150 | 0.110 | 0.030 | 0.540 |
| AN4019pax | 1 | 1.520 | 2.265 | 1.045 | 0.765 | 3.090 | 1.225 |
| JH0116pax | 1 | 0.035 | 1.465 | 0.520 | 0.830 | 1.040 | 1.120 |
| JH0132pax | 1 | −0.460 | 0.010 | −0.310 | 0.095 | 0.365 | −0.005 |
| JH0170pax | 1 | 2.050 | 2.960 | 1.645 | 0.855 | 3.655 | 3.370 |
| NK1001pax | 1 | 0.415 | 0.990 | −0.050 | −0.025 | 1.805 | 0.975 |
| OL0065pax | 1 | 0.280 | 0.730 | 0.445 | 0.530 | 1.630 | 0.690 |
| BE3011Apax | 1 | 0.640 | 1.825 | 0.600 | 0.680 | 2.150 | 1.105 |
| KW0004pax | 1 | 0.895 | 2.485 | 1.415 | 1.290 | 1.975 | 1.935 |
| JH0022pax | 1 | −0.265 | 0.255 | 0.040 | 0.145 | 0.375 | 0.945 |
| JH0100pax | 1 | 0.550 | 1.420 | 1.020 | 0.955 | 1.955 | 1.405 |
| CD1690pax | 1 | 0.120 | 0.145 | 0.110 | 0.165 | 1.040 | −0.315 |
| MH0063pax | 1 | 0.265 | −0.295 | −0.305 | −0.215 | 2.185 | −0.590 |
| MIP1017pax | 1 | −0.260 | 0.825 | −0.250 | 0.000 | 0.670 | 0.800 |
| JH0109pax | 1 | 1.190 | 2.160 | 1.000 | 0.405 | 2.055 | 2.640 |
| CC0001pax | 1 | 0.170 | 0.765 | 0.295 | 0.315 | 1.785 | 1.305 |
| PB3545pax | 1 | −0.520 | 1.150 | −0.380 | 0.170 | 0.795 | 0.475 |
| IS4001pax | 1 | −0.855 | −0.065 | −0.915 | −0.770 | −0.370 | 1.630 |
| DC0005pax | 1 | 1.085 | 1.960 | 1.220 | 0.715 | 1.895 | 1.965 |
| MH0070pax | 1 | 0.380 | 0.945 | 0.685 | 0.515 | 1.575 | 1.395 |
| JH0114pax | 1 | −1.875 | −1.485 | −1.400 | −0.540 | −1.710 | −1.970 |
| CD1351pax | 1 | 0.510 | 0.515 | 0.015 | −0.295 | 1.830 | 0.785 |

TABLE 17-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| OL0093pax | 1 | −2.055 | −0.120 | −1.075 | 0.025 | −0.430 | 0.560 |
| JH0058pax | 1 | −0.610 | 0.305 | 0.165 | 0.240 | −0.060 | 1.195 |
| DC5008Apax | 1 | −0.395 | 0.160 | −0.190 | −0.155 | 1.135 | 1.540 |
| OL0085pax | 1 | −0.985 | −0.050 | −0.750 | −0.290 | 0.505 | 0.520 |
| FS1022pax | 1 | −0.530 | 0.295 | 0.400 | 0.675 | 0.655 | 0.040 |
| OL0063pax | 1 | −0.915 | −0.430 | −0.335 | −0.025 | 0.055 | −0.085 |
| MH0108Apax | 1 | 0.215 | 0.810 | 0.225 | −0.005 | 0.885 | 0.570 |
| MIP2006pax | 1 | −0.590 | 0.470 | −0.025 | 0.265 | 0.505 | 0.080 |
| NK2016pax | 1 | −0.220 | 0.425 | 0.075 | 0.215 | 1.975 | 0.835 |
| OL0057pax | 1 | −0.975 | −0.970 | −1.340 | −1.210 | −0.630 | −0.575 |
| JH0137pax | 1 | 0.265 | 1.395 | 0.095 | −0.125 | 1.190 | 1.175 |
| JH0118pax | 1 | 0.030 | −0.565 | 0.010 | −0.405 | 0.610 | 0.125 |
| MH0097pax | 1 | −0.785 | −0.180 | −0.195 | −0.015 | 0.345 | 0.430 |
| JH0147pax | 1 | 0.770 | 2.080 | 0.915 | 0.855 | 3.475 | 1.255 |
| BE4002pax | 1 | 0.160 | 0.420 | 0.015 | −0.445 | 0.760 | 1.265 |
| MH0036pax | 1 | −0.090 | 0.620 | 0.370 | 0.240 | 1.430 | 1.440 |
| JH0142pax | 1 | −0.585 | 0.220 | −0.185 | 0.055 | 0.285 | −0.605 |
| MIP2010Apax | 1 | 0.285 | 0.555 | −0.075 | −0.280 | 1.550 | −0.070 |
| JH0169pax | 1 | −0.305 | 0.255 | −0.120 | −0.320 | 0.455 | 1.110 |
| FS1010pax | 1 | 0.435 | 1.705 | 1.210 | 0.800 | 1.520 | 2.145 |
| JGA0036pax | 1 | −0.515 | 0.390 | −0.595 | −0.995 | −0.725 | 2.090 |
| MH0079pax | 1 | 0.395 | 0.625 | 0.275 | −0.375 | 0.500 | 1.020 |
| OL0064pax | 1 | 0.030 | 0.500 | 0.305 | 0.120 | 1.345 | 0.580 |
| JH0135pax | 1 | −1.480 | −1.890 | −1.505 | −1.320 | −1.655 | −1.480 |
| OL0017pax | 1 | −0.790 | −0.650 | −0.375 | −0.315 | 0.900 | 0.765 |
| CC2001pax | 1 | −0.285 | 1.450 | 0.335 | 0.480 | 1.315 | 1.210 |
| DC6002Apax | 1 | −0.570 | 0.975 | 0.200 | 0.395 | 0.930 | 1.000 |
| JH0149pax | 1 | 0.485 | 1.165 | 0.240 | −0.065 | 2.395 | 0.980 |
| DC2009pax | 1 | −0.715 | 0.050 | 0.195 | 0.155 | −0.350 | 0.365 |
| MP0033Bpax | 1 | 0.145 | 1.045 | 0.320 | 0.075 | 1.285 | 0.715 |
| MP0030Bpax | 1 | −0.875 | 0.445 | 0.270 | 0.690 | 2.285 | 1.790 |
| JH0133pax | 1 | −0.335 | 0.500 | 0.045 | −0.220 | 0.210 | 1.150 |
| OL0059pax | 1 | −1.335 | −0.180 | −0.735 | −0.290 | −0.065 | −0.145 |
| AN4026Bpax | 1 | −0.175 | 0.485 | 0.215 | −0.160 | 0.510 | 1.130 |
| AN4022Apax | 1 | −0.540 | 0.830 | −0.290 | −0.355 | 0.020 | 0.710 |
| OL0077pax | 1 | −1.055 | −0.525 | −0.085 | 0.035 | 0.200 | 0.165 |
| OL0094pax | 1 | −0.305 | 0.535 | 0.190 | 0.015 | 0.710 | 0.460 |
| KW0002pax | 1 | −0.625 | 0.165 | −0.505 | −0.695 | 0.470 | 1.215 |
| MH0066pax | 1 | −1.180 | −0.855 | −0.710 | −0.595 | −0.320 | −0.480 |
| DC5006Apax | 1 | −0.210 | 0.160 | 0.105 | −0.385 | −0.220 | 0.280 |
| NK4001pax | 1 | −0.975 | 1.135 | −0.090 | 0.260 | 0.500 | 0.810 |
| JGA0029pax | 1 | −0.870 | 0.590 | −0.575 | −0.195 | 1.295 | 0.185 |
| MW0008Apax | 1 | −1.080 | −0.505 | −0.480 | −0.440 | −0.300 | −0.285 |
| JH0131pax | 1 | −0.640 | −0.890 | −0.935 | −1.555 | −1.150 | 0.180 |
| JH0106pax | 1 | −0.720 | −0.200 | −0.105 | −0.290 | 0.845 | 1.115 |
| OL0056pax | 1 | −0.495 | −1.310 | −0.470 | −0.925 | 1.175 | 0.450 |
| MH0076pax | 1 | 0.515 | 1.955 | 0.540 | −0.075 | 2.340 | 2.570 |
| NK2005pax | 1 | −1.575 | −1.090 | −0.925 | −1.055 | −2.160 | −0.020 |
| MP0029Apax | 1 | −1.700 | −0.870 | −1.100 | −0.670 | 0.275 | 0.060 |
| MH0080pax | 1 | −0.310 | 0.215 | 0.340 | 0.120 | 1.530 | 0.510 |
| FS1014pax | 1 | −0.580 | 0.050 | −0.030 | 0.045 | 1.850 | −0.105 |
| JH0110pax | 1 | −0.565 | 0.185 | −0.375 | −0.830 | −0.420 | 0.735 |
| JH0145pax | 1 | −2.030 | −0.365 | −0.940 | −0.500 | −1.170 | 0.445 |
| MH0125Apax | 1 | −0.550 | 1.265 | 0.135 | −0.170 | 0.465 | 2.310 |
| OL0058pax | 1 | −0.935 | −1.050 | −0.840 | −0.870 | 0.115 | −1.495 |
| DC0008pax | 1 | 0.545 | 0.990 | 0.665 | −0.070 | 1.875 | 0.815 |
| MH0073pax | 1 | −1.290 | −0.595 | −1.165 | −1.040 | 0.040 | −0.285 |
| MIP0002pax | 1 | −2.285 | −0.925 | −1.240 | −0.595 | −0.575 | 0.055 |
| JH0138pax | 1 | −0.680 | 0.150 | −0.065 | −0.315 | 0.120 | 0.340 |
| OL0074pax | 1 | −1.255 | −0.530 | −0.680 | −0.410 | 1.280 | 0.145 |
| OL0079pax | 1 | −0.920 | −0.125 | −0.510 | −0.755 | −0.360 | 0.460 |
| MR1001pax | 1 | −0.120 | 0.795 | 0.015 | −0.490 | 0.650 | 0.495 |
| DES5001Bpax | 1 | −1.335 | 0.395 | −1.095 | −0.735 | 0.770 | 0.315 |
| MH0093pax | 1 | −2.215 | −1.375 | −1.240 | −0.880 | −0.800 | 0.255 |
| MP0027Apax | 1 | −0.415 | 0.765 | −0.140 | −0.350 | 0.940 | 0.200 |
| IS1005Apax | 1 | −1.180 | −1.030 | −0.340 | −0.445 | 0.325 | −0.025 |
| KW0003pax | 1 | −0.295 | 0.830 | 0.335 | −0.580 | −0.325 | 2.740 |
| CD1260pax | 1 | −0.730 | −1.005 | −0.325 | −0.795 | 0.725 | 0.510 |
| JH0130pax | 1 | −1.110 | −0.400 | −0.940 | −1.210 | −0.505 | 0.220 |
| MH0096pax | 1 | −1.225 | 0.790 | −0.670 | −0.420 | 0.865 | 0.665 |
| OL0052pax | 1 | −1.075 | −1.005 | −0.060 | −0.315 | 0.040 | −0.265 |

TABLE 17-continued

Sample test set levels of RNA encoded by ANXA3, CLEC4D, LMNB1, PRRG4, TNFAIP6 and VNN1 in blood of subjects having colorectal cancer (Group 1) and subjects not having any colorectal pathology (Group 0), normalized to levels of RNA encoded by IL2RB. Levels shown correspond to ΔCt.

| | | Gene | | | | | |
|---|---|---|---|---|---|---|---|
| Sample ID | Group | ANXA3 | CLEC4D | LMNB1 | PRRG4 | TNFAIP6 | VNN1 |
| MIP0005pax | 1 | −2.020 | −1.140 | −1.305 | −0.835 | −0.420 | −1.190 |
| OL0014pax | 1 | −2.000 | −2.250 | −1.480 | −1.640 | −1.645 | −0.705 |
| WJ0003RTpax | 1 | −1.935 | −1.860 | −1.760 | −1.735 | −1.070 | −1.055 |
| MIP2013Bpax | 1 | 0.025 | 1.825 | 0.110 | −0.890 | −0.500 | 1.975 |
| JH0164pax | 1 | −0.115 | 0.335 | 0.015 | −0.615 | 1.275 | 0.005 |
| JH0123pax | 1 | −2.050 | −1.365 | −1.125 | −0.920 | −1.165 | −1.315 |
| OL0089pax | 1 | −1.415 | 0.130 | −0.455 | −0.365 | −0.305 | −0.520 |
| DES1013Bpax | 1 | −1.130 | 0.105 | −0.450 | −0.595 | 0.160 | 0.065 |
| AN4011pax | 1 | −0.155 | 0.805 | 0.770 | 0.280 | 2.110 | 0.880 |
| JH0093pax | 1 | 0.095 | 1.090 | 0.085 | −0.695 | 1.290 | 0.885 |
| OL0043pax | 1 | −0.705 | −0.475 | −0.555 | −1.105 | 0.230 | −0.335 |
| JH0097pax | 1 | −0.280 | −0.285 | 0.270 | −0.445 | 0.780 | −0.415 |
| DC3003pax | 1 | −0.265 | 0.975 | 0.030 | −0.625 | 1.600 | 1.845 |
| OL0068pax | 1 | −1.790 | −0.720 | −1.340 | −1.230 | −0.665 | −0.895 |
| KW0006pax | 1 | −1.320 | 0.575 | 0.155 | 0.080 | 0.700 | 1.540 |
| NK5008pax | 1 | −1.150 | −1.435 | −1.000 | −1.300 | 0.610 | −1.040 |
| DC6001Apax | 1 | −0.965 | 0.725 | −0.225 | −0.670 | 0.135 | 1.500 |
| OL0034pax | 1 | −1.155 | −0.515 | −0.985 | −1.375 | 0.485 | 0.545 |
| MH0062pax | 1 | −1.040 | −0.245 | −0.205 | −0.600 | 0.450 | 0.300 |
| MIP1019Apax | 1 | −1.415 | −0.495 | −1.060 | −1.125 | 0.800 | −0.060 |
| MR1002pax | 1 | −0.890 | 0.295 | 0.315 | −0.070 | 0.645 | 0.355 |
| MH0090pax | 1 | −0.995 | 0.240 | −0.365 | −0.705 | 0.000 | −0.495 |
| NK2010pax | 1 | −1.505 | −1.070 | −0.985 | −1.320 | −0.870 | −1.045 |
| NK2009pax | 1 | 0.060 | 0.745 | 0.470 | −0.370 | 1.920 | 0.300 |
| NK2018pax | 1 | −2.160 | −1.415 | −1.155 | −1.090 | −0.640 | −1.100 |
| JH0144pax | 1 | 0.475 | 2.560 | 1.160 | 0.215 | 2.295 | 1.575 |
| OL0078pax | 1 | −2.540 | −2.250 | −1.570 | −1.555 | −1.350 | −1.325 |
| MIP1009pax | 1 | −2.950 | −1.590 | −2.030 | −1.500 | −0.685 | −1.165 |
| OL0025pax | 1 | −2.010 | −0.060 | −0.940 | −0.855 | −0.380 | −0.445 |
| MH0078pax | 1 | −0.910 | 0.290 | −0.405 | −1.410 | −0.335 | 1.345 |
| KW0007pax | 1 | −0.655 | 0.930 | 0.090 | −0.640 | 0.830 | 0.495 |
| AN0013pax | 1 | 0.060 | 1.905 | 0.875 | −0.085 | 2.740 | 2.020 |
| JH0076pax | 1 | −0.535 | −0.795 | −0.360 | −1.735 | −0.300 | −0.065 |
| OL0090pax | 1 | −1.105 | 0.150 | 0.090 | −0.745 | 0.075 | 0.990 |
| JH0120pax | 1 | −0.040 | 0.595 | 0.215 | −0.935 | 1.860 | 0.390 |
| JH0126pax | 1 | −1.570 | −0.110 | −0.455 | −1.020 | −0.435 | 0.415 |
| JH0113pax | 1 | −0.055 | 0.805 | 0.605 | −0.715 | 0.835 | 0.570 |
| JH0085pax | 1 | −0.960 | −0.445 | −0.075 | −1.095 | 0.185 | 0.295 |
| MH0081pax | 1 | 0.390 | 1.375 | 0.640 | −0.845 | 2.085 | 1.300 |
| AN0001pax | 1 | −1.830 | −1.010 | −0.840 | −1.320 | 0.110 | −0.175 |
| MH0095pax | 1 | −2.145 | −1.475 | −1.350 | −1.795 | −0.915 | −0.830 |
| DS0007pax | 1 | −3.365 | −2.210 | −1.965 | −1.820 | −3.555 | −2.965 |
| JH0136pax | 1 | −2.355 | −1.670 | −0.970 | −1.215 | −0.845 | −1.710 |
| OL0072pax | 1 | −1.135 | −0.315 | −0.375 | −1.170 | 0.415 | −0.875 |
| BE1006pax | 1 | −2.635 | −1.570 | −1.580 | −1.735 | −0.580 | −0.740 |
| JH0048pax | 1 | −2.285 | −0.250 | −1.315 | −1.350 | −1.075 | −2.025 |
| OL0073pax | 1 | −2.980 | −2.425 | −1.650 | −1.685 | −0.100 | −0.650 |
| FS0002pax | 1 | −2.275 | −1.035 | −0.730 | −1.030 | −0.780 | −1.700 |
| OL0041pax | 1 | −1.890 | −1.030 | −1.595 | −2.325 | −0.970 | −1.465 |
| AN0007pax | 1 | −3.105 | −1.775 | −2.300 | −3.180 | −2.690 | −1.255 |

The test set results confirmed the surprising finding based on the training set that ANXA3, CLEC4D, LMNB1, PRRG4, TNFAIP6 and VNN1 each express RNA on average at a significantly higher level (p-value less than 0.05) in blood of subjects having colorectal cancer relative to subjects having no colorectal pathology (Table 18). The ranges of fold-change in the levels of RNA encoded by ANXA3, CLEC4D, LMNB1, PRRG4, TNFAIP6 and VNN1 normalized to levels of RNA encoded by IL2RB in blood of the test set subjects having colorectal cancer relative to the test set subjects not having any colorectal pathology are also shown in Table 18.

TABLE 18

Sample test set ranges of fold-changes in levels of RNA encoded by ANXA3, CLEC4D, LMNB1, PRRG4, TNFAIP6 and VNN1 normalized to levels of RNA encoded by IL2RB in blood of subjects having colorectal cancer relative to subjects not having any colorectal pathology.

| | Gene | | | | | |
|---|---|---|---|---|---|---|
| | ANXA3 | CLEC4D | LMNB1 | PRRG4 | TNFAIP6 | VNN1 |
| Average normalized RNA level in subjects having colorectal cancer ($\Delta$Ct) | −0.37 | 0.39 | −0.04 | −0.07 | 0.76 | 0.74 |
| Average normalized RNA level in subjects not having any colorectal pathology ($\Delta$Ct) | 0.72 | 1.21 | 0.65 | 0.90 | 1.73 | 1.51 |
| Average RNA level fold-change | 2.12 | 1.77 | 1.61 | 1.97 | 1.95 | 1.70 |
| p-value for average RNA level fold-change | 2.8E−24 | 3.0E−14 | 3.3E−19 | 1.9E−26 | 5.0E−17 | 2.4E−12 |
| Maximum observed RNA level directional fold-change | 16.95 | 12.44 | 7.71 | 16.96 | 38.96 | 22.19 |

As can be seen in Table 18, a test subject having a blood level of RNA encoded by ANXA3, normalized to a level of RNA encoded by IL2RB, which is 2.1 to 17.0 fold higher than the average level of RNA encoded by this gene in blood of subjects not having any colorectal pathology is more likely to have colorectal cancer than to not have any colorectal pathology.

As can be seen in Table 18, a test subject having a blood level of RNA encoded by CLEC4D, normalized to a level of RNA encoded by IL2RB, which is 1.8 to 12.4 fold higher than the average level of RNA encoded by this gene in blood of subjects not having any colorectal pathology is more likely to have colorectal cancer than to not have any colorectal pathology.

As can be seen in Table 18, a test subject having a blood level of RNA encoded by LMNB1, normalized to a level of RNA encoded by IL2RB, which is 1.6 to 7.7 fold higher than the average level of RNA encoded by this gene in blood of subjects not having any colorectal pathology is more likely to have colorectal cancer than to not have any colorectal pathology.

As can be seen in Table 18, a test subject having a blood level of RNA encoded by PRRG4, normalized to a level of RNA encoded by IL2RB, which is 2.0 to 17.0 fold higher than the average level of RNA encoded by this gene in blood of subjects not having any colorectal pathology is more likely to have colorectal cancer than to not have any colorectal pathology.

As can be seen in Table 18, a test subject having a blood level of RNA encoded by TNFAIP6, normalized to a level of RNA encoded by IL2RB, which is 2.0 to 39.0 fold higher than the average level of RNA encoded by this gene in blood of subjects not having any colorectal pathology is more likely to have colorectal cancer than to not have any colorectal pathology.

As can be seen in Table 18, a test subject having a blood level of RNA encoded by VNN1, normalized to a level of RNA encoded by IL2RB, which is 1.7 to 22.2 fold higher than the average level of RNA encoded by this gene in blood of subjects not having any colorectal pathology is more likely to have colorectal cancer than to not have any colorectal pathology.

Furthermore, the test set results confirmed the surprising finding based on the training set that logistic regression model #191 based on blood expression levels of the combination of ANXA3, CLEC4D, LMNB1, PRRG4, TNFAIP6 and VNN1, each of which normalized against expression levels of IL2RB, can be used to discriminate, with a ROC AUC of at least 0.80 (Table 16), between subjects having colorectal cancer and subjects not having any colorectal pathology. As such, the novel logistic regression model #191 can be used to determine the probability that a test subject has colorectal cancer as opposed to not having any colorectal pathology, based on blood levels of expression of ANXA3, CLEC4D, LMNB1, PRRG4, TNFAIP6 and/or VNN1 normalized to those of IL2RB.

Example 7

Determination of the Probability that a Test Subject has Colorectal Cancer as Opposed to not Having Colorectal Cancer Using Blood Levels of RNA Encoded by the Colorectal Cancer Markers: ANXA3, CLEC4D, IL2RB, LMNB1, PRRG4, TNFAIP6 and VNN1 Normalized to Those of IL2RB A blood sample from a test subject is analyzed for levels of RNA encoded by ANXA3, CLEC4D, IL2RB, LMNB1, PRRG4, TNFAIP6 and VNN1 as described in Example 1, above, thereby generating test data. Logistic regression model #191 of Table 16 is applied to the test data, thereby providing the probability that the test subject has colorectal cancer as opposed to not having any colorectal pathology.

All patents, patent applications, and published references cited herein are hereby incorporated by reference in their entirety.

One skilled in the art will appreciate readily that the invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining whether a human test subject requires an invasive screening procedure for colon cancer, the method comprising:
    identification of whether the human test subject is more likely to have colorectal cancer than to not have colorectal cancer, the identification comprising:
        a) amplifying test cDNA complementary to test mRNA to obtain values of levels of test cDNA corresponding to the test mRNA expressed specifically by each gene of a set of genes consisting of IL2RB, ANXA3, CLEC4D, LMNB1, PRRG4, TNFAIP6 and VNN1 comprising the steps of:
            i) generating test cDNA from the test mRNA expressed specifically by each gene of the set of genes from blood of the human test subject;
            ii) reacting each test cDNA under conditions to amplify the test cDNA with a primer pair for said cDNA, wherein each primer pair consists of a forward primer and a reverse primer; and
            iii) obtaining the values of the levels of the test cDNA corresponding to the test mRNA expressed specifically by each of the IL2RB, ANXA3, CLEC4D, LMNB1, PRRG4, TNFAIP6, and VNN1 genes:
        b) obtaining a set of 6 ratios, each ratio being obtained by normalizing the level of the test cDNA corresponding to the test mRNA expressed specifically by each of the ANXA3, CLEC4D, LMNB1, PRRG4, TNFAIP6, and VNN1 genes against the level of the test cDNA corresponding to the test mRNA expressed by the IL2RB gene; and
        c) applying each of the 6 ratios to a mathematical model formulated by analyzing, using logistic regression, a training set of training set ratios, said training set ratios being obtained from levels of cDNA corresponding to mRNA expressed by each of the ANXA3, CLEC4D, LMNB1, PRRG4, TNFAIP6, and VNN1 genes, in blood of training subjects having colorectal cancer and training subjects not having colorectal cancer, normalized to levels cDNA corresponding to mRNA expressed by the IL2RB gene in the blood of said training subjects, to determine the probability that a test subject has colorectal cancer as opposed to not having colorectal cancer
    wherein when the human test subject is identified as more likely to have colorectal cancer than to not have colorectal cancer as a result of said identification, determining that the human test subject requires the invasive screening procedure for colon cancer, the invasive screening procedure being selected from the group consisting of colonoscopy, sigmoidoscopy, and combinations thereof.

2. The method of claim 1, wherein the forward primer and reverse primer pair for ANXA3, CLEC4D, IL2RB, LMNB1, PRRG4, TNFAIP6, and VNN1 test cDNA consists, respectively, of a primer pair identified as SEQ ID NO: 10 and SEQ ID NO:11, a primer pair identified as SEQ ID NO: 19 and SEQ ID NO: 20, a primer pair identified as SEQ ID NO: 28 and SEQ ID NO: 29, a primer pair identified as SEQ ID NO: 37 and SEQ ID NO: 38, a primer pair identified as SEQ ID NO: 46 and SEQ ID NO: 47, a primer pair identified as SEQ ID NO: 55 and SEQ ID NO: 56, and a primer pair identified as SEQ ID NO: 64, and SEQ ID NO: 65.

3. The method of claim 1, wherein the conditions to amplify the test cDNA comprise:
    a. combining each test cDNA with a primer pair, a thermostable DNA polymerase, and a plurality of free nucleotides comprising adenine, thymine, cytosine, and guanine in a reaction mixture;
    b. heating the reaction mixture to a predetermined temperature for a first predetermined time to separate the strands of the test cDNA from each other;
    c. cooling the reaction mixture to a second predetermined temperature for a second predetermined time under conditions to allow the first primer and the second primer to hybridize with their complementary sequences on the first strand and the second strand of the test cDNA, and to allow the thermostable DNA polymerase to extend the primers; and
    d. repeating steps (b) and (c).

* * * * *